United States Patent
Tao

(10) Patent No.: US 10,612,019 B2
(45) Date of Patent: Apr. 7, 2020

(54) METHODS AND COMPOSITIONS FOR WEED CONTROL

(71) Applicant: Monsanto Technology LLC, St. Louis, MO (US)

(72) Inventor: Nengbing Tao, O'Fallon, MO (US)

(73) Assignee: Monsanto Technology LLC, St. Louis, MO (US)

( * ) Notice: Subject to any disclaimer, the term of this patent is extended or adjusted under 35 U.S.C. 154(b) by 538 days.

(21) Appl. No.: 14/774,427

(22) PCT Filed: Mar. 11, 2014

(86) PCT No.: PCT/US2014/023503
§ 371 (c)(1),
(2) Date: Sep. 10, 2015

(87) PCT Pub. No.: WO2014/164797
PCT Pub. Date: Oct. 9, 2014

(65) Prior Publication Data
US 2016/0015035 A1    Jan. 21, 2016

Related U.S. Application Data

(60) Provisional application No. 61/779,532, filed on Mar. 13, 2013.

(51) Int. Cl.
| | | |
|---|---|---|
| *C12N 15/82* | (2006.01) | |
| *C12N 15/113* | (2010.01) | |
| *A01N 57/16* | (2006.01) | |
| *A01N 25/30* | (2006.01) | |

(52) U.S. Cl.
CPC ............ *C12N 15/113* (2013.01); *A01N 25/30* (2013.01); *A01N 57/16* (2013.01); *C12N 15/8274* (2013.01)

(58) Field of Classification Search
CPC .............. C12N 15/8218; C12N 15/113; C12N 2310/14; C12N 15/8274
See application file for complete search history.

(56) References Cited

U.S. PATENT DOCUMENTS

| | | |
|---|---|---|
| 3,687,808 A | 8/1972 | Merigan et al. |
| 3,791,932 A | 2/1974 | Schuurs et al. |
| 3,839,153 A | 10/1974 | Schuurs et al. |
| 3,850,578 A | 11/1974 | McConnell |
| 3,850,752 A | 11/1974 | Schuurs et al. |
| 3,853,987 A | 12/1974 | Dreyer |
| 3,867,517 A | 2/1975 | Ling |
| 3,879,262 A | 4/1975 | Schuurs et al. |
| 3,901,654 A | 8/1975 | Gross |
| 3,935,074 A | 1/1976 | Rubenstein et al. |
| 3,984,533 A | 10/1976 | Uzgiris |
| 3,996,345 A | 12/1976 | Ullman et al. |
| 4,034,074 A | 7/1977 | Miles |
| 4,098,876 A | 7/1978 | Piasio et al. |
| 4,469,863 A | 9/1984 | Ts'o et al. |
| 4,476,301 A | 10/1984 | Imbach et al. |
| 4,535,060 A | 8/1985 | Comai |
| 4,581,847 A | 4/1986 | Hibberd et al. |
| 4,666,828 A | 5/1987 | Gusella |
| 4,683,202 A | 7/1987 | Mullis |
| 4,761,373 A | 8/1988 | Anderson et al. |
| 4,769,061 A | 9/1988 | Comai |
| 4,801,531 A | 1/1989 | Frossard |
| 4,810,648 A | 3/1989 | Stalker |
| 4,879,219 A | 11/1989 | Wands et al. |
| 4,940,835 A | 7/1990 | Shah et al. |
| 4,971,908 A | 11/1990 | Kishore et al. |
| 5,004,863 A | 4/1991 | Umbeck |
| 5,011,771 A | 4/1991 | Bellet et al. |
| 5,013,659 A | 5/1991 | Bedbrook et al. |
| 5,015,580 A | 5/1991 | Christou et al. |
| 5,023,243 A | 6/1991 | Tullis |
| 5,034,506 A | 7/1991 | Summerton et al. |
| 5,094,945 A | 3/1992 | Comai |
| 5,141,870 A | 8/1992 | Bedbrook et al. |
| 5,145,783 A | 9/1992 | Kishore et al. |
| 5,159,135 A | 10/1992 | Umbeck |
| 5,166,315 A | 11/1992 | Summerton et al. |
| 5,177,196 A | 1/1993 | Meyer, Jr. et al. |
| 5,185,444 A | 2/1993 | Summerton et al. |
| 5,188,642 A | 2/1993 | Shah et al. |

(Continued)

FOREIGN PATENT DOCUMENTS

| | | |
|---|---|---|
| AU | 2008258254 B2 | 7/2014 |
| CN | 101279950 A | 10/2008 |

(Continued)

OTHER PUBLICATIONS

Yu, Qin, Andrew Cairns, and Stephen Powles. "Glyphosate, paraquat and ACCase multiple herbicide resistance evolved in a Lolium rigidum biotype." Planta 225.2 (2007): 499-513. (Year: 2007).*
Yu, Qin, et al. "Diversity of acetyl-coenzyme A carboxylase mutations in resistant Lolium populations: evaluation using clethodim." Plant physiology 145.2 (2007): 547-558. (Year: 2007).*
Morozov, Ivan Vladimirovitch. Evaluation and Characterization of Herbicide Resistance in Italian Ryegrass (*Lolium multiflorum* Lam.) Biotypes to Diclofop-methyl and Alternative Management Options. Diss. Virginia Tech, 2004. (Year: 2004).*
Guttieri, Mary J., et al. "DNA sequence variation in Domain A of the acetolactate synthase genes of herbicide-resistant and-susceptible weed biotypes." Weed Science 40.4 (1992): 670-677. (Year: 1992).*

(Continued)

*Primary Examiner* — Weihua Fan
(74) *Attorney, Agent, or Firm* — Amanda Carmany-Rampey; Arnold & Porter Kaye Scholer LLP

(57) ABSTRACT

The present invention provides novel compositions for use to enhance weed control. Specifically, the present invention provides for methods and compositions that modulate gene expression in *Lolium*. The present invention also provides for combinations of compositions and methods that enhance *Lolium* control.

9 Claims, No Drawings

Specification includes a Sequence Listing.

(56) References Cited

U.S. PATENT DOCUMENTS

| | | |
|---|---|---|
| 5,188,897 A | 2/1993 | Suhadolnik et al. |
| 5,192,659 A | 3/1993 | Simons |
| 5,214,134 A | 5/1993 | Weis et al. |
| 5,216,141 A | 6/1993 | Benner |
| 5,235,033 A | 8/1993 | Summerton et al. |
| 5,264,423 A | 11/1993 | Cohen et al. |
| 5,264,562 A | 11/1993 | Matteucci |
| 5,264,564 A | 11/1993 | Matteucci |
| 5,272,057 A | 12/1993 | Smulson et al. |
| 5,276,019 A | 1/1994 | Cohen et al. |
| 5,281,521 A | 1/1994 | Trojanowski et al. |
| 5,286,634 A | 2/1994 | Stadler et al. |
| 5,286,717 A | 2/1994 | Cohen et al. |
| 5,304,732 A | 4/1994 | Anderson et al. |
| 5,310,667 A | 5/1994 | Eichholtz et al. |
| 5,312,910 A | 5/1994 | Kishore et al. |
| 5,321,131 A | 6/1994 | Agrawal et al. |
| 5,331,107 A | 7/1994 | Anderson et al. |
| 5,339,107 A | 8/1994 | Henry et al. |
| 5,346,107 A | 9/1994 | Bouix et al. |
| 5,378,824 A | 1/1995 | Bedbrook et al. |
| 5,384,253 A | 1/1995 | Krzyzek et al. |
| 5,390,667 A | 2/1995 | Kumakura et al. |
| 5,392,910 A | 2/1995 | Bell et al. |
| 5,393,175 A | 2/1995 | Courville |
| 5,399,676 A | 3/1995 | Froehler |
| 5,405,938 A | 4/1995 | Summerton et al. |
| 5,405,939 A | 4/1995 | Suhadolnik et al. |
| 5,416,011 A | 5/1995 | Hinchee et al. |
| 5,453,496 A | 9/1995 | Caruthers et al. |
| 5,455,233 A | 10/1995 | Spielvogel et al. |
| 5,459,127 A | 10/1995 | Felgner et al. |
| 5,460,667 A | 10/1995 | Moriyuki et al. |
| 5,462,910 A | 10/1995 | Ito et al. |
| 5,463,174 A | 10/1995 | Moloney et al. |
| 5,463,175 A | 10/1995 | Barry et al. |
| 5,466,677 A | 11/1995 | Baxter et al. |
| 5,470,967 A | 11/1995 | Huie et al. |
| 5,476,925 A | 12/1995 | Letsinger et al. |
| 5,489,520 A | 2/1996 | Adams et al. |
| 5,489,677 A | 2/1996 | Sanghvi et al. |
| 5,491,288 A | 2/1996 | Chaubet et al. |
| 5,510,471 A | 4/1996 | Lebrun et al. |
| 5,518,908 A | 5/1996 | Corbin et al. |
| 5,519,126 A | 5/1996 | Hecht |
| 5,536,821 A | 7/1996 | Agrawal et al. |
| 5,538,880 A | 7/1996 | Lundquist et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,550,318 A | 8/1996 | Adams et al. |
| 5,550,398 A | 8/1996 | Kocian et al. |
| 5,550,468 A | 8/1996 | Häberlein et al. |
| 5,558,071 A | 9/1996 | Ward et al. |
| 5,561,225 A | 10/1996 | Maddry et al. |
| 5,561,236 A | 10/1996 | Leemans et al. |
| 5,563,253 A | 10/1996 | Agrawal et al. |
| 5,569,834 A | 10/1996 | Hinchee et al. |
| 5,571,799 A | 11/1996 | Tkachuk et al. |
| 5,587,361 A | 12/1996 | Cook et al. |
| 5,591,616 A | 1/1997 | Hiei et al. |
| 5,593,874 A | 1/1997 | Brown et al. |
| 5,596,086 A | 1/1997 | Matteucci et al. |
| 5,597,717 A | 1/1997 | Guerineau et al. |
| 5,602,240 A | 2/1997 | De Mesmaeker et al. |
| 5,605,011 A | 2/1997 | Bedbrook et al. |
| 5,608,046 A | 3/1997 | Cook et al. |
| 5,610,289 A | 3/1997 | Cook et al. |
| 5,618,704 A | 4/1997 | Sanghvi et al. |
| 5,623,070 A | 4/1997 | Cook et al. |
| 5,625,050 A | 4/1997 | Beaton et al. |
| 5,627,061 A | 5/1997 | Barry et al. |
| 5,633,360 A | 5/1997 | Bischofberger et al. |
| 5,633,435 A | 5/1997 | Barry et al. |
| 5,633,448 A | 5/1997 | Lebrun et al. |
| 5,639,024 A | 6/1997 | Mueller et al. |
| 5,646,024 A | 7/1997 | Leemans et al. |
| 5,648,477 A | 7/1997 | Leemans et al. |
| 5,663,312 A | 9/1997 | Chaturvedula |
| 5,677,437 A | 10/1997 | Teng et al. |
| 5,677,439 A | 10/1997 | Weis et al. |
| 5,719,046 A | 2/1998 | Guerineau et al. |
| 5,721,138 A | 2/1998 | Lawn |
| 5,731,180 A | 3/1998 | Dietrich |
| 5,739,180 A | 4/1998 | Taylor-Smith |
| 5,746,180 A | 5/1998 | Jefferson et al. |
| 5,767,361 A | 6/1998 | Dietrich |
| 5,767,373 A | 6/1998 | Ward et al. |
| 5,780,708 A | 7/1998 | Lundquist et al. |
| 5,804,425 A | 9/1998 | Barry et al. |
| 5,824,877 A | 10/1998 | Hinchee et al. |
| 5,837,848 A | 11/1998 | Ely et al. |
| 5,859,347 A | 1/1999 | Brown et al. |
| 5,866,775 A | 2/1999 | Eichholtz et al. |
| 5,874,265 A | 2/1999 | Adams et al. |
| 5,879,903 A | 3/1999 | Strauch et al. |
| 5,914,451 A | 6/1999 | Martinell et al. |
| 5,919,675 A | 7/1999 | Adams et al. |
| 5,928,937 A | 7/1999 | Kakefuda et al. |
| 5,939,602 A | 8/1999 | Volrath et al. |
| 5,969,213 A | 10/1999 | Adams et al. |
| 5,981,840 A | 11/1999 | Zhao et al. |
| 5,985,793 A | 11/1999 | Sandbrink et al. |
| RE36,449 E | 12/1999 | Lebrun et al. |
| 6,040,497 A | 3/2000 | Spencer et al. |
| 6,056,938 A | 5/2000 | Unger et al. |
| 6,069,115 A | 5/2000 | Pallett et al. |
| 6,084,089 A | 7/2000 | Mine et al. |
| 6,084,155 A | 7/2000 | Volrath et al. |
| 6,118,047 A | 9/2000 | Anderson et al. |
| 6,121,513 A | 9/2000 | Zhang et al. |
| 6,130,366 A | 10/2000 | Herrera-Estrella et al. |
| 6,140,078 A | 10/2000 | Sanders et al. |
| 6,153,812 A | 11/2000 | Fry et al. |
| 6,160,208 A | 12/2000 | Lundquist et al. |
| 6,177,616 B1 | 1/2001 | Bartsch et al. |
| 6,194,636 B1 | 2/2001 | McElroy et al. |
| 6,225,105 B1 | 5/2001 | Sathasivan et al. |
| 6,225,114 B1 | 5/2001 | Eichholtz et al. |
| 6,232,526 B1 | 5/2001 | McElroy et al. |
| 6,245,968 B1 | 6/2001 | Boudec et al. |
| 6,248,876 B1 | 6/2001 | Barry et al. |
| 6,252,138 B1 | 6/2001 | Karimi et al. |
| RE37,287 E | 7/2001 | Lebrun et al. |
| 6,268,549 B1 | 7/2001 | Sailland et al. |
| 6,271,359 B1 | 8/2001 | Norris et al. |
| 6,282,837 B1 | 9/2001 | Ward et al. |
| 6,288,306 B1 | 9/2001 | Ward et al. |
| 6,288,312 B1 | 9/2001 | Christou et al. |
| 6,294,714 B1 | 9/2001 | Matsunaga et al. |
| 6,326,193 B1 | 12/2001 | Liu et al. |
| 6,329,571 B1 | 12/2001 | Hiei |
| 6,348,185 B1 | 2/2002 | Piwnica-Worms |
| 6,365,807 B1 | 4/2002 | Christou et al. |
| 6,384,301 B1 | 5/2002 | Martinell et al. |
| 6,385,902 B1 | 5/2002 | Schipper et al. |
| 6,399,861 B1 | 6/2002 | Anderson et al. |
| 6,403,865 B1 | 6/2002 | Koziel et al. |
| 6,414,222 B1 | 7/2002 | Gengenbach et al. |
| 6,421,956 B1 | 7/2002 | Boukens et al. |
| 6,426,446 B1 | 7/2002 | McElroy et al. |
| 6,433,252 B1 | 8/2002 | Kriz et al. |
| 6,437,217 B1 | 8/2002 | McElroy et al. |
| 6,453,609 B1 | 9/2002 | Soll et al. |
| 6,479,291 B2 | 11/2002 | Kumagai et al. |
| 6,506,559 B1 | 1/2003 | Fire et al. |
| 6,642,435 B1 | 11/2003 | Rafalski et al. |
| 6,644,341 B1 | 11/2003 | Chemo et al. |
| 6,645,914 B1 | 11/2003 | Woznica et al. |
| 6,768,044 B1 | 7/2004 | Boudec et al. |
| 6,992,237 B1 | 1/2006 | Habben et al. |
| 7,022,896 B1 | 4/2006 | Weeks et al. |
| 7,026,528 B2 | 4/2006 | Cheng et al. |
| RE39,247 E | 8/2006 | Barry et al. |

(56) References Cited

U.S. PATENT DOCUMENTS

| | | |
|---|---|---|
| 7,105,724 B2 | 9/2006 | Weeks et al. |
| 7,119,256 B2 | 10/2006 | Shimizu et al. |
| 7,138,564 B2 | 11/2006 | Tian et al. |
| 7,297,541 B2 | 11/2007 | Moshiri et al. |
| 7,304,209 B2 | 12/2007 | Zink et al. |
| 7,312,379 B2 | 12/2007 | Andrews et al. |
| 7,323,310 B2 | 1/2008 | Peters et al. |
| 7,371,927 B2 | 5/2008 | Yao et al. |
| 7,392,379 B2 | 6/2008 | Le Pennec et al. |
| 7,405,347 B2 | 7/2008 | Hammer et al. |
| 7,406,981 B2 | 8/2008 | Hemo et al. |
| 7,462,379 B2 | 12/2008 | Fukuda et al. |
| 7,485,777 B2 | 2/2009 | Nakajima et al. |
| 7,525,013 B2 | 4/2009 | Hildebrand et al. |
| 7,550,578 B2 | 6/2009 | Budworth et al. |
| 7,622,301 B2 | 11/2009 | Ren et al. |
| 7,657,299 B2 | 2/2010 | Huizenga et al. |
| 7,671,254 B2 | 3/2010 | Tranel et al. |
| 7,714,188 B2 | 5/2010 | Castle et al. |
| 7,738,626 B2 | 6/2010 | Weese et al. |
| 7,807,791 B2 | 10/2010 | Sekar et al. |
| 7,838,263 B2 | 11/2010 | Dam et al. |
| 7,838,733 B2 | 11/2010 | Wright et al. |
| 7,842,856 B2 | 11/2010 | Tranel et al. |
| 7,884,262 B2 | 2/2011 | Clemente et al. |
| 7,910,805 B2 | 3/2011 | Duck et al. |
| 7,935,869 B2 | 5/2011 | Pallett et al. |
| 7,943,819 B2 | 5/2011 | Baum et al. |
| 7,973,218 B2 | 7/2011 | McCutchen et al. |
| 8,090,164 B2 | 1/2012 | Bullitt et al. |
| 8,143,480 B2 | 3/2012 | Axtell et al. |
| 8,226,938 B1 | 7/2012 | Meikle et al. |
| 8,548,778 B1 | 10/2013 | Hart et al. |
| 8,554,490 B2 | 10/2013 | Tang et al. |
| 9,121,022 B2 | 9/2015 | Sammons et al. |
| 9,422,557 B2 | 8/2016 | Ader |
| 9,445,603 B2 | 9/2016 | Baum et al. |
| 2001/0006797 A1 | 7/2001 | Kumagai et al. |
| 2001/0042257 A1 | 11/2001 | Connor-Ward et al. |
| 2002/0069430 A1 | 6/2002 | Kiaska et al. |
| 2002/0114784 A1 | 8/2002 | Li et al. |
| 2003/0150017 A1 | 8/2003 | Mesa et al. |
| 2003/0154508 A1 | 8/2003 | Stevens et al. |
| 2003/0167537 A1 | 9/2003 | Jiang |
| 2003/0221211 A1 | 11/2003 | Rottmann et al. |
| 2004/0029275 A1 | 2/2004 | Brown et al. |
| 2004/0053289 A1 | 3/2004 | Allen et al. |
| 2004/0055041 A1 | 3/2004 | Labate et al. |
| 2004/0072692 A1 | 4/2004 | Hoffman et al. |
| 2004/0082475 A1 | 4/2004 | Hoffman et al. |
| 2004/0123347 A1 | 6/2004 | Hinchey et al. |
| 2004/0126845 A1 | 7/2004 | Eenennaam et al. |
| 2004/0133944 A1 | 7/2004 | Hake et al. |
| 2004/0147475 A1 | 7/2004 | Li et al. |
| 2004/0177399 A1 | 9/2004 | Hammer et al. |
| 2004/0216189 A1 | 10/2004 | Houmard et al. |
| 2004/0244075 A1 | 12/2004 | Cai et al. |
| 2004/0250310 A1 | 12/2004 | Shukla et al. |
| 2005/0005319 A1 | 1/2005 | della-Cioppa et al. |
| 2005/0044591 A1 | 2/2005 | Yao et al. |
| 2005/0215435 A1 | 9/2005 | Menges et al. |
| 2005/0223425 A1* | 10/2005 | Clinton .................. A01N 57/20 800/279 |
| 2005/0246784 A1 | 11/2005 | Plesch et al. |
| 2005/0250647 A1 | 11/2005 | Hills et al. |
| 2006/0009358 A1 | 1/2006 | Kibler et al. |
| 2006/0021087 A1 | 1/2006 | Baum et al. |
| 2006/0040826 A1 | 2/2006 | Eaton et al. |
| 2006/0111241 A1 | 5/2006 | Gerwick, III et al. |
| 2006/0130172 A1 | 6/2006 | Whaley et al. |
| 2006/0135758 A1 | 6/2006 | Wu |
| 2006/0200878 A1 | 9/2006 | Lutfiyya et al. |
| 2006/0223708 A1 | 10/2006 | Hoffman et al. |
| 2006/0223709 A1 | 10/2006 | Helmke et al. |
| 2006/0247197 A1 | 11/2006 | Van De Craen et al. |
| 2006/0272049 A1 | 11/2006 | Waterhouse et al. |
| 2006/0276339 A1 | 12/2006 | Windsor et al. |
| 2007/0011775 A1 | 1/2007 | Allen et al. |
| 2007/0021360 A1 | 1/2007 | Nyce et al. |
| 2007/0050863 A1 | 3/2007 | Tranel et al. |
| 2007/0124836 A1 | 5/2007 | Baum et al. |
| 2007/0199095 A1 | 8/2007 | Allen et al. |
| 2007/0250947 A1 | 10/2007 | Boukharov et al. |
| 2007/0259785 A1 | 11/2007 | Heck et al. |
| 2007/0269815 A1 | 11/2007 | Rivory et al. |
| 2007/0281900 A1 | 12/2007 | Cui et al. |
| 2007/0300329 A1 | 12/2007 | Allen et al. |
| 2008/0022423 A1 | 1/2008 | Roberts et al. |
| 2008/0050342 A1 | 2/2008 | Fire et al. |
| 2008/0092256 A1 | 4/2008 | Kohn |
| 2008/0113351 A1 | 5/2008 | Naito et al. |
| 2008/0155716 A1 | 6/2008 | Sonnewald et al. |
| 2008/0214443 A1 | 9/2008 | Baum et al. |
| 2009/0011934 A1 | 1/2009 | Zawierucha et al. |
| 2009/0018016 A1 | 1/2009 | Duck et al. |
| 2009/0036311 A1 | 2/2009 | Witschel et al. |
| 2009/0054240 A1 | 2/2009 | Witschel et al. |
| 2009/0075921 A1 | 3/2009 | Ikegawa et al. |
| 2009/0098614 A1 | 4/2009 | Zamore et al. |
| 2009/0118214 A1 | 5/2009 | Paldi et al. |
| 2009/0137395 A1 | 5/2009 | Chicoine et al. |
| 2009/0165153 A1 | 6/2009 | Wang et al. |
| 2009/0165166 A1 | 6/2009 | Feng et al. |
| 2009/0172838 A1 | 7/2009 | Axtell et al. |
| 2009/0188005 A1 | 7/2009 | Boukharov et al. |
| 2009/0205079 A1 | 8/2009 | Kumar et al. |
| 2009/0215628 A1 | 8/2009 | Witschel et al. |
| 2009/0285784 A1 | 11/2009 | Raemaekers et al. |
| 2009/0293148 A1 | 11/2009 | Ren et al. |
| 2009/0298787 A1 | 12/2009 | Raemaekers et al. |
| 2009/0306189 A1 | 12/2009 | Raemaekers et al. |
| 2009/0307803 A1 | 12/2009 | Baum et al. |
| 2010/0005551 A1 | 1/2010 | Roberts et al. |
| 2010/0048670 A1 | 2/2010 | Biard et al. |
| 2010/0068172 A1 | 3/2010 | Van De Craen |
| 2010/0071088 A1 | 3/2010 | Sela et al. |
| 2010/0099561 A1 | 4/2010 | Selby et al. |
| 2010/0100988 A1 | 4/2010 | Tranel et al. |
| 2010/0152443 A1 | 6/2010 | Hirai et al. |
| 2010/0154083 A1 | 6/2010 | Ross et al. |
| 2010/0192237 A1 | 7/2010 | Ren et al. |
| 2010/0247578 A1 | 9/2010 | Salama |
| 2010/0248373 A1 | 9/2010 | Baba et al. |
| 2011/0015084 A1 | 1/2011 | Christian et al. |
| 2011/0015284 A1 | 1/2011 | Dees et al. |
| 2011/0028412 A1 | 2/2011 | Cappello et al. |
| 2011/0035836 A1 | 2/2011 | Eudes et al. |
| 2011/0041400 A1 | 2/2011 | Trias Vila et al. |
| 2011/0053226 A1 | 3/2011 | Rohayem |
| 2011/0098180 A1 | 4/2011 | Michel et al. |
| 2011/0105327 A1 | 5/2011 | Nelson |
| 2011/0105329 A1 | 5/2011 | Song et al. |
| 2011/0112570 A1 | 5/2011 | Mannava et al. |
| 2011/0126310 A1 | 5/2011 | Feng et al. |
| 2011/0126311 A1 | 5/2011 | Velcheva et al. |
| 2011/0152339 A1 | 6/2011 | Brown et al. |
| 2011/0152346 A1 | 6/2011 | Karleson et al. |
| 2011/0152353 A1 | 6/2011 | Koizumi et al. |
| 2011/0160082 A1 | 6/2011 | Woo et al. |
| 2011/0166022 A1 | 7/2011 | Israels et al. |
| 2011/0166023 A1 | 7/2011 | Nettleton-Hammond et al. |
| 2011/0171176 A1 | 7/2011 | Baas et al. |
| 2011/0171287 A1 | 7/2011 | Saarma et al. |
| 2011/0177949 A1 | 7/2011 | Krapp et al. |
| 2011/0185444 A1 | 7/2011 | Li et al. |
| 2011/0185445 A1 | 7/2011 | Bogner et al. |
| 2011/0191897 A1 | 8/2011 | Poree et al. |
| 2011/0201501 A1 | 8/2011 | Song et al. |
| 2011/0203013 A1 | 8/2011 | Peterson et al. |
| 2011/0296555 A1 | 12/2011 | Ivashuta et al. |
| 2011/0296556 A1* | 12/2011 | Sammons .............. A01N 57/16 800/298 |
| 2012/0036594 A1 | 2/2012 | Cardoza et al. |
| 2012/0107355 A1 | 5/2012 | Harris et al. |

(56) References Cited

U.S. PATENT DOCUMENTS

| | | |
|---|---|---|
| 2012/0108497 A1 | 5/2012 | Paldi et al. |
| 2012/0137387 A1 | 5/2012 | Baum et al. |
| 2012/0150048 A1 | 6/2012 | Kang et al. |
| 2012/0156784 A1 | 6/2012 | Adams, Jr. et al. |
| 2012/0157512 A1 | 6/2012 | Ben-Chanoch et al. |
| 2012/0164205 A1 | 6/2012 | Baum et al. |
| 2012/0174262 A1 | 7/2012 | Azhakanandam et al. |
| 2012/0185967 A1 | 7/2012 | Sela et al. |
| 2012/0198586 A1 | 8/2012 | Narva et al. |
| 2012/0230565 A1 | 9/2012 | Steinberg et al. |
| 2012/0258646 A1 | 10/2012 | Sela et al. |
| 2013/0003213 A1 | 1/2013 | Kabelac et al. |
| 2013/0041004 A1 | 2/2013 | Drager et al. |
| 2013/0047297 A1 | 2/2013 | Sammons et al. |
| 2013/0047298 A1 | 2/2013 | Tang |
| 2013/0060133 A1 | 3/2013 | Kassab et al. |
| 2013/0067618 A1 | 3/2013 | Ader et al. |
| 2013/0084243 A1 | 4/2013 | Goetsch et al. |
| 2013/0096073 A1 | 4/2013 | Sidelman |
| 2013/0097726 A1 | 4/2013 | Ader et al. |
| 2013/0212739 A1 | 8/2013 | Giritch et al. |
| 2013/0226003 A1 | 8/2013 | Edic et al. |
| 2013/0247247 A1 | 9/2013 | Ader et al. |
| 2013/0254940 A1 | 9/2013 | Ader et al. |
| 2013/0254941 A1 | 9/2013 | Ader et al. |
| 2013/0288895 A1 | 10/2013 | Ader et al. |
| 2013/0318657 A1 | 11/2013 | Avniel et al. |
| 2013/0318658 A1 | 11/2013 | Ader et al. |
| 2013/0324842 A1 | 12/2013 | Mittal et al. |
| 2013/0326731 A1 | 12/2013 | Ader et al. |
| 2014/0018241 A1 | 1/2014 | Sammons et al. |
| 2014/0057789 A1 | 2/2014 | Sammons et al. |
| 2014/0109258 A1 | 4/2014 | Van De Craen et al. |
| 2014/0230090 A1 | 8/2014 | Avniel et al. |
| 2014/0274712 A1 | 9/2014 | Finnessy et al. |
| 2014/0275208 A1 | 9/2014 | Hu et al. |
| 2014/0296503 A1 | 10/2014 | Avniel et al. |
| 2015/0096079 A1 | 4/2015 | Avniel et al. |
| 2015/0143580 A1 | 5/2015 | Beattie et al. |
| 2015/0159156 A1 | 6/2015 | Inberg et al. |
| 2015/0203867 A1 | 7/2015 | Beattie et al. |
| 2015/0240258 A1 | 8/2015 | Beattie et al. |
| 2016/0015035 A1 | 1/2016 | Tao |
| 2016/0029644 A1 | 2/2016 | Tao |

FOREIGN PATENT DOCUMENTS

| | | |
|---|---|---|
| CN | 101279951 A | 10/2008 |
| CN | 101892247 A | 11/2010 |
| CN | 101914540 A | 12/2010 |
| CN | 102481311 A | 5/2012 |
| CN | 102822350 A | 12/2012 |
| DE | 288618 A5 | 4/1991 |
| DE | 10000600 A1 | 7/2001 |
| DE | 10116399 A1 | 10/2002 |
| DE | 10256353 A1 | 6/2003 |
| DE | 10256354 A1 | 6/2003 |
| DE | 10256367 A1 | 6/2003 |
| DE | 10204951 A1 | 8/2003 |
| DE | 10234875 A1 | 2/2004 |
| DE | 10234876 A1 | 2/2004 |
| DE | 102004054666 A1 | 5/2006 |
| DE | 102005014638 A1 | 10/2006 |
| DE | 102005014906 A1 | 10/2006 |
| DE | 102007012168 A1 | 9/2008 |
| DE | 102010042866 A1 | 5/2011 |
| EP | 0 804 600 A1 | 11/1997 |
| EP | 1 155 615 A1 | 11/2001 |
| EP | 1 157 991 A2 | 11/2001 |
| EP | 1 238 586 A1 | 9/2002 |
| EP | 1 416 049 A1 | 5/2004 |
| EP | 1 496 123 A1 | 1/2005 |
| EP | 1 889 902 A1 | 2/2008 |
| EP | 1 964 919 A1 | 9/2008 |
| EP | 2 147 919 A1 | 1/2010 |
| EP | 2 160 098 B1 | 11/2010 |
| EP | 2 530 159 A1 | 3/2011 |
| EP | 2 305 813 A2 | 4/2011 |
| EP | 2 545 182 A1 | 1/2013 |
| JP | 2001253874 A | 9/2001 |
| JP | 2002080454 A | 3/2002 |
| JP | 2002138075 A | 5/2002 |
| JP | 2002145707 A | 5/2002 |
| JP | 2002220389 A | 8/2002 |
| JP | 2003064059 A | 3/2003 |
| JP | 2003096059 A | 4/2003 |
| JP | 2004051628 A | 2/2004 |
| JP | 2004107228 A | 4/2004 |
| JP | 2005008583 A | 1/2005 |
| JP | 2005239675 A | 9/2005 |
| JP | 2005314407 A | 11/2005 |
| JP | 2006232824 A | 9/2006 |
| JP | 2006282552 A | 10/2006 |
| JP | 2007153847 A | 6/2007 |
| JP | 2007161701 A | 6/2007 |
| JP | 2007182404 A | 7/2007 |
| JP | 2008074840 A | 4/2008 |
| JP | 2008074841 A | 4/2008 |
| JP | 2008133207 A | 6/2008 |
| JP | 2008133218 A | 6/2008 |
| JP | 2008169121 A | 7/2008 |
| JP | 2009067739 A | 4/2009 |
| JP | 2009114128 A | 5/2009 |
| JP | 2009126792 A | 6/2009 |
| JP | 2009137851 A | 6/2009 |
| JP | 2009-508481 A | 12/2009 |
| WO | WO 89/11789 A1 | 12/1989 |
| WO | WO 95/34659 A1 | 12/1995 |
| WO | WO 95/34668 A2 | 12/1995 |
| WO | WO 96/005721 A1 | 2/1996 |
| WO | WO 96/033270 A1 | 10/1996 |
| WO | WO 96/038567 A2 | 12/1996 |
| WO | WO 96/040964 A2 | 12/1996 |
| WO | WO 97/49816 A1 | 12/1997 |
| WO | WO 99/024585 A1 | 5/1999 |
| WO | WO 99/26467 A1 | 6/1999 |
| WO | WO 99/27116 A2 | 6/1999 |
| WO | WO 99/32619 A1 | 7/1999 |
| WO | WO 99/61631 A1 | 12/1999 |
| WO | WO 99/67367 A1 | 12/1999 |
| WO | WO 00/32757 A2 | 6/2000 |
| WO | WO 00/044914 A1 | 8/2000 |
| WO | WO 01/07601 A2 | 2/2001 |
| WO | WO 2001/07601 A2 | 2/2001 |
| WO | WO 02/14472 A2 | 2/2002 |
| WO | WO 02/066660 A2 | 8/2002 |
| WO | WO 03/000679 A2 | 1/2003 |
| WO | WO 03/006422 A1 | 1/2003 |
| WO | WO 03/012052 A2 | 2/2003 |
| WO | WO 03/013247 A1 | 2/2003 |
| WO | WO 03/016308 A1 | 2/2003 |
| WO | WO 03/020704 A1 | 3/2003 |
| WO | WO 03/022051 A1 | 3/2003 |
| WO | WO 03/022831 A1 | 3/2003 |
| WO | WO 03/022843 A1 | 3/2003 |
| WO | WO 03/029243 A2 | 4/2003 |
| WO | WO 03/037085 A1 | 5/2003 |
| WO | WO 03/037878 A1 | 5/2003 |
| WO | WO 03/045878 A2 | 6/2003 |
| WO | WO 03/050087 A2 | 6/2003 |
| WO | WO 03/051823 A1 | 6/2003 |
| WO | WO 03/051824 A1 | 6/2003 |
| WO | WO 03/051846 A2 | 6/2003 |
| WO | WO 03/064625 A2 | 8/2003 |
| WO | WO 03/076409 A1 | 9/2003 |
| WO | WO 03/077648 A2 | 9/2003 |
| WO | WO 03/087067 A1 | 10/2003 |
| WO | WO 03/090539 A1 | 11/2003 |
| WO | WO 03/091217 A1 | 11/2003 |
| WO | WO 03/093269 A2 | 11/2003 |
| WO | WO 03/104206 A2 | 12/2003 |
| WO | WO 2004/002947 A1 | 1/2004 |
| WO | WO 2004/002981 A2 | 1/2004 |
| WO | WO 2004/005485 A2 | 1/2004 |

(56) References Cited

FOREIGN PATENT DOCUMENTS

| | | |
|---|---|---|
| WO | WO 2004/009761 A2 | 1/2004 |
| WO | WO 2004/011429 A1 | 2/2004 |
| WO | WO 2004/022771 A2 | 3/2004 |
| WO | WO 2004/029060 A1 | 4/2004 |
| WO | WO 2004/035545 A2 | 4/2004 |
| WO | WO 2004/035563 A1 | 4/2004 |
| WO | WO 2004/035564 A1 | 4/2004 |
| WO | WO 2004/037787 A1 | 5/2004 |
| WO | WO 2004/049806 A1 | 6/2004 |
| WO | WO 2004/062351 A2 | 7/2004 |
| WO | WO 2004/067518 A1 | 8/2004 |
| WO | WO 2004/067527 A1 | 8/2004 |
| WO | WO 2004/074443 A2 | 9/2004 |
| WO | WO 2004/077950 A1 | 9/2004 |
| WO | WO 2005/000824 A1 | 1/2005 |
| WO | WO 2005/003362 A2 | 1/2005 |
| WO | WO 2005/007627 A1 | 1/2005 |
| WO | WO 2005/007860 A1 | 1/2005 |
| WO | WO 2005/040152 A1 | 5/2005 |
| WO | WO 2005/047233 A1 | 5/2005 |
| WO | WO 2005/047281 A1 | 5/2005 |
| WO | WO 2005/061443 A2 | 7/2005 |
| WO | WO 2005/061464 A1 | 7/2005 |
| WO | WO 2005/068434 A1 | 7/2005 |
| WO | WO 2005/070889 A1 | 8/2005 |
| WO | WO 2005/089551 A1 | 9/2005 |
| WO | WO 2005/095335 A1 | 10/2005 |
| WO | WO 2005/107437 A2 | 11/2005 |
| WO | WO 2005/110068 A2 | 11/2005 |
| WO | WO 2006/006569 A1 | 1/2006 |
| WO | WO 2006/024820 A1 | 3/2006 |
| WO | WO 2006/029828 A1 | 3/2006 |
| WO | WO 2006/029829 A1 | 3/2006 |
| WO | WO 2006/037945 A1 | 4/2006 |
| WO | WO 2006/050803 A1 | 5/2006 |
| WO | WO 2006/074400 A2 | 7/2006 |
| WO | WO 2006/090792 A1 | 8/2006 |
| WO | WO 2006/123088 A2 | 11/2006 |
| WO | WO 2006/125687 A1 | 11/2006 |
| WO | WO 2006/125688 A1 | 11/2006 |
| WO | WO 2006/132270 A1 | 12/2006 |
| WO | WO 2006/138638 A1 | 12/2006 |
| WO | WO 2007/003294 A1 | 1/2007 |
| WO | WO 2007/007316 A1 | 1/2007 |
| WO | WO 2007/024783 | 3/2007 |
| WO | WO 2007/026834 A1 | 3/2007 |
| WO | WO 2007/035650 A2 | 3/2007 |
| WO | WO 2007/038788 A2 | 4/2007 |
| WO | WO 2007/039454 A1 | 4/2007 |
| WO | W 2007/050715 A2 | 5/2007 |
| WO | WO 2007/050715 A2 | 5/2007 |
| WO | WO 2007/051462 A2 | 5/2007 |
| WO | WO 2007/070389 A2 | 6/2007 |
| WO | WO 2007/071900 A1 | 6/2007 |
| WO | WO 2007/051462 A3 | 7/2007 |
| WO | WO 2007/074405 A2 | 7/2007 |
| WO | WO 2007/077201 A1 | 7/2007 |
| WO | WO 2007/077247 A1 | 7/2007 |
| WO | WO 2007/080126 A2 | 7/2007 |
| WO | WO 2007/080127 A2 | 7/2007 |
| WO | WO 2007/083193 A2 | 7/2007 |
| WO | WO 2007/096576 A1 | 8/2007 |
| WO | WO 2007/119434 A1 | 10/2007 |
| WO | WO 2007/134984 A1 | 11/2007 |
| WO | WO 2008/007100 A2 | 1/2008 |
| WO | WO 2008/009908 A1 | 1/2008 |
| WO | WO 2008/029084 A1 | 3/2008 |
| WO | WO 2008/042231 A2 | 4/2008 |
| WO | WO 2008/059948 A1 | 5/2008 |
| WO | WO 2008/063203 A2 | 5/2008 |
| WO | WO 2008/071918 A1 | 6/2008 |
| WO | WO 2008/074991 A1 | 6/2008 |
| WO | WO 2008/084073 A1 | 7/2008 |
| WO | WO 2008/100426 A2 | 8/2008 |
| WO | WO 2008/102908 A1 | 8/2008 |
| WO | WO 2008/148223 A1 | 12/2008 |
| WO | WO 2008/152072 A2 | 12/2008 |
| WO | WO 2008/152073 A2 | 12/2008 |
| WO | WO 2009/000757 A1 | 12/2008 |
| WO | WO 2009/005297 A2 | 1/2009 |
| WO | WO 2009/029690 A1 | 3/2009 |
| WO | WO 2009/035150 A2 | 3/2009 |
| WO | WO 2009/037329 A1 | 3/2009 |
| WO | WO 2009/046384 A1 | 4/2009 |
| WO | WO 2009/063180 A1 | 5/2009 |
| WO | WO 2009/068170 A2 | 6/2009 |
| WO | WO 2009/068171 A2 | 6/2009 |
| WO | WO 2009/086041 A1 | 7/2009 |
| WO | WO 2009/090401 A2 | 7/2009 |
| WO | WO 2009/090402 A2 | 7/2009 |
| WO | WO 2009/115788 A1 | 9/2009 |
| WO | WO 2009/116558 A1 | 9/2009 |
| WO | WO 2009/125401 A2 | 10/2009 |
| WO | WO 2009/144079 A1 | 12/2009 |
| WO | WO 2009/152995 A1 | 12/2009 |
| WO | WO 2009/158258 A1 | 12/2009 |
| WO | WO 2010/012649 A1 | 2/2010 |
| WO | WO 2010/026989 A1 | 3/2010 |
| WO | WO 2010/034153 A1 | 4/2010 |
| WO | WO 2010/049270 A1 | 5/2010 |
| WO | WO 2010/049369 A1 | 5/2010 |
| WO | WO 2010/049405 A1 | 5/2010 |
| WO | WO 2010/049414 A1 | 5/2010 |
| WO | WO 2010/056519 A1 | 5/2010 |
| WO | WO 2010/063422 A1 | 6/2010 |
| WO | WO 2010/069802 A1 | 6/2010 |
| WO | WO 2010/078906 A2 | 7/2010 |
| WO | WO 2010/078912 A1 | 7/2010 |
| WO | WO 2010/093788 A2 | 8/2010 |
| WO | WO 2010/104217 A1 | 9/2010 |
| WO | WO 2010/108611 A1 | 9/2010 |
| WO | WO 2010/112826 A2 | 10/2010 |
| WO | WO 2010/116122 A2 | 10/2010 |
| WO | WO 2010/119906 A1 | 10/2010 |
| WO | WO 2010/130970 A1 | 11/2010 |
| WO | WO 2011/001434 A1 | 1/2011 |
| WO | WO 2011/003776 A2 | 1/2011 |
| WO | WO 2011/035874 A1 | 3/2011 |
| WO | WO 2011/045796 A1 | 4/2011 |
| WO | WO 2011/065451 A1 | 6/2011 |
| WO | WO 2011/067745 A2 | 6/2011 |
| WO | WO 2011/075188 A1 | 6/2011 |
| WO | WO 2011/080674 A2 | 7/2011 |
| WO | WO 2011/112570 A1 | 9/2011 |
| WO | WO 2011/132127 A1 | 10/2011 |
| WO | WO 2012/001626 A1 | 1/2012 |
| WO | WO 2012/056401 A1 | 5/2012 |
| WO | WO 2012/092580 A2 | 7/2012 |
| WO | WO 2012/164100 A2 | 12/2012 |
| WO | WO 2013/010691 A1 | 1/2013 |
| WO | WO 2013/025670 A1 | 2/2013 |
| WO | WO 2013/039990 A1 | 3/2013 |
| WO | WO 2013/040005 A1 | 3/2013 |
| WO | WO 2013/040021 A1 | 3/2013 |
| WO | WO 2013/040033 A1 | 3/2013 |
| WO | WO 2013/040049 A1 | 3/2013 |
| WO | WO 2013/040057 A1 | 3/2013 |
| WO | WO 2013/040116 A9 | 3/2013 |
| WO | WO 2013/040117 A9 | 3/2013 |
| WO | WO 2013/153553 A2 | 10/2013 |
| WO | WO 2013/175480 A1 | 11/2013 |
| WO | WO 2014/022739 A2 | 2/2014 |
| WO | WO 2014/106837 A2 | 7/2014 |
| WO | WO 2014/106838 A2 | 7/2014 |
| WO | WO 2014/151255 A1 | 9/2014 |
| WO | WO 2014/164761 A1 | 10/2014 |
| WO | WO 2014/164797 A2 | 10/2014 |
| WO | WO 2015/010026 A2 | 1/2015 |

(56) References Cited

OTHER PUBLICATIONS

Duhoux, Arnaud, and Christophe Délye. "Reference genes to study herbicide stress response in *Lolium* sp.: up-regulation of P450 genes in plants resistant to acetolactate-synthase inhibitors." PloS one 8.5 (2013): e63576. (Year: 2013).*

Delye, Christophe, Annick Matejicek, and Jacques Gasquez. "PCR-based detection of resistance to acetyl-CoA carboxylase-inhibiting herbicides in black-grass (*Alopecurus myosuroides* Huds) and ryegrass (*Lolium rigidum* Gaud)." Pest Management Science 58.5 (2002): 474-478. (Year: 2002).*

Délye, Christophe, et al. "Variation in the gene encoding acetolactate-synthase in *Lolium* species and proactive detection of mutant, herbicide-resistant alleles." Weed research 49.3 (2009): 326-336. (Year: 2009).*

Agricultural Chemical Usage 2006 Vegetables Summary, Agricultural Statistics Board, NASS, USDA, pp. 1-372 (2007).

Agrios, *Plant Pathology* (Second Edition), 2:466-470 (1978).

Alarcón-Reverte et al., "Resistance to ACCase-inhibiting herbicides in the weed *Lolium multiflorum*," *Comm. Appl. Biol. Sci.*, 73(4):899-902 (2008).

Al-Kaff et al., "Plants rendered herbicide-susceptible by cauliflower mosaic virus—elicited suppression of a 35S promoter-regulated transgene," *Nature Biotechnology*, 18:995-999 (2000).

Amarzguioui et al., "An algorithm for selection of functional siRNA sequences," *Biochemical and Biophysical Research Communications*, 316:1050-1058 (2004).

Ambrus et al., "The Diverse Roles of RNA Helicases in RNAi," *Cell Cycle*, 8(21):3500-3505 (2009).

An et al., "Transient RNAi Induction against Endogenous Genes in *Arabidopsis* Protoplasts Using in Vitro-Prepared Double-Stranded RNA," *Biosci Biotechnol Biochem*, 69(2):415-418 (2005).

Andersson et al., "A novel selection system for potato transformation using a mutated AHAS gene," *Plant Cell Reports*, 22(4):261-267 (2003).

Anonymous, "A handbook for high-level expression and purification of 6xHis-tagged proteins," *The QiaExpressionist*, (2003).

Anonymous, "Agronomy Facts 37: Adjuvants for enhancing herbicide performance," n.p., 1-8, (Jan. 26, 2000), *Web*, (Jan. 21, 2014).

Anonymous, "Devgen, The mini-Monsanto," KBC Securities (2006).

Anonymous, "Do Monsanto have the next big thing?," *Austalian Herbicide Resistance Initiative (AHRI)*, (Apr. 23, 2013) Web. (Jan. 19, 2015).

Aoki et al., "In Vivo Transfer Efficiency of Antisense Oligonucleotides into the Myocardium Using HVJ—Liposome Method," *Biochem Biophys Res Commun*, 231:540-545 (1997).

Arpaia et al., "Production of transgenic eggplant (*Solanum melongena* L.) resistant to Colorado Potato Beetle (*Leptinotarsa decemlineata* Say)," (1997) *Theor. Appl. Genet.*, 95:329-334 (1997).

Artymovich, "Using RNA interference to increase crop yield and decrease pest damage," *MMG 445 Basic Biotech.*, 5(1):7-12 (2009).

Axtell et al., "A Two-Hit Trigger for siRNA Biogenesis in Plants," *Cell*, 127:565-577 (2006).

Baerson et al., "Glyphosate-Resistant Goosegrass. Identification of a Mutation in the Target Enzyme 5-Enolpyruvylshikimate-3-Phosphate Synthase," *Plant Physiol.*, 129(3):1265-1275 (2002).

Bai et al., "Naturally Occurring Broad-Spectrum Powdery Mildew Resistance in a Central American Tomato Accession Is Caused by Loss of Mlo Function," *MPMI*, 21(1):30-39 (2008).

Balibrea et al., "Extracellular Invertase is an Essential Component of Cytokinin-Mediated Delay of Senescence," *The Plant Cell*, 16(5):1276-1287 (2004).

Bannerjee et al., "Efficient production of transgenic potato (*S. tuberosum* L. ssp. *andigena*) plants via *Agrobacterium tumefaciens*-mediated transformation," *Plant Sci.*, 170:732 738 (2006).

Bart et al., "A novel system for gene silencing using siRNAs in rice leaf and stem-derived protoplasts," *Plant Methods*, 2(13):1-9 (2006).

Basu et al., "Weed genomics: new tools to understand weed biology," *Trends in Plant Science*, 9(8):391-398 (2004).

Baulcombe, "RNA silencing and heritable epigenetic effects in tomato and *Arabidopsis*," Abstract 13th Annual Fall Symposium, Plant Genomes to Phenomes, Donald Danforth Plant Science Center, 28-30 (2011).

Bayer et al., "Programmable ligand-controlled riboregulators of eukaryotic gene expression," *Nature Biotechnol.*, 23(3):337-343 (2005).

Beal, et al., "Second Structural Motif for Recognition of DNA by Oligonucleotide-Directed Triple-Helix Formation," *Science*, 251:1360-1363 (1992).

Becker et al., "Fertile transgenic wheat from microprojectile bombardment of scutellar tissue," *The Plant Journal*, 5(2):299-307 (1994).

Bhargava et al., "Long double-stranded RNA-mediated RNA interference as a tool to achieve site-specific silencing of hypothalamic neuropeptides," *Brain Research Protocols*, 13:115-125 (2004).

Boletta et al., "High Efficient Non-Viral Gene Delivery to the Rat Kidney by Novel Polycationic Vectors," *J. Am Soc. Nephrol.*, 7:1728 (1996).

Bolognesi et al., "Characterizing the Mechanism of Action of Double-Stranded RNA Activity against Western Corn Rootworm(*Diabrotica virgifera virgifera* LeConte)," *PLoS ONE* 7(10):e47534 (2012).

Bolter et al., "A chloroplastic inner envelope membrane protease is essential for plant development," *FEBS Letters*, 580:789-794 (2006).

Bourgeois et al., "Field and producer survey of ACCase resistant wild oat in Manitoba," *Canadian Journal of Plant Science*, 709-715 (1997).

Breaker et al., "A DNA enzyme with Mg2+-dependent RNA phosphoesterase activity," *Chemistry and Biology*, 2:655-660 (1995).

Brodersen et al., "The diversity of RNA silencing pathways in plants," *Trends in Genetics*, 22(5):268-280 (2006).

Brugière et al., "Glutamine Synthetase in the Phloem Plays a Major Role in Herewith Controlling Proline Production," *The Plant Cell*, 11:1995-2011 (1999).

Busch et al., "RNAi for discovery of novel crop protection products," *Pflanzenschutz-Nachrichten Bayer*, 58(1):34-50 (2005).

Busi et al., "Gene flow increases the initial frequency of herbicide resistance alleles in unselectedpopulations," *Agriculture, Ecosystems and Environments*, Elsevier, Amsterdam, NL, 142(3):403-409 (2011).

Butler et al., "Priming and re-drying improve the survival of mature seeds of *Digitalis purpurea* during storage," *Annals of Botany*, 103:1261-1270 (2009).

Bytebier et al., "T-DNA organization in tumor cultures and transgenic plants of the monocotyledon *Asparagus officinalis*," *Proc. Natl. Acad. Sci. U.S.A.*, 84:5345-5349 (1987).

Campbell et al., "Gene-knockdown in the honey bee mite *Varroa destructor* by a non-invasive approach: studies on a glutathione S-transferase," *Parasites & Vectors*, 3(1):73, pp. 1-10 (2010).

Chabannes et al., "In situ analysis of lignins in transgenic tobacco reveals a differential impact of individual transformations on the spatial patterns of lignin deposition at the cellular and subcellular levels," *The Plant Journal*, 28(3):271-282 (2001).

Chabbouh et al., "Cucumber mosaic virus in artichoke," *FAO Plant Protection Bulletin*, 38:52-53 (1990).

Chakravarty et al., "Genetic Transformation in Potato: Approaches and Strategies," *Amer J Potato Res*, 84:301 311 (2007).

Chang et al., "Cellular Internalization of Fluorescent Proteins via Arginine-rich Intracellular Delivery Peptide in Plant Cells," *Plant Cell Physiol.*, 46(3):482-488 (2005).

Chee et al., "Transformation of Soybean (*Glycine max*) by Infecting Germinating Seeds with *Agrobacterium tumefaciens*," *Plant Physiol.*, 91:1212-1218 (1989).

Chen et al., "In Vivo Analysis of the Role of atTic20 in Protein Import into Chloroplasts," *The Plant Cell*, 14:641-654 (2002).

Chen et al., "Transfection and Expression of Plasmid DNA in Plant Cells by an Arginine-Rich Intracellular Delivery Peptide without Protoplast Preparation," *FEBS Letters* 581, pp. 1891-1897 (2007).

Cheng et al., "Production of fertile transgenic peanut (*Arachis hypogaea* L.) plants using *Agrobacterium tumefaciens*," *Plant Cell Reports*, 15:653-657 (1996).

Chi et al., "The Function of RH22, a DEAD RNA Helicase, in the Biogenesis of the 50S Ribosomal Subunits of *Arabidopsis* Chloroplasts," *Plant Physiology*, 158:693-707 (2012).

(56) References Cited

OTHER PUBLICATIONS

Chupp et al., "Chapter 8: White Rust," *Vegetable Diseases and Their Control*, The Ronald Press Company, New York, pp. 267-269 (1960).
Clough et al., "Floral dip: a simplified method for Agrobacterium-mediated transformation of *Arabidopsis thaliana*," *The Plant Journal*, 16(6):735-743 (1998).
CN101914540 Patent Diclosure, "Introduction of RNA into plant by interference," (2010).
Colbourne et al., "The Ecoresponsive Genome of Daphnia pulex," *Science*, 331(6017):555-561 (2011).
Colliver et al., "Differential modification of flavonoid and isoflavonoid biosynthesis with an antisense chalcone synthase construct in transgenic *Lotus corniculatus*," *Plant Molecular Biology*, 35:509-522 (1997)
Communication pursuant to Article 94(3) EPC dated Jan. 14, 2016, in European Patent Application No. 12 832 415.9.
Communication pursuant to Article 94(3) EPC dated Jun. 26, 2015, in European Patent Application No. 11 753 916.3.
Communication pursuant to Article 94(3) EPC dated Mar. 18, 2016, in European Patent Application No. 12 832 160.1.
Communication pursuant to Article 94(3) EPC dated Mar. 24, 2016, in European Patent Application No. 12 831 684.1.
Communication pursuant to Article 94(3) EPC dated Mar. 4, 2016, in European Patent Application No. 12 830 932.5.
Communication pursuant to Article 94(3) EPC dated Mar. 9, 2016, in European Patent Application No. 12 831 166.9.
Communication pursuant to Article 94(3) EPC dated Oct. 23, 2015, in European Patent Application No. 12 831 945.6.
Concise Descriptions of Relevance filed by a third party on Nov. 29, 2012, in U.S. Appl. No. 13/042,856.
Cooney et al., "Site-Specific Oligonueleotide Binding Represses Transcription of the Human c-myc Gene in Vitro," *Science*, 241:456-459 (1988).
COST Action FA0806 progress report "Plant virus control employing RNA-based vaccines: A novel non-transgenic strategy" (2010).
Coticchia et al., "Calmodulin modulates Akt activity in human breast cancer cell lines," *Breast Cancer Res. Treat*, 115:545-560 (2009).
Dalakouras et al., "Induction of Silencing in Plants by High-Pressure Spraying of In vitro-Synthesized Small RNAs," Frontiers in Plant Science, 7(1327):1-5 (2016).
Dalmay et al., "An RNA-Depenedent RNA Polymerase Gene in *Arabidopsis* Is Required for Posttranscriptional Gene Silencing Mediated by a Transgene but Not by a Virus," *Cell*, 101:543-553 (2000).
Davidson et al., "Engineering regulatory RNAs," *TRENDS in Biotechnology*, 23(3):109-112 (2005).
Dawson et al., "cDNA cloning of the complete genome of tobacco mosaic virus and production of infectious transcripts," *Proc. Natl. Acad. Sci. USA*, 83:1832-1836 (1986).
De Block, et al. "Engineering herbicide resistance in plants by expression of a detoxifying enzyme," *EMBO J.* 6(9):2513-2519 (1987).
De Framond, "MINI-Ti: A New Vector Strategy for Plant Genetic Engineering," *Nature Biotechnology*, 1:262-269 (1983).
Della-Cioppa et al., "Import of a precursor protein into chloroplasts is inhibited by the herbicide glyphosate," *The EMBO Journal*, 7(5):1299-1305 (1988).
Desai et al., "Reduction in deformed wing virus infection in larval and adult honey bees (*Apis mellifera* L.) by double-stranded RNA ingestion," *Insect Molecular Biology*, 21(4):446-455 (2012).
Diallo et al., "Long Endogenous dsRNAs Can Induce Complete Gene Silencing in Mammalian Cells and Primary Cultures," *Oligonucleotides*, 13:381-392 (2003).
Dietemann et al.,"*Varroa destructor*: research avenues towards sustainable control," *Journal of Apicultural Research*, 51(1):125-132 (2012).
Du et al., "A systematic analysis of the silencing effects of an active siRNA at all single-nucleotide mismatched target sites," *Nucleic Acids Research*, 33(5):1671-1677 (2005).
Dunoyer et al., "Small RNA Duplexes Function as Mobile Silencing Signals Between Plant Cells," *Science*, 328:912-916 (2010).
Ellington et al., "In vitro selection of RNA molecules that bind specific ligands," *Nature*, 346:818-822 (1990).
Emery et al., "Radial Patterning of *Arabidopsis* Shoots by Class III HD-ZIP and KANADI Genes," *Current Biology*, 13:1768-1774 (2003).
European Cooperation in the field of Scientific and Technical Research—Memorandum of Understanding for COST Action FA0806 (2008).
Extended European Search Report dated Feb. 2, 2015, in European Patent Application No. 12 830 932.5.
Extended European Search Report dated Feb. 27, 2015, in European Patent Application No. 12 832 160.1.
Extended European Search Report dated Feb. 3, 2015, in European Patent Application No. 12 831 945.6.
Extended European Search Report dated Jan. 20, 2016, in European Patent Application No. 13 794 339.5.
Extended European Search Report dated Jan. 21, 2015, in European Patent Application No. 12 832 415.9.
Extended European Search Report dated Jan. 29, 2015, in European Patent Application No. 12 831 567.8.
Extended European Search Report dated Jun. 29, 2015, in European Patent Application No. 12 831 494.5.
Extended European Search Report dated Mar. 17, 2015, in European Patent Application No. 12 831 684.1.
Extended European Search Report dated Mar. 3, 2015, in European Patent Application No. 12 831 166.9.
Extended European Search Report dated Oct. 8, 2013, in European Patent Application No. 11753916.3.
Extended European Search Report dated Sep. 29, 2016, in European Patent Application No. 14778840.0.
Farooq et al., "Rice seed priming," *IPRN*, 30(2):45-48 (2005).
Feuillet et al., "Crop genome sequencing: lessons and rationales," *Trends Plant Sci.*, 16:77-88 (2011).
Final Office Action dated Apr. 7, 2016, in U.S. Appl. No. 13/619,980.
Final Office Action dated Dec. 17, 2015, in U.S. Appl. No. 14/335,135.
Final Office Action dated Feb. 17, 2016, in U.S. Appl. No. 13/612,929.
Final Office Action dated Feb. 4, 2016, in U.S. Appl. No. 13/612,936.
Final Office Action dated Jun. 30, 2016, in U.S. Appl. No. 13/901,326.
Final Office Action dated Mar. 2, 2016, in U.S. Appl. No. 13/612,995.
Final Office Action dated Mar. 21, 2016, in U.S. Appl. No. 13/612,925.
Final Office Action dated May 26, 2016, in U.S. Appl. No. 14/532,596.
Final Office Action dated Sep. 9, 2016, in U.S. Appl. No. 13/612,954.
Final Office Action dated Nov. 10, 2015, in U.S. Appl. No. 13/612,985.
Final Office Action dated Nov. 19, 2015, in U.S. Appl. No. 13/612,941.
Final Office Action dated Nov. 10, 2016, in U.S. Appl. No. 13/583,302.
Final Office Action dated Nov. 30, 2015, in U.S. Appl. No. 13/612,948.
Final Office Action dated Sep. 9, 2016, in U.S. Appl. No. 14/608,951.
Final Office Action dated Sep. 9, 2016, in U.S. Appl. No. 14/603,347.
Final Office Action dated Nov. 7, 2013, in U.S. Appl. No. 13/042,856.
Final Office Action dated Oct. 20, 2016, in U.S. Appl. No. 14/480,199.
Final Office Action dated Oct. 22, 2015, in U.S. Appl. No. 14/608,951.
Fire et al., "Potent and specific genetic interference by double-stranded RNA in *Caenorhabditis elegans*," *Nature*, 391:806-811 (1998).
First Examination Report dated Apr. 23, 2013, in New Zealand Patent Application No. 601784.
First Examination Report dated Jul. 28, 2014, in New Zealand Patent Application No. 627060.
First Office Action dated Aug. 31, 2015, in Chinese Patent Application No. 201280053985.3.
First Office Action dated Feb. 2, 2016, in Chinese Patent Application No. 201380039346.6.
First Office Action dated Jul. 7, 2015, in Chinese Patent Application No. 201280054820.8.
First Office Action dated Mar. 12, 2015, in Chinese Patent Application No. 201280053984.9.
First Office Action dated Mar. 2, 2015, in Chinese Patent Application No. 201280054819.5.

(56) References Cited

OTHER PUBLICATIONS

First Office Action dated May 27, 2015, in Chinese Patent Application No. 201280054179.8.
First Office Action dated Sep. 9, 2015, in Chinese Patent Application No. 201280055409.2.
Fraley et al., "Liposome-mediated delivery of tobacco mosaic virus RNA into tobacco protoplasts: A sensitive assay for monitoring liposome-protoplast interactions," *Proc Natl Acad Sci U S A.*, 79(6):1859-1863 (1982).
Fukuhara et al., "Enigmatic Double-Stranded RNA in Japonica Rice," *Plant Molecular Biology*, 21:1121-1130 (1993).
Fukuhara et al., "The Unusual Structure of a Novel RNA Replicon in Rice," *The Journal of Biological Chemistry*, 270(30):18147-18149 (1995).
Fukuhara et al., "The wide distribution of endornaviruses, large double-stranded RNA replicons with plasmid-like properties," *Archives of Virology*, 151:995-1002 (2006).
Fukunaga et al., "dsRNA with 5' overhangs v contributes to endogenous and antiviral RNA silencing pathways in plants," *The EMBO Journal*, 28(5):545-555 (2009).
Further Examination Report dated May 16, 2014, in New Zealand Patent Application No. 601784.
Gaines et al., "Gene amplification confers glyphosate resistance in *Amaranthus palmeri*," *Proc. Natl. Acad. Sci. USA*, 107(3):1029-1034 (2010).
Gan et al., "Bacterially expressed dsRNA protects maize against SCMV infection," *Plant Cell Rep*, 11:1261-1268 (2010).
Gan et al., "Inhibition of Leaf Senescence by Autoregulated Production of Cytokinin," *Science*, 270:1986-1988 (1995).
Gao et al., "Down-regulation of acetolactate synthase compromises 01-1-mediated resistance to powdery mildew in tomato," *BMC Plant Biology*, 14 (2014).
Gao et al., "Nonviral Methods for siRNA Delivery," *Molecular Pharmaceutics*, 6(3):651-658 (2008).
Garbian et al., "Bidirectional Transfer of RNAi between Honey Bee and *Varroa destructor*: *Varroa* Gene Silencing Reduces *Varroa* Population," 8(12):1-9:e1003035 (2012).
Ge et al., "Rapid vacuolar sequestration: the horseweed glyphosate resistance mechanism," *Pest Management Sci.*, 66:345-348 (2010).
GenBank Accession No. AY545657.1 (2004).
GenBank Accession No. CB377464, "CmaE1_37_J02_T3 Cowpea weevil larvae Lambda Zap Express Library Callosobruchus maculatus cDNA, mRNA sequence," (2007).
GenBank Accession No. DY640489, "PU2_plate27_F03 PU2 Prunus persica cDNA similar to expressed mRNA inferred from Prunus persica hypothetical domain/motif cont aining IPR011005:Dihydropteroate synthase-like, MRNA sequence" (2006).
GenBank Accession No. EU024568, "Amaranthus hypochondriacus acetolactate synthase (ALS) gene" (2007).
GenBank Accession No. EW765249, "ST020010B10C12 Normalized and subtracted western corn rootworm female head cDNA library Diabrotica virgifera virgifera cDNA clone STO20010B10C12 5-, mRNA sequence," (2007).
GenBank Accession No. EW771198, "ST020010B10C12 Normalized and subtracted western corn rootworm female head cDNA library Diabrotica virgifera virgifera cDNA clone STO20010B10C12 5-, mRNA sequence," (2007).
GenBank Accession No. FE348695, "CBIB7954.fwd CBIB_Daphnia_pulex_Chosen_One_Library_2 Daphnia pulex cDNA clone CBIB7954 5', mRNA sequence" (2011).
GenBank Accession No. FJ972198, "Solanum lycopersicum cultivar Ailsa Craig dihydropterin pyrophosphokinase-dihydropteroate synthase (HPPK-DHPS) gene, complete cds" (2010).
GenBank Accession No. GI:186478573 (2014).
GenBank Accession No. GU120406, "Chrysomela tremulae ribosomal protein L7 (RpL7) mRNA, complete cds" (2009).
GenBank Accession No. HD315444, "Sequence 192160 from Patent EP2213738" (2010).
GenBank Accession No. Q4GXM3_BIPLU, "Ribosomal protein L7e" (2006).
GenBank Accession No. U87257.1, "Daucus carota 4-hydroxyphenylpyruvate dioxygenase mRNA, complete cds" (1997).
GenBank Accession No. XM_014456745.1, Predicted: Myotis lucifugus ribonucleoprotein, PTB-binding 2 (RAVER2), transcript variant X3, mRNA,: (2015).
GenBank Accession No. Y08611.1, "P.sativum mRNA for dihydropterin pyrophosphokinase/dihydropteroate synthase." (2006).
GenEmbl Accession No. FJ861243 (2010).
Gong et al., "Silencing of Rieske iron-sulfur protein using chemically synthesised siRNA as a potential biopesticide against Plutella xylostella," *Pest Manag Sci*, 67:514-520 (2011).
Gossamer Threads, Compendium of Herbicide Adjuvants: Organo-Silicone Surfactant, p. 1-4 (1998).
Gressel et al., "A strategy to provide long-term control of weedy rice while mitigating herbicide resistance transgene flow, and its potential use for other crops with related weeds," *Pest Manag Sci*, 65(7):723-731 (2009).
Gudkov, "Minireview: The L7/L12 ribosomal domain of the ribosome: structural and functional studies," *FEBS Letters*, 407:253-256 (1997).
Gutensohn et al., "Functional analysis of the two *Arabidopsis* homologues of Toc34, a component of the chloroplast protein import apparatus," *The Plant Journal*, 23(6):771-783 (2000).
Haigh, "The Priming of Seeds: Investigation into a method of priming large quantities of seeds using salt solutions," Thesis submitted to Macquarie University (1983).
Hajirezaei et al., "Impact of elevated cytosolic and apoplastic invertase activity on carbon metabolism during potato tuber development," *Journal of Experimental Botany*, 51:439-445 (2000).
Hamilton et al., "Guidelines for the Identification and Characterization of Plant Viruses," *J. gen. Virol.*, 54:223-241 (1981).
Hamilton et al., "Two classes of short interfering RNA in RNA silencing," *EMBO J.*, 21(17):4671-4679 (2002).
Han et al., "Molecular Basis for the Recognition of Primary microRNAs by the Drosha-DGCR8 Complex," *Cell*, 125(5):887-901 (2006).
Hannon, "RNA interference," *Nature*,481:244-251 (2002).
Hardegree, "Drying and storage effects on germination of primed grass seeds," *Journal of Range Management*, 47(3):196-199 (1994).
Harrison et al., "Does Lowering Glutamine Synthetase Activity in Nodules Modigy Nitrogen Metabolism and Growth of *Lotus japonicus?,*" *Plant Physiology*, 133:253-262 (2003).
Heffer et al., "Rapid isolation of gene homologs across taxa: Efficient identification and isolation of gene orthologs from non-model organism genomes, a technical report," *EvoDevo Journal*, 2(7):1-5 (2011).
Herman et al., "A three-component dicamba O-demethylase from *Pseudomonas maltophilia*, strain DI-6: gene isolation, characterization, and heterologous expression," *J. Biol. Chem.*, 280: 24759-24767 (2005).
Hewezi et al., "Local infiltration of high- and low-molecular-weight RNA from silenced sunflower (*Helianthus annuus* L.) plants triggers post-transcriptional gene silencing in non-silenced plants," *Plant Biotechnology Journal*, 3:81-89 (2005).
Hidayat et al., "Enhanced Metabolism of Fluazifop Acid in a Biotype of *Digitaria sanguinalis* Resistant to the Herbicide Fluazifop-P-Butyl," *Pesticide Biochem Physiol.*, 57:137-146 (1997).
Himber et al., "Transitivity-dependant and -independent cell-to-cell movement of RNA silencing," *The EMBO Journal*, 22(17):4523-4533 (2003).
Hirschberg et al., "Molecular Basis of Herbicide Resistance in *Amaranthus hybridus*," *Science*, 222:1346-1349 (1983).
Hoekema et al., "A binary plant vector strategy based on separation of vir- and T-region of the *Agrobacterium tumefaciens* Ti-plasmid," *Nature*, 303:179-180 (1983).
Hofgen et al., "Repression of Acetolactate Synthase Activity through Antisense Inhibition: Molecular and Biochemical Analysis of Transgenic Potato (*Solanum tuberosum* L. cv Desiree) Plants," *Plant Physiol.*, 107(2):469-477 (1995).
Holtra et al., "Assessment of the Physiological Condition of *Salvinia natans* L. Exposed to Copper(II) Ions," *Environ. Protect. Eng.*, 41:147-158 (2015).

(56) References Cited

OTHER PUBLICATIONS

Hsieh et al., "A library of siRNA duplexes targeting the phosphoinositide 3-kinase pathway: determinants of gene silencing for use in cell-based screens," *Nucleic Acids Res.*, 32(3):893-901 (2004).
Huesken et al., "Design of a genome-wide siRNA library using an artificial neural network," *Nature Biotechnology*, 23(8): 995-1001 (2005).
Hunter et al., "RNA Interference Strategy to suppress Psyllids & Leafhoppers," *International Plant and Animal Genome XIX*, 15-19 (2011).
Ichihara et al., "Thermodynamic instability of siRNA duplex is a prerequisite for dependable prediction of siRNA activities," *Nucleic Acids Res.*, 35(18):e123 (2007).
International Preliminary Report on Patentability (Chapter II) dated Jul. 24, 2015, in International Application No. PCT/US2014/047204.
International Preliminary Report on Patentability dated Sep. 11, 2012, in International Application No. PCT/US2011/027528.
International Preliminary Report on Patentability dated Sep. 11, 2014, in International Application No. PCT/IL2013/050447.
International Rice Genome Sequencing Project, The map-based sequence of the rice genome, *Nature*, 436(11):793-800 (2005).
International Search Report and the Written Opinion dated Feb. 25, 2013, in International Application No. PCT/US2012/054883.
International Search Report and the Written Opinion dated Feb. 27, 2013, in International Application No. PCT/US2012/054814.
International Search Report and the Written Opinion dated Feb. 27, 2013, in International Application No. PCT/US2012/054842.
International Search Report and the Written Opinion dated Feb. 27, 2013, in International Application No. PCT/US2012/054862.
International Search Report and the Written Opinion dated Feb. 27, 2013, in International Application No. PCT/US2012/054894.
International Search Report and the Written Opinion dated Feb. 27, 2013, in International Application No. PCT/US2012/054974.
International Search Report and the Written Opinion dated Feb. 27, 2013, in International Application No. PCT/US2012/054980.
International Search Report and the Written Opinion dated Jul. 15, 2014, in International Application No. PCT/US2014/025305.
International Search Report and the Written Opinion dated Jul. 22, 2014, in International Application No. PCT/IL2013/051083.
International Search Report and the Written Opinion dated Jul. 22, 2014, in International Application No. PCT/IL2013/051085.
International Search Report and the Written Opinion dated Jul. 24, 2014, in International Application No. PCT/US2014/026036.
International Search Report and the Written Opinion dated May 10, 2011, in International Application No. PCT/US2011/027528.
International Search Report and the Written Opinion dated Oct. 1, 2013, in International Application No. PCT/IL2013/050447.
International Search Report and Written Opinion dated Aug. 25, 2014, in International Application No. PCT/US2014/023503.
International Search Report and Written Opinion dated Aug. 27, 2014, in International Application No. PCT/US2014/023409.
International Search Report and Written Opinion dated Feb. 23, 2015, in International Application No. PCT/US2014/063832.
International Search Report and Written Opinion dated Jul. 8, 2015, in International Application No. PCT/US2015/011408.
International Search Report and Written Opinion dated Mar. 26, 2015, in International Application No. PCT/US2014/069353.
International Search Report and Written Opinion dated May 26, 2016, in International Application No. PCT/US2016/014344.
International Search Report and Written Opinion dated Nov. 24, 2015, in International Application No. PCT/US2015/037522.
International Search Report and Written Opinion dated Nov. 27, 2015, in International Application No. PCT/US2015/037015.
International Search Report dated Mar. 12, 2013, in International Application No. PCT/US2012/054789.
Invitation to Pay Additional Fees dated May 6, 2014, in International Application No. PCT/IL2013/051083.
Invitation to Pay Additional Fees dated May 6, 2014, in International Application No. PCT/IL2013/051085.
Invitation to Pay Additional Fees dated Nov. 25, 2014, in International Application No. PCT/US2014/047204.
Invitation to Pay Additional Fees dated Sep. 8, 2015, in International Application No. PCT/US2015/037015.
Invitation to Pay Additional Fees dated Sep. 9, 2015, in International Application No. PCT/US2015/037522.
Isaacs et al., "Engineered riboregulators enable post-transcriptional control of gene expression," *Nature Biotechnology*, 22(7):841-847 (2004).
Ji et al., "Regulation of small RNA stability: methylation and beyond," *Cell Research*, 22:624-636 (2012).
Jin et al., "Posttranslational Elevation of Cell Wall Invertase Activity by Silencing its Inhibitor in Tomato Delays Leaf Senescence and Increases Seed Weight and Fruit Hexose Level," *The Plant Cell*, 21:2072-2089 (2009).
Jofre-Garfias et al., "*Agrobacterium*-mediated transformation of Amaranthus *hypochondriacus*: light- and tissue-specific expression of a pea chlorophyll a/b-binding protein promoter," *Plant Cell Reports*, 16:847-852 (1997).
Jones-Rhoades et al., "MicroRNAs and Their Regulatory Roles in Plants," *Annu. Rev. Plant Biol.*, 57:19-53 (2006).
Josse et al., "A DELLA in Disguise: SPATULA Restrains the Growth of the Developing *Arabidopsis* Seedling," *Plant Cell*, 23:1337-1351 (2011).
Kaloumenos et al., "Identification of a Johnsongrass (*Sorghum halepense*) Biotype Resistant to ACCase-Inhibiting Herbicides in Northern Greece," *Weed Technol*, 23:470-476 (2009).
Kam et al., "Nanotube Molecular Transporters: Internalization of Carbon Nanotube-Protein Conjugates into Mammalian Cells," *J. Am. Chem. Soc.*, 126(22):6850-6851 (2004).
Kambiranda et al., "Relationship Between Acid Invertase Activity and Sugar Content in Grape Species," *Journal of Food Biochemistry*, 35:1646-1652 (2011).
Katoh et al., "Specific residues at every third position of siRNA shape its efficient RNAi activity," *Nucleic Acids Res.*, 35(4): e27 (2007).
Kertbundit et al., "In vivo random β-glucuronidase gene fusions in *Arabidopsis thaliana*," *Proc. Natl. Acad. Sci. U S A.*, 88:5212-5216 (1991).
Khachigian, "DNAzymes: Cutting a path to a new class of therapeutics," *Curr Opin Mol Ther* 4(2):119-121 (2002).
Khan et al., "Matriconditioning of Vegetable Seeds to Improve Stand Establishment in Early Field Plantings," *J. Amer. Soc. Hort. Sci.*, 117(1):41-47 (1992).
Khodakovskaya et al., "Carbon Nanotubes Are Able to Penetrate Plant Seed Coat and Dramatically Affect Seed Germination and Plant Growth," *ACS Nano*, 3(10):3221-3227 (2009).
Kim et al., "Optimization of Conditions for Transient Agrobacterium-Mediated Gene Expression Assays in *Arabidopsis*," *Plant Cell Reports*, 28:1159-1167 (2009).
Kim et al., "Synthetic dsRNA Dicer substrates enhance RNAi potency and efficacy," *Nature Biotechnology*, 23(2):222-226 (2005).
Kirkwood, "Herbicides and Plants," *Botanical Journal of Scotland*, 46(3):447-462 (1993).
Kirkwood, "Use and Mode of Action of Adjuvants for Herbicides: A Review of some Current Work," *Pestic Sci.*, 38:93-102 (1993).
Klahre et al., "High molecular weight RNAs and small interfering RNAs induce systemic posttranscriptional gene silencing in plants," *Proc. Natl. Acad. Sci. USA*, PNAS, 99(18):11981-11986 (2002).
Knudsen, "Promoter2.0: for the recognition of PolI promoter sequences," *Bioniformatics*, 15(5):356-361 (1999).
Kronenwett et al., "Oligodeoxyribonucleotide Uptake in Primary Human Hematopoietic Cells Is Enhanced by Cationic Lipids and Depends on the Hematopoietic Cell Subset," *Blood*, 91(3):852-862 (1998).
Kumar et al., "Sequencing, De Novo Assembly and Annotation of the Colorado Potato Beetle, *Leptinotarsa decemlineata*, Transcriptome," *PLoS One*, 9(1):e86012 (2014).
Kusaba et al., "Low glutelin content1: A Dominant Mutation That Suppresses the *Glutelin* Multigene Family via RNA Silencing ni Rice," *The Plant Cell*, 15(6):1455-1467 (2003).
Kusaba, "RNA interference in crop plants," *Curr Opin Biotechnol*, 15(2):139-143 (2004).

(56) References Cited

OTHER PUBLICATIONS

Lavigne et al., "Enhanced antisense inhibition of human immunodeficiency virus type 1 in cell cultures by DLS delivery system," *Biochem Biophys Res Commun*, 237:566-571 (1997).
Lee et al., "Aptamer Database," *Nucleic Acids Research*, 32:D95-D100 (2004).
Lein et al., "Target-based discovery of novel herbicides," *Current Opinion in Plant Biology*, 7:219-225 (2004).
Leopold et al., "Chapter 4: Moisture as a Regulator of Physiological Reaction in Seeds," *Seed Moisture, CSSA Special Publication No. 14*, pp. 51-69 (1989).
Lermontova et al., "Reduced activity of plastid protoporphyrinogen oxidase causes attenuated photodynamic damage during high-light compared to low-light exposure," *The Plant Journal*, 48(4):499-510 (2006).
Lesnik et al., "Prediction of rho-independent transcriptional terminators in *Escherichia coli*," *Nucleic Acids Research*, 29(17):3583-3594 (2001).
Li et al., "Establishment of a highly efficient transformation system for pepper (*Capsicum annum* L.)," *Plant Cell Reports*, 21: 785-788 (2003).
Li et al., "The FAST technique: a simplified Agrobacterium-based transformation method for transient gene expression analysis in seedlings of *Arabidopsis* and other plant species," *Plant Methods*, 5(6):1-15 (2009).
Liu et al., "Carbon Nanotubes as Molecular Transporters for Walled Plant Cells," *Nano Letters*, 9(3):1007-1010 (2009).
Liu et al., "Comparative study on the interaction of DNA with three different kinds of surfactants and the formation of multilayer films," *Bioelectrochemistry*, 70:301-307 (2007).
Liu et al., "DNAzyme-mediated recovery of small recombinant RNAs from a 5S rRNA-derived chimera expressed in *Escherichia coli*," *BMC Biotechnology*, 10:85 (2010).
Liu et al., "Identification and Application of a Rice Senescence-Associated Promoter," *Plant Physiology*, 153:1239-1249 (2010).
Liu, "Influence of Sugars on the Foliar Uptake of Bentazone and Glyphosate," *New Zealand Plant Protection*, 55:159-162 (2002).
Llave et al., "Endogenous and Silencing-Associated Small RNAs in Plants," *The Plant Cell*, 14:1605-1619 (2002).
Lu et al., "OligoWalk: an online siRNA design tool utilizing hybridization thermodynamics," *Nucleic Acids Research*, 36:W104-W108 (2008).
Lu et al., "RNA silencing in plants by the expression of siRNA duplexes," *Nucleic Acids Res.*, 32(21):e171 (2004).
Luft "Making sense out of antisense oligodeoxynucleotide delivery: getting there is half the fun," *J Mol Med*, 76:75-76 (1998).
Luque et al., "Water Permeability of Isolated Cuticular Membranes: A Structural Analysis," *Archives of Biochemistry and Biophysics*, 317(2):417-422 (1995).
Maas et al., "Mechanism and optimized conditions for PEG mediated DNA transfection into plant protoplasts," *Plant Cell Reports*, 8:148-149 (1989).
MacKenzie et al., "Transgenic *Nicotiana debneyii* expressing viral coat protein are resistant to potato virus S infection," *Journal of General Virology*, 71:2167-2170 (1990).
Maher III et al., "Inhibition of DNA binding proteins by oligonucleotide-directed triple helix formation," *Science*, 245(4919):725-730 (1989).
Makkouk et al., "Virus Diseases of Peas, Beans, and Faba Bean in the Mediterranean region," *Adv Virus Res*, 84:367-402 (2012).
Mandal et al., "Adenine riboswitches and gene activation by disruption of a transcription terminator," *Nature Struct. Mol. Biol.*, 11(1):29-35 (2004).
Mandal et al., "Gene Regulation by Riboswitches," *Nature Reviews | Molecular Cell Biology*, 5:451-463 (2004).
Manoharan, "Oligonucleotide Conjugates as Potential Antisense Drugs with Improved Uptake, Biodistribution, Targeted Delivery, and Mechanism of Action," *Antisense & Nucleic Acid Drug Development*, 12:103-128 (2002).

Maori et al., "IAPV, a bee-affecting virus associated with Colony Collapse Disorder can be silenced by dsRNA ingestion," *Insect Molecular Biology*, 18(1):55-60 (2009).
Masoud et al., "Constitutive expression of an inducible β-1,3-glucanase in alfalfa reduces disease severity caused by the oomycete pathogen *Phytophthora megasperma* f. sp *medicaginis*, but does not reduce disease severity of chitincontaining fungi," *Transgenic Research*, 5:313-323 (1996).
Matveeva et al., "Prediction of antisense oligonucleotide efficacy by in vitro methods," *Nature Biotechnology*, 16:1374-1375 (1998).
Meinke, et al., "Identifying essential genes in *Arabidopsis thaliana*," *Trends Plant Sci.*, 13(9):483-491 (2008).
Meins et al., "RNA Silencing Systems and Their Relevance to Plant Development," *Annu. Rev. Cell Dev. Biol.*, 21:297-318 (2005).
Melnyk et al., "Intercellular and systemic movement of RNA silencing signals," *The EMBO Journal*, 30:3553-3563 (2011).
Migge et al., "Greenhouse-grown conditionally lethal tobacco plants obtained by expression of plastidic glutamine synthetase antisense RNA may contribute to biological safety," *Plant Science* 153:107-112 (2000).
Misawa et al., "Expression of an *Erwinia* phytoene desaturase gene not only confers multiple resistance to herbicides interfering with carotenoid biosynthesis but also alters xanthophyll metabolism in transgenic plants," *The Plant Journal*, 6(4):481-489 (1994).
Misawa et al., "Functional expression of the *Erwinia uredovora* carotenoid biosynthesis gene crtI in transgenic plants showing an increase of β-carotene biosynthesis activity and resistance to the bleaching herbicide norflurazon," *The Plant Journal*, 4(5):833-840 (1993).
Miura et al., "The Balance between Protein Synthesis and Degradation in Chloroplasts Determines Leaf Variegation in *Arabidopsis* yellow variegated Mutants," *The Plant Cell*, 19:1313-1328 (2007).
Molina et al., "Inhibition of protoporphyrinogen oxidase expression in *Arabidopsis* causes a lesion-mimic phenotype that induces systemic acquired resistance," *The Plant Journal*, 17(6):667-678 (1999).
Molnar et al., "Plant Virus-Derived Small Interfering RNAs Originate redominantly from Highly Structured Single-Stranded Viral RNAs," *Journal of Virology*, 79(12):7812-7818 (2005).
Molnar et al., "Small Silencing RNAs in Plants Are Mobile and Direct Epigenetic Modification in Recipient Cells," *Science*, 328:872-875 (2010).
Mora et al., "How Many Species Are There on Earth and in the Ocean?," *PLOS Biol.*, 9(8):e100127, p. 1-8 (2011).
Moriyama et al., "Double-stranded RNA in rice: a novel RNA replicon in plants," *Molecular & General Genetics*, 248(3):364-369 (1995).
Moriyama et al., "Stringently and developmentally regulated levels of a cytoplasmic double-stranded RNA and its high-efficiency transmission via egg and pollen in rice," *Plant Molecular Biology*, 31:713-719 (1996).
Morrissey et al., "Potent and persistent in vivo anti-HBV activity of chemically modified siRNAs," *Nat Biotechnol.* 23(8):1002-1007 (2005).
Moser et al., "Sequence-Specific Cleavage of Double Helical DNA by Triple Helix Formation," *Science*, 238:645-646 (1987).
Mount et al., "Gene and Metabolite Regulatory Network Analysis of Early Developing Fruit Tissues Highlights New Candidate Genes for the Control of Tomato Fruit Composition and Development," *Plant Physiology*, 149:1505-1528 (2009).
Non-Final Office Action dated Apr. 11, 2013, in U.S. Appl. No. 13/042,856.
Non-Final Office Action dated Aug. 19, 2016, in U.S. Appl. No. 13/612,925.
Non-Final Office Action dated Aug. 19, 2016, in U.S. Appl. No. 13/612,929.
Non-Final Office Action dated Apr. 29, 2016, in U.S. Appl. No. 13/583,302.
Non-Final Office Action dated Aug. 10, 2016, in U.S. Appl. No. 13/612,995.
Non-Final Office Action dated Aug. 12, 2015, in U.S. Appl. No. 13/612,936.
Non-Final Office Action dated Nov. 9, 2016, in U.S. Appl. No. 14/901,003.

(56) References Cited

OTHER PUBLICATIONS

Non-Final Office Action dated Aug. 13, 2015, in U.S. Appl. No. 13/612,929.
Non-Final Office Action dated Aug. 3, 2016, in U.S. Appl. No. 14/015,715.
Non-Final Office Action dated Aug. 5, 2016, in U.S. Appl. No. 14/015,785.
Non-Final Office Action dated Aug. 8, 2016, in U.S. Appl. No. 13/612,936.
Non-Final Office Action dated Dec. 17, 2015, in U.S. Appl. No. 14/532,596.
Non-Final Office Action dated Feb. 10, 2016, in U.S. Appl. No. 13/901,326.
Non-Final Office Action dated Feb. 23, 2016, in U.S. Appl. No. 14/603,347.
Non-Final Office Action dated Feb. 23, 2016, in U.S. Appl. No. 14/608,951.
Non-Final Office Action dated Sep. 6, 2016, in U.S. Appl. No. 14/335,135.
Non-Final Office Action dated Jul. 23, 2015, in U.S. Appl. No. 14/335,135.
Non-Final Office Action dated Jul. 30, 2014, in U.S. Appl. No. 13/042,856.
Non-Final Office Action dated Jun. 5, 2015, in U.S. Appl. No. 13/612,948.
Non-Final Office Action dated Jun. 8, 2015, in U.S. Appl. No. 13/612,941.
Non-Final Office Action dated Mar. 1, 2016, in U.S. Appl. No. 13/612,954.
Non-Final Office Action dated Mar. 30, 2015, in U.S. Appl. No. 13/583,302.
Non-Final Office Action dated May 15, 2015, in U.S. Appl. No. 14/608,951.
Non-Final Office Action dated May 22, 2015, in U.S. Appl. No. 13/612,985.
Non-Final Office Action dated Oct. 3, 2016, in U.S. Appl. No. 14/403,491.
Non-Final Office Action dated Sep. 1, 2015, in U.S. Appl. No. 13/612,954.
Non-Final Office Action dated Sep. 11, 2015, in U.S. Appl. No. 13/612,925.
Non-Final Office Action dated Sep. 4, 2015, in U.S. Appl. No. 13/612,995.
Nookaraju et al., "Molecular approaches for enhancing sweetness in fruits and vegetables," *Scientia Horticulture*, 127:1-15 (2010).
Nord-Larsen et al., "Cloning, characterization and expression analysis of tonoplast intrinsic proteins and glutamine synthetase in ryegrass (*Lolium perenne* L.)," *Plant Cell Reports*, 28(10):1549-1562 (2009).
Notice of Allowance dated Apr. 11, 2016, in U.S. Appl. No. 13/612,985.
Notice of Allowance dated Apr. 19, 2016, in U.S. Appl. No. 13/612,941.
Notice of Allowance dated Apr. 20, 2016, in U.S. Appl. No. 13/612,948.
Notice of Allowance dated Feb. 23, 2015, in U.S. Appl. No. 13/042,856.
Notice of Allowance dated Jun. 2, 2015, in U.S. Appl. No. 13/042,856.
Notice of Allowance dated Oct. 5, 2015, in U.S. Appl. No. 13/583,302.
Nowak et al., "A new and efficient method for inhibition of RNA viruses by DNA interference," *The FEBS Journal*, 276:4372-4380 (2009).
Office Action dated Apr. 13, 2016, in Chinese Patent Application No. 201280053985.3.
Office Action dated Aug. 28, 2013, in Chinese Patent Application No. 201180012795.2.
Office Action dated Jul. 18, 2016, in Indonesian Patent Application No. W00201203610.
Office Action dated Sep. 5, 2016, in Ukrainian Patent Application No. a 2014 03846.
Office Action dated Aug. 25, 2016, in Eurasian Patent Application No. 201201264.
Office Action dated Feb. 17, 2014, in Mexican Patent Application No. MX/a/2012/010479.
Office Action dated Feb. 24, 2014, in Eurasian Patent Application No. 201201264.
Office Action dated Jul. 23, 2015, in Ukrainian Patent Application No. 201211548.
Office Action dated Jun. 20, 2016, in Chinese Patent Application No. 201280054819.5.
Office Action dated Jun. 24, 2016, in Chinese Patent Application No. 201280053984.9.
Office Action dated Nov. 3, 2014, in Chinese Patent Application No. 201180012795.2.
Office Action dated Jan. 6, 2015, in Japanese Patent Application No. 2012-557165.
Office Action dated Nov. 19, 2014, in Eurasian Patent Application No. 201201264/28.
Office Action dated Oct. 5, 2015, in Eurasian Patent Application No. 201201264/28.
Ongvarrasopone et al., "A Simple and Cost Effective Method to Generate dsRNA for RNAi Studies in Invertebrates," *Science Asia*, 33:35-39 (2007).
Orbović et al., "Foliar-Applied Surfactants and Urea Temporarily Reduce Carbon Assimilation of Grapefruit Leaves," *J. Amer. Soc. Hort. Sci.*, 126(4):486-490 (2001).
Ouellet et al., "Members of the Acetohydroxyacid Synthase Muligene Family of Brassica Napus Have Divergent Patterns of Expression," *The Plant Journal*, Blackwell Scientific Publications, Oxford, GB, 2(3):321-330 (1992).
Paddison et al., "Stable suppression of gene expression by RNAi in mammalian cells," *Proc. Natl Acad. Sci. USA*, 99(3):1443-1448 (2002).
Palauqui et al., "Activation of systemic acquired silencing by localised introduction of DNA," *Current Biology*, 9:59-66 (1999).
Parera et al., "Dehydration Rate after Solid Matrix Priming Alters Seed Performance of Shrunken-2 Corn," *J. Amer. Soc. Hort. Sci.*, 119(3):629-635 (1994).
Partial Supplementary European Search Report dated Mar. 2, 2015, in European Patent Application No. 12 831 494.5.
Patent Examination Report No. 1 dated Feb. 8, 2016, in Australian Patent Application No. 2014262189.
Patent Examination Report No. 1 dated Jun. 17, 2016, in Australian Patent Application No. 2012308659.
Patent Examination Report No. 1 dated Jun. 17, 2016, in Australian Patent Application No. 2012308660.
Patent Examination Report No. 1 dated Nov. 11, 2013, in Australian Patent Application No. 2011224570.
Paungfoo-Lonhienne et al., "DNA is Taken up by Root Hairs and Pollen, and Stimulates Root and Pollen Tube Growth," *Plant Physiology*, 153:799-805 (2010).
Paungfoo-Lonhienne et al., "DNA uptake by *Arabidopsis* induces changes in the expression of CLE peptides which control root morphology," *Plant Signaling & Behavior*, 5(9):1112-1114 (2010).
Pei et al., "On the art of identifying effective and specific siRNAs," *Nature Methods*, 3(9):670-676 (2006).
Peretz et al., "A Universal Expression/Silencing Vector in Plants," *Plant Physiology*, 145:1251-1263 (2007).
Pornprom et al., "Glutamine synthetase mutation conferring target-site-based resistance to glufosinate in soybean cell selections," *Pest Manag Sci*, 2009; 65(2):216-222 (2009).
Pratt et al., "Amaranthus rudis and A. tuberculatus, One Species or Two?," *Journal of the Torrey Botanical Society*, 128(3):282-296 (2001).
Preston et al., "Multiple effects of a naturally occurring proline to threonine substitution within acetolactate synthase in two herbicide-resistant populations of *Lactuca serriola*," *Pesticide Biochem. Physiol.*, 84(3):227-235 (2006).
Promoter Prediction for SEQ ID No. 1702 from 13/612929/MK/, Promoter 2.0 Prediction Results, pp. 1-4 (2016).
Promoter Prediction for SEQ ID No. 4 from 13/612995/MK/, Promoter 2.0 Prediction Results, pp. 1-3 (2016).

(56) References Cited

OTHER PUBLICATIONS

Promoter Prediction for SEQ ID No. 7 from 13/612936/MK/, Promoter 2.0 Prediction Results, pp. 1-2 (2016).
Promoter Prediction for SEQ ID No. 8 from 13/612,925/MK/, Promoter 2.0 Prediction Results, pp. 1-6 (2016).
Qiwei,"Advance in DNA interference," *Progress in Veterinary Medicine*, 30(1):71-75 (2009).
Rajur et al., "Covalent Protein—Oligonucleotide Conjugates for Efficient Delivery of Antisense Molecules," *Bioconjug Chem.*, 8:935-940 (1997).
Reddy et al "Organosilicone Adjuvants Increased the Efficacy of Glyphosate for Control of Weeds in Citrus (*Citrus* spp.)" *HortScience* 27(9):1003-1005 (1992).
Reddy et al., "Aminomethylphosphonic Acid Accumulation in Plant Species Treated with Glyphosate," *J. Agric. Food Chem.*, 56(6):2125-2130 (2008).
Reither et al., "Specificity of DNA triple helix formation analyzed by a FRET assay," *BMC Biochemistry*, 3:27 (2002).
Restriction Requirement dated Apr. 21, 2015, in U.S. Appl. No. 13/612,954.
Restriction Requirement dated Feb. 12, 2015, in U.S. Appl. No. 13/612,985.
Restriction Requirement dated Jul. 15, 2016, in U.S. Appl. No. 14/143,748.
Restriction Requirement dated Jul. 18, 2016, in U.S. Appl. No. 14/143,836.
Restriction Requirement dated Mar. 12, 2015, in U.S. Appl. No. 13/612,948.
Restriction Requirement dated Mar. 4, 2015, in U.S. Appl. No. 13/612,941.
Restriction Requirement dated May 4, 2015, in U.S. Appl. No. 13/612,929.
Restriction Requirement dated May 5, 2015, in U.S. Appl. No. 13/612,936.
Restriction Requirement dated May 7, 2015, in U.S. Appl. No. 13/612,925.
Restriction Requirement dated May 7, 2015, in U.S. Appl. No. 13/612,995.
Restriction Requirement dated Oct. 2, 2012, in U.S. Appl. No. 13/042,856.
Restriction Requirement dated Oct. 13, 2016, in U.S. Appl. No. 14/206,707.
Restriction Requirement dated Oct. 21, 2014, in U.S. Appl. No. 13/583,302.
Restriction Requirement dated Oct. 28, 2015, in U.S. Appl. No. 14/603,347.
Restriction Requirement dated Sep. 2, 2015, in U.S. Appl. No. 14/532,596.
Rey et al., "Diversity of Dicotyledenous-Infecting Geminiviruses and Their Associated DNA Molecules in Southern Africa, Including the South-West Indian Ocean Islands," *Viruses*, 4:1753-1791 (2012).
Reynolds et al., "Rational siRNA design for RNA interference," *Nature Biotechnology*, 22:326-330 (2004).
Riggins et al., "Characterization of de novo transcriptome for waterhemp (*Amaranthus tuberculatus*) using GS-FLX 454 pyrosequencing and its application for studies of herbicide target-site genes," *Pest Manag. Sci.*, 66:1042-1052 (2010).
Roberts, "Fast-track applications: The potential for direct delivery of proteins and nucleic acids to plant cells for the discovery of gene function," *Plant Methods*, 1(12):1-3 (2005).
Robson et al., "Leaf senescence is delayed in maize expressing the Agrobacterium IPT gene under the control of a novel maize senescence-enhanced promoter," *Plant Biotechnology Journal*, 2:101-112 (2004).
Roitsch et al., "Extracellular invertase: key metabolic enzyme and PR protein," *Journal of Experimental Botany*, 54(382):513-524 (2003).
Roitsch et al., "Function and regulation of plant invertases: sweet sensations," *Trades in Plant Science*, 9(12):606-613 (2004).
Rose et al., "Functional polarity is introduced by Dicer processing of short substrate RNAs," *Nucleic Acids Research*, 33(13):4140-4156 (2005).
Rothnie et al., Pararetroviruses and Retroviruses: A Comparative Review of Viral Structure and Gene Expression Strategies, *Advances in Virus Research*, 44:1-67 (1994).
Ruan et al., "Suppression of Sucrose Synthase Gene Expression Represses Cotton Fiber Cell Initiation, Elongation, and Seed Development," *The Plant Cell*, 15:952-964 (2003).
Ryabov et al., "Cell-to-Cell, but Not Long-Distance, Spread of RNA Silencing That Is Induced in Individual Epidermal Cells," *Journal of Virology*, 78(6):3149-3154 (2004).
Ryan, "Human endogenous retroviruses in health and disease: a symbiotic perspective," *Journal of the Royal Society of Medicine*, 97:560-565 (2004).
Salanenka et al., "Seedcoat Permeability: Uptake and Post-germination Transport of Applied Model Tracer Compounds," *HortScience*, 46(4):622-626 (2011).
Santoro et al., "A general purpose RNA-cleaving DNA enzyme," *Proc. Natl. Acad. Sci. USA*, 94:4262-4266 (1997).
Sathasivan et al., "Nucleotide sequence of a mutant acetolactate synthase gene from an imidazolinone-resistant *Arabidopsis thaliana* var. Columbia," *Nucleic Acids Research*, 18(8):2188-2193 (1990).
Schönherr, "Water Permeability of Isolated Cuticular Membranes: The Effect of pH and Cations on Diffusion, Hydrodynamic Permeability and Size of Polar Pores in the Cutin Matrix," Planta, 128:113-126 (1976).
Schwab et al., "RNA silencing amplification in plants: Size matters," *PNAS*, 107(34):14945-14946 (2010).
Schweizer et al., "Double-stranded RNA interferes with gene function at the single-cell level in cereals," *The Plant Journal*, 24(6):895-903 (2000).
Schwember et al., "Drying Rates following Priming Affect Temperature Sensitivity of Germination and Longevity of Lettuce Seeds," *HortScience*, 40(3):778-781 (2005).
Scott et al., "Botanical Insecticides for Controlling Agricultural Pests: Piperamides and the Colorado Potato Beetle *Leptinotarsa decemlineata* Say (Coleoptera: Chrysomelidae), *Archives of Insect Biochemistry and Physiology*, 54:212-225 (2003).
Second Chinese Office Action dated Jun. 10, 2014, in Chinese Patent Application No. 201180012795.2.
Second Office Action dated Feb. 25, 2016, in Chinese Patent Application No. 201280054179.8.
Second Office Action dated Mar. 4, 2016, in Chinese Patent Application No. 201280054820.8.
Seidman et al., "The potential for gene repair via triple helix formation," *J Clin Invest.*, 112(4):487-494 (2003).
Selvarani et al., "Evaluation of seed priming methods to improve seed vigour of onion (*Allium cepa* cv. *Aggregatum*) and carrot (*Daucus carota*)," *Journal of Agricultural Technology*, 7(3):857-867 (2011).
Senthil-Kumar et al., "A systematic study to determine the extent of gene silencing in Nicotiana benthamiana and other *Solanaceae* species when heterologous gene sequences are used for virus-induced gene silencing," *New Phytologist*, 176:782-791 (2007).
Sharma et al., "A simple and efficient *Agrobacterium*-mediated procedure for transformation of tomato," *J. Biosci.*, 34(3):423 433 (2009).
Shintani et al., "Antisense Expression and Overexpression of Biotin Carboxylase in Tobacco Leaves," *Plant Physiol.*, 114:881-886 (1997).
Showalter, "Structure and Function of Plant Cell Wall Proteins," *The Plant Cell*, 5:9-23 (1993).
Sijen et al., "On the Role of RNA Amplification in dsRNA-Triggered Gene Silencing," *Cell*, 107:465-476 (2001).
Silwet L-77 Spray Adjuvant for agricultural applications, product description from Momentive Performance Materials, Inc. (2003).
Singh et al., "Absorption and translocation of glyphosate with conventional and organosilicone adjuvants," *Weed Biology and Management*, 8:104-111 (2008).
Snead et al., "Molecular basis for improved gene silencing by Dicer substrate interfering RNA compared with other siRNA variants," *Nucleic Acids Research*, 41(12):6209-6221 (2013).

(56) References Cited

OTHER PUBLICATIONS

Song et al., "Herbicide," *New Heterocyclic Pesticide*, Chemical Industry Press, 354-356 (2011).

Steeves et al., "Transgenic soybeans expressing siRNAs specific to a major sperm protein gene suppress *Heterodera glycines* reproduction," *Funct. Plant Biol.*, 33:991-999 (2006).

Stevens et al., "New Formulation Technology—Silwet® Organosilicone Surfactants Have Physical and Physiological Properties Which Enhance the Performance of Sprays," *Proceedings of the 9th Australian Weeds Conference*, pp. 327-331 (1990).

Stevens, "Organosilicone Surfactants as Adjuvants for Agrochemicals," *Journal of Pesticide Science*, 38:103-122 (1993).

Stock et al., "Possible Mechanisms for Surfactant-Induced Foliar Uptake of Agrochemicals," *Pestic. Sci.*, 38:165-177 (1993).

Strat et al., "Specific and nontoxic silencing in mammalian cells with expressed long dsRNAs," *Nucleic Acids Research*, 34(13):3803-3810 (2006).

Street, "Why is DNA (and not RNA) a stable storage form for genetic information?," *Biochemistry Revisited*, pp. 1-4 (2008).

Sudarsan et al., "Metabolite-binding RNA domains are present in the genes of Herewith.eukaryotes," *RNA*, 9:644-647 (2003).

Sun et al., "A Highly efficient Transformation Protocol for Micro-Tom, a Model Cultivar for Tomato Functional Genomics," *Plant Cell Physiol.*, 47(3):426-431 (2006).

Sun et al., "Sweet delivery—sugar translocators as ports of entry for antisense oligodeoxynucleotides in plant cells," *The Plant Journal*, 52:1192-1198 (2007).

Sutton et al., "Activity of mesotrione on resistant weeds in maize," *Pest Manag. Sci.*, 58:981-984 (2002).

Takasaki et al., "An Effective Method for Selecting siRNA Target Sequences in Mammalian Cells," *Cell Cycle*, 3:790-795 (2004).

Tang et al., "Efficient delivery of small interfering RNA to plant cells by a nanosecond pulsed laser-induced stress wave for post-transcriptional gene silencing," *Plant Science*, 171:375-381 (2006).

Tank Mixing Chemicals Applied to Peanut Crops: Are the Chemicals Compatible?, College of Agriculture & Life Sciences, NC State University, AGW-653, pp. 1-11 (2004).

Taylor, "Seed Storage, Germination and Quality," *The Physiology of Vegetable Crops*, pp. 1-36 (1997).

Temple et al., "Can glutamine synthetase activity levels be modulated in transgenic plants by the use of recombinant DNA technology?" *Transgenic Plants and Plant Biochemistry*, 22(4):915-920 (1994).

Temple et al., "Down-regulation of specific members of the glutamine synthetase gene family in Alfalfa by antisense RNA technology," *Plant Molecular Biology*, 37:535-547 (1998).

Templeton et al., "Improved DNA: liposome complexes for increased systemic delivery and gene expression," *Nature Biotechnology*, 15:647-652 (1997).

Tenllado et al., "Crude extracts of bacterially expressed dsRNA can be used to protect plants against virus infection," *BMC Biotechnology*, 3(3):1-11 (2003).

Tenllado et al., "Double-Stranded RNA-Mediated Interference with Plant Virus Infection," *Journal of Virology*, 75(24):12288-12297 (2001).

Tenllado et al., "RNA interference as a new biotechnological tool for the control of virus diseases plants," *Virus Research*, 102:85-96 (2004).

Tepfer, "Risk assessment of virus resistant transgenic plants," *Annual Review of Phytopathology*, 40:467-491 (2002).

The Seed Biology Place, Website Gerhard Leubner Lab Royal Holloway, University of London, <http://www.seedbiology.de/seedtechnology.asp.

Third Party Submission filed on Nov. 29, 2012 in U.S. Appl. No. 13/042,856.

Thomas et al., "Size constraints for targeting post-transcriptional gene silencing and for RNA-directed methylation in *Nicotiana benthamiana* using a potato virus X vector," *The Plant Journal*, 25(4):417-425 (2001).

Thompson, et al., "Clustal W: improving the sensitivity of progressive multiple sequence alignment through sequence weighting, position-specific gap penalties and weight matrix choice," *Nucl. Acids Res.*, 22(22):4673-4680 (1994).

Timmons et al., "Specific interference by ingested dsRNA," *Nature*, 395:854 (1998).

Tomari et al., "Perspective: machines for RNAi," *Genes & Dev.*, 19:517-529 (2005).

Tomlinson et al., "Evidence that the hexose-to-sucrose ratio does not control the switch to storage product accumulation in oilseeds: analysis of tobacco seed development and effects of overexpressing apoplastic invertase," *Journal of Experimental Botany*, 55(406):2291-2303 (2004).

Töpfer et al., "Uptake and Transient Expression of Chimeric Genes in Seed-Derived Embryos," *Plant Cell*, 1:133-139 (1989).

Toriyama et al., "Transgenic Rice Plants After Direct Gene Transfer Into Protoplasts," *Bio/Technology*, 6:1072-1074 (1988).

Tran et al., "Control of specific gene expression in mammalian cells by co-expression of long complementary RNAs," *FEBS Lett.*;573(1-3):127-134 (2004).

Tranel et al., "Resistance of weeds to ALS-inhibiting herbicides: what have we learned?," *Weed Science*, 50:700-712 (2002).

Tsugawa et al., "Efficient transformation of rice protoplasts mediated by a synthetic polycationic amino polymer," *Theor Appl Genet*, 97:1019-1026 (1998).

Turina et al., "Tospoviruses in the Mediterranean Area," *Advances in Virus Research*, 84:403-437 (2012).

Tuschl, "Expanding small RNA interference," *Nature Biotechnol.*, 20: 446-448 (2002).

Tuschl, "RNA Interference and Small Interfering RNAs," *ChemBiochem.* 2(4):239-245 (2001).

Ui-Tei et al., "Guidelines for the selection of highly effective siRNA sequences for mammalian and chick RNA interference," *Nucleic Acids Res.*, 32(3): 936-948 (2004).

Unnamalai et al., "Cationic oligopeptide-mediated delivery of dsRNA for post-transcriptional gene silencing in plant cells," *FEBS Letters*, 566:307-310 (2004).

Unniraman et al., "Alternate Paradigm for Intrinsic Transcription Termination in Eubacteria," *The Journal of Biological Chemistry*, 276(45)(9):41850-41855 (2001).

Unniraman et al., "Conserved Economics of Transcription Termination in Eubacteria," Nucleic Acids Research, 30(3):675-684 (2002).

Urayama et al., "Knock-down of OsDCL2 in Rice Negatively Affects Maintenance of the Endogenous dsRNA Virus, *Oryza sativa* Endornavirus," *Plant and Cell Physiology*, 51(1):58-67 (2010).

Van de Wetering et al., "Specific inhibition of gene expression using a stably integrated, inducible small-interfering-RNA vector," *EMBO Rep.*, 4(6):609-615 (2003).

Vasil et al., "Herbicide Resistant Fertile Transgenic Wheat Plants Obtained by Microprojectile Bombardment of Regenerable Embryogenic Callus," *Bio/Technology*,10:667-674 (1992).

Vaucheret, "Post-transcriptional small RNA pathways in plants: mechanisms and regulations," *Genes Dev.*, 20:759-771 (2006).

Vencill et al., "Resistance of Weeds to Herbicides," *Herbicides and Environment*, 29:585-594 (2011).

Verma et al., "Modified oligonucleotides: synthesis and strategy for users," *Annu. Rev. Biochem.*, 67:99-134 (1998).

Vermeulen et al. "The contributions of dsRNA structure to Dicer specificity and efficiency," *RNA*, 11(5):674-682 (2005).

Vert et al., "An accurate and interpretable model for siRNA efficacy prediction," *BMC Bioinformatics*, 7:520 (2006).

Voinnet et al., "Systemic Spread of Sequence-Specific Transgene RNA Degradation in Plants Is Initiated by Localized Introduction of Ectopic Promoterless DNA," *Cell*, 95:177-187 (1998).

Wakelin et al., "A target-site mutation is present in a glyphosate-resistant *Lolium rigidum* population," *Weed Res.* (*Oxford*), 46(5):432-440 (2006).

Walton et al., "Prediction of antisense oligonucleotide binding affinity to a structured RNA target," *Biotechnol Bioeng* 65(1):1-9 (1999).

Wan et al., "Generation of Large Numbers of Independently Transformed Fertile Barley Plants," *Plant Physiol.*, 104:37-48 (1994).

(56) References Cited

OTHER PUBLICATIONS

Wang et al., "Foliar uptake of pesticides—Present status and future challenge," ScienceDirect, 87:1-8 (2007).
Wardell, "Floral Induction of Vegetative Plants Supplied a Purified Fraction of Deoxyribonucleic Acid from Stems of Flowering Plants," *Plant Physiol*, 60:885-891 (1977).
Wardell, "Floral Activity in Solutions of Deoxyribonucleic Acid Extracted from Tobacco Stems," *Plant Physiol*, 57:855-861 (1976).
Waterhouse et al., "Virus resistance and gene silencing in plants can be induced by simultaneous expression of sense and antisense RNA," *Proc Natl Acad Sci USA*, 95 13959-13964 (1998).
Welch et al., "Expression of ribozymes in gene transfer systems to modulate target RNA levels," *Curr Opin Biotechnol.* 9(5):486-496 (1998).
Widholm et al., "Glyphosate selection of gene amplification in suspension cultures of 3 plant species," *Phyisologia Plantarum*, 112:540-545 (2001).
Wiesman et al., "Novel cationic vesicle platform derived from vernonia oil for efficient delivery of DNA through plant cuticle membranes," *Journal of Biotechnology*, 130:85-94 (2007).
Wild Carrot, Noxious Weed Control Board (NWCB) of Washington State (2010) <www.nwcb.wa.gov/detail.asp?weed=46>.
Wilson, et al., "Transcription termination at intrinsic terminators: The role of the RNA hairpin," *Proc. Natl. Acad. Sci. USA*, 92:8793-8797 (1995).
Winkler et al., "Thiamine derivatives bind messenger RNAs directly to regulate bacterial gene expression," *Nature*, 419:952-956 (2002).
Written Opinion dated Apr. 7, 2016, in Singapore Patent Application No. 201206152-9.
Written Opinion dated May 8, 2014, in International Application No. PCT/IL2013/050447.
Written Opinion dated Sep. 1, 2014, in Singapore Patent Application No. 201206152-9.
Xu et al., Characterization and Functional Analysis of the Calmodulin-Binding Domain of Rac1 GTPase, *Plos One*, 7(8)1-12:e42975 (2012).
Yin et al., "Production of double-stranded RNA for interference with TMV infection utilizing a bacterial prokaryotic expression system," *Appl. Microbiol. Biotechnol.*, 84(2):323-333 (2009).
YouTube video by General Electric Company "Silwet Surfactants," screen shot taken on Jan. 11, 2012 of video of www.youtube.com/watch?v=WBw7nXMqHk8 (uploaded Jul. 13, 2009).
Zagnitko, "Lolium regidum clone LS1 acetyl-CoA carboxylase mRNA, partial cds; nuclear gene for plastid product," GenBank: AF359516.1, 2 pages (2001).
Zagnitko, et al., "An isoleucine/leucine residue in the carboxyltransferase domain of acetyl-CoA carboxylase is critical for interaction with aryloxyphenoxypropionate and cyclohexanedione inhibitors," *PNAS*, 98(12):6617-6622 (2001).
Zhang et al., "A novel rice gene, NRR responds to macronutrient deficiency and regulates root growth," *Mol Plant*, 5(1):63-72 (2012).
Zhang et al., "*Agrobacterium*-mediated transformation of *Arabidopsis thaliana* using the floral dip method," *Nature Protocols*, 1(2):1-6 (2006).
Zhang et al., "Cationic lipids and polymers mediated vectors for delivery of siRNA," *Journal of Controlled Release*, 123:1-10 (2007).
Zhang et al., "Chapter 10: New Characteristics of Pesticide Research & Development," *New Progress of the world agriculture chemicals*, p. 209 (2010).
Zhang et al., "DEG: a database of essential genes," *Nucleic Acids Res.*, 32:D271-D272 (2004).
Zhang et al., "Transgenic rice plants produced by electroporation-mediated plasmid uptake into protoplasts," *The Plant Cell Rep.*, 7:379-384 (1988).
Zhao et al., "*Phyllotreta striolata* (Coleoptera: Chrysomelidae):Arginine kinase cloning and RNAi-based pest control," *European Journal of Entomology*, 105(5):815-822 (2008).
Zhu et al., "Ingested RNA interference for managing the populations of the Colorado potato beetle, *Leptinotarsa decemlineata*," *Pest Manag Sci*, 67:175-182 (2010).

Bachman et al., "Characterization of the spectrum of insecticidal activity of a double-stranded RNA with targeted activity against Western Corn Rootworm (*Diabrotica virgifera virgifera* LeConte)," Transgenic Res., pp. 1-16 (2013).
Office Action dated Dec. 13, 2016, in Ukrainian Patent Application No. a 2014 03843.
Office Action dated Dec. 14, 2016, in Ukrainian Patent Application No. a 2014 03850.
Office Action dated Dec. 15, 2016, in Ukrainian Patent Application No. a 2014 03845.
Office Action dated Dec. 15, 2016, in Ukrainian Patent Application No. a 2014 03852.
Office Action dated Dec. 15, 2016, in Ukrainian Patent Application No. a 2014 03849.
Office Action dated Dec. 27, 2016, in Ukrainian Patent Application No. a 2012 11548.
Office Action dated Mar. 16, 2017, in Chinese Patent Application No. 201280054819.5.
Office Action dated Nov. 15, 2016, in Mexican Patent Application. No. MX/a/2014/003068.
Shaoquan, "The action target of herbicide and the innovation of a new variety," Chemical Industry Press, pp. 23-24 (2001).
Written Opinion dated Mar. 6, 2017, in Singaporean Patent Application No. 2012061529.
Fassler, BLAST Glossary, National Center for Biotechnology Information (2011).
GenBank Accession No. EF143582 (2007).
"Jacque et al., ""Modulation of HIV-1 replication by RNA interference,"" Nature, 418, 435-438 (2002)".
Office Action dated Aug. 1, 2017, in European Patent Application No. 12 830 932.5.
Office Action dated Aug. 14, 2017, in Israeli Patent Application No. 235878.
Office Action dated Aug. 22, 2017, in Korean Patent Application No. 10-2012-7023415.
Office Action dated Aug. 3, 2017, in Chinese Patent Application No. 201480014392.5 (with English translation).
Office Action dated Aug. 3, 2017, in European Patent Application No. 12 831 684.1.
Office Action dated Aug. 8, 2017, in Chilean Patent Application No. 201501874.
Office Action dated Jul. 11, 2017, in Mexican Patent Application No. MX/a/2015/013118 (with English translation).
Office Action dated Jul. 3, 2017, in Mexican Patent Application No. MX/a/2015/012632 (with English translation).
Office Action dated Jul. 6, 2017, in Mexican Patent Application No. MX/a/2015/013103 (with English translation).
Office Action dated May 3, 2016, in Chilean Patent Application No. 201601057.
Office Action dated Nov. 15, 2016, in Mexican Patent Application No. MX/a/2014/003068 (with English translation).
Office Action dated Sep. 6, 2017, in Chinese Patent Application No. 2014800154012 (with English translation).
Patent Examination Report No. 1 dated Jun. 8, 2017, in Australian Patent Application No. 2012308686.
Search Report dated Jul. 24, 2017, in Chinese Patent Application No. 201480014392.5 (with English translation).
Statement of Grounds and Particulars dated Sep. 1, 2017, in Australian Patent No. 2014262189.
"Stevens, ""Formulation of Sprays to Improve the Efficacy of Foliar Fertilisers,"" New Zealand Journal of Forestry Science, 24(1):27-34 (1994)".
"Stevens, ""Organosilicone Surfactants as Adjuvants for Agrochemicals,"" New Zealand Journal of Forestry Science, 24:27-34 (1994)".
Zhang, Chapter 10: New Characteristics of Pesticide Research & Development, p. 209 (2010).
Andersen et al., Delivery of siRNA from lyophilized polymeric surfaces, *Biomaterials*, 29:506-512 (2008).
Anonymous, Resistant Weeds Spur Research Into New Technologies, *Grains Research & Development Corporation* (2013).

(56) References Cited

OTHER PUBLICATIONS

Ascencio-Ibanez et al., DNA abrasion onto plants is an effective method for geminivirus infection and virus-induced gene silencing, *Journal of Virological Methods*, 142:198-203 (2007).
Bauer et al., The major protein import receptor of plastids is essential for chloroplast biogenesis, *Nature*, 403:203-207 (2000).
Bedell et al., Sorghum Genome Sequencing by Methylation Filtration, *PLOS Biology*, 3(1):E13/104-115 (2005).
Burgos et al., Review: Confirmation of Resistance to Herbicides and Evaluation of Resistance Levels, *Weed Science*, 61 (1):4-20 (2013).
Chang et al., Dual-target gene silencing by using long, sythetic siRNA duplexes without triggering antiviral responses, *Molecules and Cells*, 27(6)689-695 (2009).
Chen et al., Exploring MicroRNA-Like Small RNAs in the Filamentous Fungus *Fusarium oxysporum*, *PLOS One*, 9(8):e104956:1-10 (2014).
Cheng et al., Transient Expression of Minimum Linear Gene Cassettes in Onion Epidermal Cells via Direct Transformation, *Appl Biochem Biotechnol*, 159:739-749 (2009).
Christiaens et al., The challenge of RNAi-mediated control of hemipterans, *Current Opinion in Insect Science*, 6:15-21 (2014).
Constan et al., An outer envelope membrane component of the plastid protein import apparatus plays an essential role in *Arabidopsis*, *The Plant Journal*, 38:93-106 (2004).
Database EMBL XP-002781749(BG442539) dated Mar. 20, 2001.
Di Stilio et al., Virus-Induced Gene Silencing as a Tool for Comparative Functional Studies in Thalictrum, PLoS One, 5(8):e12064 (2010).
Eamens et al., RNA Silencing in Plants: Yesterday, Today, and Tomorrow, *Plant Physiology*, 147(2):456-468 (2008).
Eudes et al., Cell-penetrating peptides, Plant Signaling & Behavior, 3(8):549-5550 (2008).
European Search Report dated Jun. 29, 2018, in European Patent Application No. 18157745.3.
European Search Report dated Sep. 7, 2017, in European Patent Application No. 17152830.0.
Examination Report dated Mar. 1, 2018, in Australian Patent Application No. 2013264742.
Extended European Search Report dated Nov. 7, 2017, in European Patent Application No. 15811092.4.
Extended European Search Report dated Nov. 8, 2017, in European Patent Application No. 15737282.2.
Extended European Search Report dated Apr. 13, 2018, in European Patent Application No. 15812530.0.
Extended European Search Report dated Mar. 15, 2018, in European Patent Application No. 17181861.0.
Fernandez et al., Uptake of Hydrophilic Solutes Through Plant Leaves: Current State of Knowledge and Perspectives of Foliar Fertilization, *Critical Reviews in Plant Sciences*, 28:36-38 (2009).
Friedberg, Automated protein function prediction—the genomic challenge, *Briefings in Bioinformatics*, 7(3):225-242 (2006).
Funke et al., Molecular basis for herbicide resistance in Roundup Ready crops, *PNAS*, 103:13010-13015 (2006).
Gallie et al., Identification of the motifs within the tobacco mosaic virus 5'-leader responsible for enhancing translation, *Nucleic Acids Res.*, 20(17):4631-4638 (1992).
Gan et al., Bacterially expressed dsRNA protects maize against SCMV infection, *Plant Cell Rep*, 29(11):1261-1268 (2010).
Gaskin et al., Novel organosillicone adjuvants to reduce agrochemical spray volumes on row crops, *New Zealand Plant Protection*, 53:350-354 (2000).
Gengling, The Transformation of Nucleic Acid Degradants in Plants, China Organic Fertilizers, Agriculture Press, ISBN: 7-1091634 (with English translation).
Gomez-Zurita et al., Recalibrated Tree of Leaf Beetles (Chrysomelidae) Indicates Independent Diversification of Angiosperms and Their Insect Herbivores, *PLoS One*, 4(e360):1-8 (2007).
Hagio, Chapter 25: Direct Gene Transfer into Plant Mature Seeds via Electroporation After Vacuum Treatment, Electroporation and Sonoporation in Developmental Biology, p. 285-293 (2009).
Hess, Surfactants and Additives, *1999 Proceedings of the California Weed Science Society*, 51:156-172 (1999).
Hoermann et al., Tic32, as Essential Component in Chloroplast Biogenesis, *The Journal of Biological Chemistry*, 279(33):34756-34762 (2004).
Hu et al., High efficiency transport of quantum dots into plant roots with the aid of silwet L-77, *Plant Physiology and Biochemistry*, 48:703-709 (2010).
Huang et al., In Vivo Analyses of the Roles of Essential Omp85-Related Proteins in the Chloroplast Outer Envelope Membrane, *Plant Physiol.*, 157:147-159 (2011).
Ivanova et al., Members of the Toc159 Import Receptor Family Represent Distinct Pathways for Protein Targeting to Plastids, *Molecular Biology of the Cell*, 15:3379-3392 (2004).
Jang et al., Resistance to herbicides caused by single amino acid mutations in acetyl-CoA carboxylase in resistant populations of grassy weeds, *New Phytologist*, 197(4):1110-1116 (2013).
Jarvis et al., An *Arabidopsis* mutant defective in the plastid general protein import apparatus, *Science*, 282:100-103 (1998).
Kikkert et al., Stable Transformation of Plant Cells by Particle Bombardment/Biolistics, *Methods in Molecular Biology*, 286:61-78 (2005).
Kovacheva et al., Further in vivo studies on the role of the molecular chaperone, Hsp93, in plastid protein import, *The Plant Journal*, 50:364-379 (2007).
Kovacheva et al., In vivo studies on the roles of Tic100, Tic40 and Hsp93 during chloroplast protein import, *The Plant Journal*, 41:412-428 (2005).
Li et al., A Simplified Seed Transformation Method for Obtaining Transgenic *Brassica napus* Plants, *Agricultural Sciences in China*, 8(6):658-663 (2009).
Li et al., Long dsRNA but not siRNA initiates RNAi in western corn rootworm larvae and adults, *Journal of Applied Entomology*, 139(6):432-445 (2015).
Liu et al., The Helicase and RNaseIIIa Domains of *Arabidopsis* Dicer-Like1 Modulate Catalytic Parameters during MicroRNA Biogenesis, *Plant Physiology*, 159:748-758 (2012).
McGinnis, RNAi for functional genomics in plants, *Brief Funct Genomics*, 9(2):111-7 (2010).
Non-Final Office Action dated Mar. 21, 2018, in U.S. Appl. No. 13/619,980.
Office Action dated Dec. 5, 2017, in Japanese Patent Application No. 2016-502033.
Office Action dated Feb. 21, 2018, in Mexican Patent Application No. MX/a/2015/012632 (with English translation).
Office Action dated Mar. 8, 2018 (with English translation), in Chilean Patent Application No. 201403192.
Partial European Search Report dated Dec. 6, 2017, in European Patent Application No. 17181861.0.
Partial Supplementary European Search Report dated Jan. 11, 2018, in European Patent Application No. 15812530.0.
Powles et al., Evolution in Action: Plants Resistant to Herbicides, *Annual Review of Plant Biology*, 61(1):317-347 (2010).
Qichuan et al., Seed Science, China Agriculture Press, pp. 101-103, Tables 2-37 (2001).
Rakoczy-Trojanowska, Alternative Methods of Plant Transformation—a short review, *Cellular & Molecular Biology Letters*, 7:849-858 (2002).
Regalado, The Next Great GMO Debate, MIT Technology Review,pp. 1-19 (2015) <https://www.technologyreview.com/s/540136/the-next-great-gmo-debate/>.
Richardson et al., Targeting and assembly of components of the TOC protein import complex at the chloroplast outer envelope membrane, *Frontiers in Plant Science*, 5:1-14 (2014).
Search Report dated Oct. 20, 2017, in Chinese Patent Application No. 201380039346.6.
Small, RNAi for revealing and engineering plant gene functions, *Current Opinion in Biotechnology*, 18:148-153 (2007).
Stevens, Formulation of Sprays to Improve the Efficacy of Foliar Fertilisers, *New Zealand Journal of Forestry Science*, 24(1):27-34 (1993).
Stevens, Organosilicone Surfactants as Adjuvants for Agrochemicals, *New Zealand Journal of Forestry Science*, 38:103-122 (1993).

(56) References Cited

OTHER PUBLICATIONS

Summons to Attend Oral Proceedings Pursuant to Rule 115(1) EPC, dated Aug. 7, 2017, in European Patent Application No. 12832160.1.
Sun et al., Antisense oligodeoxynucleotide inhibition as a potentstrategy in plant biology: identification of SUSIBA2 as atranscriptional activator in plant sugar signalling, *The Plant Journal*, 44:128-138 (2005).
Sun, Characterization of Organosilicone Surfactants and Their Effects on Sulfonylurea Herbicide Activity, Thesis Submitted to the Faculty of the Virginia Polytechnic Institute and State University dated Apr. 5, 1996.
Teng et al., Tic21 Is an Essential Translocon Component for Protein Translocation across the Chloroplast Inner Envelope Membrane, *The Plant Cell*, 18:2247-2257 (2006).
Trucco et al., Amaranthus hybridus can be pollinated frequently by *A. tuberculatus* under filed conditions, *Heredity*, 94:64-70 (2005).
Ulrich et al., Large scale RNAi screen in Tribolium reveals novel target genes for pest control and the proteasome as prime target, *BMC genomics*, 16(1):671 (2015).
Voinnet, Origin, Biogenesis, and Activity of Plant MicroRNAs, Cell, 136:669-687 (2009).
Wang et al., Principle and technology of genetic engineering in plants, in Plant genetic engineering principles and techniques, Beijing: *Science Press*, pp. 313-315 (1998).
Wool et al., Structure and evolution of mammalian ribosomal proteins, *Biochem. Cell Biol.*, 73:933-947 (1995).
Xu et al., Characterization and Functional Analysis of the Calmodulin-Binding Domain of Rac1 GTPase, *PLoS One*, 7(8):e42975 (2012).
Zaimin et al., Chapter III Seeds and Seedlings, Botany, Northwest A&F University Press, pp. 87-92 (2009).
Zhang et al., Development and Validation of Endogenous Reference Genes for Expression Profiling of Medaka (*Oryzias latipes*) Exposed to Endocrine Disrupting Chemicals by Quantitative Real-Time RT-PCR, *Toxicological Sciences*, 95(2):356-368 (2007).
Zhang, Artificial trans-acting small interfering RNA: a tool for plant biology study and crop improvements, *Planta*, 239:1139-1146 (2014).
Zhong et al., A forward genetic screen to explore chloroplast protein import in vivo identifies Moco sulfurase, pivotal for ABA and IAA biosynthesis and purine turnover, *The Plant Journal*, 63:44-59 (2010).
Zhong et al., A pea antisense gene for the chloroplast stromal processing peptidase yields seedling lethals in *Arabidopsis*: survivors show defective GFP import in vivo, *The Plant Journal*, 34:802-812 (2003).
Zotti et al., RNAi technology for insect management and protection of beneficial insects from diseases: lessons, challenges and risk assessments, *Neotropical Entomology*, 44(3):197-213 (2015).
Asad et al., "Silicon Carbide Whisker-Mediated Plant Transformation," Properties and Applications of Silicon Carbide, pp. 345-358 (2011).
Baker, "Chlorophyll Fluorescence: A Probe of Photosynthesis In Vivo," *Annu. Rev. Plant Biol.*, 59:89-113 (2008).
Baum et al., "Progress Towards RNAi-Mediated Insect Pest Management" *Advances in Insect Physiology*, 47:249-295 (2014).
Belhadj et al., "Methyl Jasmonate Induces Defense Responses in Grapevine and Triggers Protection against Erysiphe necator," *J. Agric Food Chem.*, 54:9119-9125 (2006).
Burleigh, "Relative Quantitative RT-PCR to Study the Expression of Plant Nutrient Transporters in Arbuscular Mycorrhizas," *Plant Science*, 160:899-904 (2001).
Communication Pursuant to Article 94(3) EPC dated Sep. 5, 2018, in European Patent Application No. 17152830.0.
Cong et al., "Multiplex Genome Engineering Using CRISPR/Cas Systems," *Science*, 339:819-823 (2013).
Declaration of Jerzy Zabkiewicz executed Nov. 28, 2017, as filed by Opponent in Australian Patent Application No. 2014262189, pp. 1-4.

Declaration of Jerzy Zabkiewicz executed Nov. 28, 2017, as filed by Opponent in Australian Patent Application No. 2014262189, pp. 1-73.
Declaration of Neena Mitter executed Nov. 30, 2017, as filed by Opponent in Australian Patent Application No. 2014262189, pp. 1-114.
Declaration of Neena Mitter executed Nov. 30, 2017, as filed by Opponent in Australian Patent Application No. 2014262189, pp. 1-25.
Delye et al., "PCR based Detection of Resistance to acetyl-CoA Carboxylase-Inhibiting Herbicides in Black-Grass (*Alopecurus myosuroides* Huds) and ryegrass (*Lolium rigidum* Gaud)," *Pest Management Science*, 58:474-478 (2002).
Delye et al., "Variation in the Gene Encoding Acetolactate-Synthase in *Lolium* Species and Proactive Detection of Mutant, Herbicide-Resistant Alleles," *Weed Research*, 49:326-336 (2009).
Desveaux et al., "PBF-2 Is a Novel Single-Stranded DNA Binding Factor Implicated in PR-10a Gene Activation in Potato," *The Plant Cell*, 12:1477-1489 (2000).
Dietzgen et al., "Transgenic Gene Silencing Strategies for Virus Control," *Australasian Plant Pathology*, 35:605-618 (2006).
Dilpreet et al., "Glyphosate Resistance in a Johnsongrass (*Sorghum halepense*) Biotype from Arkansas," *Weed Science*, 59(3):299-304 (2011).
Drobyazko R.V., "Reliable and Environmentally friendly insecticide," *Protection and quarantine of plants*, 2012 (pp. 52, 53) (in Russian).
Duhoux et al., "Reference Genes to Study Herbicide Stress Response in *Lolium* sp.: Up-Regulation of P3450 Genes in Plants Resistant to Acetolactate-Synthase Inhibitors," *PLoS One*, 8(5):e63576 (2013).
Egli et al., "A Maize Acetyl-Coenzyme A Carboxylase cDNA Sequence," *Plant Physiol.*, 108: 1299-1300 (1995).
Extended European Search Report dated Dec. 19, 2018, in European Patent Application No. 16804395.8.
Extended European Search Report dated Nov. 16, 2018, in European Patent Application No. 18182238.8.
Extended European Search Report dated Nov. 21, 2018, in European Patent Application No. 18175809.5.
Extended European Search Report dated Sep. 28, 2018, in European Patent Application No. 16740770.9.
Gao et al., "DNA-guided Genome Editing Using the *Natronobacterium gregoryi* Argonaute," *Nature Biotechnology*, 34(7):768-773 (2016).
Gasser et al., "Structure, Expression, and Evolution of the 5-Enolpyruvylshikimate-3-phosphate Synthase Genes of Petunia and Tomato," *J. Biol. Chem.*, 263: 4280-4287 (1988).
Gilmer et al., "Latent Viruses of Apple I. Detection with Woody Indicators," *Plant Pathology*, 1(10):1-9 (1971).
Guttieri et al., "DNA Sequence Variation in Domain A of the Acetolactate Synthase Genes of Herbicide-Resistant and -Susceptible Weed Biotypes," *Weed Science*, 40:670-679 (1992).
Horsch et al., "Inheritance of Functional Foreign Genes in Plants," *Science*, 223:496-498 (1984).
Hsu et al., "DNA targeting specificity of RNA-guided Cas9 nucleases," *Nature Biotechnology*, 31:827-832 (2013).
Huggett et al., "Real-Time RT-PCR Normalisation, Strategies and Considerations," *Genes and Immunity*, 6:279-284 (2005).
Inaba et al., "*Arabidopsis* Tic110 Is Essential for the Assembly and Function of the Protein Import Machinery of Plastids," *The Plant Cell*, 17:1482-1496 (2005).
International Search Report dated Oct. 13, 2016, in International Patent Application No. PCT/US2016/35500.
Jacque et al., "Modulation of HIV-1 Replication by RNA Interference," *Nature* (2002).
Jiang et al., "Chapter III Seeds and Seedlings, Botany, Northwest A&F," *University Press*, pp. 87-92 (2009).
Kim et al., "Synthesis and Characterization of Mannosylated Pegylated Polyethylenimine as a Carrier for siRNA," *International Journal of Pharmaceutics*, 427:123-133 (2012).
Kirkwood, "Recent Developments in our Understanding of the Plant Cuticle as a Barrier to the Foliar Uptake of Pesticides," *Pestic. Sci.*, 55:69-77 (1999).

(56) References Cited

OTHER PUBLICATIONS

Liu, "Calmodulin and Cell Cycle," *Foreign Medical Sciences Section of Pathophysiology and Clinical Medicine*, 18(4):322-324 (1998).
Liu, "Confocal Laser Scanning Microscopy—An Attractive Tool for Studying the Uptake of Xenobiotics into Plant Foliage," *Journal of Microscopy*, vol. 213(Pt 2):87-93 (2004).
Liu, "The Transformation of Nucleic Acid Degradants in Plants," *China Organic Fertilizers, Agriculture Press*, ISBN: 7-1091634-X (1991) (with English translation).
Lodish et al., "Molecular Cell Biology," Fourth Edition, p. 210 (2000).
Lucas et al., "Plasmodesmata—Bridging the Gap Between Neighboring Plant Cells," *Trends in Cell Biology*, 19:495-503 (2009).
Morozov et al., "Evaluation of Preemergence Herbicides for Control of Diclofop-resistant Italian Ryegrass (*Lolium multiflorum*) in Virginia," Virginia Polytechnic Institute and State University, pp. 43-71 (2004).
Nemeth, "Virus, Mycoplasma and Rickettsia Diseases of Fruit Trees," *Martinus Nijhoff Publishers*, pp. 197-204 (1986).
N-TER Nanoparticle siRNA, Sigma Aldrich TM website, Web. Nov. 20, 2018.
Office Action dated Aug. 9, 2018, in Canadian Patent Application No. 2,848,371.
Office Action dated Jul. 30, 2018, in Canadian Patent Application No. 2,848,576.
Office Action dated Sep. 20, 2018, in Chilean Patent Application No. 201601440 (with English translation).
Partial European Search Report dated Jun. 29, 2018, in European Patent Application No. 18157745.3.
Partial Supplementary European Search Report dated Jan. 11, 2018, in European Patent Application No. 15812530.2.
Pratt et al., "Sorghum Expressed Sequence Tags Identify Signature Genes for Drought, Pathogenesis, and Skotomorphogenesis from a Milestone Set of 16,801 Unique Transcripts," *Plant Physiology*, 139:869-884 (2005).
Qi et al., "RNA Processing Enables Predictable Programming of Gene Expression," *Nature Biotechnology*, 30:1002-1007 (2012).
Reverdatto et al., "A Multisubunit Acetyl Coenzyme A Carboxylase from Soybean," *Plant Physiol.*, 119: 961-978 (1999).
Schönherr et al., "Size Selectivity of Aqueous Pores in Astomatous Cuticular Membranes Isolated from *Populus canescens* (Aiton) Sm. Leaves," *Planta*, 219:405-411 (2004).
Simeoni et al., "Insight into the Mechanism of the Peptide-Based Gene Delivery System MPG: Implications for Delivery of siRNA into Mammalian Cells," *Nucleic Herewith Acids Research*, 31(11):2717-2724 (2003).
Swarts et al., "Argonaute of the Archaeon *Pyrococcus furiosus* is a DNA-Guided Nuclease that Targets Cognate DNA," *Nucleic Acid Res.*, 43(10):5120-5129 (2015).
Swarts et al., "DNA-Guided DNA Interference by a Prokaryotic Argonaute," *Nature*, 507(7491):258-61 (2014).
Tenllado et al., "Crude Extracts of Bacterially Expressed dsRNA Can be Used to Protect Plants Against Virus Infections," *BMC Biotechnology*, 3:1-11 (2003).
Tice, "Selecting the Right Compounds for Screening: Does Lipinski's Rule of 5 for Pharmaceuticals Apply to Agrochemicals?" *Pest Management Science*, 57(1):3-16 (2001).
Townsend et al., "High Frequency Modification of Plant Genes Using Engineered Zinc Finger Nucleases," *Nature*, 459:442-445 (2009).
TransIT-TKO® Transfection Reagent, Frequently Asked Questions, Web. 2019.
Van der Meer et al., "Promoted Analysis of the Chalcone Synthase (chs A) Gene of *Petunia hybrida*: a 67 bp Promoter Region Directs Flower-Specific Expression," *Plant Mol. Biol.*, 15:95-109 (1990).
Watson et al., "RNA silencing platforms in plants," *FEBS Letters*, 579:5982-5987 (2005).
Yan et al., "Seed Science," China Agriculture Press, pp. 101-103, Tables 2-37 (2001).
Yu et al., "Diversity of Acetyl-Coenzyme A Carboxylase Mutations in Resistant *Lolium* Populations: Evaluation Using Clethodim," *Plant Physiology*, 145:547-558 (2007).
Yu et al., "Glyphosate, Paraquat and ACCase Multiple Herbicide Resistance Evolved in a *Lolium rigidum* biotype," *Planta*, 225:499-513 (2007).
Zabkiewicz, "Adjuvants and Herbicidal Efficacy—Present Status and Future Prospects," *Weed Research*, 40:139-149 (2000).
Zhao et al., "PsOr1, a Potential Target for RNA Interference-Based Pest Management," *Insect Molecular Biology*, 20(1):97-104 (2011).
Zhao et al., "Vegetable Standardized Production Technology," Hangzhou: Zhejiang Science and Technology Press, p. 19 (2008).
Zidack et al., "Promotion of Bacterial Infection of Leaves by an Organosilicone Surfactant: Implications for Biological Weed Control," *Biological Control*, 2:111-117 (1992).
Zipperian, "Silicon Carbide Abrasive Grinding," Quality Matters Newsletter, *PACE Technologies* 1(2):1-3 (2002).

\* cited by examiner

SEQUENCE LISTING

<160> NUMBER OF SEQ ID NOS: 155

<210> SEQ ID NO 1
<211> LENGTH: 880
<212> TYPE: DNA
<213> ORGANISM: Lolium rigidum

<400> SEQUENCE: 1

```
cctatgcagc gtgctgctgg gctcaatgac attggtatgg tagcctggat cttggacatg     60
tccactcccg aatttcccag tggcagacag attattgttg tcgcaaatga tattactttt    120
agagctggat catttggccc aagggaagat gcattttttg aagctgttac caacctggct    180
tgtgagagaa agcttcctct tatctatatg gctgcaaact ctggtgctcg gattggcatt    240
gctgatgaag ttaaatctat cttccgtgtt aaatggattg atgatagcaa ccctgaacgt    300
ggatttgatt acgtttatct gtctgaagaa gactatggcc gtattagctc ttctgttata    360
gcgcacaaga cacagctaga tagtggcgaa ataaggtcgg ttatcgattc tgttgtgggc    420
aaggaggatg gactaggtgt ggagaacata catggaagtg ctgctattgc cagtgcgtat    480
tctagggcat acgaggagac atatacactt acatttgtga ctggacgaac tgttggaata    540
ggagcctatc ttgctcgact tggcatacgg tgcatacagc gtgaagatca gcccattatc    600
ttaactgggt attctgccct gaacaagctt ctcggacggg aagtgtacag ctctcacatg    660
cagttgggtg gtcccaaaat catggcaact aatggtattg accatctgac tgttccagat    720
gaccttgcag gtgtttctca tatattgagg tggctcagct atgttcctgc taacattggt    780
ggacctcttc ctattacaaa acctttggat ccaatagaca gacctgttgc atacattcct    840
gagaatacat gtgatcctcg tgcagccata agtggcattg                          880
```

<210> SEQ ID NO 2
<211> LENGTH: 895
<212> TYPE: DNA
<213> ORGANISM: Lolium rigidum

<400> SEQUENCE: 2

```
ctctacagga cttctatttt ttttggcaat catttacatt gttaaatggt ctgcattcag     60
gttgagcacc cagtcactga gtggatagct gaagtaaatt tgcctgcagc tcaagttgca    120
gttggaatgg gtatacccct ttggcaggtt ccaggtaata ataaaagcat cgtaatatct    180
ttattttctg tcccatgtta tttcgttgtc taattatctc cttatacaga gatcagacgt    240
ttctacggaa tggacaatgg aggtggctat gacatttgga ggaaaacagc agctcttgct    300
actccattca actttgatga agtagattct caatggccga agggtcattg tgttgcagtt    360
cggataacta gtgagaatcc agatgatgga ttcaagccta ctggtggaaa agtaaaggtg    420
ggatttccta atgcgatatc tatatttcaa gcagactagg gttagtaaac tgatgtggtc    480
ttgatttttc gtatgtttca ggagataagt tttaaaagta agccgaatgt ctggggatat    540
ttctcagtta aggtaagcta agctgttcat agctctgttg cagtgtcatg ttgttttgag    600
ttctgcagaa aattggtctg caagattttt tatttgaatt agtattctca tttgggtttt    660
gattgactaa gtactgatcc aatcaaaaaa tctccccccc cctcttaatc tgttttcagt    720
ctggtggagg cattcatgaa tttgcagatt ctcagtttgg tatgtaaaat tttacccagt    780
gcatattcct ctttgctatt tgtattgatc cttacattgg aaattgctcc ttcgactaca    840
ggacatgttt ttgcctatgg agtgactaga tcagcagcaa taaccagcat gtctc          895
```

<210> SEQ ID NO 3
<211> LENGTH: 4919
<212> TYPE: DNA
<213> ORGANISM: Lolium rigidum

<400> SEQUENCE: 3

```
tccttttatg gacagaggtt gtacatatta ttgattgcat cagaaccttt tttcgtaatt      60
aagtaccaaa tattctgtac atggcttaag aaattgattg atttccccaa aatgtgttat     120
tttgtagtct gacgtgattg aacgactacg cctacaatat agtaaagacc ttcagaaggt     180
tgtagacatt gttttgtctc accaggtaag ttacttttgg cctaatgact tggtgcaatt     240
gatcactgaa gcaatcttcg tcactgatag tttgattttt ttctagggtg tgagaaacaa     300
aactaagctg atactcacgc tcatggagaa actggtttat ccaaatcctg ctgcctacag     360
ggatcagttg attcgctttg cttccctcaa ccataaaaga tattataagg tgacaatggc     420
gacctaaaag aaatggaagc ttttggataa tcttaatgtg atatcttagg ctaacgaatt     480
actttcattg taataatgta gttggcccctt aaagcgagtg aacttcttga acaaaccaag     540
ctcagtgaac tccgcacaag cattgcaagg aacctttcag ctctggagat gtttactgag     600
gaaagggcag gttctccctt gcaagccaga aaattggcca ttgatgagag catggtagat     660
ttagtcactg ccccactgcc agttgaagat gcacttattt ccttgtttga ttgtagtgat     720
caaactctcc agcagagagt gattgagaca tacatatctc gattataccca ggtattgcat     780
gagctatttt ttggatcttc tgcttttctg gatgcaaaca ctaaagtttc taatgaataa     840
gatgatcagt gtggaagtat ttgatttaga acttgtaaga catttactgc tctataagtg     900
ggctaacttg ccaatgatat tttcagcctc aacttgtgaa ggatagtatc cagctgaaat     960
atcaggattc tggtgttact gctttatggg aattcacccca agggcatcct gagaagagat    1020
tgggtgctat ggttatcctg aagtcgcttg aatctgtgtc gacagccatt ggagctgctc    1080
taaaggatac atcgcattat gcaagctctg cgggtaacac gatgcacatt gctttgttgg    1140
gtgatactca attgaataca gctgaagata ggtatgttca tgtgcatatt agtgctgatg    1200
agtttatttg gtgcaattct taaaataact taacctattt ctttcagtgg tgacaatgac    1260
cgagctcaag acaggataga ccaactttct ttgatactga acaggatac tgtcacggct    1320
gatctatgtg ctgctggtgt caaggttatt agttgcattg tccaaagaga tggagcactc    1380
atgcccatgc gccgtacctt cctcctgtca gatgagaagc ttggttatga ggaagagccg    1440
attctccggc atgtggagcc tccacttttct tcacttcttg agttggtatg caactcatca    1500
aactgactgc atgatgtttt gatacaactt aaaatgctat tattttgtta tctgctactt    1560
gtatttattt agcctgcttt ggatacagga taaactgaaa gtgaaaggat acaatgagat    1620
gaagtataca ccgtcacgtg atcggcagtg gcatatatac acacttagaa atactgaaaa    1680
ccccaaaatg ttgcacagag tattttttccg aactcttgtc agacaaccca gtgctggcaa    1740
caggtttacg tcaggccata tcagcgatgt tgaaggggga cgtgctgagg aatctctttc    1800
atttacgtct agcagcataa tgaaatcgct gacgactgct atagaagaac tggagcttca    1860
cgcgatcagg actggccatt ctcatatgta cttgtgcata ttgaaggagc aaaagcttct    1920
tgaccttatt cccgtttcag ggtaagcttg gacattgttc tttttacata acatatatgc    1980
cttgctcttg tgtctcacct tctcaatgag cttttcttcg tacacaggag cactgttgtg    2040
gatgttggtc aggatgaagc tactgcatgc tctcttttga aagaaatggc tctaaagata    2100
catgaacttg ttggtgcaag aatgcatcat ctttctgtat gtcagtggga agtgaaactt    2160
```

```
aagttggata gcgatggacc tgccagtggt agctggagag ttgtaacaac caatgtcact    2220
cctcacacct gcactgtaga tgtaagtttt attgccttgc atcttgtttt cctgtatgga    2280
actaatgaaa ctaaagtgaa cacatgatac ttatatacat agaactacca tcttacttag    2340
tttgttgtca tttccacctc atttagacat atggtctgaa gctcatggtg cttttaatgc    2400
ttttagatct accgggaggt cgaagataca gaatcacaga aactagtata ccactctgcc    2460
tcatcgtcat ctggtccttt gcatggtgtc gcactgagta attcgtatca gcctttgagc    2520
attattgatc taaaacgatg ctctgccagg gccaacagaa ctacatactg ctacgatttt    2580
ccattggtta gtatctatct ctacgtattg tgtattctgt tagcagatta ctattggtat    2640
tacatgtcct cctaaagctg ataagaactc aaaaatgtag gcatttgaaa ctgcagtgag    2700
gaagtcatgg tctaacattc ctagaaacaa ccaatgttat gttaaagcga cagagctggt    2760
gtttgctgac aagaatgggt cgtggggcac tcctataatt cctatgcagc gtgctgctgg    2820
gctcaatgac atcggtatgg tagcctggat cttggacatg tccactcccg aatttcccag    2880
tggcagacag attattgttg tcgcaaatga tattactttt agagctggat catttggccc    2940
aagggaagat gcattttttg aagctgttac caacctggct tgtgagagaa agcttcctct    3000
tatctatttg gctgcaaact ctggtgctcg gattggcatt gccgatgaag ttaaatctat    3060
cttccgtgtt aaatggattg atgatagcaa ccctgaacgt ggatttgatt acgtttatct    3120
gtctgaagaa gactatggcc gtattagctc ttctgttata gcgcacaaga cacagctaga    3180
tagtggcgaa ataaggtggg ttatcgattc tgttgtgggc aaggaggatg gactaggtgt    3240
ggagaacata catggaagtg ctgctattgc cagtgcgtat tctagggcat atgaggagac    3300
atttacactt acatttgtga ctggacgaac tgttggaata ggagcctatc ttgctcgact    3360
tggcatacgg tgcatacagc gtgaagatca gcccattatc ttaactgggt attctgccct    3420
gaacaagctt ctcgggcggg aagtgtacag ctctcacatg cagttgggtg gtcccaaaat    3480
catggcgact aatggtattg accatctgac tgttcgagat gaccttgaag gtgtttctaa    3540
tatattgagg tggctcagct atgttcctgc taacattggt ggacctcttc ctattacaaa    3600
acctttggat ccaatagaca gacctgttgc atacattcct gagaatacat gtgatcctcg    3660
tgcagccata agtggcattg atgacagcca agggaaatgg ctgggtggta tgtttgacaa    3720
agacagtttt gtggagacat ttggaggatg ggcgaagaca gtagttactg gcagagcaaa    3780
acttggaggg attcctgtgg gtgttatagc tgtggagaca cagaccatga tgcagctcgt    3840
cccagctgat ccaggacagc ctgattccca tgagcggtct gttcctcgtg ctgggcaagt    3900
ctggtttcca gattctgcta ccaagacagc gcaggcaatg ttggacttca accgtgaagg    3960
gttacctctg ttcatccttg ctaactggag aggcttctct ggtgggcaaa gagacctttt    4020
tgaaggaatt ctgcaggctg gatcaacaat tgttgagaac cttaggacat ataatcagcc    4080
tgcctttgta tatatcccca aggctgcaga gcttcgtgga ggtgcttggg tcgtgattga    4140
tagcaagata aatccagatc gcattgagtg ctatgctgag acaactgcaa aagggaatgt    4200
tctcgagcct caagggttga ttgagatcaa gttcaggtca gaggaacttc aagaatgcat    4260
gggtaggctt gatccagaat tgataaatct gaaagcacaa ctccagggag caaagcatga    4320
aaatggaagt ctatctgacg gagaatccat tcagaagagc atagaagctc gaaagaaaca    4380
gttgctgcct ttgtacactc aaatcgcgat acggtttgct gaattgcatg atacttccct    4440
cagaatgctt gctaaaggtg tgattaggaa aattgtagat tgggaagaat ctcggtcttt    4500
cttctacaag agattacggc ggaggatatc tgaggacgtt cttgcaaaag aaataagaag    4560
```
tgttattggt gtcgagtctt ctcacaaatc agcaatggag ttgattaaga agtggtactt 4620
ggcttctgag acagctggag gaagcactga atgggatgat gacgatgctt ttgttgcctg 4680
gagggagaac cctgaaaact acaaggagca tatcaaagag cttagggctc aaagggtatc 4740
tcaggtgctc tcagatgttg cagactccag ttcggattta caagccttgc cacagggtct 4800
ttccatgcta ctagataagg tacacatgct tacagtttta gctgcatcta ttttgtttgc 4860
aagttatttg ctgagggtga gtaaaatgtt gctatcttca tatacactta gtctgtaac 4919

<210> SEQ ID NO 4
<211> LENGTH: 9711
<212> TYPE: DNA
<213> ORGANISM: Lolium rigidum

<400> SEQUENCE: 4
tgtacagcat ggagacaggc gaatattatt tcctggagct taatccaaga ttgcaggttg 60
aacaccctgt gaccgaatgg attgctgaag taaacttacc tgcatctcaa gttgcagtcg 120
gaatgggcat acccctctac aacattccag gtagatcagt tttccaactt gatggttgat 180
gagattttct cttttcctcc atattactaa tcaataaaag gatcattgca gagatcagac 240
gcttttatgg aatggaacat gggggtggct accatgcttg gagggaaata tcagctgttg 300
caactaaatt tgatttggat aaagcacagt ctgtaaagcc aaaaggtcat tgtgtagcag 360
ttagagttac aagcgaggat ccagatgatg ggtttaagcc tactagtggg agagtggaag 420
agctaaactt taaaagtaaa cccaatgttt gggcctattt ctccgttaag gcaagtgtac 480
atccatgcat ttgattcttt tataccacat gtcatgtcac aacaaccgca acttataatt 540
accctttagt tttcatgctt cttttgtcga taaatttcct ggaaaagtta tatcctcttg 600
tgcggcaacc taatctgaat catcattttt cttactttca gtcgggagga gcaattcatg 660
aattttctga ttctcagttt ggtaagtaac acacataatt ttctcttttc ttctggtctc 720
tcataatgca ttgtcgtaaa cagtatcatt tttttgcagg tcatgttttt gcttttgggg 780
aatctagatc gttggcaata gccaatatgg tacttgggct aaaagagatc caaattcgtg 840
gagagatacg cactaatgtt gattacaccg tggatctctt gaaggtaaga taatcccata 900
gtaaatgttc tctggttaca atgtatatat ttttcctttt gtgtaatttg tgttcaaatt 960
ttccatatgt tcagactgca gaataccgag aaaataagat ccacactggt tggctagaca 1020
gcagaatagc tatgcgtgtt agagcagaga ggcccccatg gtacctttca gttgttggag 1080
gagctctata tgtatgattt ctttgtctgc agaactatga tttattggat gttatgactt 1140
atgagcttgc acactagata ccatttccat cctcaagtac tgtatttctt acattccagg 1200
aagcatcaag caggagttcg agcgttgtta gtgattatgt cggttatctc agcaaaggtc 1260
aaataccacc aaaggtatct tattttatga tgaatacact tactacttac attaatttct 1320
ataaataaaa aacttactaa ctgttttccc tttacagcac atctctcttg tcaatttgac 1380
tgtaacacta aatatagagg ggagtaaata tacggtaatt ctctggaatt ttctctttaa 1440
ccttatccat gccgttatcc cgttggtatc cttcagctac tcatgatcat cttcttcttt 1500
agattgagac agcaagaggt ggaccccgta gctacaaatt aagaattaat aaatcagaga 1560
tagaagcgga ggtacatccg ttgcgagatg gtgggctgtt aatgcaggta aacatattta 1620
ccacaggaca agtttatata tacaaatatg acttatcttt tgttctgttt ttgttttgga 1680
aggatctgat ctattttcat tttttaactc tccagttgga tggaaacagt catgtaattt 1740

-continued

```
acgcagagac agaggcggct ggtacgcgcc ttctaatcaa tgggagaaca tgcttattac    1800
aggtgaagat agcttctcct cttggtttct aactaaaagt tagctctgag ttattactag    1860
gcgaagagta ctttgtatgt caaaattatg atagatctag acaaaattta cgctactgtc    1920
tgacaagtta tgttgcattt ttattccctc aaaaaaatgt tgcatttttt atgatcatgt    1980
gaaggtcata gaaatggaa  acttctcttt gttgaaggat gagaataata agctagaatg    2040
aactgaacgg aagtttgggc aactgctgat gaagggtagc ctgtaattat attatagttt    2100
tttctgttgc tttgtttcat gcacctccta gttaatttgg aattaggtaa caaattaata    2160
acatagatat ttcatttccc tcgtcaagtg cttttttgg  catctgctat cactgtggtg    2220
ttgcatctgc cattctgcct aatagtcatg tcttggcaac cgcatatgat actcaatgtg    2280
agaatgacct aagatcttat tagagaaatc ctcactatgt gaatatttaa ctgaagggct    2340
actgggtcca ttgttattgt tgactgctaa ttgtatgaaa gtacagaaat taatcatgtc    2400
ctgtgaatga taaattacag aaagaacatg atccttcaaa gttgttggct gatacaccat    2460
gcaaacttct tcggtttctg gtcacggatg gttctcatgt ggttgctgat acaccatatg    2520
cggaagtgga ggtcatgaag atgtgcatgc ccctgttact accggcctct ggcgtcattc    2580
actttgtcat gcctgagggt caggccatga aggttccttt cttctccacc cccttgcttg    2640
catgtttgca gtgctatatg tacattctgg ttatagtact ttatgcttgt aatatgcatg    2700
catcttttac atactagctg aaatagctgt cattgtgcag gcaagtgacc tgatagcaag    2760
gttggatctg gatgacccat cttctgtgag gaaagctgaa ccatttcatg gcacttttcc    2820
aaaacttgga ccacctactg ctatttctgg caaagttcac caaaagtttg ctgcaagcat    2880
gaattctgcg ctcatgatcc ttgcaggata tgaacataat actgaacgag taagacagca    2940
aacttttctg actatcgttg ttcttccact tttgtttctc cttgtttatc ttgttgccat    3000
tgtcctcgtc tactgaggga aactaacctc ttagtgccaa attaactttc tttaatcaac    3060
aagttcctga ctatatcttc tctttcaggt tgtagatgat ttgctaaact tcctagacag    3120
ccctgagctc cctttctac  agtggcaaga gctcatgtcc gttttggcaa cccggctacc    3180
aaaggatctt aggaatgagg tgattatgtg ttcagttat tttttattta ttttacatgc     3240
catctttatt ttgatttttc ctgtctgcat atggaatgta taactaattt tcctgtattc    3300
agttggatgg taagtacaag gattatgagt tcaatgctga cttcgggaag agcaaggatt    3360
tccctgccaa gttgctaagg ggagtcattg aggtcagttt gagactgtta cttggcattc    3420 ttttctttt  tgttatcatg ttgtttcctt acaaaaccat cactgcaggc aaatcttgca    3480
tactgttctg agaaagacag agttgctaat gagaggcttg tagagccact tatgagcctt    3540
gtcaagtcat atgagggtgg aagagaaagc aatgctcgtg ttgttgtgaa gtctctgttt    3600
gaggagtatt tgtctgttga agaactgttc agtgatgaca ttcaggtacc cttcattatt    3660
acttggaatg ggtcgattaa tgcccactct ctcaccaaaa tgtgctaaac ttttgggcat    3720
cttttctttt ctattttcag tctgatgtga tagaacgcct acgacttcaa catgcaaaag    3780
acctcgagaa agtcgtatat attgtgttct cccaccaggt aatgtcttta ttgtgctacc    3840
tgtgttgatt tacttgttat gcaaaggcat ttcgtgctga cagttttgt tcctttgaag     3900 ggcgtgaaaa acaaaaatga attactacta cggcttatgg aacaaatggt ctatccaaat    3960
ccatctgctt acagggacca gttgattcgc ttctctgccc tgaaccatac agcatactct    4020
ccggtaaaat tgagtttcga cgatctgcat cttttgtattt tgcacatatg acagtctaga   4080
gaaataatgc aaatttatat aattgatgca gctcgcactt aaagcaagcc aacttctcga    4140
```

```
gcaaaccaaa ttgagtgaac tccgcgcaag cattgcaaga agcctttcag agctagagat    4200
gtttactgag gaaggagagc gggtttcaac acctaggaga aagatggcca tcaatgaaag    4260
aatggaagat ttagtatgtg ccccgcttgc agttgaagat gcccttgtgg ctttgtttga    4320
tcacagtgat cctactcttc agcggagagt agttgagaca tacatacgca gattgtatca    4380
ggtatcacat gatttatcaa ctaatctctt tcttcacaca gcttggactt aagacatat     4440 acgttggcta acccactatc atattccagc attatcttgt aagggcagt  gtccggatgc    4500 aatggcacag gtctggtcta attgctttat gggaattttc tgaagagcat attgaacaaa    4560
gaaacgggca atctaagaca cttctaaagc acaagtagaa ggatcccatt cgcaggcgat    4620
ggggtgtaat ggttgtaatc aagtctcttc agcttctgcc aactgcaatt gaagctgcat    4680
taaaggagac ttcacattat ggagcaggtg atgcaaatgt ctccaatggt agtcctataa    4740
gatctaataa tagcaatatg ctgcatattg ctttggttgg tatcagaaat cagatgagta    4800
ctcttcaaga caggttcgtt tacactctct actctttgcg attctttatt cttgatgaaa    4860
cgcaaaatat cataagagtg attctatgaa ctggttctga atttcatgaa attttagtt     4920 acaccctcca ctttgttttc tcttttttagt ggtgatgagg atcaagcaca agaaaggatc   4980
aacaaacttt ccaagatttt gagggatacc actataacat cacatctcaa tggtgctggt    5040
gttaggactg tcagctgcat tatccaaaga gatgaagggc gtcctccaat gcgccattcc    5100
ttccaatggt catttgacaa gctatattat gaggaggagc cgatgctccg ccatgtggaa    5160
cctcctctgt ccacattcct tgaattggta tgcagcttta gttttggctt atgttctctt    5220
caacaatacc agtacctcta ataacttatc tgtaaataca ggacaaagtg aaattagaag    5280
gttacagtga catgaaatac aatccatcgc gtgatcgcca gtggcacatt tacacactga    5340
acagtgaaga tccaaaatca aatgaccaaa ggatattcct tcgtacagtt gttagacagc    5400
caagtttaac caatggtttt gtttggaagt atcgacaatg aagtaggccg ttctcaggcc    5460
acatcgtcat tcacatctaa cagcatactt agatcattga ttgcagcgct agaagaaata    5520
gagttacatg ctcataataa ggccatgagt tcacgccatt cccacatgta tctgtgcatg    5580
ttgagagaac aacggttgtc tgatctaatt ccattttcaa ggtcagtcaa aatatactta    5640
tgttctcaat aaaatacact gcattaaatg tgctcataga tgctcacttg gtttgtgctt    5700
ctcatggtgt taggatgatg ggtgaagttg gtcaagatga ggagacagca tgcacacttt    5760
tgaagcatat ggttatgaat atatatgaac atgttggtgt caggatgcat cgcctttctg    5820
tgtgccaatg ggaagtgaag ctatggttag attgtgatgg tcaagccagt ggtgcttgga    5880
gagttgtcat taccaacata actgggcata cctgcactgt tgatgtaagt taccttagcg    5940
attgctgtat tgcactacta tgtgaacaac agcatctaca gttctgcata tcataaagaa    6000
tgctacctct gatggcccca tagatcatca tatatgatta tattttagtt agtaaataga    6060
acatggtcat catttccatc attcgtgtca tggacattct ctcaactgat gcctttaaag    6120
ggtctattaa agaccactta aaaataatta agtactattt tctctttatt ccaatactct    6180
tatatgctca cattcgtttg actttcagat ttaccgagaa gtagaagact ccaatacgca    6240
tcagattttc taccgctctg ccacacacac agctggtcct ttgcatggca ttgcattgca    6300
tgagccatac aaacgtttgg ctcctattga catgaaacgg tctgcggcta ggaaaaacga    6360
aactacatac tgctatgatt tcccattggt gagttggttg cgtttgttaa tttacttttt    6420
atctaacatt agttcgcatg attaacctga tcaactgagt ttgctaataa tactctgtcc    6480
```

```
acaggcattt gaaacagcat tgaagaaatt gtggaaatct agtgcttcac atcttgcaga    6540
aactaaccag cataatcagc agtatgctga agtgacagag cttttatttg ctgattcaac    6600
tggatcatgg ggtactcctt tggttccagt tgaacgttct ccatgtgtca atgatatcgg    6660
cattgttgct tggaagatga agctctccac gccagaattt ccaggcggcc gggagattat    6720
agttgttgca aatgacgtga cgtttaaagc tgggtctttt ggtcctagag aagggcatt     6780 cttcgatgct gctaccaagc ttgcttgtga gaggaaaatt cctctaatct acttgtcagc    6840
aactgctggt gctaggcttg gtgtggcaga ggaaataaag tcctgcttcc atgttggatg    6900
gtctgatgag cagagtcctg aacgtggttt tcactacatt tacctcactg aagaagacta    6960
ttcacgtcta agctcttcag ttatagccca tgaactgaaa ctagacagcg gagaaaccag    7020
atggattgtt gataccattg ttgggaaaga ggatggactt ggttgtgaga atctgcatgg    7080
tagtggtgcc attgccagtg cctttgctaa ggcatataga gagacctta ctctgacatt     7140 tgtgactgga aacgcagttg gaattgggc ttatcttgct cggctaggaa tgcggtgtat     7200
acagcgactt gatcaatcaa ttcttttaac tggttttct gccctgaaca aacttctggg     7260
gcgcgaggtt tatagctctc agatgcaact gggtggcccc aaaattatgg gtacaaatgg    7320
agtcgtccat ctgacagtgc cagatgatct tgaaggtgtt tctgctatct tgaaatggct    7380
cagctatgtt cctgcctatg ttggcggtcc tcttcctatt ctgaagcctc ttgatccacc    7440
agatagagct gtaacatatt cccagagaa ttcatgtgat gcccgtgcag ccatctgtgg     7500
gattcaggac actcaaggca gtggttggg tggtatgttt gacagagaaa gctttgtgga    7560
aacattagaa ggatgggcaa aaactgttat tactggaagg gcaaagctgg gtgggattcc    7620
agttggcgtc atagcagtgg aaacccagac aatgatgcaa gtaatccctg ctgaccctgg    7680
tcagcttgat tccgctgagc gtgtagtccc tcaagcagga caggtgtggt tcccagattc    7740
ggcctcaaaa acagcgcagg cattgctgga tttcaaccat gaagggctcc cattgttcat    7800
acttgctaac tggagaggct tctctggtgg gcaaagggat ctgtttgaag gaatccttca    7860
ggctggctct acaattgttg agaacctgag gacctacaag cagccagctt ttgtgtacat    7920
cccaaaggct ggagagctgc gtggaggtgc atgggttgtg gtggacagca agatcaatcc    7980
tgagcacatt gagatgtatg cggagaggac tgcaaaggga aatgtccttg agccagaagg    8040
gctgattgag attaaattta agccaaaaga agtggaagag agtatgataa ggcttgaccc    8100
tgagctggcc agccttgatt ctagactcaa agaaatgaag aaagcaaatg ctagcctgca    8160
ggaaacggag gccatcaaca ggagcatcaa caaccggata aagaagctga tgcccatcta    8220
tacgcaggtt gccacacggt tgctgaatt gcacgacacc tcttccagaa tgactgccaa    8280
aggtgtgatc agtaaggtgg ttgattggga ggagtctcgg agcttcttct acaggaggtt    8340
gcgaaggcgg gtcgcggagg attcccttgc ccaggaagtt aaagaagccg ctggtgagcc    8400
gatgcctcac agagcagcac tggagcgtat caagcagtgg tatctggcct ccaagggttc    8460
ggaaggagac ggtgagaagt ggaacgatga cgaggctttc ttcgcctgga agacgatgc     8520 caagaactac gagaaccatc ttcaggagtt gaaggctgaa agagtatcta gactgttctc    8580
ggatcttgct gaaagctcgg acgtgaaggc cttgcccaac ggtctttcgc gcctccttgg    8640
caaagtaagt tctgcttctt ctttcttat taataaaatt ggcccgaatt aagttttgct     8700
tccgcttttt tttttctgtc tctaaatacga tcatatcttt gatacgttgt gcagatgaat    8760
ccttcaaaga gggaacaagt tctcgatggc ctcaggcagc ttcttggtta atcgttggcc    8820
tctacgtatc cagcataaac gtgcacagac gacgacgaac ttgtctggcg agctatagga    8880
```

```
ggactcaatg gactagaaca cattgttttg tttgtttgca cataggcact tggtgacggt    8940
caagaccgta tattgttatc atacacacaa agaataggtt gttctctgct ctgctggata    9000
cttgtttgtg gttgtagatt gccagttctc cttttaagga agttattatg tgttgctcag    9060
tttgctggcg ccaaagcttc tttctctccc tcctggtgac catgtatgca taaattttct    9120
tatgctttgc caagtgaacc tcttgatatg acaacatacc caatgaacaa tgactaaaga    9180
aaatagaaat ttacatttta tgatagcata tacaattttc taacttttt aagggttaca    9240 aaaggcatga tccactttcc attttgtcac gaatcacccc aaaccccttt aggggttgca    9300
atcttgggat gaccaccagc tccggcgact ccctccatca ggatacgaaa caacaacaaa    9360
atcttataaa aaactgaact atccaactat tttgcagagc tccctttatc ctatctggat    9420
atttcatcac gctccaacca tcgaacatgt tgtcacattg catgctatat gctccttca    9480 ctgcaggaac cagctccatg atatgttctg gtaggggagc taatcctgcc agatggccaa    9540
gttttttttt gcgaaagttt cgccgatcaa ttaataatca tcaatagcag tacaaacaga    9600
tccaaaagta acaaaaatta caaataggtc tttgtagcga cgactagctg aaggcgcgcc    9660
accgtcctcg accctccatc atcggagcca gaaaaagctt attgtagtag a            9711

<210> SEQ ID NO 5
<211> LENGTH: 3281
<212> TYPE: DNA
<213> ORGANISM: Lolium rigidum

<400> SEQUENCE: 5
gttttgatca catggttcaa ctccgtcctt ttttttcttg ttataacaga taattgagga      60
aggaccagtt actgttgctc cacgtgagac agtgaaggag ctagagcaag cagcaaggag     120
gcttgctaag gctgtgggat atgttggtgc tgctactgtt gaatatctct acagcatgga     180
gactggtgaa tactattttc tggagcttaa tccacggttg caggtttgtt cttttgaaca     240
ctctacagga cttctatttt ttttggcagt catttacatg gttaaatggt ctacattcag     300
gttgagcacc cagtcactga gtggatagct gaagtaaatt tgcctgcagc tcaagttgca     360
gttggaatgg gtataccct ttggcaggtt ccaggtaata ataaaatcat cgtaatatct     420
ttagtttctg gcccatgtta tttcgttgtc taattatctc cttacacaga gatcagacgt     480
ttctacggaa tggacaatgg aggtggctat gacatttgga ggaaaacagc agctcttgct     540
actccattca actttgatga agtagattct caatggccga agggtcattg tgttgcagtt     600
aggataacta gtgagaatcc agatgatgga ttcaagccta ctggtggaaa agtaaaggtg     660
ggttttccta atgtgatatc tatgtttcaa gcacactagg ttagtaaac tcatctggtt     720 ttgattttc gtatatttca ggagataagt tttaaagta agccgaatgt ctggggatat     780
ttctcagtta aggtaagcta agctgttcat agctctattg cagtgccatg ttattttgag     840
ttctgcagaa aattggtctg caagattttt tatttgaatt agtattctca ttttggtttt     900
gattgactaa gtactgatcc aatcaaaaaa tcttttccta ccctcttcat ctgttttcag     960
tctggtggag gcattcatga atttgcagat tctcagttcg gtatgtatac ccagtgcata    1020
ttcctctttg ctatttgtat tgatccttac attgtaaatt gctccttcga ttacaggaca    1080 tgttttttgcc tatggagtga ctagatcagc agcaataacc agcatgtctc ttgcattaaa    1140
agagattcaa atccgcggag aaattcattc aaacgttgat tacacggttg atctcttgaa    1200
tgtaagtaat aatagcaact tgttgaaccc tacttttga ttttacatct ggctttcctt    1260
```

-continued

```
caaaataatc ccttcttgtg gtttctgcat ctttaattca ggccccagac ttcagagaaa      1320
acacgatcca taccggctgg ctggatacca gaatagctat gcgtgttcaa gctgagaggc      1380
ctccctggta catttcagtg gttggaggag ctctatatgt aagccaatga aactagttaa      1440
tgttacagca acttttggca agccaattgt gaaaaacaca actagtgttg aaatgattgt      1500
tttgtgttgt agaaaacaat aaccaccaac gcggagactg tttctgaata tgtcagctac      1560
ctcatcaagg gtcagattcc accaaaggta gtgtcttaat tggcgtaaac tctgtatatt      1620
acttgaaggt gaacgttgtt gaccattatt tttgtgcagc atatatccct tgtgcattca      1680
actatttctt tgaatataga ggaaatcaaa tatacagtaa gtgcgacatt ccttaagaaa      1740
gattcagtta taatgcaatg atagctacca ttgatgctca tctacaccat gtcacagatt      1800
gagattgtga ggagtggaca gggtagctac agattgagaa tgaatggatc gcttattgaa      1860
gcaaatgtac aaacattatg tgatggtggc cttctaatgc aggtatttat acttgctcat      1920
aaatataatc taaggttgaa aagtactgcc gaaagagttc tgattctttg gttgtaattt      1980
ctccagctgg atggaaacag ccatgttatt tatgctgaag aagaagcagg tggtacacgg      2040
cttcttattg atggaaagac atgcttgtta caggtaagga tattctcttt gtttgttcct      2100
ttatctataa tcttggtgtt tgatgattgg atttcgtatt cctatttgtg acttgttact      2160
gacttactgc agtcaccttc tgatcattag cactttagtt tgaaaagaaa agataaatcg      2220
gtattatgaa ctaatgaatg gtacaacatg atgtttttca aggtcacacc aggaccaggt      2280
gatattaaat tttaccgaca gcaggttttg tgatgtataa gggcaagtta catagctgca      2340
atatagctaa gagggctcca gctctttat attgcttctt ctatttctca aatctaggtt      2400
ttccagcaac actagtattt ttaacaagca ctaatgatca taataaggca caaaaagagt      2460
tagaaggtgt cctttaacac tatgtcatgt aaccctttaaa agcttgtgat cagatcattt      2520
tagtgataca aaagaacaat tgaatacttt atgattttt tcttacacaa aaactttatg      2580
attcctgatc acactgcatt gtatcctcaa ctaaataaat gacaaatcat tctgcagaat      2640
gatcatgatc cgtcaaggtt attagctgaa acaccctgca aacttcttcg tttcttggtt      2700
gctgatggtc tcatgtcga tgctgatgta ccatatgcgg aagttgaggt tatgaagatg      2760
tgcatgcccc tcttgtcacc tgctgctggt gtcattaatg ttttgttgtc tgagggccag      2820
gcgatgcagg ttatattact gcactttttt gttgcttatg ctgttaataa cgattgcatg      2880
tgaagcatct gaatttaata ttttttttcag gctggtgatc ttatagcgag acttgatctc      2940 gatgacccctt ctgctgtgaa gagagccgaa ccattcgaag gatcttttcc agaaattagc      3000
cttcctattg ctgcttctgg ccaagttcac aaaaaatgtg ctgcaagttt gaatgctgct      3060
cgaatggtcc ttgcaggata tgagcatgcg atcaacaaag taaactttaa daccccctgca      3120 gtaactatat ttcgaatata ttgtctcata tttcctgttt ttctcaaata ccattatgta      3180
ttattattat tatgaagttc tggattattc tgagttcctc attgaccttt ttctgccttt      3240
cgctacaaaa tggtttctaa tatatagaag ttattgatgc t                         3281
```

<210> SEQ ID NO 6
<211> LENGTH: 1356
<212> TYPE: DNA
<213> ORGANISM: Lolium rigidum

<400> SEQUENCE: 6

```
ccacttgtgt ttccgattca tactaggcaa tactatgtca catgtattat ggtgaccaca        60
gtaatgactt tcctcgtttc ttttctagtg ggtctggaga ccacatgggc tcctaccaaa       120
```

-continued

| | |
|---|---|
| tgaatgggat actgaatgaa tcacataacg ggagacacgc ttcgctgtct aaggttgttg | 180 |
| aattttgtat ggcattgggt ggaaagacac caattcacag tgtattagtc gccaacaatg | 240 |
| gaatggcagc agctaagttc atgcggagtg tccggatatg ggctaatgat acatttgggt | 300 |
| cagagaaggc gattcagttg atagctatgg caactccgga agacatgaga ataaatgcag | 360 |
| agcatattag aattgctgat cagtttgttg aagtacctgg tggaacaaac aataacaact | 420 |
| atgcaaatgt ccaactcata gtggaggtca gtactgttca cccctttgat gtgcaattta | 480 |
| tgcacaagct cctctttgtt cttttagcat gaaatttgac atggcaactt tgcttttgca | 540 |
| gatagcagag agaacaggtg tttcggccgt ttggcctggt tggggccatg catctgagaa | 600 |
| tcctgaactt ccagatgcac tcactgcaaa aggaattgtt tttctcgggc caccagcatc | 660 |
| atcaatgaac gcattaggtg acaaggttgg ttcagctctc attgctcagg cagcaggggt | 720 |
| tccgactctt gcttggagtg atcacatgt aagagttaca ttctctcgga taatccatcg | 780 |
| ccttatattt gtggtggatg cattttataa tgacacttta ttataggtgg aaattccatt | 840 |
| agaactttgc ttggactcga tacctgagga gatgtatagg aaagcttgtg ttactaccgc | 900 |
| ggatgaagca gttgcaagtt gtcagatgat tggttatcct gccatgatca aggcatcctg | 960 |
| gggtggtggt ggtaaaggga ttagaaaggt acattattca tttggttgca ctgtactcaa | 1020 |
| gagattctgt tattatgtgt gcagtgttag acctaacctt tttaacatat taactcgata | 1080 |
| tctcttgcag gttaataatg atgatgaggt taaagcactg tttaagcaag tacagggtga | 1140 |
| agttcctggc tccccaatat ttatcatgag acttgcatct caggttagac ttgtcttgaa | 1200 |
| tttctatttt ccaaggatgc tgtttctggg tggtatattg tacacctgga agcttcattt | 1260 |
| gctcttcctt gcaggctaga attgtatttt gtaatctgta ctcatatggt aattttcagt | 1320 |
| ttaatctctt ctcccttttcc ttttgtagag tcgaca | 1356 |

<210> SEQ ID NO 7
<211> LENGTH: 1418
<212> TYPE: DNA
<213> ORGANISM: Lolium rigidum

<400> SEQUENCE: 7

| | |
|---|---|
| tttatatacc tgctgtaatt tcatatccgt gcacttcatt ttgttcgttc gcgaaaagtt | 60 |
| tgatgaggac tttcatggtc tggctaaaca tagtcgtgtt tttgtcgata tcgttttagc | 120 |
| atcaagttca gaaacaacaa attccttcct catgcagaat taaagttatt cgtgcaacgg | 180 |
| ttcgctaaca gaatcgacaa tgctaacgat tcttttttgtc ccttgctttt ccagcgctga | 240 |
| aggctagagg gtggcgacaa tggtggcgga accggaccag acaaacggga cgcccaacag | 300 |
| gatgtccagt aacaggcacc tgtcctcgcc gtccgtggtc gacgagttct gcaaggcgct | 360 |
| cgggggcgat tcgcccatcc acagcgtgct ggtcgccaac aatggaatgg ccgcggtcaa | 420 |
| gttcatgcgc agcatccgca cctgggcccct cgagacgttt ggaccgaga aggccattct | 480 |
| cctggtggcc atggcaactc cggaggacct caggataaac gcggagcaca taaggatcgc | 540 |
| cgaccagttc ttggaagtcc ctggcggaac aaacaataac aattatgcga atgtgcagct | 600 |
| cattgtggag gttagcacaa tgaccattct cccggtcctt tttactagct tgttgattta | 660 |
| gcctatccat gttctttgtg ctggatattt gactagttac ttaatgtttc taccttcact | 720 |
| gtcacagata gcagagagaa ctcgggtttc tgccggtttgg cctggctggg gccatgcttc | 780 |
| tgagaacccg gaacttccag acgcgctcaa ggagaaggga atcatttttc ttgggccacc | 840 |

-continued

```
atcagccgcg atggctgcac ttggtgataa gattggttct tctcttattg cgcaagcagc    900
aggagttccg actcttccat ggagtggatc acatgtatac gttcttctat ttctgtatag    960
ttttgatcct cttttttta tcggctgcta tgttgcttaa aattaaatcc aaatcaactc   1020
taggtgaaag ttccgcaaga aacctgccac ttgatacctg aggacatcta taagaaagct   1080
tgtgttacaa ctacagagga agcggtggct agttgtcagg tggtggggta tcctgcaatg   1140
atcaaggcat catggggtgg tggtggtaaa ggaataagga aggttggtct tctttttagt   1200
tcaactctac cgcaattata tggaaagtct ctgctcacaa acgatacatg gaaatgtcca   1260
ctgtccatgc aaaatgaagc taaggttttc ggtaaatatt gtagaataaa cgaaagatga   1320
ttttgatgtc atccaaatgg tttttatagg tccacaatga tgatgaggtg agagccttgt   1380
ttaagcaagt gcaaggagaa gtccccggat cacctata                          1418
```

<210> SEQ ID NO 8
<211> LENGTH: 572
<212> TYPE: DNA
<213> ORGANISM: Lolium rigidum

<400> SEQUENCE: 8

```
agttcttgtt tggtttagcc agttcttgtt tattgatctt ttgtaccttg tgttctgcct     60
caacggattc taatttttat gcaatcagtt ggagcgtaaa tacgatgaat ttaagttgaa    120
tattgaccat atgaagacca aggatttccc caccgagatg cttagagaga caatcaaggt    180
cagtttttgg tttctgatgg catcccggtc taagttgtac tattttttgt aacaagtttt    240
cttttaggaa aatcttgcat atgtttctga gaatgaaatg gcgacaattg aaaggcttgt    300
tgagcctctg atgagcctac tgaagtcata tgagggtggg ctagaaagcc atgcccactt    360
tattgtcaag tccctttcg aggagtatct cttggttgag gaactattca gtgatggcat    420
tcaggtattc tttcatttca aaactgagaa aatctactag attcattttt acgggtcatt    480
ccttttaaac atatatgaac tgatgttata tactccatcc gtccataaaa ggatgtcgga    540
ggtttgtcca aattcggatg tatctgtaca ct                                 572
```

<210> SEQ ID NO 9
<211> LENGTH: 735
<212> TYPE: DNA
<213> ORGANISM: Lolium rigidum

<400> SEQUENCE: 9

```
ttttactcct gtcagtattc agcgagtgct tctgtactga tatatcttat atcatgtcta     60
aaagcttgcc ttttctgtta tttctctgta gagccgacat ctagaggttc agctgctctg    120
tgacaaacac ggcaatgtag cagcactgca cagtcgagac tgtagtgttc aaagaaggca    180
ccaaaaggtt agaaattctc ctgaaaaatt atgttgtcca atatcagttt ccttggagct    240
aatacatgcc gaaacattgt atactgagta ctggtagaag ttctgtagct ttagggattg    300
gcaaagtgct aaactctgca gaagctatac aaaatttgag ttcaatattt ttttaaatgg    360
aaacatttat ttctgtcaag tactgtattg taagtagttg aaccttgaac gttatgtttt    420
gaactcaaga actaactttt tctctatagt gatacgtgtt gcaattatta ttgaaaagtc    480
taatttactg cattactaat tagtccttcc gatccaaatt aattgacaca gatatgccta    540
catttgcatg tatctacaca ctaaaactcg tctatatcat gtgtatctag acaaatccgc    600
gtcaattgtt tggaaccaag ggaccatttc ataaccacaa gttaactagt ccaactgtgc    660
aagacaaaaa aaaaatataa taataatatg agctgacaag ccttgccaaa actgtgcttc    720
```

```
ttacattttt gtgaa                                                    735
```

<210> SEQ ID NO 10
<211> LENGTH: 1887
<212> TYPE: DNA
<213> ORGANISM: Lolium rigidum

<400> SEQUENCE: 10

```
ctacaagaga ttacggcgga ggatatctga ggacgttctt gcaaaagaaa taagaagtgt     60
aattggtgtc gagtcttctc acaaatcagc aatggagttg attaagaagt ggtacttggc    120
ttctgagaca gctggaggaa gcactgaatg ggatgatgac gatgcttttg tagcctggag    180
ggagaaccct gaaaactaca aggagcatat cagggagctt agggctcaaa gggtatctca    240
ggagctctca gatgatgcag actccagatc ggatttacaa gccttgccac agggtctttc    300
catgctacta gataaggtac acatgcttac agttttagct gcatctattt tgtttgcaag    360
ttatttgctg agggtgagta aaatgttgct tagtctgtaa ccaaacaatg caaatatctt    420
tttcatgtag tatgacccca ataatgtct gacacacttt tctttggaca cttgtagat     480
ggatccctct aggagagcag agtttattga ggaggtcaag aaggtcctca atgatcaaa    540
tgataccacc acatccaaca cagaatgtgc atgatatctg tttctcttga agtacatata    600
tagaaggata caaggcggct gtaaccgatc gtagccaatc tgggccaacc attattattg    660
tgaacttgtt ggtggtcttg cttttgggac cccctccggc tggttgagga gtgtaagtgg    720
gatgtgttag ttctgctgcc acatgatttg agagaatagg ggcagcgggt tacctaagaa    780
cactggtgat cttctctctgg tgctttagtt ctgtgatgtt actatggtct gttcgttgct    840
gtaactctag tcttgaagtg tgattcagat gtccattcaa ttttgaactt gaataatgtg    900
ttttgtaggc ttatgtgtac ctgtacgtgg aataaatgtc cgttgagcta gcattcaaca    960
tgtaaatctg ctcggattgt aatgtatgtt agaattctga tcttgtatgt ctttccactt   1020
gatagcatgt cgcctggctt ctggcaacat acacgctatc agaatggtta gcttgcgtta   1080
ggtgttactg aagctcataa ctgtcgccca tcctgtttct caccggcttt acttaatatc   1140
tagcccatgt ttgtcagcaa agggtttact ctgctgaaag tttcaagttc tcaagaaata   1200
ttttgggttg gatctatcgt aagagttgta agttggcgtg agctaatgca gtttgcgaca   1260
gggataaggt gtttacgttt ctatgtcggg agcaattctc tctgacatcc tcaaattgac   1320
gagcagaggg gtgaacttat gtttacagat atgtaaatga tatgtgctac tgatgacact   1380
cctatgtaat gacatgaact atttaccccct ggactgctct ccccgtttct cctctcgtat   1440
cactgtgcac acaaaatttt cttctgttga ctctggtaac taattcacat tccccacatt   1500
cccctggact tgttactatg ctagggctgc cctgcgccat tttggtattt gttcattctt   1560
cagctagtgc agttccgatt gttttattgc atgcatgtgg ttgtttcgtt ggggtaaaat   1620
gctcgcacag tgtcacaact atgggtagaa ttttcccctca aaagaaaaac tatagctaga   1680
attttgagtt cagaactata cacgtatgca tggattagtg gcaccatcgt acttctggta   1740
gttgatgaac agggacccaa ctcccggtta actaacgcat agaaacgaaa ccatccgaca   1800
tagttcttac atatacacag ttaactaatg cagtgtaaca accaagtggc ttcacatagg   1860
aacacccaca tgcaagaaaa tagatta                                       1887
```

<210> SEQ ID NO 11
<211> LENGTH: 402
<212> TYPE: DNA

<213> ORGANISM: Lolium rigidum

<400> SEQUENCE: 11

```
gctcatcacc aaccacctct tccgccacga gcaggggag gccttcgcgg cgtccgggta        60
cgcccgcgcg tccggccgcg tcggggtctg cgtcgccacc tccggcccgg gggccaccaa      120
cctcgtctcc gcgctcgccg acgccctcct cgactccatc cccatggtgg ccatcacggg      180
gcaggtcccg cgccgcatga tcggcacgga cgccttccag gagacgccca tcgtcgaggt      240
caccgctcc atcaccaagc acaactacct cgtcctcgac gtcgaggaca tccccgcgt       300
catccaggaa gccttcttcc tcgcctcctc tggccgcccg ggcccggtgc tcgtcgacat      360
ccccaaggac attcagcagc agatggctgt gcccgtctgg ga                         402
```

<210> SEQ ID NO 12
<211> LENGTH: 280
<212> TYPE: DNA
<213> ORGANISM: Lolium rigidum

<400> SEQUENCE: 12

```
ctctggcggt gccggcgcta tgggctactg catttcggcg gccttgggcg ccaaaactgg       60
tcgtccggag gctatcgtct ggggtatcga cggcgacgtg tgtttccaac tggaccaacg      120
ggaactcgct actgttgccc ttaatagtgc tcctgccaag aatagtgctc ctgtcaagat      180
cgccatcatt gacaccgttg ctctacttcg tgccaaggcc gttgacgcct cactggaatc      240
gctgacgatc gaggccaccg ggagacgtga aagctggat                             280
```

<210> SEQ ID NO 13
<211> LENGTH: 337
<212> TYPE: DNA
<213> ORGANISM: Lolium rigidum

<400> SEQUENCE: 13

```
cccttcgcc ttcgccctcg cccgccctc ctgccaccgc gctccgtcca tgggcccat         60
ccgagccccg caagggcgcc gacatcctcg tcgaggccct cgagcgctgc ggcatcagcg      120
acgtcttcgc ctacccgggc ggcgcctcaa tggagatcca ccaggcgctc acgcgctcgc      180
cgctcatcac caaccacctc ttccgccacg agcaggggga ggccttcgcg cgtccgggt      240
acgcccgcgc gtccggccgc gtcggggtct gcgtcgccac tccggcccg ggggccacca      300
acctcgtctc cgcgctcgcc gacgccctcc tcgactc                              337
```

<210> SEQ ID NO 14
<211> LENGTH: 795
<212> TYPE: DNA
<213> ORGANISM: Lolium rigidum

<400> SEQUENCE: 14

```
ctcctcgact ccatcccgat ggtggccatc acggggcagg tccgcgccg catgatcggc        60
acggacgcct tccaggagac gcccatcgtc gaggtcaccc gctccatcac caagcacaac      120
tacctcgtcc tcgacgtcga ggacatcccc gcgtcatcc aggaggcctt cttcctcgcc      180
tcctctggcc gccgggccc ggtgctcgtc gacatcccca aggacatcca gcagcagatg      240
gctgtgcccg tctgggacgc gcccatgagt ctgccaggct acattgcccg cctgcctaag      300
ccgccggcta ctgaattgct tgagcaggtc ctgcgtttgg ttggtgaggc gagacgccca      360
attctctatg ttggcggtgg ctgctctgca tccgagagg agctgcgccg ctttgttgag      420
ctcactggga tcccagttac aactacccctc atgggtcttg gcaacttccc cagcgacgac      480
```

-continued

```
ccgctgtctc tgcgtatgct tgggatgcat ggcactgtct acgcaaacta cgccgtagat    540
aaggctgacc tgttgcttgc gtttggcgtg aggtttgatg atcgcgtgac tgggaaaatc    600
gaggcttttg cgagcaggtc caagattgtg cacattgaca ttgatccagc tgagattggc    660
aagaacaagc agccgcatgt ctccatttgt gcagatgtca agctcgcttt gcagggcctg    720
aatgctctgc taactgggag caaagcacac aagagtttcg attttggttc ctggcatgag    780
gagttggagc agcag                                                      795
```

<210> SEQ ID NO 15
<211> LENGTH: 878
<212> TYPE: DNA
<213> ORGANISM: Lolium rigidum

<400> SEQUENCE: 15

```
cgctttgcag ggcctgaatg ctctgctaac tgggagcaaa gcacaaaaga gtttcgattt     60
tgcctcgtgg catgaggagt tggagcagca gaaaagggag tttcctctgg gatacaaaac    120
tttcggggag gccatcccac cgcaatatgc tatccaggta ctggatgagc tcaccaaagg    180
cgaggccatc attgccactg gtgttgggca gcaccagatg tgggcggctc agtattacac    240
ctacaagcgc ccacggcagt ggctgtcttc ggctggtctg gggcaatgg gctttgggtt    300 gccagctgca gctggcgccg ctgtggctaa cccaggtgtc acagttgttg acattgatgg    360
ggatggtagc ttcctcatga acattcagga gttagcgctg attcgcattg agaacctccc    420
agttaaggtg atgatattga acaaccaaca tcttggaatg gtggtgcagt gggaggacag    480
gttttacaag gccaatcggg cgcatacata ccttgggaac ccagaaaatg agagtgagat    540
atatccagat tttgtgacca ttgctaaagg gttcaatgtt cctgcagttc gggtgacaaa    600
gaggagtgaa gtccgtgcag caatcaagaa gatgcttgag actcctgggc catacttgtt    660
ggatatcatc gtccctcacc aggagcatgt gctgcctatg atccctagcg gtggtgcttt    720
taaggacatt atcatggaag gtgatggcag gattgcgtat taatcgggac ttctgcaaga    780
gctccaccta caagacctac aagtgcaata tgcctaatca gcatgatgct ggtgtatgtt    840
atatccatgt gttcgctaat ttgcttgttt gatgagct                            878
```

<210> SEQ ID NO 16
<211> LENGTH: 273
<212> TYPE: DNA
<213> ORGANISM: Lolium rigidum

<400> SEQUENCE: 16

```
gccccgagct gattttctga cggggaattt ggtctggttg cagggtgcgg cgccacacga     60
tctcggtctt cgtcggggac gagagcggca tgatcaaccg gatcgccggg gtgttcgcca    120
ggaggggcta caacatcgag tcgctcgccg tggggctcaa caaggacaag gcgctattca    180
ccatcgtcgt ctccgggacg gacagggtgc tcaagcaggt catcgagcag ctcaacaagc    240
tcgtcaacgt cctgaacgtg agttttccgc cgc                                 273
```

<210> SEQ ID NO 17
<211> LENGTH: 5106
<212> TYPE: DNA
<213> ORGANISM: Lolium rigidum

<400> SEQUENCE: 17

```
cgccggtgcc accccgcccc aggggctcgt aagtttctcg ccccgctgag gactagtttt     60
```

```
ctcatgccct tccgatcttc aagtcgaggt acagtaacat tttatttcca atggggtata    120
taggactgta aagcgccaca cggtatcggt gttcgttggg gacgagagcg ggatgatcaa    180
ccgaattgcc ggggttttcg ccaggagagg gtacaacatc gagtcgttgg ccgttgggct    240
gaacaaggac aaggcgctgt tcacgatagt agtgtccgga acagagaaag tactccaaca    300
ggttgtggag cagctctaca aacttgttaa tgttatacag gtcagtaggt tcctccaatg    360
ccacttgaat tacaagatca ttgctaactg atacgtagta atgctccatc aattgaatca    420
ttcgtttcag ttttcatgct tatttcagtc gtcagatcct ctgatattcg tagctttgta    480
tattgatgga acaggttgag gatttgtcaa aggagccaca agttgagaga gagctcatgc    540
tgataaagct gaatgtagag ccagagcagc gcctcgaggt aaagtttgta tgtgcgtagg    600
atgctcgatt atatgcttca gctggactgg atgtgagggt aaaacgttgg tactcttgc     660 ttatttctcc actgggacat gcaggtgatg gggttggttg acattttcag agcaaaagtg    720
gttgatcttt cagaccggac actgactatt gaggtaaaat ccatggtgtg ttgtatcttg    780
ctgatcgctt acatcgtcac ttgtatgctt ttattaaacc aaagtatgct ctctgttttt    840
tttacacatt ccaaaggtaa ctggagatcc tggaaaaatg gtagctgtac agaggaacct    900
gagcaaattt gggatcaaag aagttgccag aactggcaag gttatacttc ttgtgtaaat    960
attaggacct catgttcttg actagattta atgggcctta ttaatatata gatagctttg    1020
cggcgtgaga aaatgggaca agcggccccc ttttggaggt tctctgtaga atcatatcct    1080
gatctggaag tgaaaaggcc ttcagaatct accctaagca ctgcatcaaa gacaaccaat    1140
ggcgagtctg aagaatcttt gcaggtagga catggtaatt ctcatcattc atatagtttt    1200
tcatgtatcc attttttctt caggattgca acaagattgt ttctttattt tgacctggtt    1260
tattgtgtta tttgagtttt tatcatgcat tcacagaaat caacacatgt aatagaatta    1320
tctctctttc attcaatatt ataaattcta ttatttactg atttggtctt aatgaagatt    1380
tcttattgtt tattttgtta aggtatgtcc taattctttt ttccgttctg agtttagaag    1440
ggaaagtaat atacacttag ataatgtacc aatattgatg cttgcaagtg caccttatat    1500
atatgcaaag cgtattgatg caattagctt gatttgccat ttatgcatat gttttgtaga    1560
caagcaggag ttgatgcatc atttaaattg ttttatgat tcataatatc agcattatgc     1620
tggcaattac tagttttttt ttttaaagca gtaagaagtt ggctgtctta tagcataact    1680
agatctcaca aacaatgtaa acatgaccat gactagttcg ttttgtgtga acaagtttat    1740
tgcaaatacc ttttctata attcacacat agttgtggtt tgcagttcga tgactgattt     1800
atatgttctt atgttttatt actagggcga tgtttatcca gtggaaactt atgaaagctt    1860
ctcgataaat caaattcttg atgctcattg gggtgtgatg actgacagtg atgtaagttc    1920
ttggattctt ctatcactag agcttctgtg ttgctgaaag ttaatggcaa gagtcccagt    1980
gcctaatgga gcataaatta catttgtttg cactaaatta caattgcaac ttaaatacct    2040
atttcgaaaa taactggaat actttgcttt cttcagccta cagggttttg ttcacatact    2100
ttgtcgatcc ttgttaatga tttccctgga gttctcaatg ttgtaactgg tatctttcc     2160 cgaaggggct acaatattca ggtttgtttt ccacctgtag atatcttatg ttccctcaat    2220
tagatcactc caggttacag tgttgcagtt cattgctaac aggttgtatc cattactttg    2280
acagagtctt gctgttggtc cagctgaaaa aataggcact tctcgcatca ctactgtcgt    2340
tcctgggagt gatgagtcta tcgccaagct aatacatcaa ctttacaagc ttatcgacgt    2400
ttatgaggtg aacttattaa tgttgtggtt tgcaggattg ttgttccaca tgtaaggtta    2460
```

```
gctcacaatc gccttgattt ttcaggtcca agatcttaca catttaccgt ttactgctag    2520
agagttaatg atcataaagg tcgctgggaa cacttcagct cgcagggcta tcctggatat    2580
tgctgaggat gttttcgggg ccaaaacggt tgacgtatca gaccacacaa taaccccttca   2640 ggtaataatt actttgttct tttggacgca actgctggat ttaggacata tatatgcttt    2700
tgctggtagg ataaatcaat gagtttgatt taagcttgtt ttacctttca tttaggcatg    2760
ttgattgtag acagtagaaa cctgaatatt tagcaaatat agccttaact tggaacaata    2820
tctgtgttgt tgtcaattag ctcataaatt tcagcataga tcaagtgaaa tcatgctatt    2880
ttgaagtatg gtatttatcc aagttgttta aagtagaaac atgaagattc atcaaatgaa    2940
gtctttactt tatctctttg agcattatta taagtgttgc tgtcagccag ctgatgaaat    3000
ttcagtatag atcaaactga aatgctgcta ttttgaatat atagggtatt tatccatttg    3060
aaaaatgcgg gagtttctag attttttcaa tgtcctgtat tataggttac agcgccgaat    3120
catatgtaca tgattactta tctaattttt gagtacttat caagaactaa tttatagcct    3180
cttttaaaag gaaatttgga tgattttaat cctttaaatt ttcatatgtg gctgtttggt    3240
atgcatttat aatccatatg attttttctt gaggattcaa ttgcagtata tttcatagaa    3300
acatttccac taattcaaac cttgtggaat gatatctttg ttttttcctgt ggcgtaatca    3360 aacacccttt ggtcgagatt cttgttgtat ttaaccctac tattcaggaa gccatgaaat    3420
tcctccttca ccttttccctg cattttttg aatcttgcaa gtcaaagagt cccttgagga    3480
caatgtattt agtggcatca atgttttta ataagtagcc atcttaatgg catgcagctc     3540
actggagacc ttcataaaat ggtcgcacta caaaggatgc ttgagccgta cggcatctgt    3600
gaggtttgta ttgaaggttc actttgcaaa tgcacaatag tgtcgataat tcgtgattgc    3660
agagtactta ttccaatgta aatcgtagtt tagcaactac aatatttcaa attattagtt    3720
acagtggatc ctttaccatc cttggccata tgcattctgc agatcgcacg aactggcagg    3780
gttgcgctga gccgtgagtc aggagtcgat tccaagtacc tccgtgggta ttctcttcct    3840
ctataacatg gcagttggcg agacttcacg ccaatcagtt tgcagattgc cattcttctg    3900
ataccggatc tcctaaactc cgaatgtgca atggttttttc gtttgtttgg agcatacagc   3960
aaaaaggcac cggtcacatt taggttaact agatttacac catcttctaa agttttttt    4020 atagatacta cagagaaatg gaattgagat ttttaatccc atgtgaatac catgttttgg    4080
gcttccttct tcgaagtagg aaacagaatt atatctgaaa ttatgcttcc aagaagattt    4140
taactttctg aatcatagtt aaatttggcg cgagcactct aaattcattt tttttactcc    4200
aagtagtttt aagagtgtat aatgaacgtt taggcttcct acttacgaat actgcaacta    4260
gcagcgatca ttagtcttct gcaaagttat agatcaaatt taagaccact ccttcaaact    4320
agttatttat gtgcccaatg tcgcattagc actcaaatgc aacttagatt cttccgtgcg    4380
aacaaatcac agataacatg ccatttcttg gcggaaggag tcatgctagt ttttgttgct    4440
gttgttgttg ttgcgacaac tcatgctaga ttgctagttg catctggcat gctagaaatt    4500
cagaactgat gcattgtttg acagcgtcga ttcatttgtg agaatataaa cgatcattgt    4560
cttgcatgga caaatgatgt ggattattat gttttgcatg cacatatgat gtggatagta    4620
cataacgcta aaaggtgatg gaattaaaaa ggtgatatcc gcgtctcgac tgaattggac    4680
ttggggcatt tgaaacgaaa gaaacccaa cgaattggct caagggtatc caaaacgatc      4740
gaaatacaat gttcctctta cgtcgataaa aatatactgt atcatccgat ggtaattaaa    4800
```

```
aaacgatcga actaattatt ccatccgttc cagataaact gaagctttgc cctaatttaa      4860
aaaaatgatc acgtctaggg aaaaagtgta cttcctccat ctaacaaaag acgtctcaac      4920
gtttgtttta gtttggatgc atcttcaaac tcttgtaagt tttgatcacg tttattgaaa      4980
aaattgccac agatacatct aaatttagat aaagtcaaga taattttttgt acaatgaagg     5040 aagtaatttta tttaaaaaaa tatacgacct ctgctcataa aagaatgtca caaatttatc     5100
taaatt                                                                 5106
```

<210> SEQ ID NO 18
<211> LENGTH: 1493
<212> TYPE: DNA
<213> ORGANISM: Lolium rigidum

<400> SEQUENCE: 18

```
taacacagct actgtgacga acctaagctg attttcatta tcatgcctgg tctgtttatc       60
tctagacctg ccatggagat gaattttaat agtttgaagt gatcttttcc gttttatcct      120
aaaaggtcat atgtcgtggg ctttgcagat ttcttttctt attgtatgtt cttatgtgat      180
tgtaataaga gtactagtat aattttttctt tgatatttat tctatttcaa tccaataaaa     240
ttgcaggttg aagatctatc taaggaacct caggttgaaa gagagctcat gcttataaaa      300
ctcaatgcca aaccagatca acgtgctgcc gtaagatatg ctgttgatct gtatttccac      360
gatatcaaaa cattgtttag tcattgaatt agtggtattg gtacttctat tttaagggt       420 tgtaacagga ctcttgcctc atggttgaca ggtcatgctt gtagctaatg tattcagagc      480
gaaggttgtt gatatttccg agaattctct aaccctagag gtaaagactt gacttcaaac      540
agtattataa ggactagggt gttccgtgtc tatgctggat taaattttct tgatgctgat      600
atggcaaatg ctgcaggtca ctggagatcc tggaaagatt gttgcggcac aaaggagcct      660
aagcaaattt gggatcgaag aaatttgtag aacgggaaaa gtatttttct ggaccatttg      720
ctacgtacat gcatgggcac atttcttcat tgtctaattc ttctatctca atgttcttag      780
attgctttga ttcgtgaaaa aattggaaca gctgcccgtt tctgggatt ttctactgct       840 tcttacccag acctcataga agcatcaccc agaaaccctc ttcttacttc tccgaaaaag      900
acggttaatg gcagttttga tcagccatcc agtgctgggg tatgtttcca tgaatataag      960
accaactaca tatttattgc atattccttc ttgttctgct tcaactgttc taaaagcgag     1020
gcaacgctta ggctataggt gccacagtct gcctagtacc tttttaaaacg ctgttactcc    1080 ctccgatcca aaatacttgt ccaaaaatgg gagaatctac acactaaaac acgtctagat     1140
acatgcattt ttgggcaagt attttggacc ggatagagta tttgtagttt taaatacttg     1200
gtaatctaca ccacgccgaa aagatgcccc ttttacatga atgacacaat caataatttg     1260
atgtgcaata acagagaaga tctcacgaac tgcgtatctt taatagctat agtgtaaaca     1320
aaggaaactg aacttctctg tcaccagtaa acatcccagt gcagccgtag cactgtaagt     1380
gaatttatag gtgaaggtaa tttgtatacc tggccttagc aaagcaaaaa aaaaattgct     1440
catacagtga aactggggag atacctgcgt gctgacaaaa ctaaaaacca cac            1493
```

<210> SEQ ID NO 19
<211> LENGTH: 473
<212> TYPE: DNA
<213> ORGANISM: Lolium rigidum

<400> SEQUENCE: 19

```
gcgtcacgcc ggtgccgccc cgccccaggg gctcgtaagt ttcataccccc gctgaacact      60
```

```
agttttctta tgcccttctg atcttcaagt cgaagtaact ttttattatt tccaatgtgc    120
tatgtaggac tgtaaagcgc cacacggtat cagtgtttgt cggggacgag agcgggatga    180
tcaaccgaat tgccggggtc ttcgcgagga gagggtacaa catcgagtcg ttggccgtcg    240
ggctgaacaa ggacaaggcg ctgttcacga tagtggtgtc cggaacagag aaagtactcc    300
aacaggttgt ggagcagctc tacaaacttg ttaatgtcat acaggtcagt atgttcctcc    360
aatatgccac ttgaattaca agatcattgc taactgatgc ttagtaatgc gccatcagtt    420
gaatcattcg tttcagtttc agtgcttatt tcagtcgtca gatcctctga tat           473
```

<210> SEQ ID NO 20
<211> LENGTH: 1324
<212> TYPE: DNA
<213> ORGANISM: Lolium rigidum

<400> SEQUENCE: 20

```
gtatgagtga ctagcccacc accaatggat agcaccataa gaagccgacc tttgacgatg     60
aaaatgtgca cacaaaagat aaccaaggtt tggtcttgca cttggttatt cccaaacaat    120
gcttggtgaa taacacaaat gtcagggcca gtgatgcaac ccatgtgccc ccttccaaaa    180
ttggattagc gcaaaaaata tgccaaatag agaataagag ggttttggat agtagaaact    240
ttgtttcgaa tatactttct atcctggtgg actaagattt tctcctaggt gctagcagcg    300
tctactagca atgcattaga aacagttgaa ccgacttccc catctttaga aaagccaaaa    360
atgtcacaaa actcatgaag tgatgtaggt tggtattccc catcgatagg gaattcgacc    420
caataattac cagaggcttc gcggatgttg tccttgaagg tggccatgaa ctcgtgggtg    480
atgctggctc aggtgtccct gcgtagcctc gagaacttcc caagtaccgc gcggttggcc    540
atcgtgttga agtctgaaag gatagagatg gtaacctgag ggttgtgaat gggttctaca    600 atttttttaaa attctcttgc aattttagga tttgcagaaa tgtaatcaaa cgtgtcaaat    660
atttgctagt catttagctt gaaaccaaat ggaagccaat gggtttgcca aaattttgga    720
ggtaccgtgg cctacaatcc aaacagccac aagttgccaa tattttggct atgccctata    780
tttggccata ccaatatttt ggccgggtta gagtgggcgc aatctaaata gcgccttggt    840
tatccgtggg agaaaaatac tagagcaggg atagttgttg tgacttgtga cctcggtatt    900
cgacgccgaa gttgagcttc atgactatag gcgggcccc gatgaactta gggaagtccg    960
acgacgtctt accggcccga tgccaccaaa gctgaccttc tcgccaccac caccgctcat   1020
ctttctttcg gtgtgtgtct tgttcgtgtg cgggtctcgc gctaggatcc gacgactcca   1080
agaaaggaac aagactttgt tgggcttgcg gagttaatat tcagtatttt cgggcctcct   1140
cacgccgcgc cctcgccgcc cccatcaggt gctccgcggt gtccccttcg ccctcgccct   1200
cgcccgcccc tcccgccacc gcgctccgtc catgggcccc atccgagccc cgcaagggcg   1260
ccgacatcct cgtcgaggcc ctcgagcgct cggcatcag cgacgtcttc gcctacccgg   1320
gcgg                                                                1324
```

<210> SEQ ID NO 21
<211> LENGTH: 912
<212> TYPE: DNA
<213> ORGANISM: Lolium rigidum

<400> SEQUENCE: 21

```
cgctagggat cataggcagc agcattcagg ccctgcaaag cgagcttgac atctgcacaa     60
```

-continued

| | |
|---|---|
| atggagacat gcggctgctt gttcttgcca atctcagcct acatacctcg ctctgctacc | 120 |
| agctgcagct ggcgccgctg tggctaaccc aggtgtcaca gttgttgaca ttgatgggga | 180 |
| tggtagcttc ctcatgaaca ttcaggagtt agcgctgagg cgataagtcg tgtcttaccc | 240 |
| accgctaggg atcataggca gcacatgctc ctggtgaggg acgatgatat ccaggtgtca | 300 |
| cagttgttga cattgatggg gatggtagct tcctcatgaa cattcaggag ttggcgctga | 360 |
| ttcgcattga gaacctccca gttaaggtga tgatattgaa caaccaacat cttggaatgg | 420 |
| tggtgcagtg ggaggacagg ttttacaagg ccaatcgggc gcatacatac cttgggaacc | 480 |
| cagaaaatga gagtgagata tatccagatt ttgtgaccat tgctaaaggg ttcaatgttc | 540 |
| ctgcagttcg ggtgacaaag aggagtgaag tccgtgcagc aatcaagaag atgcttgaga | 600 |
| ctcctgggcc atacttgttg gatatcatcg tccctcacca ggagcatgtg ctgcctatga | 660 |
| tccctagcgg tggtgctttt aaggacatta tcatggaagg tgatggcagg attgcgtatt | 720 |
| aatcgaaact tctgcaggag ctccacctac aagacctaca agtgcaatat gcctgatcag | 780 |
| catgatgctg gtgtatgtta tatccatgtg ttcgctaatt tgcttgtttg atgagcatgg | 840 |
| tttggtaatc ttacctagct ctgaaccttc taggttttct agtctgttct tttccgtagg | 900 |
| catatgctgt ca | 912 |

<210> SEQ ID NO 22
<211> LENGTH: 5106
<212> TYPE: DNA
<213> ORGANISM: Lolium rigidum

<400> SEQUENCE: 22

| | |
|---|---|
| cgccggtgcc accccgcccc aggggctcgt aagtttctcg ccccgctgag gactagtttt | 60 |
| ctcatgccct tccgatcttc aagtcgaggt acagtaacat tttatttcca atggggtata | 120 |
| taggactgta aagcgccaca cggtatcggt gttcgttggg gacgagagcg ggatgatcaa | 180 |
| ccgaattgcc ggggttttcg ccaggagagg gtacaacatc gagtcgttgg ccgttgggct | 240 |
| gaacaaggac aaggcgctgt tcacgatagt agtgtccgga acagagaaag tactccaaca | 300 |
| ggttgtggag cagctctaca aacttgttaa tgttatacag gtcagtaggt tcctccaatg | 360 |
| ccacttgaat tacaagatca ttgctaactg atacgtagta atgctccatc aattgaatca | 420 |
| ttcgttttcag ttttcatgct tatttcagtc gtcagatcct ctgatattcg tagctttgta | 480 |
| tattgatgga acaggttgag gatttgtcaa aggagccaca agttgagaga gagctcatgc | 540 |
| tgataaagct gaatgtagag ccagagcagc gcctcgaggt aaagtttgta tgtgcgtagg | 600 |
| atgctcgatt atatgcttca gctggactgg atgtgagggt aaaacgttgg tactctttgc | 660 |
| ttatttctcc actgggacat gcaggtgatg gggttggttg acatttttcag agcaaaagtg | 720 |
| gttgatcttt cagaccggac actgactatt gaggtaaaat ccatggtgtg ttgtatcttg | 780 |
| ctgatcgctt acatcgtcac ttgtatgctt ttattaaacc aaagtatgct ctctgttttt | 840 |
| tttacacatt ccaaaggtaa ctggagatcc tggaaaaatg gtagctgtac agaggaacct | 900 |
| gagcaaattt gggatcaaag aagttgccag aactggcaag gttatacttc ttgtgtaaat | 960 |
| attaggacct catgttcttg actagattta atgggcctta ttaatatata gatagctttg | 1020 |
| cggcgtgaga aaatgggaca agcggccccc ttttggaggt tctctgtaga atcatatcct | 1080 |
| gatctggaag tgaaaaggcc ttcagaatct accctaagca ctgcatcaaa gacaaccaat | 1140 |
| ggcgagtctg aagaatcttt gcaggtagga catggtaatt ctcatcattc atatagtttt | 1200 |
| tcatgtatcc atttttttctt caggattgca acaagattgt ttctttattt tgacctggtt | 1260 |

```
tattgtgtta tttgagttttt tatcatgcat tcacagaaat caacacatgt aatagaatta    1320
tctctctttc attcaatatt ataaattcta ttatttactg atttggtctt aatgaagatt    1380
tcttattgtt tattttgtta aggtatgtcc taattctttt ttccgttctg agtttagaag    1440
ggaaagtaat atacacttag ataatgtacc aatattgatg cttgcaagtg caccttatat    1500
atatgcaaag cgtattgatg caattagctt gatttgccat ttatgcatat gttttgtaga    1560
caagcaggag ttgatgcatc atttaaattg tttttatgat tcataatatc agcattatgc    1620
tggcaattac tagtttttttt ttttaaagca gtaagaagtt ggctgtctta tagcataact    1680
agatctcaca aacaatgtaa acatgaccat gactagttcg ttttgtgtga acaagtttat    1740
tgcaaatacc ttttttctata attcacacat agttgtggtt tgcagttcga tgactgattt    1800
atatgttctt atgttttatt actagggcga tgtttatcca gtggaaactt atgaaagctt    1860
ctcgataaat caaattcttg atgctcattg gggtgtgatg actgacagtg atgtaagttc    1920
ttggattctt ctatcactag agcttctgtg ttgctgaaag ttaatggcaa gagtcccagt    1980
gcctaatgga gcataaatta catttgtttg cactaaatta caattgcaac ttaaatacct    2040
atttcgaaaa taactggaat actttgctttt cttcagccta cagggttttg ttcacatact    2100
ttgtcgatcc ttgttaatga tttccctgga gttctcaatg ttgtaactgg tatcttttcc    2160
cgaaggggct acaatattca ggtttgtttt ccacctgtag atatcttatg ttccctcaat    2220
tagatcactc caggttacag tgttgcagtt cattgctaac aggttgtatc cattactttg    2280
acagagtctt gctgttggtc cagctgaaaa aataggcact tctcgcatca ctactgtcgt    2340
tcctgggagt gatgagtcta tcgccaagct aatacatcaa ctttacaagc ttatcgacgt    2400
ttatgaggtg aacttattaa tgttgtggtt tgcaggattg ttgttccaca tgtaaggtta    2460
gctcacaatc gccttgattt ttcaggtcca agatcttaca catttaccgt ttactgctag    2520
agagttaatg atcataaagg tcgctgggaa cacttcagct cgcagggcta tcctggatat    2580
tgctgaggat gtttttcgggg ccaaaacggt tgacgtatca gaccacacaa taacccttca    2640
ggtaataatt actttgttct tttggacgca actgctggat ttaggacata tatatgcttt    2700
tgctggtagg ataaatcaat gagtttgatt taagcttgtt ttaccttcca tttaggcatg    2760
ttgattgtag acagtagaaa cctgaatatt tagcaaatat agccttaact tggaacaata    2820
tctgtgttgt tgtcaattag ctcataaatt tcagcataga tcaagtgaaa tcatgctatt    2880
ttgaagtatg gtatttatcc aagttgttta aagtagaaac atgaagattc atcaaatgaa    2940
gtctttactt tatctctttg agcattatta taagtgttgc tgtcagccag ctgatgaaat    3000
ttcagtatag atcaaactga aatgctgcta ttttgaatat atagggtatt tatccatttg    3060
aaaaatgcgg gagtttctag atttttttcaa tgtcctgtat tataggttac agcgccgaat    3120
catatgtaca tgattactta tctaattttt gagtacttat caagaactaa tttatagcct    3180
cttttaaaag gaaatttgga tgattttaat cctttaaatt ttcatatgtg ctgtttggt    3240 atgcatttat aatccatatg atttttttctt gaggattcaa ttgcagtata tttcatagaa    3300
acatttccac taattcaaac cttgtggaat gatatctttg ttttttcctgt ggcgtaatca    3360 aacacccttt ggtcgagatt cttgttgtat ttaaccctac tattcaggaa gccatgaaat    3420
tcctccttca ccttttccctg catttttttg aatcttgcaa gtcaaagagt cccttgagga    3480
caatgtattt agtggcatca atgttttttta ataagtagcc atcttaatgg catgcagctc    3540
actggagacc ttcataaaat ggtcgcacta caaaggatgc ttgagccgta cggcatctgt    3600
```

```
gaggtttgta ttgaaggttc actttgcaaa tgcacaatag tgtcgataat tcgtgattgc    3660
agagtactta ttccaatgta atcgtagtt tagcaactac aatatttcaa attattagtt    3720
acagtggatc ctttaccatc cttggccata tgcattctgc agatcgcacg aactggcagg    3780
gttgcgctga gccgtgagtc aggagtcgat tccaagtacc tccgtgggta ttctcttcct    3840
ctataacatg gcagttggcg agacttcacg ccaatcagtt tgcagattgc cattcttctg    3900
ataccggatc tcctaaactc cgaatgtgca atggttttc gtttgtttgg agcatacagc    3960
aaaaaggcac cggtcacatt taggttaact agatttacac catcttctaa agttttttt    4020 atagatacta cagagaaatg gaattgagat ttttaatccc atgtgaatac catgttttgg    4080
gcttccttct tcgaagtagg aaacagaatt atatctgaaa ttatgcttcc aagaagattt    4140
taactttctg aatcatagtt aaatttggcg cgagcactct aaattcattt tttttactcc    4200
aagtagtttt aagagtgtat aatgaacgtt taggcttcct acttacgaat actgcaacta    4260
gcagcgatca ttagtcttct gcaaagttat agatcaaatt taagaccact ccttcaaact    4320
agttatttat gtgcccaatg tcgcattagc actcaaatgc aacttagatt cttccgtgcg    4380
aacaaatcac agataacatg ccatttcttg gcggaaggag tcatgctagt ttttgttgct    4440
gttgttgttg ttgcgacaac tcatgctaga ttgctagttg catctggcat gctagaaatt    4500
cagaactgat gcattgtttg acagcgtcga ttcatttgtg agaatataaa cgatcattgt    4560
cttgcatgga caaatgatgt ggattattat gttttgcatg cacatatgat gtggatagta    4620
cataacgcta aaggtgatg gaattaaaaa ggtgatatcc gcgtctcgac tgaattggac    4680 ttgggggcatt tgaaacgaaa gaaaacccaa cgaattggct caagggtatc caaaacgatc    4740
gaaatacaat gttcctctta cgtcgataaa aatatactgt atcatccgat ggtaattaaa    4800
aaacgatcga actaattatt ccatccgttc cagataaact gaagctttgc cctaatttaa    4860
aaaaatgatc acgtctaggg aaaaagtgta cttcctccat ctaacaaaag acgtctcaac    4920 gtttgttta gtttggatgc atcttcaaac tcttgtaagt tttgatcacg tttattgaaa    4980
aaattgccac agatacatct aaatttagat aaagtcaaga taattttgt acaatgaagg    5040 aagtaattta tttaaaaaaa tatacgacct ctgctcataa aagaatgtca caatttatc    5100 taaatt                                                             5106
```

<210> SEQ ID NO 23
<211> LENGTH: 1423
<212> TYPE: DNA
<213> ORGANISM: Lolium rigidum

<400> SEQUENCE: 23

```
ctgtggtttc attatcacca catagatgac aatatccaaa gtcatgtatc actgtatcac      60
tttaccataa cacctcagca ttcaaatttt tgttggcagt tcttatattg gtcatagcta     120
cattactagt aataaatgaa ctttctggcc tggacagtac tgacaatttt aaaagcagaa     180
ctgaagcaac ataccctctga gtaaaatgtt cccagacttc cattgcacat acgagatact     240
gtattacagt atatctgttg ctgctgattc ttataatatg tggttgtatt gacttttgaa     300
ttttgtgttc agggtgatgt gtatcctgtg gaaccttatg aaagcatgtc catgaaccaa     360
gtacttgatg cccattgggg tgttcttgac gatgaagatg taagctaaaa gatttccatt     420
tctgcaaaag aaacatcatt tgtttagtta aactaaatga cctataaact gtatctaaaa     480
ctgttgtggc tgcagtgtgt tctcattttg tgtcttcatt atctttgcaa ccagtcagtg     540
taaacagatg cctctatcgt aatagtgcca gcttctaagc taatgatgcc tttgtttggt     600
```

```
acagtcaagc ggactttgct cacatacccc ttccatcctt gtgaatgatt gtcctggtgt    660
cctcaacatt ataacaggcg tctttgctcg cagggctac agtatacagg ttttttttcaa    720
```
(best-effort; see image)

```
acagtcaagc ggactttgct cacatacccct ttccatcctt gtgaatgatt gtcctggtgt   660
cctcaacatt ataacaggcg tctttgctcg cagggctac  agtatacagg ttttttttcaa   720
aactttattg gttatgtagt gccaagctat ttttcaatga aaccatacta tttcccagag    780
tcttgctgtt ggccgagctg aaaggaagg  catttcacgt attacaacag ttgttcccgg    840
aactgatgaa tccattgaga agttagttca gcagctttac aagcttatcg atgtacttaa    900
ggtaaatggc atgcaatttc ttagggcaat cattgacgat ataaaatatg ttgtgtaatg    960
caaaacatgt gactgtccca ggttgaggac ttgactcact tacctttttgc cgaaagagaa   1020
ctgatgctta tcaaggtatc tgggaacacc gctgctcgga gggagatact agatatcggt   1080
caaatcttcc gggcagaatg tctggatctt tctgatcaca cagttacgtt aatggtgagc   1140
ttctggcttt ataaggtgtt gttttttatt gtcgatttta cacagtagat ttaccaactc    1200
tcaagtgtgc tacggtgagt gttaaagcag cttgggtaca aacttaagat caagagaacc   1260
atctcatgta taaacaaaaa gttagaggcc ttgctttcag aaactatttt tttgtatgat   1320
ggtctttaga attcatatgt gcccagtgaa ttatcttgtg attttactgt tttgttttga   1380
acagttgttc tggtagtatc aggatgaatt gcttacataa aaa                      1423

<210> SEQ ID NO 24
<211> LENGTH: 418
<212> TYPE: DNA
<213> ORGANISM: Lolium rigidum

<400> SEQUENCE: 24
agggtagaca agtttattgc agaaaccttt tctattatcc acatagtttt ttttacagtt     60
tcatgattga tttatatatt cttatgttct tattactagg gtgatgttta cccagtggaa    120
tcttatgaaa gcttctcaat gaatcaaatt cttgatgctc attggggtgt gatgactgac    180
actgatgtaa gttcttgcat tcttctttca caagagctgc tgtgttgctg aaagttaatg    240
gcaagagtcc caaaatctag tggagcataa attattaatt tatgtgcact aaattgcaat    300
ttaaatgccc atttcgaaaa taactggcac acttttcttt cttcagccta caggattttg    360
ttcacatact ttgtcaatcc ttgtgaatga tttccctgga gttctcaatg ttgtaacg     418

<210> SEQ ID NO 25
<211> LENGTH: 5106
<212> TYPE: DNA
<213> ORGANISM: Lolium rigidum

<400> SEQUENCE: 25

```
atgctcgatt atatgcttca gctggactgg atgtgagggt aaaacgttgg tactctttgc    660
ttatttctcc actgggacat gcaggtgatg gggttggttg acattttcag agcaaaagtg    720
gttgatcttt cagaccggac actgactatt gaggtaaaat ccatggtgtg ttgtatcttg    780
ctgatcgctt acatcgtcac ttgtatgctt ttattaaacc aaagtatgct ctctgttttt    840
tttacacatt ccaaaggtaa ctggagatcc tggaaaaatg gtagctgtac agaggaacct    900
gagcaaattt gggatcaaag aagttgccag aactggcaag gttatacttc ttgtgtaaat    960
attaggacct catgttcttg actagattta atgggcctta ttaatatata gatagctttg   1020
cggcgtgaga aaatgggaca gcggccccc ttttggaggt tctctgtaga atcatatcct    1080
gatctggaag tgaaaaggcc ttcagaatct acccctaagca ctgcatcaaa gacaaccaat   1140
ggcgagtctg aagaatcttt gcaggtagga catggtaatt ctcatcattc atatagtttt   1200
tcatgtatcc atttttctt caggattgca acaagattgt ttctttattt tgacctggtt    1260
tattgtgtta tttgagtttt tatcatgcat tcacagaaat caacacatgt aatagaatta   1320
tctctctttc attcaatatt ataaattcta ttatttactg atttggtctt aatgaagatt   1380
tcttattgtt tattttgtta aggtatgtcc taattctttt ttccgttctg agtttagaag   1440
ggaaagtaat atacacttag ataatgtacc aatattgatg cttgcaagtg caccttatat   1500
atatgcaaag cgtattgatg caattagctt gatttgccat ttatgcatat gttttgtaga   1560
caagcaggag ttgatgcatc atttaaattg tttttatgat tcataatatc agcattatgc   1620
tggcaattac tagtttttt ttttaaagca gtaagaagtt ggctgtctta tagcataact    1680
agatctcaca acaatgtaa acatgaccat gactagttcg ttttgtgtga acaagtttat    1740
tgcaaatacc tttttctata attcacacat agttgtggtt tgcagttcga tgactgattt   1800
atatgttctt atgtttatt actagggcga tgtttatcca gtggaaactt atgaaagctt    1860
ctcgataaat caaattcttg atgctcattg gggtgtgatg actgacagtg atgtaagttc   1920
ttggattctt ctatcactag agcttctgtg ttgctgaaag ttaatggcaa gagtcccagt   1980
gcctaatgga gcataaatta catttgtttg cactaaatta caattgcaac ttaaatacct   2040
atttcgaaaa taactggaat actttgcttt cttcagccta cagggttttg ttcacatact   2100
ttgtcgatcc ttgttaatga tttccctgga gttctcaatg ttgtaactgg tatcttttcc   2160
cgaagggct acaatattca ggtttgtttt ccacctgtag atatcttatg ttccctcaat    2220
tagatcactc caggttacag tgttgcagtt cattgctaac aggttgtatc cattactttg   2280
acagagtctt gctgttggtc cagctgaaaa aataggcact tctcgcatca ctactgtcgt   2340
tcctgggagt gatgagtcta tcgccaagct aatacatcaa ctttacaagc ttatcgacgt   2400
ttatgaggtg aacttattaa tgttgtggtt tgcaggattg ttgttccaca tgtaaggtta   2460
gctcacaatc gccttgattt tcaggtcca agatcttaca catttaccgt ttactgctag    2520
agagttaatg atcataaagg tcgctgggaa cacttcagct cgcagggcta tcctggatat   2580
tgctgaggat gttttcgggg ccaaaacggt tgacgtatca gaccacacaa taacccttca   2640
ggtaataatt actttgttct tttggacgca actgctggat ttaggacata tatatgcttt   2700
tgctggtagg ataaatcaat gagtttgatt taagcttgtt ttacctttca tttaggcatg   2760
ttgattgtag acagtagaaa cctgaatatt tagcaaatat agccttaact tggaacaata   2820
tctgtgttgt tgtcaattag ctcataaatt tcagcataga tcaagtgaaa tcatgctatt   2880
ttgaagtatg gtatttatcc aagttgttta aagtagaaac atgaagattc atcaaatgaa   2940
gtctttactt tatctctttg agcattatta taagtgttgc tgtcagccag ctgatgaaat   3000
```

```
ttcagtatag atcaaactga aatgctgcta ttttgaatat ataggg tatt tatccatttg   3060
aaaaatgcgg gagtttctag attttttcaa tgtcctgtat tataggttac agcgccgaat   3120
catatgtaca tgattactta tctaatttt gagtacttat caagaactaa tttatagcct    3180
cttttaaaag gaaatttgga tgattttaat cctttaaatt ttcatatgtg ctgtttggt    3240
atgcatttat aatccatatg atttttctt gaggattcaa ttgcagtata tttcatagaa    3300
acatttccac taattcaaac cttgtggaat gatatctttg ttttcctgt ggcgtaatca    3360
aacacccttt ggtcgagatt cttgttgtat ttaaccctac tattcaggaa gccatgaaat   3420
tcctccttca ccttccctg cattttttg aatcttgcaa gtcaaagagt cccttgagga    3480
caatgtattt agtggcatca atgttttta ataagtagcc atcttaatgg catgcagctc    3540
actggagacc ttcataaaat ggtcgcacta caaaggatgc ttgagccgta cggcatctgt   3600
gaggtttgta ttgaaggttc actttgcaaa tgcacaatag tgtcgataat cgtgattgc    3660
agagtactta ttccaatgta aatcgtagtt tagcaactac aatatttcaa attattagtt   3720
acagtggatc ctttaccatc cttggccata tgcattctgc agatcgcacg aactggcagg   3780
gttgcgctga gccgtgagtc aggagtcgat tccaagtacc tccgtgggta ttctcttcct   3840
ctataacatg gcagttggcg agacttcacg ccaatcagtt tgcagattgc cattcttctg   3900
ataccggatc tcctaaactc cgaatgtgca atggttttc gttgtttgg agcatacagc     3960
aaaaaggcac cggtcacatt taggttaact agatttacac catcttctaa gttttttt    4020
atagatacta cagagaaatg gaattgagat ttttaatccc atgtgaatac catgttttgg   4080
gcttccttct tcgaagtagg aaacagaatt atatctgaaa ttatgcttcc aagaagattt   4140
taactttctg aatcatagtt aaatttggcg cgagcactct aaattcattt tttttactcc   4200
aagtagtttt aagagtgtat aatgaacgtt taggcttcct acttacgaat actgcaacta   4260
gcagcgatca ttagtcttct gcaaagttat agatcaaatt taagaccact ccttcaaact   4320
agttatttat gtgcccaatg tcgcattagc actcaaatgc aacttagatt cttccgtgcg   4380
aacaaatcac agataacatg ccatttcttg gcggaaggag tcatgctagt ttttgttgct   4440
gttgttgttg ttgcgacaac tcatgctaga ttgctagttg catctggcat gctagaaatt   4500
cagaactgat gcattgtttg acagcgtcga ttcatttgtg agaatataaa cgatcattgt   4560
cttgcatgga caaatgatgt ggattattat gttttgcatg cacatatgat gtggatagta   4620
cataacgcta aaaggtgatg aattaaaaa ggtgatatcc gcgtctcgac tgaattggac    4680
ttggggcatt tgaaacgaaa gaaaacccaa cgaattggct caagggtatc caaaacgatc   4740
gaaatacaat gttcctctta cgtcgataaa aatatactgt atcatccgat ggtaattaaa   4800
aaacgatcga actaattatt ccatccgttc cagataaact gaagctttgc cctaatttaa   4860
aaaaatgatc acgtctaggg aaaagtgta cttcctccat ctaacaaaag acgtctcaac    4920
gtttgtttta gtttggatgc atcttcaaac tcttgtaagt tttgatcacg tttattgaaa   4980
aaattgccac agatacatct aaatttagat aaagtcaaga taattttgt acaatgaagg    5040
aagtaatta tttaaaaaaa tatacgacct ctgctcataa aagaatgtca caatttatc     5100
taaatt                                                              5106

<210> SEQ ID NO 26
<211> LENGTH: 1423
<212> TYPE: DNA
<213> ORGANISM: Lolium rigidum
```

<400> SEQUENCE: 26

```
ctgtggtttc attatcacca catagatgac aatatccaaa gtcatgtatc actgtatcac      60
tttaccataa cacctcagca ttcaaatttt tgttggcagt tcttatattg gtcatagcta     120
cattactagt aataaatgaa cttctggcc tggacagtac tgacaatttt aaaagcagaa      180
ctgaagcaac atacctctga gtaaaatgtt cccagacttc cattgcacat acgagatact    240
gtattacagt atatctgttg ctgctgattc ttataatatg tggttgtatt gacttttgaa     300
ttttgtgttc agggtgatgt gtatcctgtg gaaccttatg aaagcatgtc catgaaccaa    360
gtacttgatg cccattgggg tgttcttgac gatgaagatg taagctaaaa gatttccatt    420
tctgcaaaag aaacatcatt tgtttagtta aactaaatga cctataaact gtatctaaaa    480
ctgttgtggc tgcagtgtgt tctcattttg tgtcttcatt atctttgcaa ccagtcagtg    540
taaacagatg cctctatcgt aatagtgcca gcttctaagc taatgatgcc tttgtttggt   600
acagtcaagc ggactttgct cacatacct ttccatcctt gtgaatgatt gtcctggtgt     660
cctcaacatt ataacaggcg tctttgctcg caggggctac agtatacagg ttttttcaa    720
aactttattg gttatgtagt gccaagctat ttttcaatga aaccatacta tttcccagag    780
tcttgctgtt ggccgagctg aaaaggaagg catttcacgt attacaacag ttgttcccgg   840
aactgatgaa tccattgaga agttagttca gcagctttac aagcttatcg atgtacttaa    900
ggtaaatggc atgcaatttc ttagggcaat cattgacgat ataaaatatg ttgtgtaatg    960
caaaacatgt gactgtccca ggttgaggac ttgactcact tacctttgc cgaaagagaa    1020
ctgatgctta tcaaggtatc tgggaacacc gctgctcgga gggagatact agatatcggt    1080
caaatcttcc gggcagaatg tctggatctt tctgatcaca cagttacgtt aatggtgagc    1140
ttctggcttt ataaggtgtt gtttttatt gtcgatttta cacagtagat ttaccaactc     1200
tcaagtgtgc tacggtgagt gttaaagcag cttgggtaca aacttaagat caagagaacc    1260
atctcatgta taaacaaaaa gttagaggcc ttgctttcag aaactatttt tttgtatgat   1320
ggtctttaga attcatatgt gcccagtgaa ttatcttgtg attttactgt tttgttttga    1380
acagttgttc tggtagtatc aggatgaatt gcttacataa aaa                     1423
```

<210> SEQ ID NO 27
<211> LENGTH: 1493
<212> TYPE: DNA
<213> ORGANISM: Lolium rigidum

<400> SEQUENCE: 27

```
taacacagct actgtgacga acctaagctg attttcatta tcatgcctgg tctgtttatc      60
tctagacctg ccatggagat gaattttaat agtttgaagt gatcttttcc gtttatcct     120
aaaaggtcat atgtcgtggg ctttgcagat ttcttttctt attgtatgtt cttatgtgat    180
tgtaataaga gtactagtat aattttttctt tgatatttat tctatttcaa tccaataaaa    240
ttgcaggttg aagatctatc taaggaacct caggttgaaa gagagctcat gcttataaaa    300
ctcaatgcca aaccagatca acgtgctgcc gtaagatatg ctgttgatct gtatttccac    360
gatatcaaaa cattgtttag tcattgaatt agtggtattg gtacttctat tttaaagggt    420
tgtaacagga ctcttgcctc atggttgaca ggtcatgctt gtagctaatg tattcagagc    480
gaaggttgtt gatatttccg agaattctct aaccctagag gtaaagactt gacttcaaac    540
agtattataa ggactagggt gttccgtgtc tatgctggat taaattttct tgatgctgat   600
atggcaaatg ctgcaggtca ctggagatcc tggaaagatt gttgcggcac aaaggagcct    660
```

-continued

```
aagcaaattt gggatcgaag aaatttgtag aacgggaaaa gtatttttct ggaccatttg    720
ctacgtacat gcatgggcac atttcttcat tgtctaattc ttctatctca atgttcttag    780
attgctttga ttcgtgaaaa aattggaaca gctgcccgtt tctggggatt ttctactgct    840
tcttacccag acctcataga agcatcaccc agaaaccctc ttcttacttc tccgaaaaag    900
acggttaatg gcagttttga tcagccatcc agtgctgggg tatgtttcca tgaatataag    960
accaactaca tatttattgc atattccttc ttgttctgct tcaactgttc taaaagcgag   1020
gcaacgctta ggctataggt gccacagtct gcctagtacc ttttaaaacg ctgttactcc   1080
ctccgatcca aaatacttgt ccaaaaatgg gagaatctac acactaaaac acgtctagat   1140
acatgcattt ttgggcaagt attttggacc ggatagagta tttgtagttt taaatacttg   1200
gtaatctaca ccacgccgaa aagatgcccc ttttacatga atgacacaat caataatttg   1260
atgtgcaata acagagaaga tctcacgaac tgcgtatctt taatagctat agtgtaaaca   1320
aaggaaactg aacttctctg tcaccagtaa acatcccagt gcagccgtag cactgtaagt   1380
gaatttatag gtgaaggtaa tttgtatacc tggccttagc aaagcaaaaa aaaaattgct   1440
catacagtga aactggggag atacctgcgt gctgacaaaa ctaaaaacca cac          1493
```

```
<210> SEQ ID NO 28
<211> LENGTH: 260
<212> TYPE: DNA
<213> ORGANISM: Lolium rigidum

<400> SEQUENCE: 28
tcccggatca agaccgagtc tctgattgtg ccgcatgaac gcatccatga gagaccgttc     60
gtcttggcgc ctcttgttga cctcctgggt tcgtcggctg aggacagtat ggagaaaaga    120
tggcactctc tctcgaagtg cagtggtggg ttctttgatt tgtggaacaa gcttggcggt    180
gaatctattg ttggaacaga gggtattaaa agggtcatgt ctgttggaaa tgcactgttg    240
gattggcgtg agaggaccct                                                260
```

```
<210> SEQ ID NO 29
<211> LENGTH: 280
<212> TYPE: DNA
<213> ORGANISM: Lolium rigidum

<400> SEQUENCE: 29
atccatcaac tatgcagaat gagcagaatt tacagtatga tgatgtctgc aaagaagttg     60
cttctgagtt atacgctcgg ctgagagcag cagagctgtc tggaattcct ttgtggagga    120
ttgttcttga ccctggcatt gggttttcca agaaatccac acagaatatt gaagtaatcg    180
cgggcttgga atccattaga gaagagatgg gtaaaatgag tctaggtgct tcacatgtgc    240
caatattact tggaccctcc aggaaaagtt tcttagggca                          280
```

```
<210> SEQ ID NO 30
<211> LENGTH: 274
<212> TYPE: DNA
<213> ORGANISM: Lolium rigidum

<400> SEQUENCE: 30
ttggatctcc ggcatcctct caactcctca agcaaaccac cgggccacgc taacccgttc     60
agggtccgct cctacacgca atgcgcgctc accaacgatt ccaccgacaa cgaaatcgtg    120
attgccctgg gcagcaacgt gggagacagg gtcagcacgt tcgacagggc gctgcggctg    180
```

-continued

```
atgaggagct cgggcatcga gatcaccagg cacgcctgcc tgtacgagac cgccccagcc    240
tacgtgaccg accagccgcg gttcctcaac tccg                                274
```

<210> SEQ ID NO 31
<211> LENGTH: 200
<212> TYPE: DNA
<213> ORGANISM: Lolium rigidum

<400> SEQUENCE: 31

```
ctccaggaaa agtttcttag ggcagatatg caatcgcgct gatccagctg agagagatgc     60
tgctactgct tctgctgtta cagttgggat attgaatggt gctaatatag taagggtcca    120
taatgttaga tacagtgtgg atgctgcaaa ggtctctgat gcatcactca agtacagaag    180
aaaataatag aaagtataca                                                200
```

<210> SEQ ID NO 32
<211> LENGTH: 7757
<212> TYPE: DNA
<213> ORGANISM: Lolium rigidum

<400> SEQUENCE: 32

```
ggttagcgtg gggcggtggt ttgcttgagg agttgagagg atgccggaga tccaatgctg     60
gtatgttcag agggggtaag tttcaagaag tggaagctgc catttctcag gccaggttgc    120
tactgtcaga aggtgctgac ataattgata ttggtgctca gtccaccagg ccctttgcaa    180
ggaggctatc cgcagaagaa gagcttgaga ggctggtccc tgttctggat gctatcacga    240
aactccccga gatggaaggg aagttgcttt cagttgacac attctacgcg caagtcgctg    300
ctgaagctgt gaaaagggga gccaccatga tcaatgatgt atctggtggg cagcttgacc    360
cagatattct tcaagttgtt gctgaactgg gagttccgta tgttaccatg cacatgagag    420
gggatccatc aactatgcag aatgaacaga atctacagta tgatgatatc tgcaaagaag    480
ttgcttctga gttatacgct cggttgagag cagcagagtt gtctggaatt cctttgtgga    540
ggattgttct tgatcctggc attgggtttt ccaagaaatc cacacagaat attgaagtaa    600
tcacgggctt ggactccatt agagaagaga tgggtaaaat gagtctaggt gcttcacatg    660
tgccaatatt acttggaccc tccaggaaaa gtttcttagg gcaaatatgc aatcgcgctg    720
atccagccga gagagatgcc gctactgctt ctgctgttac agttgcgatc ttaaatggtg    780
ctaatatagt aagggtccat aatgttagat acagtgtgga tgctgcaaag gtctctgatg    840
catcactcaa gtacagaaga aaataataga aagtatacag ccaggataga agccatacca    900
gttgccagtt ttgtgcaagg gaatgctgat gtggagctca aaccatacgg ggtgtatcat    960
cacttaaagc aataaaagca tgtgtgaata actattacat tgaacaagag atatacagtt   1020
ttttcgtgcg cctcctcccc cgtagaatct tcagacaagc aaaggtaaca cagaccaagg   1080
cctctagggt tggtatatga tgtaaccagt tttgcgaggg tttaataatt atctaatagc   1140
gagacctaag agtaagacct ttgtaatatg ctttgcttgg aattgtctac ttgagagcat   1200
catttggtgc tgcagagtta atttccatct caggcagttt tcttagggtt acaaaatttt   1260
atctgactcc ttatgtgtgt tctgaactta ttgtccccga tgaggaaact catgcattgc   1320
aagtgccgta tgacattact tggcctcaag gcttggtcta tgatctaacc agttttctga   1380
ggggtttatt gcctaactgt gagtacttta ttatgctgtc tatgtgggag catcatttct   1440
tcttgctgag tcaagttcca gctctcttgc agttttttga ggttttcatg aaacttctcc   1500
tcgtgactcc ttatttgtgt tttgatcttg ctgtacccaa tgaggaaact catgcattgc   1560
```

```
aagtgccata tgacattact aggcctcaag gcttggtcta tgatctaacc agttttctga    1620
gggttttatt atcaaattgt gagacctttg taatgcactt tgcttcgatc gtctacttga    1680
gagaatcatt tgttgctgca gagttaattt ccatctcttg tgcatattta gattttaatc    1740
ttcaataact tctagcgtgt tttaaaaaga acatagcaaa ggcatccgac agaagtttga    1800
attggtttgt gacccaatga ggaaactcat gcattgcaag tgccgcatga cattactagg    1860
tctcaaggct tggtctatga tctaaccagt tgtctgaggg ttttattttc taattacgac    1920
ctttgtaatg tactttttta tgctgtctat gtgggagcat catttgttct tgtggagtaa    1980
atttccagct ctcatgcagt ttttttgagg ttttttcatg aaacttctcc ttgtgagtcc    2040
ttatttctgt tttcatcttg ctgtacccaa tgaagaaact catgcattgc aagtgccgta    2100
tgacattact aggcctcaag gcttggtcta tgatctaacc agttttctga ggttttatt    2160 gtcaaattgt gagacctttg taatgtactt tcttcgaat gtctacttga gagaatcatt    2220
tgttgctgca gagttaattt ccacctcttg tgcatatttc gattttaatt ttcaattaac    2280
ttctagcgtg ttttaaaagg aatatagcaa aggcatccaa cagaagttcg gattggtttg    2340
tgacccaatg aggaaactaa tgcattgcaa gtgccatatg acattactag gcgtcaaggc    2400
ttggtttatg atctaaacag aattctgagg gtttgtattg tctagatgca agacctttt    2460 actgcacgct gcatgtaatt ttctacttgt gagcttaatt tattcttaca caagatttga    2520
gttttaaatc tgaactgttt ttttggttcg ttttaaactt gaactttggt atattttcc    2580 gcatgcatgt gctcttttgga gccaaattgc atccccgtgg cttcttgtgc atttatatcc    2640
ctcctttgtt cactgatgag tgatgagacc ttaagaactg caggtgctgg atgattatgc    2700
tttcatcaag aatggccatg tcaatgatat caccacaggt tgttgtggt gttatctgtt    2760 ttttatacta ttgaacattt gtttgcattt ttacatgttt tttgtataat ttgaagctat    2820
tttagcttgc ttttgacctt gttctaccca atgatgaaat tcatgcattg caagtgccgt    2880
atgacatgct tggcctcaag gcttagtctt tgattcaacc agatttgtga gggttttata    2940
ttgtctaaat gcatgacctt tttaatttgc tcttatttga attgtctact taagatcatc    3000
atttgttcct acattatttg tttctgcatt tcatacagat ttggattta aatctgagct    3060 gctttggcca ttttaacaaa tatccatagg tcgctttgca ttttttcctgc tatgtttact    3120 gatgaaatct taagaattgc aagtgcccgg tgattacagt gttcatggca atgatgttaa    3180
cgcaggattc tgtggtcttg tcttgtttat actattcaaa atttatgttg tatgaagtga    3240
agctattctg gctcgccttt gatcaatctt caccttgtaa ctccttaatt ttcttgatga    3300
tgttctaccc aatgagggtc ttctccttgt aactccttaa ttttcttgat gatgttctac    3360
ccaatgagga aacccatatg agcgaggcct caactcctca accctcagta tttgatttaa    3420
ccaggtttcc tacggtttat attgtctaaa cgcagaacat ttttgatgtg ccctcatccg    3480
gatactctat agattgccat tgttcctgca gatttgctg tctacctcat aatacatatt    3540
tgaattttaa atctgacccg ttttgtactg ccttcactcc tgaaaccttt taataactgc    3600
aagtgtgaga tgattacgca ttggctcact tgttgttgcc accctgttct tgacactcac    3660
ctggaaaccc gaaggttttg ttttccttcc ctgaagtgca gtaatgcccg tcatcaagaa    3720
agccaaacat gaaaagtctg aatggaattt gaagaccagc atgcagggtt ctcatgatac    3780
cagcggtaac tttcttccct ttctctattg tcctatcgta ttatttatgc tgttgttttt    3840
gttcttttta atatttcttg aatcctttgt tctgcagagt atcaacaaaa ttagccaagt    3900
```

```
aatatcaaac gagctacttt ttttgttctt gggcactcat gtactaaggt ctcactcaag    3960
tttgcttctc gggaaaatgt acaagagtgc atcaggctaa cgggagaatt tactctgttt    4020
ccaaacggga caagctagag gtctatcgat cagtttatcc atactctcat gttgtatgca    4080
taatttatct gtttgttcat tgctaatcct tatcttcata tctctataac tgttccatgc    4140
tctctttgct gcaagagtca atttgtaaac atgaattggg agattaaaaa gatagtttca    4200
tgcaattaat attgtagcct ctgtgtgcac cattcagcaa tttcttttat tgaatcttga    4260
aattagtgtt gccttagtta tttatttgca ttctttccga ttctaagtaa agtttacttt    4320
attttagtta atggattatc tctgtcctac tatatttcct ttccatgttt caagttagca    4380
gattgcagtc ttgattaata cattttactg cttcgagttt gcttggatta agtgatgctg    4440
agtgtcgtgc ggcaaaaaac tccaaatcga aatgagatct tttatgcact attttcagat    4500
attgtctgga taaatgagc ttcagcacct gttttgtga accacataca gtatctatca    4560
gtgatgttct cgaaacattc tgaaatgaac ttgatctatc aacagctgag agggttttgg    4620
tattggactt ttcctgtcag attttaggaa tatataggat tgaatctgaa aggcaagtgt    4680
tttttagaac aaaatttgtt gatgattagt tataggtgct tagtcgcacc acccattatt    4740
tgttttgcag gccaaagatt ttcaattgct caaatcaagg aactgtgttg aaattcttca    4800
atctatgtca aaagaccaga ttcatgatat tgttgtgttt tcttcattgt acagactgat    4860
ggcctttcaa accgtataga attttttact aacattatct cttatgcaaa gtcaaataca    4920
tgtcattcca tgtccctgtc cccattcaag atggtaacgt ccggccagat tcaaggattc    4980
agaaattttc atacttatac atatttcgtt gtttcccgtg attttatatt catgtatatt    5040
cctttgcctt ttccagactt aaagatgtgt tggtagctta gatgacgatt tgattccag     5100 tttatctcaa attgggaaag aaataagcat ggttggcatc attactgaac tggattacgg    5160
atgtagcgct gacattgcac attgtaaaga tatattatca cgctttgagc ctcagtgatt    5220
ttgtattatc agatcatatg gcatatcgag tcgcggtctc ctcacattgc acttcgtgag    5280
ggtaaggctt gccactaaca tcttccccag accccgcaca gtgcgggagc tctcagcact    5340
gggtacgtcc tttagatcat atggcatatg ctccttttta ctgaagtggg agaagtgcag    5400
ttttcaggta agatgtgttg ctgaattcac tgttgttata ttgcagtaat aaatatatga    5460
agatacatat ttttctgctg atttagataa cggtggcact gtcataacca tgcttcctcg    5520
cgcactttct aggacatata cacagtttta atgtgcgaat cctagcatct cttttcacta    5580
aaatattctt ggtttcgagt attgtgtact agaaagcata gtcccaattt agtcacaggtt   5640 tctaacttag tcccatggat tcagtactgt ctataccatg ctgatgttac cacatagttc    5700
ccagtttacc ataggaggta acctaacttg gtgttcttat ttttgtgtgc agaaaatgca    5760
tgttgcagat tagattacag attagaaagt gccgccctct tttaggccag cggcgattgc    5820
aaaaatcttt ctctaagaaa tctttcttaa attgttatac tctctaaaac tggagcaggt    5880
ctctttctta gaccagtgca gtcacttagt agtcacttac acaacgacca cttgaaatat    5940
ctctcctttt cgtcttcaag atcatgattt attgtatgat tatttttat tgttggtaaa     6000 ctacattcat ttcatggtaa catatgtcgg tgttgttgca ggtcctgtgt tttttacccg    6060
ccggtgtttc agtcttcgtt atttcacaga tatgcttatt cttacatgga tgttggtgca    6120
tcatcttgga agaggtaaag attggaaagt atttctgctg aattttattc tcgaaatggt    6180
gaatatatac tatatacatg taccactaac tcaaaggatc acacatgaac tttataattt    6240
cattggcagt ttcaaggaag taacccgcat ttgctcattg gcagtttcaa gaaaagtaac    6300
```

-continued

```
cccatctgc attgggatct tccgatctaa agcttctttc aagtgtatgc ttattctgaa      6360
cactttactt ccttgaatcc tcttcaaagg ttttatgcaa agtgcagtta gcttaggccg      6420
cacaaggact agatgtacct gtagatgtgg tttattttt ggaagttcat atttagtttt      6480
tatttgctca gctgagagaa atggcatgtt gacagaagaa actaagcagc ctcatgtttt      6540
gtataaatag taccagaata tcttttgcaa tgtaaaacag caggtcaccg aaccattgtg      6600
cattgtgcta aaagcacata tattactcag tttacgttgt ataatagttg caagctggca      6660
agctattgct cattgaccaa aacgtcatgt attcacaaca gtgtctgatc agactcacga      6720
agaacacaat tctgtcgaaa cacctccaa catcaacata tagaattctt atctgagcta      6780
aaacgcttct tgcttataat ttaacaatga cgcaacggga aacttcctag tatcgttaac      6840
agcaacatcc atgctctact cacctcctcc tcacttatct cttttctctt gtgtatgtgc      6900
ctgtcgccgc ctcttcaatt tgctcccctc agctcttgta ctatccacta ccatgcccct      6960
gccatctgtc ctcaccagtc tgtcctctca ctaccaaagt agaaaagaac acaaggatg      7020 tgtgtattta atgaaatca gttggtgaga ttgttagtct atggaattta gtagtaatca      7080
agcggattca ctaaataaga gaaatataca catagtgagt actatttgtc tggcagtgct      7140
cttccacgaa atccaacaca caaattttct ctgctggctt catgcctaga aagctggtag      7200
aatatgaagc aaaaaagag tgatttaata tgttagtcaa aatggaaatg tactggtaaa      7260
atatagatta caaacctcgc ctagtgacta atagttgatg ttaggtgatc ttttctttt      7320 tttggtagtg cacgtggaaa aggaactgaa aataaaacat atgagataat tacctacaag      7380
atgcaggtgt aatccaacct gatccttgtg attagcacaa ttccctgaaa atgtgaaatt      7440
ttataggatc aggcataata tcactcagtg aggcttaaat atgtagttgg atcgcacaca      7500
catacatgtg caacataatg cctcagcgtg gagcataaaa ggagaattgg ccaacctcac      7560
gaatgggctt atgggcatta ctaaatgaat atctccggat atcagctgca taaagccttt      7620
atctactgaa ccagtgacaa ttctgcaata cttgccctat taggtaacca ctaacatcat      7680
attacccata tcagcgagtt gtataatcca agtttgtcgt ttacaaataa aaatcatcag      7740
aatagtaaga tagcatc                                                    7757
```

<210> SEQ ID NO 33
<211> LENGTH: 647
<212> TYPE: DNA
<213> ORGANISM: Lolium rigidum

<400> SEQUENCE: 33

```
cgccacgtcc gtggccgcgc ccgcggcgcc ggccggcgcg gaggaggtcg tgctgcagcc       60
catccgggag atctccggcg ccgtgcagct gcccggctcc aagtcgctct ccaaccggat      120
ccttctcctc tccgccttgt ccgaggtgag aaaacaagca gacaaagccc ctctccctac      180 ttctccccctt tgtgtgaatt gggtgccgag atgggatttt aggagggtta ggtgcatctt      240
atcatgctag gtgctcgtga gatcataaga ttttttttctt tttacttaaa acgatctagc      300
cataggattt agttcaaggt tactcttctt agtagccaat tcctatgttc gtttatcgaa      360
tcgttagaat tatgtagtta gttggatcaa tattatatga ggccttggat gagcaaaagt      420
cagttaatgg taattagaat tatgtaggac ctggtgatcc tcttatgtca gtctgatggc      480
ttcctcatga agtattacg ctgcaacgct gtcatggaca cctagtattc atatacctgc      540
attcaagatg cacgactttc aaatcttgtt atcgctaaag gttttcacaa gctataagat      600
```
cctaaatcta ggatcccctc cagagtttat tcactttcca ctcatcg       647

<210> SEQ ID NO 34
<211> LENGTH: 305
<212> TYPE: DNA
<213> ORGANISM: Lolium rigidum

<400> SEQUENCE: 34
aacaatcatt agtaatataa aaataaaatc agtttgaaca atccaacaag gcagtggcca    60
attcccatga ataagagcat tttaggtcgc gccctccaaa gggctcccca aaggactttg   120
gaggcgccag actaaaacat gcgcctaacc acggccgcag aggtgatttg tgtacgatgc   180
aaccccccaaa aaaactgcct gatactcata ggaagattct gctccttgtc agttggacaa   240
accataatct attttacttt ccctttttgtt ccctccacac attccatttc tcccgcctta   300
cattt                                                               305

<210> SEQ ID NO 35
<211> LENGTH: 4472
<212> TYPE: DNA
<213> ORGANISM: Lolium rigidum

<400> SEQUENCE: 35
tcctctccgc cttgtccgag gtgaccaaac aacccgaaac gcttcccct cctcccttc     60
ctttggggtg aattgggtgt actaaagatg ggattttttgg aggtttaggg gcgcacttgt   120
atcttgtcat gctaggtgct ggccagatca taagatattc tttcattctt attaagacga   180
tctagccata agacatatac ttaagaaggt agtctgttca gtaggcaatt cataagtctg   240
ttcacccaat tattgcatac atactgtagc ttgtatttga atgaagatga tctcaccata   300
ggatactcta ctccattcca aatagattca agttgtatgt gtcctaatta aaactatttc   360
tggtttcaca gaaaagtgtg tcactttaat ttcgttagtt tcatcataaa atatattttt   420
tgtactgtac tatagagatt tgatgttgta tatattatca tttttctcgt ctacaaactg   480
ggtcaaacgt agacaaggtt gacacaggac aaacataaga cttcgattaa tttggaaccg   540
agggagtggt atgtttacca gacaaatcct atgttcgttt attgaatcat tagaattatg   600
tactagctat tagttggatc aagatgatac ataaggttaa aaggtattag tataatcagg   660
tgatccttag gctggtcttt ttttttttctt ctgatggctt cttatgaaa gatttgtatt   720
gcaatggtgt cgtggacact tgataagaaa ctgaaactgg tttactttgc tggcatctct   780
agttgatcgt tagctgacta ttttgctctt cagggaacaa cggtggtgga taacctgttg   840
aacagtgagg atgtccacta catgctcgag gccctggacg cgctcgggct tccgtggaa    900
gcagacaaag ttgcaaaaag agctctagtc gtcggctgtg gcggcaggtt cccgattgag   960
aaggatgcca aggaggaagt aaagctcttc ttgggcaacg ctggaactgc gatgcggcca  1020
ttgacggcgg ctgtagtagc tgctggtgga aatgcaacgt atgtttcttt tctttaatcc  1080
ttattatggg aataagtatg agttccgtgg ttatgctttg agactgatgg tttatgtctc  1140
tcttctgaac ttcagttatg ttcttgatgg agtaccaaga atgagggagc gacctatcgg  1200
tgacttagtt gtcggtttga aacaactagg tgcgaatgtt gattgtttcc tcggcaccga  1260
ctgcccacct gttcggatca acggcattgg agggctacct ggtggcaagg ttagcctcat  1320
caacttccct tttatgcgct tttgtacaca catttcagtt ctctgaaaaa aacaagatta  1380
tgcgaccttt aaaatagcca taaccattag gccctatttc gtgtaaaaca gatatgctga  1440
ttgtgttgtg gtcttagatc acacggccta tcataaatta gcacttaaca ttgaattgca  1500

```
ttccacaggt taagctatct ggttccatca gcagccagta cttgagttcc ttgctgatgg   1560
ctgctccttt ggctcttggg gatgttgaga ttgaaatcat tgataaacta atctctgttc   1620
cttatgttga aatgacattg agattgatgg agcgttttgg cgtgacggca gagcattctg   1680
atagctggga cagattctac attaaaggag gacagaagta caagtaagtt ttgaattgtt   1740
ctgcttattc taaacatttg tccaaacatt tgacttctgg ataaactagg gaattgaaca   1800
ttggaaagaa ctattgactg ctcaacttac tgttattagc taagtcaagc tttactagga   1860
aatgagtaac tctgctactt acaatgcact ggctgcacag ctatgttttc tggtgcataa   1920
actattgtct gcccaaataa ctttaatcat ctggttagga ccaaacttgt agtagttatg   1980
aactgtacaa ggaaatcagt gtgacaaatc tccgctactt acaatgacat tggacggtta   2040
tattttcttg tgcataaact tggtcacatc agaagtgcca tccatctaaa aaagggtgag   2100
aattgagaac atatgcagct taatgacagc tgtttggcaa taagcatttc ttttgcggat   2160
gattcttgat ttgcttcttt tagccttttt tattgttact agttgaatgt ccgtgcttcg   2220
ccacggctcc ttagtgtata tttaatggca ttcgtgttat acggataaag atactatgta   2280
tgtaaatatt gaaagtactt ttttggacc cccttccggc atgttctatt gtcttcatcg   2340
tcgaagccaa atgttacatt gggatatctg ctgccaaatg ttgcagcagg atatgcatcc   2400
tgattttact gagcatactt cactgatgta attgaaactg tcagttcaaa cttcataaaa   2460
gttgcagtaa tcgcttccta acaagccct cccttgctct ggaattgaca attgacaggt   2520
cccctggaaa tgcctatgtc gaaggtgatg cctcaagtgc gagctatttc ttggctggcg   2580
ctgcaatcac tggaggaact gtgactgtcc aaggttgcgg caccaccagt ttgcaggtac   2640
aaccagtttt aaccatttgg ttaagcatac ttgcggtata taacataatc aaagatatac   2700
tgctgtcaac caaactgatt taagtggaca ttcatttatg aatctatata actacagtac   2760
tgtaagtcgg tttcttgtgc tatctccctg acgatgatta atattgcagg gtgatgtgaa   2820
atttgctgag gtactagaaa tgatgggagc gaaagttaca tggaccgaca ctagtgtaac   2880
tgttactggt ccaccacgtc agcccttttgg aaggaaacac ctaaaagctg ttgatgtcaa   2940
catgaacaaa atgcctgatg ttgccatgac tcttgccgtt gttgcccttt ttgccgatgg   3000
tccaactgct atcagagatg gtaaaccctc ttatgtgttg ctgttgattt cttttggatg   3060
gattccgcta cagcacatga tttgttcctg acacttgtcc attctcctct gtagttgcct   3120
cttggagagt gaaggaaacc gagagaatgg tggcaatccg gacggaacta acaaaggtag   3180
cacacctatc tccacttctt atatttcagc tcactgttgc actccccagt gcttagtctc   3240
acctgttgtg tgcctctgtg ctatagctgg gagcaacggt agaggaaggc ccagactact   3300
gcattatcac accaccagag aagctgaacg tcacggcaat cgacacctac gatgaccacc   3360
ggatggcgat ggccttctcc ctcgccgcct gcgctgaggt gcctgtcacg atcagggacc   3420
ctgggtgcac ccgcaagacc ttccccaact actttgacgt gctaagcacc ttcgtgaaga   3480
actagctcga tgaaaatcta cagtgtatcg catttgtact tttgtagcct gtccatggtc   3540
cgaggaaatt tttactgttt tggtcttctt gcgaaatgat ttatgagtgt aatactagtt   3600
ttgtagcatg gcgtggggct tttgaggtaa atgagttgat atgcatactg agttcgtttt   3660
gaataagaag caagttagga gtaccataga ccatactgtg acctacatgt tcttccgttt   3720
ccagaggtat tatgttggct gctggtactc aagtgtgttc gaaaactact cgacagccat   3780
ggaatttggg agatgccatt tgggtatgtg gatgcttgag gaagatcatc aaagcaaaca   3840
```

| | | | | | |
|---|---|---|---|---|---|
| agaacaccag | tcgatggtaa | aacagtgcag | cttgcaccaa | gaatgtttgc | ctatcagagt | 3900 |
| aaacaaacca | gactcagcag | atatgaaaaa | aactcagcac | tgtgacactc | gtgctaaaac | 3960 |
| taatttcatt | taggccgtgg | agtaggccat | tgcatactta | cgtattagag | catctctagt | 4020 |
| cgagtcctag | agcatctcta | gtcgagtccc | cacaaacggc | gccggatcga | gcgcttgggg | 4080 |
| gacgagtttt | gttcgtgccg | tgtttggggt | acatcgctcc | ctagtcgcgt | ccccaaacg | 4140 |
| ccgtccccaa | tgaggaattc | aaaatagttt | gtgcatttaa | aaaagatggt | gttcgtcgaa | 4200 |
| gtcgtcgcga | tcaaagtact | tggcgcgcga | tcatattaca | ggccgacttg | cacaaacata | 4260 |
| gatcctccag | aacggtccac | ttgggacagt | gtgccctacg | ccttcttctt | cttttcctcc | 4320 |
| ggaccgggtc | ctggctcgta | cgtcggggag | tagaacatag | cgttggggtt | gaagccgtca | 4380 |
| cgaggcagcg | catcctcgta | ccgcggcaac | aagtttggtg | tcacgcaccc | gggagtggcg | 4440 |
| gaggggccgt | cgttgtagaa | cccggatgtc | ga | | | 4472 |

<210> SEQ ID NO 36
<211> LENGTH: 1880
<212> TYPE: DNA
<213> ORGANISM: Lolium rigidum

<400> SEQUENCE: 36

| | | | | | |
|---|---|---|---|---|---|
| tacgtcgcat | ttccaccagc | aaatttcaca | tcaccctgca | ttaagatgca | caactttcaa | 60 |
| attttgttat | cgctaaaggt | tttcacgagc | tataagatcc | taaatctagg | atcccctcca | 120 |
| tggtttattc | ggtttccact | tgttagactg | aacataactg | aatactcatt | ggaatgttat | 180 |
| agtgcagcat | accttatttt | cattaagata | cgaaattggc | actgctttac | ttcgctgcca | 240 |
| tctcttgttg | atcattaact | gacttttgct | catcagggaa | caacggtcgt | ggataacctg | 300 |
| ttgaacagtg | aggatgtcca | ctacatgctc | gaggccctgg | acgccctcgg | gctctctgtg | 360 |
| gaagcagaca | aagttgcaaa | aagagctgta | gtcgttggct | gtggcggcag | gttcccgatt | 420 |
| gaaaaggatg | ccaaggagga | agtcaagctc | ttcttgggca | acgctggaac | tgcaatgcgg | 480 |
| tcattgacgg | ctgctgtagt | agctgctggt | ggaaatgcga | cgtatgtttc | ttttttatc | 540 |
| cttatgggaa | taagtatgag | ttccgtgggt | atgctttgag | actgactgat | ggtttatgtc | 600 |
| tctcttctga | acttcagtta | tgttcttgat | ggagtaccaa | gaatgaggga | gcgacctatc | 660 |
| ggtgacttag | ttgtcggttt | gaaacagcta | ggtgcgaatg | ttgattgttt | ccttggcact | 720 |
| gactgcccac | ctgttcggat | caacggcatt | ggagggctac | ctggtggcaa | ggttagcctc | 780 |
| atgaacttcc | acgttatgcc | cttttgtaca | cacatttcag | ttctataaaa | aaaaaaacaa | 840 |
| tgcgaccata | caataactcc | aaaattgcgc | atcaaaaaaa | aataactcca | aaattgccat | 900 |
| aaccaatagg | gcctgtttcg | tgtaaaacag | atatgctgat | tgtgttgtgg | tcttagatca | 960 |
| caaggtctat | cataaattag | cacttaacat | tgaattgcat | tccacaggtt | aagctgtctg | 1020 |
| gttccatcag | cagccaatac | ttgagttcct | tgctgatggc | tgctcctttg | gctcttgggg | 1080 |
| atgtcgagat | tgaaatcatt | gataaactaa | tctctgttcc | ttacgttgaa | atgacattga | 1140 |
| gattgatgga | gcgttttggc | gtgacagcag | agcattctga | tagctgggac | agattctaca | 1200 |
| ttaaaggagg | acagaagtac | aagtaagttt | tgaattgttc | tgcttattct | aaacatttgt | 1260 |
| ccaaacattt | gacttctgga | taaactaggg | aattgagcat | tggaaagaac | tattgactgc | 1320 |
| tcaactttat | tcatctggaa | atgaccatac | tgttattagt | taagtcaagc | tttactatga | 1380 |
| aatcagtgac | tctgctactt | acaatgcact | ggctgcacaa | ctatgttttc | tggtgcataa | 1440 |
| actatagtct | gcccaaataa | ctttattcat | ctggctagga | ccaacttgta | gtagctatga | 1500 |

```
actgtacaag gaaatcagtg tggcaaaact ctgctactta caatgacatt gcacggttat    1560 atttcttgt  gcataaactt ggtcacatca gaagtgccat ccatctaaaa aagagtgaaa    1620
attgagaaca tatgcagctt aatgacagct gtttggcaat aagcattttt tttgcagacg    1680
attcttgctt tgcttctttt agccttttt  ttattgttat gctctgctgc caaatgttgc    1740
accaggatat gcatcctgat tttactgagc atacttcacc gatgtaattg aaactgtcag    1800
ttcgaacttc ataaaagttg cagtaattgc ttcctaaaca agccctccct tgctctggaa    1860
ttaacaattg acaggtcccc                                                1880

<210> SEQ ID NO 37
<211> LENGTH: 692
<212> TYPE: DNA
<213> ORGANISM: Lolium rigidum

<400> SEQUENCE: 37
tgcgagctat ttcttggctg gtgctgcaat cactggagga actgtgactg tccaaggttg      60
cggcaccacc agtttgcagg tagaactcta ctataagtat ttaccatttg gttaagcata     120
cttgcagtat ataacataat tgaagataca gtgctgtcaa ccaaacacgc tttaagtgga     180
catccattta tgaatctata taactacagt actgtgagtc ggttttcttg tgctatctac     240
cttacgatgc ttaatattgc agggtgatgt gaaatttgct gaggtactag aaatgatggg     300
agcgaaggtt acatggaccg acactagtgt aactgttact ggtccaccgc gtcagccctt     360
tggaaggaaa cacctaaaag ctgttgatgt caacatgaac aaaatgcctg atgttgccat     420
gactctagcc gttgttgccc tttttgccga tggtccaact gctatcagag atggtaaacc     480
ctcttacgtg ttgctgttaa tttcttttgg atagattcag ctacagcgca tgatttgttc     540
ctgacacttg tccattctcc tctgcagttg cctcctggag agtgaaggaa accgagagaa     600
tggtggcaat ctgcacggaa ctaacaaagg tagcacacct gtctccactt cttatttca      660 gctcactgtt gcaccccccc cccccccccc cc                                    692

<210> SEQ ID NO 38
<211> LENGTH: 260
<212> TYPE: DNA
<213> ORGANISM: Lolium rigidum

<400> SEQUENCE: 38
gtccgtgcca gggccggggg aagggtgtgg ggcgtcagga aggccgcccg cggcacggcc      60
gggttcaagg tgctggccct cggcccggag accaccgggg tcgtgcagag gatgaaccag     120
ctgctcgaca tggacaccac gcccttcacc gacaagatca tcgcagagta catctggtac     180
gtacgtcctc ccaatgttgc attcctcggt tgcgccggag cgggctttgt tcgcacccat     240
tggctcgccc cagataggcc                                                  260

<210> SEQ ID NO 39
<211> LENGTH: 1061
<212> TYPE: DNA
<213> ORGANISM: Lolium rigidum

<400> SEQUENCE: 39
atctcatttc tacgcttgat taattggtgc taagtatgtt gaagtgtaac ctaactaatc      60
tcgactttat gtgtgtgtag ggtccttact actgcagtat tggtgctgag aagtcctttg     120
ggcgtgacat cgttgactcc cactacaagg cctgcctcta tgcaggcatc aacatcagtg     180
```

```
gcatcaatgg cgaggtcatg cccggacagg tgaatactaa ctacttcaca ttatcatctt    240
ctgtacctga aaatttatta ctgactttc taaccatgta aaattatgat tggttttcag    300
tgggagttcc aagttggccc aagtgttggc atttctgctg gtgaccaagt ctgggttgct    360
cgctacattc ttgaggtata atactcttca accaggaaga taatctgaaa tagccatatg    420
atcttgttca gacagtatcc ttgcatttag tattcagtta atattattgc ggttattaag    480
tgagaccatc cctttcttca gaggatcact gagatcgccg gagttgtcgt cacattcgac    540
cccaagccca tcccaggtga ctggaacggt gctggtgctc acacaaacta caggtaagac    600
tatcaagatg aacacacagt tcgaaacacc tcgttcatct gaactttgtt actgatcgtg    660
aattttgcat tcagcactga gtcgatgagg aaggatggtg ggttcgaggt cattgtggcc    720
gcagttgaga agctcaagct gaggcataag gagcacattg ccgcctacgg cgagggcaac    780
gagcgtcgtc tcactggcaa gcacgagacc gctgacatcc acaccttcag ctgggtacgt    840
gcattgctcc gaatcacctg aatccttgta tttattacag gagtggttct gagaaactgt    900
ttttgctctg cagggtgttg ccaaccgtgg cgcgtccatc cgtgttggcc gcgagacgga    960
gcagaaggca agggctactt cgaggaccgc cggccggcgt ccaacatgga cccctacgtc   1020
gtgaccgcca tgatcgccga caccaccctc ctgtggaagc c                      1061
```

<210> SEQ ID NO 40
<211> LENGTH: 3587
<212> TYPE: DNA
<213> ORGANISM: Lolium rigidum

<400> SEQUENCE: 40

```
taacaattct gcctttctct cttcacattc tgcagggttg gagggtctgg aatcgacatc     60
agaagcaaat caagggtacg cagcccacta tcttcatgga attgacatta gatttgtttt    120
ttgaaaggat tttttctaga agtttagggg atgagcagtt ggttttgtac gcagagtact    180
ccttccttac ttccttcttg gctcctgaca agaaaattta atgctcgcat ttcagacgat    240
atcgaaaccg gtggaggacc cttccgagct accgaagtgg aactacgatg gatcgagcac    300
agggcaagct ccgggagaag acagtgaagt catcctatag taaggggggaa attacagtat    360 atgtgtttct tcaagcttgc atataagaag tatcctagat ttatacatgt gttactctat    420
ttatgttttt tcctatcctg tttcagccca caggctatat tcaaggaccc attccgagga    480
ggcaacaaca tcatagtacc gtccatttc ccacttgcat tattcatttc tgattttgct    540
tttatgcagc tatactgaaa gggtcaatag tggacacttt tacctgtttg ttacatgtgc    600
aaagtgccat gtgagttaaa atgatttttt ttgcctttca ggttatgtgt gacacgtaca    660
caccacaagg ggaaccccatc cctaccaaca aacgcgccag ggctgcacaa attttcagtg    720
acccaaaggt ttcttcgcaa gtgccatggt aattatgcgt tgagcacctg tatgccgtgc    780
aaaggcctgc tgttcttta cctccctta ttcgcctaca gactgtagag ttgaaaaatc    840
ttcttttcta ggtttggaat cgaacaggag tacactttga tgcagagaga cgtgaactgg    900
cctcttggct ggcctgttgg agggtaccct ggcccccagg tactgtacca agaagcttca    960
tttactatac aaaaaataaa tcttaggctg cctgaaatac acttttagt taaacactat   1020 tgagtagtaa tattgtgctg aaatattgca gggtccatac tactgcgccg tgggatcaga   1080
caagtcattt ggccgtgaca tatcggatgc tcactacaag gcatgccttt acgctggaat   1140
tgaaatcagt ggaacaaacg gggaggtcat gcctggtcag gtgagccttt atatttatat   1200
gtgcgcatgt attcttattt tgtgtgaacc agagatgttt tttacatttt ctttctaatg   1260
```

```
aagtgtttaa taagtggaat ttcacaaacc ttatccatgc agtgggagta ccaggttgga    1320
cctagtgtgg gtattgatgc tggagatcac atatgggctt caagatatct tctcgaggta    1380
cttcaagcaa taatccgtgg ttccctaatg tgatgaaact ttgtttattt tcttttgatg    1440
accagaatat ggtcaataaa tcaattggtt ggttaaccct ttagctgcat gcactatgaa    1500
cttgtgattt gttcttgaaa cttcagtttt aattcatttc ctgaaaaccg tcagaccatt    1560
tttcttcaaa atatgatgaa accaaatcct ataactggcc agcccttttgg tcaaatcata   1620 tttcccatct gtaaagcctt ctaattatca tcgtactgac cttaatcaga gaatcacgga    1680
gcaagctggt gtagtgctca ctttggaccc aaaaccaatc caggtatatc cctgtaagtt    1740
gttggaagca ctttatatat tggaacttag taaactgaag attaatttga tatagggtga    1800
ctggaatgga gctggctgcc acacaaatta caggttccaa tctcttctgt taaataatca    1860
tttttcctgc ttaacattta cagaatatct tgttgtatat taacaataca tcagaaaacc    1920
taatatagct ttgctttagt aaatgctgtg gggttcacat cagaaggaaa tgtatgctgg    1980
gactaataga aaaaaaccct ccaaatacac atttaaactg gctataaatg ggaaaccatt    2040
attagtcgtc ggtttttttat tgagcatgat tcagaataag catttattca cattagttaa    2100
tcgctaaatt tggttagttg tttttctcaa tacacgatgc agttagtcct taatgtgcaa    2160
gcgtgaaact atcttttctt gttgttgcaa atatagcaca aagagcatgc gtgaagatgg    2220
aggttttgaa gtgattaaga aagcaatcct gaacctttca cttcgtcacg acttgcacat    2280
cagtgaatat ggtgaaggaa atgaacggag attgacaggg ttacatgaga cagctagcat    2340
atcagacttt tcatgggtac gggtggagca gcctttcatt attttttcagc tgtaatttac    2400 ttcatgttta tttgcaagtt atactaatta taatacatca tctatcaggg tgtagcaaac    2460
cgtggttgtt ctattcgggt ggggcgagac actgaggcaa aagggaaagg tatgtgctct    2520
cccttggttc ctgaaactac ttgcactgtt tggaaatgca ggaaagagtt ctacccagaa    2580
ataaaattca aggacattat gcaagcataa ttcttgggga gtagaaagcc cttaaactgt    2640
ctaacttgga tcttaggttc tttagctcat tttacccata tggccatata acgaatatgg    2700
atgccattct gatgattttg aatagttctg ggccaaatcc acgcccttaa atttgctatt    2760 ctgcacccctc tacgtgttga gtgttatcaa tttgaaaaat gttccttcac tcatacatat    2820
ctagtcacca actgatggcc tagctcacag ttgaaagaaa aatacattgg cacaaaatcg    2880
atatcttact atactattat cagtacccat tcattatgac atggtaattt gcatggagcc    2940
atacactgac agcgctgctg actgaaacta aaaggacttc atcttcatgc caacaggata    3000
cctggaggac cggcgtccgg cctcaaacat ggacccatac actgtgactg ccctactggc    3060 tgaaccacg attctctggg agccgaccct tgaagcagag gctcttgctg ccaagaagct    3120
ggcgatgaac gtatgaagga ctgaaaagga tgaatttctg ggaaaaataa atcgacagcg    3180
acactgtttg tcgtccattc ttccggatct tgtggttcca tcgggcact gtctgtacaa    3240 aatttacagt ttgtagaacc actttgcctt tcgcttgaac ttcacatttg atctgggtct    3300
gtatctgatt ccacttggaa ctacgttaaa ggataatgaa acacacagga ttttgattca    3360
gctattttat ttcctttgaa tggttcatct ttaagactag tgtcatgggt ggttcgtctg    3420
tctcgagaat ttatctatag cgttaaagtt tctcatgttt ataaagcttt gatggggaat    3480
gttggtgcta ttcctgcaat taaatggatg tgggatggtt gttgtcaaca gaggcacaag    3540
gttttctttt ggccgcttgt tcataattgc ctcaacacca gggccct                  3587
```

<210> SEQ ID NO 41
<211> LENGTH: 296
<212> TYPE: DNA
<213> ORGANISM: Lolium rigidum

<400> SEQUENCE: 41

| | | | | | |
|---|---|---|---|---|---|
| aaaacaggta | cggtatcgag | caggagtaca | ccctccttca | gaaggacgtg | aactggcccc | 60 |
| ttggctggcc | cattggtggc | taccctggtc | ctcagggccc | ctactactgc | gccgccggcg | 120 |
| cggacaaggc | gttcggccgt | gacatcgttg | acgctcacta | caaggcctgc | ctctacgccg | 180 |
| ggatcaacat | cagcggcatc | aacggggagg | tcatgcccgg | ccaggtacta | cacatcatct | 240 |
| tgcagcgact | tgctttcaga | aacacttcca | gttgcgtgtg | ccgccaactc | tgactg | 296 |

<210> SEQ ID NO 42
<211> LENGTH: 2162
<212> TYPE: DNA
<213> ORGANISM: Lolium rigidum

<400> SEQUENCE: 42

| | | | | | |
|---|---|---|---|---|---|
| tgaaattatt | gcaaacagat | gacgctccta | aaaccggtaa | tctgggcctc | caattattgg | 60 |
| tgcgcctggt | cagagccttc | caagttccaa | aactatgaat | ggaaaacaat | aacaatggcc | 120 |
| atgccggtca | atcactgtac | atataaacaa | cccaggccgt | tgaggtttgg | ctgttgctcg | 180 |
| tgtttatttt | gattggagag | gtcgcctggg | cttggccggc | tcgcatgtgg | agacggacgt | 240 |
| gacaaggaga | ggcagccgca | tctttcatat | ccagagcaca | aaaacacatt | gtaaactcta | 300 |
| tccaagatgt | gtgtgccttg | cctgccttct | gagcggcgct | tccctttgct | gtctttgcct | 360 |
| ccggtggtgc | tgcaagggcc | gccagaaatc | tcgtccaccc | aaagccctat | cgcctaatca | 420 |
| agagccagat | gccactgccc | cagccgcggc | cactagaatc | tctctcgcaa | atctaaaata | 480 |
| cttatacgcc | tcttgctctg | ccccgtaga | tagataaata | attccagcgc | gatcttgcag | 540 |
| tcgccgaccg | tttctcctcc | tctccccctcg | tctgcccgtc | tgctgccgcc | tctggtgagt | 600 |
| ggtcgaacca | atgcctagtt | tcgttccttc | tctgttgcat | tcgctgctgg | ctagcgatcg | 660 |
| atccgatgtg | gtaatggcgc | ctatctgctt | tggttggttc | atcagctagc | gttgacaagc | 720 |
| aaggcggcag | agtagctacc | tactagctag | cctgatggcg | caggcggtgg | tgccggcgat | 780 |
| gcagtgccag | atgggcgcgc | tgggcaagtc | ggccgtccgt | gccagggccg | ggggaagggt | 840 |
| gtggggcgtc | aggagggccg | cccgcggcac | ggccgggttc | aaggtgctgg | ccctcggccc | 900 |
| ggagaccacc | ggggtggtgc | agaggatgaa | ccagctgctc | gacatggaca | ccacgccctt | 960 |
| caccgacaag | atcatcgcag | agtacatctg | gtacgtacgt | cctcccaatg | ttgcattcct | 1020 |
| cggttgcgcc | ggagcgggct | tgttcgcac | ccattgactc | gccccagata | ggccacaccc | 1080 |
| gcacttttgg | ggactagatt | agtgccgggg | caagcagatt | cgccccctttt | ttaagtggta | 1140 |
| atttaatttt | ctgtctaaag | cttccagggc | atggtgggtg | atgagtgacg | atttcaaaag | 1200 |
| tgcttgcttt | ttagttagtt | ccagcacttg | aataagctta | ggaaaatgca | catcgcactt | 1260 |
| tgggggagca | ataagggtca | aacaaattgg | tcctggcatc | tactaagtat | tatacctctg | 1320 |
| tggcaaaata | caagacgttt | tggtagtcta | tttttgggac | agaggtaata | gtactttaac | 1380 |
| aattctgtct | tcctctcttt | acattccgca | gggttggagg | gtctggaatc | gacatcagaa | 1440 |
| gcaaatcaag | ggtacgcagc | ccactatctt | catggaattg | acattagatt | tgtttttttt | 1500 |
| tttgaaagga | ttttttttcta | aagtttagc | ggatgagaag | ttggttttgt | atgcagagtt | 1560 |
| ctccttcctt | acatccttttt | tggttcctga | caagaaaatt | taatgcttgc | atttcagacg | 1620 |

| | |
|---|---|
| atatcgaaac cggtggagga cccttccgag ctaccgaaat ggaactacga tggatcgagc | 1680 |
| acagggcaag ctccgggaga agacagtgaa gtcatcctat agtaaggggg aaattacagt | 1740 |
| atatgtgttt cttcaagctt gcatataaga agtatcctag atttatacat gtgttactct | 1800 |
| atttatgttt tttcctatcc tgtttcagcc cacaggctat attcaaggac ccattccgag | 1860 |
| gaggcaacaa catcatagta ccgtccattt tcccacttgc attattcatt tctggatttt | 1920 |
| cttttatgca gctatactga aagggtcaat agtggacagt tttacctgtt tgttacatgt | 1980 |
| gcagagtggc atgtgagtta aaatgatttt ttttgccttt caggttatgt gtgacacgta | 2040 |
| cacaccacaa ggggaaccca tccctaccaa caaacgcgcc agggctgcac aaattttcag | 2100 |
| tgacccaaag gtttcttcgc aagtgccatg gtaattatgc gttgagcacc tgtatgccgt | 2160 |
| gc | 2162 |

<210> SEQ ID NO 43
<211> LENGTH: 5926
<212> TYPE: DNA
<213> ORGANISM: Lolium rigidum

<400> SEQUENCE: 43

| | |
|---|---|
| aacccgatga aatcaggaaa agcctgtttg gacaaaagga atctgacttt gaaaagtttg | 60 |
| tgctgatgta ctgggaaagc tcaccttatt tgtacaggag gaaacaaagt ggtctggaag | 120 |
| gggatcctgt gtacactgca ttgcgtaatg cgtttgatct tacaacacct gatgctatca | 180 |
| ttgagtcatt tatacagggc cttgtttctt gccctgctat tgcttcggat gaactcaaca | 240 |
| tagactcatt tctccatgag gttcgtgatt cttgggtgc cctgtgaag tacaggcaag | 300 |
| atgtaagagt tgtcagaaca cgagatcaga cctcaacagg gtctgggatg gaggagcatt | 360 |
| tcttcgatga tggtattgcc ttcccggatg catctgcatt tgttgacaaa tgtaaggacg | 420 |
| cagtcaagaa tggcttctca attgccttgc gtggcatgga gttccggtca gaaaaggttg | 480 |
| ctgctatagc ttctgctctg gctgatctgt ttggtcagcc ttctgtagga gccaatgtat | 540 |
| acttctcacc tcctagatct caaggcctgg cccggcatta tgacgaccac tgtgtgcttg | 600 |
| tttggcagct acttggttgc aagaagtgga agatttggcc caatacgagg tcaatttgc | 660 |
| ctagactgta tgaaccttt cactctttag atgacttggt ggatgatagt ggtggaaggg | 720 |
| tggaagtgtt acatgaagga gacataatgt atgttcctag aggctgtgtc cacgaggctc | 780 |
| atactgacat tgatgatggt gaatccgagg tcaatgcatc agccaattac tcactccatt | 840 |
| tgacccttgc cattgaagtc gagcaaccct ttgagtgagt attcctactt ctgcaaacaa | 900 |
| aggcattctt tgcatgcatg cccagtggtt ctgtgtttca ccatttatct tttgttacag | 960 |
| gtgggaagga tttgcacaca ttgctcttca ctgttggttg ttggaggagc agacacttgg | 1020 |
| atgtagctct ggatctatca actccaaggt ggatgaacaa gctccattat tttctctcct | 1080 |
| gctgcatctg gcgatcaggc tgctctccga caatgatcct agtctgagga aggcgtgcat | 1140 |
| ggttgcggcg aagcttccat catccagcaa ctcctgttca acttctcact ccaactccct | 1200 |
| cagaagccac catatgtcaa ccttcatcga gatactcaac aagatcgata acacctgcaa | 1260 |
| cctcaaggag gtgctgagat tggtcgagct tgtggttaaa ggaaagacgg atgagcccct | 1320 |
| ccagtggatg tcctggctcc ggcatctcca acagcagcag tacggcgaca cggcggctca | 1380 |
| caagatcgac ttctgcgacc tcctgggacc tttcaaagag cttcttgaca tgtttggctc | 1440 |
| cgatcctgaa caagcctcgg ctgagttcac tgatttcaag tcgaggttct gtaggtgtgc | 1500 |

-continued

```
tgggtatgat gatgcttgca agagcttcga gatgctgctc cacatgtata ggacaactag      1560
gactcagtac acaaagggca tgctggcatt gcacgggaga cataggaatt agcctctgga      1620
gtggagatca aatccttaat tcctagctca tgacagataa gtttcagtga ttaggtaggc      1680
aggcatattt tttggtcagc ttagctcgga tttagtactc ggatcccacg aattctgatg      1740
ctacattcaa gtgtgtgagt gggaaatcac attgcaaagc tagaaaagag aagaatctga      1800
agcatctctg tggaaatcgc cagttgcagt tggttacgca gaaacaacag cttgttttca      1860
tgaaagatat acagctactg gtgccaaatt tgcaccgtcg ggagccgtac atctgtggta      1920
ctgatcagtt ggactgactg agcggaatat gttaattcca ggtcccgcaa tcattgcaaa      1980
tagacgacgc tcctaaaacc ggtgatcttg tccccaatta ttgcagcctg gtcagagcct      2040
tccaaagtga tgaaaaataa acatatcacg atgcgggtca atcccaataa ggttttgggt      2100
ttggagaggt cacctgggtt cggccggatg gcctctggag atggacgtga caattattgt      2160
ttgttggatg atagcggtcg accgataaaa gttttgcgtg gacacataac atatcttcct      2220
tagaggttgt gtccatgagg caccaatgca tctgccaatt actcactcta tttgacccett      2280 gacattgaag tcgagccacc ctttgacttt gagtatgtat tcttcctgtt gcaaacaaag      2340
gcatcttggc atatacaatt atgcatgtct aatggttctg ctcctcacca tttacctttg      2400
ttacagatgg tgagatggga atggtttgca cacatcgctc ttcgctgttg gttagagaag      2460
gagactcttt ttttttttga aacggaggca aaagttttgc ctcatccatt cattaagcag      2520
aaggtgtctg gttttagga gaaaaccggg caaaaaccta caaagacagg gccaaaccca      2580
cacccaccca cacgacgcca caaggcaca ccgagccacc ctgactaccc acataagcta      2640
cacaaacgcg aagctcaagt tggcctatgc caaatagatg gctccccaag aaaaagccgg      2700
tagctccgat tctgacgacg agccgcggag aggagatgca caagacctgc gccgaaaagg      2760
atcttcaccg tcgaatcgcc cctccagaga aggagactct ggaggagctc tggatctgtc      2820
aagtccgagg tggaagaaca agcttcattg taatgctctc ctgctccaag tggccatcag      2880
gctgctctct gacaatgatc ccgctctcat gaaagcctgc atggtcgcag caaggcttcc      2940
atcatccagc aactcctgtg agacagctgt ctcagaagca gccatagatc aagctttgcc      3000
aagatactca acaagatcaa caacacctgc aacctcaagg aggtgctgag gtcgatcaag      3060
ctcgcgatta aaggaaagtt ggactgagtc ctgtatccgg catctgccac agaagcagca      3120
gcacggagac gcgatggctc tcaggatcga cttgtgcggc gtcctgagac tgctcgaaga      3180
gcttcttgat gtgtttggct gaggggttcg agacgctgct gaagatgtgc agaacggttc      3240
agaaccggta catgagggat tgaggggcat gctggcgttg cacgcgaggc atggtggtta      3300
gctgttggag tgcaggtcga attcctccta gctcctgacc gacaagtttc gcggtgattg      3360
ggcagctagg cctgttttag tttgggtcag ttttagttcg gctctgctac ttggcttcac      3420
ggtttttagc tgttagttcc tctgttcatc tagatacatg tagtacttct agacaaatct      3480
ggcacacttg tttccgaacg gagggagtac tagcgagtga gaaatcactt tgcaatagtg      3540
agaaatctga agcatctccg ctgaatcaca tcagctggta caaggaagaa tagcctcttt      3600
tcagcaaaga cacacagttg tgctggtacc aacttgtact atcaggaacc gtacatcagc      3660
agctcgactg accgacttaa cggaatctga taataatacc aagacgtgca attattgcga      3720
acagatgacg ttcctaaaac cggtatcttg gccccaggta attgctgtgc ctggtcagag      3780
ccttccaaag tgatgaaaaa atggccacgc tgcgagtcaa tctctcagtg cacataaaca      3840
aagctgggtt ttttatttt tggttggaga cttggagagg tcgcctgggc ttggccgggc      3900
```

```
tcgccggcgt gcgtcggggg gagacggacg tgacaaggag aggcagccgc atctttcata    3960
tccagaggcc agagcacaag aaacattgta aactctatct atccgtgatg tgtgttgcat    4020
cggtgtgttt gtgtctcttt gccccgatg gtgctgcaag ggccgccaga aatctcgtcc    4080
acccgaagcc ctatcgccta atcaaaagcc agatgccact gcccgcgccg cggccactag    4140
aatctctctc gcaaatccaa agtctttttt gctctgctcc cataaataaa taattccacc    4200
gcgatctcgc agttgctccg ccctctccct ctccctctc gtctcgtctg ccgcctgctg    4260
ccgcctctgg tgagtggtcg aaccaatgct tacctcgctt cttcaattcc ctgttgcacg    4320
agtgatcgat gttgtaatgg cgcttgtctg ctttggtttc ttggttgatc agctagcgtt    4380
gacaagcaag gcggcagagt acctagctag ctccggtagc tagccgagat ggcgcaggcg    4440
gtggtgccgg cgatgcagtg ccagatgggc gcgctgggca gtcggccgt ccgcgcgagg    4500
ccggcggcgg ccgggggaag ggtgtggggc atcaggaagg ccgcccgcgg cacggccggg    4560
ttcaaggtgc tggccctcgg tccggagacc accggggtgg tgcagaggat gaaccagctg    4620
ctcgacatgg acaccacgcc cttcaccgac aagatcatcg cagagtacat ctggtacgta    4680
cgtcctccca atgttgcatt cctaggttgc gccgagcgg gctaccattg actccccga    4740
cacagcagca ccagccacca gtagcttcag ataggccaaa cccgcacttt ctgggagtag    4800
attagtgccg gtgcaagcag attcgacccc ttttaaggt ttgatgatag tggtaattta    4860
attctctgtc taaagcttcc agggcatggg tgggtgatga ctgacgaatt caaaagtgct    4920
cgcttttag ttagttccag cacttgaata agcttaggaa aatgcacatc gcactttggg    4980
ggagcaataa gggtcaacta ctaagtacta cctctgtggc aaaatataag acgcttttgt    5040
agggacgcct atttttgaga cagatgtaat attactagta tttaacaatt ctgcctttct    5100
ctcttcgcat tctgcagggt tggagggtct ggaatcgaca tcagaagcaa atcaagggta    5160
cgcagcccac tatcttcatg gaattgacat tatatttgtt tttggaaatg attttttta    5220
aaagtttaca cgatgagcag ttggttttgt acgcagcata ctccttactt acttccttct    5280
tggcttctga caaaaaaat taatgctcgc atttcagacg atatcgaaac cggtggagga    5340
ccccttccgag ctaccgaagt ggaactacga tggatcgagc acagggcaag ctcctggaga    5400
agacagtgaa gtcatcctat agtaaggggg aaattacagt atatgtgttt cttcaagctt    5460
gcatataaga agtatcctag atttatacat gtgttaactc catttatgtt tttcctatcc    5520
tgtttcagcc cacaggctat attcaaggac ccattccgag gaggcaacaa catcatagta    5580
ccgtccattt tccccacttg cattattcat ttctggtttt gcttttatgc agctatactg    5640
aaagggtcaa tagtggacgg ttttacctgt ttgttacatg ttgcaaagtg ccatgtgagt    5700
taaaatgatt ttttttgcc tttcaggtta tgtgtgacac gtacacacca caaggggaac    5760
ccatccctac caacaaacgc gccagggctg cacaaatttt cagtgaccca aaggtttctt    5820
cgcaagtgcc atggtaatta tgcgttgagc acctgtatgc cgtgcaaagg cctgctgttc    5880
ttttacctcc ctttattcgc ctacagactg tagagttgaa aaaact    5926
```

<210> SEQ ID NO 44
<211> LENGTH: 8388
<212> TYPE: DNA
<213> ORGANISM: Lolium rigidum
<220> FEATURE:
<221> NAME/KEY: unsure
<222> LOCATION: (1)..(8388)
<223> OTHER INFORMATION: unsure at all n locations

<400> SEQUENCE: 44

```
atctccgcgg aaatcaccag ttgcagttgg ttgtgcagaa acaacttgtt ttaatgaaag      60
atatacagct gctggtgcca aatttgtact gtcaggagcc gtacatctct ggtaccgagc     120
agttggactg actgagcgga acatgttaat tacaggccct gcaatgattg caaatagatg     180
acactcctaa aaccggtgat cctgtcccca attattgccg cctggtcaga gccttccaaa     240
tgatgaaaat tgaaaaataa acatatcacg atgcaggtca atcccaataa ggttttgggt     300
ttggagaggt cacctgggtt cggtgggctg cctctggag atggaagtaa caattatgat      360
ttgttggatg acagcagctg acgcatgaaa gttttgcatg cacacataat atatcttcct     420
taaccacgag gcatcaatgc atctgctaat tactcactct atttgaccct tgacattgaa     480
gtcgagccac cgtttgactt tgagtatgta ttctccctgt tgcaaacaaa ggcatcttgg     540
catatgcaat tatgcatgtc taatggttcc gcttctcacc atttactttt tgttacagat     600
ggtgagatgg gaatggtttg cacacatcgc tcttcgctgt tggttagaga aggagatact     660
ctggaggagc tctggatctg tcaagtccga ggtggaagaa caggctcctt ttttagccct     720
cctgctgcat gtggccatca ggctgctctc ggacaatgat cccgctttca tgaaagcctg     780
catggtcgcg gcaaggcttc catcatctag caactcctgt gagacaactg tctctaattc     840
tatcagaagc agccataggt caacctttgc cgaggtactc aacaaaatca caacacctg      900
caacctcaag gaggcgctga ggtcgatcaa gctcacgatt acaggaaagg tggactgaac     960
ccttccggtg gatgtcctgg ctccggcatc tgctgcagaa tcagcagcac ggagccgcag    1020
cggcttgcag gatcgacttg tgggacgtcc tggggctgct cgaagagctt cttgacgtgt    1080
ttggctctga cagtgagggg ttcgagatgc tgctgaagat ttacagtacg gttaggaacc    1140
ggtacatgag ggattgacgg gcatgctggc gttgccttgc acgggaggtg tggtggttag    1200
ctgttggagt gcagatggaa ttcctcctag cccctgacca ataagtttcg caatgattgg    1260
ttagctagtt ttagctcagc tccgctactt gggttcacgg ttttaagctg ttacttcctc    1320
cgttcatctg gacacatgta aatctagaca aatccgcacc tagcgagtga gaaatcactt    1380
cgcaatagta gaaaagaaga agaaatctga agcatctctg ctgaatcaca ccagctggtg    1440
catcggaaga atagcctctt ttcagcaaag acacacagtt gtgctggtac caacttgtac    1500
tatcaggaac cgtacatcag cagctcgact gaccgactta acggaatctg ataatgatac    1560
caagtcgtac aattattgcg aacagatgac gttcctaaaa ccggtatctt ggccccaggt    1620
aattgctgtg cctggtcaga gccttgcaaa atgatgaaa atggtcacg ctgcgagtca      1680
atctcacagt gcacataaac aaagctggga ttttttttgg ttggagactt ggagaggtcg    1740
cctgggcttg gcatgcgttg gggggagacg gacgtgacaa ggagaggcag ccgcatcttt    1800
catatccaga ggcgagagca caagaaacat tgtaaactct atctatccgt gatgtgtgtt    1860
gcatcggtgt gtttgtgtct ctttgccccc gatggtgctg caaggccgc cagaaatctc     1920
gtccacccga agccctatcg cctaatcaaa agccagatgc cactgcccgc gccgcggcca    1980
ctagaatctc gctcgcaaat ctgaagcctg tgcttctccc ataaataaat aattccaccg    2040
cgatcttgca accgctccgc tccgccttct ctccctctc gtctcgtctc gtctgccgcc     2100
tctggtgagt ggtcgaacca atgctcaact cgcttcttca attctctgac cagtgatcga    2160
tcgatgtgcc gatgtggtaa tggcgcctgt ctgctctgct ttgttggttg atcagctagc    2220
gttgacgagg agcgcggcag agtacctagc tagctagctc cggtagctag ccgagatggc    2280
gcaggcggtg gtgccggcga tgcagtgcca gatgggcgcg ctgggcaagt cggccgtccg    2340
```

-continued

```
cgcgaggccg gcggcggccg ggggaagggt gtggggcgtc aggaggaccg cccgcggcac    2400
ggccgggttc aaggtgctgg cactcggccc ggagaccacc ggggtggtgc agaggatgaa    2460
ccagctgctc gacatggaca ccacgcccttt caccgacaag atcatcgcag agtacatctg   2520
gtacgtacgt cctcccaatg ttgcattcct cggttgcgcc ggagcgggct ttgttcgctt    2580
ccattgactc cccccgacag aacatcacca gtagcttcag ataggccaaa cccgcacttt    2640
ttgggactag attagtgccg gtgcaagcag attcgcctcc tttttaaggt ttgatgatag    2700
tggtaattta attctctgtc taaagcttcc tgggcatggt gggtgatgag tgacgaattc    2760
aaaagtgctc gcttttagt tagttccagc aattgaataa gcttagggaa atgcacatcg     2820
cgctttgcgg gagcaataag ggtcaaacac taagtagtac ctctgttgca aaatataaga    2880
agcttttgta gcctattttt gggacagatg taatattact actagtattt aacaattctt    2940
cctttctctc tttacattct gcagggttgg agggtctgga atcgacatca gaagcaaatc    3000
aagggtacgc agcccacaat cttcatggac ttgacattat atatttttt taaatgattt     3060 cttttctaga agtttagggg atgggaagtt ggttttgtac gcagagtact acttccttac    3120 tacctttcg gctcctgaca agaaaatta atgcttgcat ttcagacgat atcgaaaccg      3180
gtggaggacc cttccgagct accgaagtgg aactacgatg gatcgagcac agggcaggct    3240
cctggagaag acagtgaagt catcctatag taagggggga attacagtac atgtgttctt    3300
caaccttgca cataaaaatc ctagatttat aaatgtgtta ctccatttat gttttttcct    3360
atcctgtttc agcccacagg ctatattcaa ggacccattc cgaggaggca acaacatcat    3420
agtaccgtcc attttcccac ttgcattatt catttctgga ttttgctttt atgcagctat    3480
actgaaaggg tcaatagtgg acagttttac ctgtttgtta catgtgcaga gtggcatgtg    3540
agttaaaatg attttttttg cctttcaggt tatgtgtgac acgtacacac cacaagggga    3600
acccatccct accaacaaac gcgccagggc tgcacaaatt ttcagtgacc caaaggtttc    3660
ttcgcaagtg ccatggtaat tatgcgttga gcacctgtat gccgtgcaaa ggcctgctgt    3720
tcttttacct cccctttattc gcctgcagac tatagagttg aaaaatcttc ttttctaggt   3780
ttggaatcga acaggagtac actttgatgc agagagatgt gaactggcct cttggctggc    3840
ctgttggagg gtaccctggc ccccaggtac tgtaccaaga agcttcattt actatacaaa    3900
aaataaatct taggctggct gaaatacact ttttagttaa acactgttga gtagtaatat    3960
tgtgctgaaa tattgcaggg tccatactac tgcgccgtgg gatcagacaa gtcatttggc    4020
cgtgacatat cagatgctca ctacaaggca tgccttacg ctggaattga aatcagtgga     4080
acaaacgggg aggtcatgcc tggtcaggtg agcctttata tttatatgtg cgcatgtatt    4140
cttattttgt gtgaaccaga gatgttttt acattttctt tcaaatgaaa gtcgaagtgt     4200
ttaataagtg gaatttcaca aaccttatcc atgcagtggg agtaccaggt tggacctagt    4260
gtgggtattg atgctggaga tcacatatgg gcttcaagat atcttctcga ggtacttcaa    4320
gcaataatcc gtggttccct aatgtgatga aactttgttt atattctttt gatgaccaga    4380
atatggtcaa taaatcaatt ggttggttaa ccctttagct gcatgcacta tgaacttgtg    4440
atttgttctg aaacttcagt tttaattcat ttgctgaaaa ccgtcagacc atttttcttc    4500
acaatgtgat gaaaccaaat cctataactg gccagccgat tggtcaaatc atatttccca    4560
tcagtaaagc cttctaatta tcatcgtact gaccttaatc agagaatcac ggagcaagct    4620
ggtgtagtgc tcactctgga cccaaaacca atccaggtat atccctgaaa gttgttggaa    4680
```

```
gcactttata tattggaact tagtaaactg aagattaatt tgatataggg tgactggaat    4740
ggagctggct gccacacaaa ttacaggttc caatctcttc tgttaaataa tcattttttcc   4800 tgcttaacat ttacagaata tcttgttgta tattaacaat acatcagaaa acctaatata   4860
gctttgcttt agtaaatgct gtggggttca catcagaagg aaatgtatgc tgggactaat   4920
agaaaaaaac cctccaaata caaatttaaa ctggctataa atgggaaacc attattagtc   4980
gtcggttttt tattgagcat gattcagaat aagcatttat tcacattagt taatcgctaa   5040
atttggttag ttgttttttct caatacacga tacagtttgt ccttaatgtg caagtgagaa   5100
actatctttt cttgttgttg caaatatagc acaaagagca tgcgtgaaga tggaggtttt   5160
gaagtgatta agaaagcaat cctgaacctt tcacttcgtc acgacttgca catcagtgaa   5220
tatggtgaag aaatgaacg gagattgaca gggttacatg agacagctag catatcagac   5280
ttttcatggg tacgggtgga gcagcctttc attatttttc agctgtgatt tacttcatgt   5340
ttatttacaa attatactaa ctacaatact tcatctatca gggtgtagca aaccgtggtt   5400
gttctattcg ggtggggcga gacactgagg caaaagggaa aggtatgtgc tctcccttgg   5460
ttcctgaaac tacttgcact gtttggaaat gcaggaaaga gttctaccca gaaataaaat   5520
tcaaggacat tatgcaagca taattcttgg ggagtagaaa gcccttaaac tgtctaactt   5580
ggatcttagg ttctttagct cattttaccc acatggccat ataacgaata tggatgccat   5640
tctgatgatt ttgaatagtt ctgggccaaa tccacgccct taaattcgct attctgcacc   5700
ctctacgtgt tgagtgttat caatttgaaa aatgttcctt cactcataca tatccagtca   5760
ccaactgatg gcctagctca cagttgaaag aaaaatacat tggcaccaaa tcgatatctt   5820
actatactat tatcagtacc cattcattat gacatggtaa tttgcatgga accatacact   5880
gacagcgctg ctgactgaaa ctaaaaggac ttcatcttca tgccaacagg atacctggag   5940
gaccggcgtc cggcctcaaa catggaccca tacactgtga ctgccctact ggctgaaacc   6000
acgattctct gggagccgac ccttgaagca gaggctcttg ctgccaagaa gctggcgatg   6060
aacgtatgaa ggactgaaaa ggatgaattt ctgggaaaaa taaatcgaca gcgacactgt   6120
ttgtcgtcca ttcttcctga tcttgtggtt ccatcggggc actgtctgta caaaatttac   6180
agtttgtaga accactttgc ctttcgcttg aacttcacat ttgatctggg tctgtatctg   6240
attccacttg gaactacgtt aaaggataat gaaacacaca ggattttgat tcagctattt   6300
tatttccttt gaatggttca tctttaagac tagtgtcatg tattctagtg atttcctcgg   6360
tggttcgtct gtctcgagaa tttatctata gcgttaaagt ttctcatgtt tataaagctt   6420
tgatggggaa tgttggtgct attcctgcaa ttaaatggat gtgggatggt tgttgtcaac   6480
agaggcacaa ggttttcttt tggccgcttg ttcataattg ccccaacacc agggccctgc   6540
tccatcgaaa gaattttgcg atgaatgatt attcttgtgt catgtgtaat cagcagcatc   6600
ttgagacaag agatcatctg ttcttccaat gtccttttgt tgtgctgtgc tggcaatatc   6660
tctgtcctct ttggatttcc ctcctttggg gtagtttgat cttcaagata cattatctgg   6720
ccttaagctt gctatctcca agcctttctt tatggagctg ataatgttga tcatatggtt   6780
tatatggctc acccgcaatg attttatcta aggctgttcc tccaatgatt ttatcttcaa   6840
ggctgttcct ccaagtgttt acagatgtcg gaagagattt aaggatgggc ttgcccttct   6900
agttcacaaa gcgaagagaa aatcttatca tggcatagtc acttgggtgg aaattttaga   6960 tagcctttt cttctctttt gggcttatgg cctcttttat ttgctcctct caagcaactg   7020
ttctcttttg tagaccttt aagctttata aataaaataa aaaatataca gtggggaaac   7080
```

```
tcactgttta gcctaaaaaa agaatttatc tatagccata ccaatataat gccatgatac    7140
taacacaagt taaaaaccag tggcgaagct agagattctg accagtaggg ccagttatct    7200
tgtttatggt gtaattttc agtaatgagc aatgtaaaga actacatcaa tgaagatttc     7260
tgaatttcta ctgggttcgt ttcaacacga aactgtatg caagnnnnnn nnnnnnnnnn     7320
nnnnnnnnnn nnnnnnnna aaaccgatgt gtatattaac aggagcattg agcaacaacc     7380
accgatttct gtgagtagca cttttccttt tttttctac ttcggaatta cattcgattt     7440
tttcgtatgg tgaagattta atctggatat gaactttctt gtaatatatc aatactatgt    7500
caatgttgcg aacacaattc aggaatattt taaacatttta actacttcta aaaaatgcta   7560
gtaccacatt atcaagtgcc aaagtacact aagtactccg actgtcaaaa aaaaaaagtg    7620
ccgaagtact cccaggacaa acacgcaccg tggcgtaatg aatgtccgt gtctggcgtg     7680 cgtggctacg ttgttctact actcgtctaa tagattagaa gcaaatgcct ccgcagaccg    7740
cagtcatgca gatcaatcat gaatttcttt gtgataataa gatcattcat ggacttgatt    7800
atgtctgcct tttggttgtg gcaaagggca caacagcaac aacagtgcag tgacggaaga    7860
tacagagacg ggagaccagg acactgaact agataagacg attgattgta cacgaactga    7920
acacccagag atggcctatg gatgcttctt cttcttgtgc gccggcgggg agctgcggtc    7980
gtgcatggcc acccgctgt agtcctcgct ggagatcagc ccttccgtga cggctccggc    8040
gtcctcatct tcctcctctc tccgaccgtc cttcctctcc gcatcgatct tcacttccat    8100
cgctgctacc tggacacgcg cagttcacga actacaaatc aaatcacatt ctcaattttg    8160
cttctcatgt gcatttgcct aagatatcac caatcaggat taatgatact ttcttctgaa    8220
caaccaaatg ttccttttcta ggatgaactg aacaaaagat ggcgtgtgca gagacagaca   8280
ggcacacgac caagcaacag cttcagctgt tgagccgccg agtctttgca caaagtgcag    8340
aagaaactct gttttttcgcg acactggatt ttttttttggg gaaatatg               8388
```

<210> SEQ ID NO 45
<211> LENGTH: 8001
<212> TYPE: DNA
<213> ORGANISM: Lolium rigidum

<400> SEQUENCE: 45

```
aaatatttcc ctcagtgttt gtaatatgtt gcaacatttc cctgtttgac acataaaaga      60
atatccaaaa ttgtttgcat cattcaaaca tactcttgca acaaaagtaa cgtgagcacg     120
agacaaatcc ccattggttt cagcagacct attaaaatag gcaaacataa aattcaaatg    180
cattcatcat ataaaacaac aatggttaat acatttgcaa cataattttg aaccttccct    240
agatatatgt tcaaataatt gcattgtgtt tctcatgtgt aaacaataaa caatgcacgc    300
ttgcaacatg ctaaaatact ccacacaaca taaacataat ttattccact aaattcccct    360
atcaacaaga ggggttgacc ttctccaatt caggagcaca ttgacaccgc atcgagcatc    420
ctatactcat tccatgtagt cccgcacctt ccttgatgtt ggccgcatgg agggcttcaa    480
ttttactcaa gctcaggtc cgtgggcaca agtgcttccc tctccaaatg aggggaataa    540
gcaacatagg actgttagag gaggaatgct acactagagt ggatggggag aagcacaaac    600
gatcattggc taaggatgaa ctccaaggag agtatgtatg gtagggaaaa aagtggtatg    660
tggatgggga ggaggagtag agagaggatg atgtaaagaa ggagaggtgg agggagagca    720
gcgaggcact catgttttaag ggagaatgtg aggtgcgaga gacaaatgca aactatagag    780
```

```
tggtcggaac caccaccgat caattggtgt tatatatatg ttttcaaaaa aggttatttt   840
tattaaaatc aaacgtttgc atcaaggcga tacaagcaac atgagcttac acatggccta   900
tgcataggta ggatgcacat ggtggtaaca ctttaagctt ccttgctagc tgcacatttc   960
acggttacgc ttggtgatga tgacacctt gcggaggtac cgcacaattt tgttttgtat  1020
ttagatgtac cttcatttca aaatgtgttt attattaaca ataaaagttg aatgtaaaat  1080
tgctctgtgc gtggaatccg tgaagacttg tgtaaattcc aatgaaggtc gtcagttgct  1140
tgcgacaatt ggatcattga caaccacccg acattgcatg ctgcaagtcg aaccctgact  1200
aaatgccgtc taaatgccac attagctggg aaggtttgca tcacaccaac gacaacatcg  1260
cttttgtgac gtgcaatatg gtgtagagat ggataatggt ctcctagggt ggtatttcct  1320
aggcgttatc ctcacaaaac cttgtcccca agatatcctt gatgataaat gttccaaaga  1380
gaaattaata tttcttcatt gtcattagac atgcaaagat gtgagtctat cggttccagc  1440
aaaccttgga gagggccttt gatcctacat acttttcatg agggtttcct ccgtaagaag  1500
cttgaaaaat tatttactaa ggaggaaata ttcttaactt gaaggtctta agtgccaaaa  1560
ccatcatgat gtttgggatt tgatcctaca tacttttcat gagggtttcc ttcataagaa  1620
gcttgaaaaa ttatttaccg aggaggaaat attcttaact tgaaggtctt aagtgccgaa  1680
accaccatga tctttgggat tgatcctac atacttttca tgagggtttc ctccataaga  1740
aggagaaaat attcttaatt tgaaagtctt aagtgccaaa accaccatga tctttgggac  1800
gatagattgc atccatttag ccaatcggta ccttttcttt tcaccgccgc ctcaccaaaa  1860
gaatgttgat agtagtaatc caaccttgt agggtatctg gagcttggaa gaaaggtaac  1920
atatataata gaaatgttac ttagtattaa attgatggga accaatgttc tgagctttgc  1980
aactcaaccc ttttcgaggc acttcacaac atgtttccac tacgctttt ttttgaacgt  2040
gcatttgtta gacgttagtc cctgacagaa catatattct acaattcagg ttgccgtgac  2100
acgtttctaa ctagtgacca gattgattta tgtaacatgt tctaatacac tctctaaacc  2160
taagatattt gcgagctgct caatcaactt acaactaggg cttcgatacg tgtagcccca  2220
tctcaagttg agatgattat taattgaggt tcttgccaca caaacggtaa tgtatcccct  2280
ccataaaaag agagagataa gagtatcttt ttttcaaact gtctatacaa ctgaaaaaca  2340
aatcatacca gcttgcgaaa agaaacttgc cagcgtaggc acctccttgc tataaatacc  2400
ggtcgcgtcc cccggctttt tcctcatccc ctgcttctcg agctgcacac ctcatcccat  2460
cgtcttcccc attgtcatcc catctctcct ttgcgattag caatggccag cctcgccgac  2520
ctcattaacc tcgacctcag ctccaccacc gacaagatca tcgtcgagta cctatggtta  2580
gcatcctcct ctgctttcca tctgctcccg atcttgacag aaaaagaaag atcctaccaa  2640
agatttagga tcacactctc gcgaaattaa actacttaca ttctacatac atgatctttg  2700
attctgctgc aagcctaacg ctgaagtttt tctgtcgagt ttaatctgcg cgatcttgta  2760
tcgtctgtaa ttctttgttt ctctctgttc agggttggag gaactggtgt tgacatcagg  2820
agcaaagcaa gggtgagtaa ttcgatctag agtctagaca tacacttctg aaaaatctca  2880
agagataccg gccggtgcaa cgatttctca ccatctgact gttttttttt ttcgatctga  2940
gcagacggtg aacggcccca tcaccgacgc gagccagctg cccaagtgga actacgacgg  3000
ctcgagcacc ggtcaggctc ccggagagga cagcgaagtc atcctctagt aagtgcaaca  3060
ccagtcttga ctttgccaac tgttgtaact ttgatcttca tgtttttttt ttttgttttt  3120
tacctggacc cctggagtaa ttttctctta attgccatct tgcagcccac aagccatctt  3180
```

```
caaggaccca ttcaggaggg gtgaccacat ccttgtaagc tcctctgcct tttatcttcc    3240
atgtttcaca ccgaacttgt tatgcaccat ggcatggcct aaagtaggaa gagtgaagag    3300
gacaggaaag gacacagcat gtacttcgaa aaaaaaatac aattctatat ttttgcaact    3360
tttaacctgg gtaaaatctt atgtaactag acccctttta cggttttact aagtatcagg    3420
atcttatttt tctaagtctg aatctttgat atggtggaca aaacaacagt gtgtgtcctg    3480
ttgtatacaa acctcaaaag tcacaagttg cccgactagt agttgcccat aactttcagt    3540
tcagagaaat tcaacttctt agtgctgatt gatgctattt gaaaaaaata ggtcaactag    3600
cacaactcat actatatctt tgtttaaata aataataaaa agcttcaccc aatgcagaac    3660
cgatgttacc actgtatttg gcactaaatt atctattcaa tattccttgt aggttatgtg    3720
cgactgctac acaccacaag gtgtgccaat ccccaccaac aagaggaaca atgctgccaa    3780
gatcttcgac aaccctaagg ttgcagctga ggtgacatgg taagaatact tctatcgaga    3840
gttcaagtta tcttttcttt tcttcctgcg gtgttgtttc agtcatgttc ttgtttcaaa    3900
catacaacat aaaattctaa ggaggagatt actaccagac actgtacttt gcatcagatg    3960 aaagtacaa atataaataa tgtccaacgt aagagctaag aaaaacatta aaaattcagt     4020
tcctggaaaa gaaaagctac taccaggaaa gtgatcagag catttggcac ctttgtatcc    4080
actttcctgc cttatctgtt ttatgatagc acacacacaa agtaggctta tctctgaatc    4140
caaaaacagg tacggtatcg agcaggagta caccctcctt cagaaggacg tgaactggcc    4200
ccttggctgg cccattggtg gctaccctgg tcctcagggc ccctactact cgccgccgg     4260 tgcggacaag gcgttcggcc gtgacatcgt tgacgcccac tacaaggcct gcctctacgc    4320
cgggatcaac atcagcggca tcaacgggga ggtcatgccc ggccaggtac tagacagcat    4380
gttgcagcaa cttggtttca gaaacacttc taactgtgat atggctgatg cgtgtgccgc    4440
caactctgac tctgaaccag tttcaaaaaa aaaaaactc tgactctgaa cctgattctg     4500
ccgtgtgaca gtgggagttc caagttggcc cgtccgttgg gatcgccgcc tccgaccagc    4560
tctgggtggc ccgctacatc ctcgaggtca gtgccctccg aacatattcg attctcaggg    4620
agaataacgt agttgcaact gtctgactga ctccaatttg atggtgattg ataacagagg    4680
atcacagagg ttgccggagt tgtgctgtcc ctggacccga agccgatccc cggcgactgg    4740
aacggcgccg gcgcgcacac caactacagc accaagtcca tgagggaggc cggtgggttc    4800
gaggtgatca agaaggccat cgagaagctc ggcaagaggc acccagagca catcgccgcc    4860
tatggcgagg caacgagcg ccgcctcact ggacaccacg agaccgccga catcaacacc     4920
ttcaaatggg tatgtagcca agtgtcagtg tggcatgtcg atcgtgctct cgtgacctga    4980
cgtgatgcta actaacaatt tgggttgact gacttgcagg gcgtcgcgaa ccgcggcgcg    5040
tctatccgcg tgggccgcga caccgagaag gagggcaagg gctacttcga ggaccgcagg    5100
cccgcctcca acatggaccc ctacgtcgtc acttccatga tcgctgagac aacgctcctc    5160
ctctgaacac acacacaacc tatacggcta tatctacatt cggcaacgat gattgttaca    5220
tcctcgactc tctcgatcga gggtggtggt gatggttaat ttctgcaaat tttcaaagtt    5280
ccattccttg tcttctttag cagtcctgtc tgttttttgg gggtgcgcct tccttcagtg    5340
tactctgaat aatgctatat ttccgcattc tgataaatga atttacggaa ccatttgtgt    5400
tgctgttcag aatctccaca tgtgtccacg ctctccactc tcttttgcca tgtcacactg    5460
atgcgaacaa attggatcat tgacaaccac ccgaaattgc atgctgcaag gcgaaccccg    5520
```

```
tctaaatgcc acattagatg gggaggtttg catcacctca acggtagcat cgcttttgtg    5580
acgtgcaata tgctgttgag atggatattg gtctcctagg gtggtactgt atttcctagg    5640
cgttatcctc acaaaacctg atctccaaga tatccttgat gatacatgtt ccaaagagaa    5700
attaatattt cttcattgtc attagacctg ctaaagatgc gagcctctcg ttttcccagt    5760
aaaccttgga gaatgagggt ttcctcctac gaagcttgaa atattattat ttactaatga    5820
ggaaatattc ttaacttgaa ggtcttaagt gccaaaacca ccatgatctt tgggatttga    5880
tcctacatac ttttcatgag ggtttcctcc gtgagaagct tgaaaaatta tttactaagg    5940
aggaaatatt cttaacttaa aaggtcttaa gtgccaaaac caccatgatc tttgggatga    6000
tagattaaat ccatttagct catcggtact ttttcttttc accgccgcct cgctaaaaga    6060
atcttaatag tagtaatcga atctttgtag ggtatttgga acttggaata aaggtagcat    6120
atacaataga aatgttactt agtgataatt ggagaatatt acttgtatag attgttgcct    6180
caatgagctg tttatataga gtacaagcct tggagaacaa ggataataaa gatagattac    6240
aactcaaact actaaaccgg tatatactct aatatcccca tgtagtgtct acctctggtg    6300
aaacgatgtt gaaactagag cgtatattat tgaatgacgc agtcgggagc cccttggtga    6360
aaatatcagg aaactgtgca cttattggaa catgaagaac acggacttct ccaagagcca    6420
cttcctcact aacaaagtgg atatcaatct caatgtgttt agtgagccga tgctgaactg    6480
gatttgaagc catatagact gctgaaatat tatcacaata tacgatggtt gcatgctcaa    6540
ttggtcgatg gagctcaaca aggagttgcc ggagctatac tgcctccacc gcagaataag    6600
caacagagcg atattcagct ttagcagaga accgtgaaac tgtgacctgc cttttagagg    6660
accaagaaac aagattatca cccaaataaa tacaatatag ccagatgtag atcatcgagt    6720
atctggacaa cctgcccagt gtcaagcttg ttggagagga tgaattaaga agaagaccat    6780
ggtcgagcct ttgggatacc gaagaatgcg tttgacatga gcgagatgag gtgtgcgagg    6840
atcatgcata aagagacatg cttgttgaac agaatatgag atgtcatgac gagttagagt    6900
ggcatattgg agagaactag tgatgctatt ttagagtgta cggtctggaa cacgaccacc    6960
atcagccgac aatttggcac caatatcagc cggggtacgg gagggttgac aatcagacat    7020
aacagaatga tggagcaaat ctaaaagata ctgacattga gaaataaaaa gagtagattt    7080
tgtgcgagaa acactaatgc cgaggaagtg atgtaggggg ccaagatcag tcattgaaaa    7140
ttcacaatta agagaggaga tgatatgttg tagaaaggaa tcagaagaac agtaagaata    7200
atatcatcaa cacaaagaag aaggtagacg gcatgagcag cggattaaaa aataaaagga    7260
aggaatcaga tttagtggga atgaagccaa tggtttgaat aaaggtgtca aaatgtataa    7320
accaagcacg aggagcttgt ttgagcccat aaagagcctt tcggaggtgg caaacatgac    7380
ccaatggaac ctcaataccc tggaggtggc tgcatgtaca cttcctcatg tagatcacca    7440
tgaaggaaag cattttttgac atctaattgg tggataggcc attgttaaga tagtgcgaga    7500
gagagaacga cgcggatggt ggcggatttg acgacggggc agaaggtctc atcgaaatca    7560
acacctcgtt ggtgggtgaa gccccgaacc acccatcgag ctttatgacg agcgagggta    7620
ccgtccgcat tgtgcttgtg acggaaaatc catttgccag agacgatgtt ggcaccgggg    7680
ggaggggtac gagtgaccag gtgttgttat gcatgagagc atcgtattcg tcctgcatag    7740
caaaagtata ctacaacagg gaaagaaaag cctattaccg tgttcgaatc gccaaattaa    7800
aaattcttga caactaccag atagcagttt cattgttttg ctttcaggta tcttaagaca    7860
actgcgaata cactagctga cacactgtct tacttcatca acatatttg actaacactc    7920
```

```
catcagcata tgttggttca gtgacaggaa agttttggtt ggtaaatgaa tcctgagttc    7980
tctttcacat attccctgtt g                                              8001

<210> SEQ ID NO 46
<211> LENGTH: 1023
<212> TYPE: DNA
<213> ORGANISM: Lolium rigidum

<400> SEQUENCE: 46
gaactggccg taaggcgtgg tgccgccttg gtgcaggagc caattgaaat tactgatgag     60
aacggcactt atatttcggc ttctgtccgc acctacggag ataccgtcca tacctttgtt    120
gatcgctcca aatacaacgg ttttgctccc ggctacaagg cagtcgccgg taagagcggt    180
cgcggtgttg gtctggcctc agtcgaccac gtagttggaa acgttgatga agacaagctc    240
ttggaatggg tggagttcta cagccgtgtt ttcggcttct atgttttcca atacttcgat    300
gcctccgata tcagcactaa atactccgcg ctggttccca agtcatggc caataagagc    360 ggctctatta agatgcctat caacgagccc tacgagcagg gtttgcgcaa atcacaaatt    420
agcgagtatc tggacttcta tcatgcaccg ggagtgcagc acattgccgt cactacccgc    480
gatatcattg ctacggtgaa agaactgcgt agccggggca tcgatttcct gcctacgccg    540
gcctcctact acgctaccct cactgagcgt gtcggcaaaa ttgatgaaga catcgatcaa    600
ttggctgaac ttggcattct tgtagaccgt gaatccgaag gttacttgct gcagattttc    660
accaagccgg tggaagatcg tcctaccctg ttctttgaaa tcattcagag aaagggcgct    720
aaaggcttcg gtaaaggtaa tttccaggct cttttcgaat ctatcgagag ggaacaggaa    780
aatagaggca atctctagac tgctgaaagc aaatctgggc cggggcggcg ctataatcaa    840
tagcgttgtc ccggagcagc agtggcgcct gacgtactca ataatcttga tgaccatatc    900
agacaggcca ggcatgctgt cgagtttctg acgtccgatt tttgtcctcc tgtaattgac    960
agcatcgagt ttttgagctc gtctctggcg gctcagatgg tggcccgaga tccttattgg   1020
ccg                                                                 1023

<210> SEQ ID NO 47
<211> LENGTH: 217
<212> TYPE: DNA
<213> ORGANISM: Lolium rigidum

<400> SEQUENCE: 47
ttctccttcg ggctcggcgt gccactcgcc gcgcagtccg acctctccac ggggaacact     60
gcgcacgcct cacgcctact acgcgcacgc tcgggctctc tctccttcct cttcaccgcg    120
ccgtacgcgc cgcacgtcgc cgactcggcg accaccgcgt ccctgccctc cttctcggcg    180
gacgccgcgc ggcgcttcac gggaacccac ggcggcc                            217

<210> SEQ ID NO 48
<211> LENGTH: 1497
<212> TYPE: DNA
<213> ORGANISM: Lolium rigidum

<400> SEQUENCE: 48
ggccgaggcc ttcgtcgcga gcgtggacgc cggagcgcgg ccagcctgcg ccccgactga     60
tctcggccac gggtttggct tcgcggaggt ggagctagcc ggggacagcg ttctccgctt    120
cgtgagctac ccggacggca ccgacgtgtc cttcctgccg gggttccagg acgtggtgag    180
```

-continued

```
ctccggcggg acgccggact tcgggctcac gcggtttgac cacgtcgacg ttaacatccc      240
ggagctggca cctgtggccg ccaatgttgc cggcttcacc gggttccaca agttctggga      300
gttcaccgcg gacgacgtgt gcccggaaga gagcggggtg aacggcgtgg tgatcgccaa      360
caactcagag aacgtgctgc tcagtatctt ggagccggtg ctcggcacca agctgcggag      420
ccacgtcgag acgttcctgg accaccacgg tggcccaggc atacagcacc tggcaatgac      480
cagccacgac atccttggcg cgctcaggaa atccgagct cggtcctcca tgggcgggtt      540
tgagctcctg ccgccgccgc cggccagcta ctatgacggt gtaaggcagc gcgccgggga      600
cgtgctgtcg gaagaacaga tcaaggagtg ccaagagctg ggcgtgcggg tggacagagg      660
gtatgacgac ggagttgtgc tccaagtctt caccaaaccg gcgggagaca ggtgcgttca      720
tttttcatgc tcaccaaatc ctctgaattc ctaaccaaaa ctctttcaag attaaatctc      780
gtcttctccc tcttatatat attcaggcca accttactgt tagagtttat ccaaagaatc      840
gggtgcatgg tcaaggacga gaaccagcag gaataccaga gaggtggatg tggcgggttt      900
gccaaaggga acgtttctga actcatcaag gacattgagg acaataataa taagactatc      960
gatgctcccg caagccaggc ttgatgacaa tacaagatga tgcacccggt actattactg     1020
ctagatcata cctggcgcct tgctgcggga acgcacaagt atatctttag aaaataattg     1080
taatgaaagt gacattgggt gcaactgata ataagagcca agttatcat attttatcaa     1140 ttaatttcag cattttcgag tactccccccc ttttttgaat ttgagtgttt cgtgaacaag     1200
tgtattaaca atgtaccaga tcgagaacca ttttattatt ttactcatcg ttaccaacgg     1260
acatatttca gtgaagatta ccgaataagc atttcaaata cgcacaatac ccctaggttg     1320
ccagtttctt tttttttgtga agaaatagac tctgaaaatt atgtacagac tctgaaagaa     1380
cataaagtcg taccaaactt tataattggt tggcaccaac aaatagttaa cctgcaatgg     1440
gtctaacaac aaaggaaacc acctatttga attgggatat tttaattagg atacaat         1497
```

<210> SEQ ID NO 49
<211> LENGTH: 691
<212> TYPE: DNA
<213> ORGANISM: Lolium rigidum

<400> SEQUENCE: 49

```
cggcggagag cggtctgaac gtggtggtgc tcgccaacaa cacggagacc gtgctcctga       60
acctcaccga gccggtgcat ggcacgaagc ggcgcagcca gaaacagacg taccttgacc      120
accacggcgg gccaggcgtg cagcacatcg cgctggccag cgacgacgtg ctgggcacgc      180
tcaggcagat gatccgggcg gccggggcct ttgaattcct ggaaccgccc ccgcccaact      240
actacgacgg cgtacggcga cgcaccgggg acgtgctgtc tgaggccag ataaaggagt      300 gccaagagct gggcgtgctg gtagacaggg atgaccaagg agtttttgcta caaatcttca     360 ccaagccggt gggagagagg tacctagctc gtcatcgatc tgtcgtctca cttacagtat     420 tttcttttgtg atcgatgatc ccagtaacag taacctacat ttgtcttctc aggcaaacac    480
ttttcctgga ggtgatccag cggatcgggt gcatggagaa agacgaggag agcgggagag    540
agcaccagag gggtggctgc ggcggctttg gcaaggaaa cttccacgag ctgttcaagg     600
ccgtggagga gtacgagaag tctcttgaag ccaagcttgt ttgtcagtaa cttggggggtg    660 tgtaatcgtg tgttcatgat gggatacgct a                                     691
```

<210> SEQ ID NO 50
<211> LENGTH: 213

<212> TYPE: DNA
<213> ORGANISM: Lolium rigidum

<400> SEQUENCE: 50

| | | |
|---|---|---|
| ccacgtcgag ttttggtgcg ccgacgcggc ctccgctgcc ggacgattct ccttcggcct | 60 |
| cggagtacca ctcgccgcgc agtccgtcat caccacgggg aacacagcgc acgcctccca | 120 |
| cgtgctccgc tcacgcacag gctctctcac gttcgtcttc agcgctccgt acgcgcggca | 180 |
| ctgcgccgcc gctacggcga cggtgccctc ctt | 213 |

<210> SEQ ID NO 51
<211> LENGTH: 782
<212> TYPE: DNA
<213> ORGANISM: Lolium rigidum

<400> SEQUENCE: 51

| | |
|---|---|
| tttgggacgg agggagtatt tgttatcggt ccttcgttat catttagtaa aagaactgcg | 60 |
| taaatttgta ggagaagcat ggctcaaaaa tggcattctt ggatggtaat ccacctgaaa | 120 |
| ggctatgtat gcctattgtc aaccacattc agtctttggg tggtgaggtc cgcctgaact | 180 |
| ctcgtattaa aaaaattgaa ctgaaccctg acgggactgt gaagcacttt gcattgagtg | 240 |
| atgggactca ataactgga gatgcttatg tttgtgctgc accaggtgtg atttattttc | 300 |
| aagaatcatg ttttctttac acctgttcag tttaactgac tagcctgtta ttcagttgat | 360 |
| atcttcaagc ttcttgtacc ggaacagtgg agagagatct cttatttcaa gaggctggat | 420 |
| aagttggtgg gagttcctgt catcaatgtt catatatggt gagttgattg aaactattgg | 480 |
| ttctaagtca agacatcttt gtgtttttgg ttcgacttat atggtcctgc ctcatgtgtt | 540 |
| atttcaggtt tgacagaaaa ctgaaaaaca catacgacca ccttcttttc agcaggtatt | 600 |
| cctttcgtca tactcatctt cctcttggca cctagtgcat tttgttgtct tgtattcaga | 660 |
| tcgggcgtct tcaatcttac ccctacatgc tttgaatgtg ttttgtttg ataccaaata | 720 |
| ccagatgtct cttatgttga ttttgttcac ttctgtttca ggagtcccct tttaagcgtc | 780 |
| ta | 782 |

<210> SEQ ID NO 52
<211> LENGTH: 2009
<212> TYPE: DNA
<213> ORGANISM: Lolium rigidum

<400> SEQUENCE: 52

| | |
|---|---|
| cagaggtgct tcacaagcag cagtgtccag ctgctgaaaa gtagttctcc aacgagcgca | 60 |
| ggtttggcgt ctcttggctc aaggaataga gggaaaaaat cacgccgtgg gcttgctgct | 120 |
| ctgcaggtta agatttcgtc cctgttcgga aaataaagtg gtttctctat tttatctcac | 180 |
| cacagccgtt tcttgtgaag taattgtttg cattttctgc aggttgtttc ccaggattta | 240 |
| ccaagacctc cactgaaaaa cacaattaac tatctggaag ctgggcagct tcttcatct | 300 |
| tttagaagca gtgaacgacc cagtaaacca ttacaggtcg tgattgctgg tgcaggtctg | 360 |
| atgtaactcc tggactagaa catatatgaa tttcacaaat tagataccc cctgagtgaa | 420 |
| gcacaaactg cctcttagcg ttactcgtct ctggtgtgaa ttgtgcagga ttggctggac | 480 |
| tatcaactgc aaaatatcta gcagatgctg gccataaacc catattgcta gaagcaagag | 540 |
| atgtttggg cggaaaggtc tgatagtttc ttacatctgt tgcttatctc atctctaaaa | 600 |
| ttgtgctggt tatttaatct gacttttcag ttgctgtcgt cattctgagt agctcacctt | 660 |

```
caccattatt gttgcttgat tgcttctatc gttgtatgcc ttgaacagtt agctgcttgg      720
aaggatgaag atggtgattg gtatgagact ggtcttcata ttttctgtaa gttacggtac      780
ttccttgttc ctttgtgccc tgtgtatagc gtgtttccac tggcagtgta tagatagtat      840
ttgatgcgtc agacaaatat ctacataata ataagataga acaccttgag taaagtacaa      900
aatgatcttt gaggagccac attgaggttc tgaaattgca aattagtgaa gagtttcata      960
ccgtcaattt tttaggttgc ttgcatttta ttaatgggcc ttattctctt aataatattt     1020
ttagtgggtt ttttttttgcg tgaccgtatg aaaacatata gcttaaattt caatgttcca    1080
tacatcgttg ttggcatggt tgaatatttc ttttgtctat aaattctctt ctaccagcat     1140
ttcctccctg ccagtagctt gtgtacggta ttcattctgt gcatgtatgt aaccatatgt     1200 tttttttttgg gttttaagtt ggagcttatc ccaacgtaca gaatttgttt ggtgagcttg    1260
gtattaatga tcgcttgcaa tggaaggaac actctatgat atttgccatg ccaaacaagc     1320
caggagaata cagccgtttt gatttcccag aggttttgcc agcgccttta aacggtaaga     1380
tcatacatag ccctggtgtt gcttaataga tgaaagaatg caagaaaac ttaggaatgc      1440 atcctagtgt tagttctttc attttgctaa tatttgaatg caactagtgg ggtatattag     1500
tgcaaacaac attgtcatgg ccatccagct gttctcttcc catcaatgtc agtttatcat     1560
tgattatgca tgtatttaac aggaatatgg gccatactga agaacaatga aatgcttact     1620
tggccggaga aggtgaagtt tgctattgga cttcttccag caatgcttgg tggccaagct     1680
tatgttgaag ctcaagatgg cttaactgtt tcagagtgga tggaaaagca ggtatgagcc     1740
caccaagtca gttagactca tctctttgta ctgaacacat agccgtctca attcacactt     1800
gatatatgag gatatgttgt aacgcgatat tgctgccttc cttcttttgt tatatttta     1860 ggaagaagcg tggctaggtc cataaatgaa actatatgct caagtttcca tacttttttt    1920
ccacccagcc cttctgtatg caatgtaggc ttaagtaatg cttatagttc tattaatctt    1980
gtaagaaaat cccaagtgca caacgatgt                                       2009
```

<210> SEQ ID NO 53
<211> LENGTH: 1173
<212> TYPE: DNA
<213> ORGANISM: Lolium rigidum

<400> SEQUENCE: 53

```
ttaaccagaa ttgtactttg aggactattg accaaaggcc caaatgcttt tgctaagaag       60
gaattcatta gtgaacttaa aattatagaa acctttggca ttgcaaattg tagttatcaa      120
ttactgaagt gtagcatttt tttcattgct aacatgtcag ttggctgttg atttcgtgaa      180
tcattttagt ttgaataact gaataaccgt gctagcttaa ctgaaagaac gaaggacatg      240
gatgcatact cgtaatttta attttccctt gttctttaac tctatgcagg agtattatga      300
tccagaccgt tcaatgctgg agttggtctt tgctccagca gaggaatgga ttggacgtag      360
cgacgctgaa atcatcgaag caaccatgca agagctagcc aagttatttc ctgatgaaat      420
tgctgctgat cagagtaaag caaaaattcg taaataccat gttgtgaaga cgccgaggtg      480
aggacatttt gctaacaccc atcctgttga ttaatcaaaa ggacacctga tgtggtcttg      540
ttctcttaca ctgtttatat ttttctggct cgctgttaca gatctgttta caagaccatc      600
ccagattgtg agccttgccg acctctgcaa cgatcaccga tcgaagggtt ctatctggct      660
ggtgattaca cgaagcagaa atatttggct tccatggagg gtgcagtttt atccgggaag      720
ctctgtgccc agtccatagt ccaggttctg gttgcacata gatgagtcaa acttctattg      780
```

-continued ttgtgttggt gcgttatggt atggcattat tgtggtctaa tcacctctct gcttgcagga 840
ttctaaattg ttgtcccgta ggagccagga aagcctgaag acaaaatccg aagttcccgt 900
cgcttcctag gtgtatttag ttagcacaca attcattctt agcacattct gtggtatttt 960
cacactgttg tagagttgaa caggtgattg agctgatatc catattgtga aaaaggaaat 1020
ctgtaaaacg agaagctgca taaaaacagc tctgatccat atagcaattc ttacgttaga 1080
cctttccgga aggcaaaagt gataaaaaaa aaagggatct tagatattat cttcgtttgc 1140
tacaattggg aactggatca ttaaccgctt act 1173

<210> SEQ ID NO 54
<211> LENGTH: 1174
<212> TYPE: DNA
<213> ORGANISM: Lolium rigidum

<400> SEQUENCE: 54
ttattcaaaa tagcaattag acatgtgttt ctattctcat tttaatttcc tttttcttat 60
ttgtaataca gatgtttctt tcttttgttc ttctcaataa tggagtcata tggtgtctga 120
tacagttatt taatcagcac agggtgttcc tgatcgagtc aacgatgagg tttttattgc 180
aatgtccaag gcactcaatt tcataaaccc tgatgagtta tccatgcagt gcattcttat 240
tgctctaaac cgatttctcc aggtacaacc caattactct attcctcctg gagagatagc 300
tacatatttg caaaatatct agtatttgtt atttcggtcc ttcgttatca tttagtaaaa 360
gaactgcgta aatttgtagg agaagcatgg ctcaaaaatg gcattcttgg atggtaatcc 420
acctgaaagg ctatgtatgc ctattgtcaa ccacattcag tctttgggtg gtgaggtccg 480
cctgaactct cgtattaaaa aaattgaact gaaccctgac gggactgtga agcactttgc 540
attgagtgat gggactcaaa taactggaga tgcttatgtt tgtgctgcac caggtgtgat 600
ttattttcaa gaatcatgtt ttctttacac ctgttcagtt taactgacta gcctgttatt 660
cagttgatat cttcaagctt cttgtaccgg aacagtggag agagatctct tatttcaaga 720
ggctggataa gttggtggga gttcctgtca tcaatgttca tatatggtga gttgattgaa 780
actattggtt ctaagtcaag acatctttgt gtttttggtt cgacttatat ggtcctgcct 840
catgtgttat ttcaggtttg acagaaaact gaaaaacaca tacgaccacc ttcttttcag 900
caggtattcc tttcttcata ctcatcttcc tgttggcacc tagtgcattt tgttgtcttg 960
tattcaaatt gagtgtcttc aatcctaccc ctacatgctt tgaatgtgtt tttgtttgat 1020
accaaatacc agatgtccct tatgttgatc ttgttcactt ctgtttcagg agtccacttt 1080
taagcgtcta tgcagacatg tcagtagcgt gcaaggtact aactcaagga gttattaata 1140
ttgcatagat actaatatga ggcatgtgat cctg 1174

<210> SEQ ID NO 55
<211> LENGTH: 9193
<212> TYPE: DNA
<213> ORGANISM: Lolium rigidum

<400> SEQUENCE: 55
caacaaggat gacatcgccg acgagatctt ctcggtgtca ctcttcagag atcccacact 60
gaagtgagac tgtgattcag aaacatggaa tcattatggg ccgaaataca ttcagtcttg 120
gaggtttact tgtttgaacc gaatgttcct acctcgaaga atgtggttct tgtgactgcc 180
cagtagaaca gcaccgtcac cagtgcgagg tacgtcccta tgacaacccc ggttgcgaag 240

```
                                               -continued
atctcgttca acctccagct atccggtctc cgcgatggct tcactcgatc cttcgatatc      300
gccatgatag tccctgatca cggtgacaca tcgataacat tgcgagctat tagcatcggt      360
tccggatgca gcaagcctca ttctcacatg ataagttcag agttactagt gcattaccat      420
cgttcagtat ggctatgatc aggaccataa atggaggaaa atcgtattcc catattgacg      480
ccagaagaac aaacccaagc tgcaaccgta caagacacag attagtgcag tgcctattga      540
tcaccgatcc attatcagat tcctgcattc ttaccactat ccgtatagtg atggacactg      600
cataaatctg cgtcggtaag gcataaatcg tcagaagcaa aattgtactg gtacaagaac      660
acgaagcgat agaaactgaa ctcaaatcta ccgtgtagtt cttcatgcgc tggaagatgg      720
tgcggctggt gaggacggcg gagacgatga cgctgagacc gggctccgtg agcacgatgt      780
cggcggcggc cctggcggcg tccgtcgcgt cggatactgc gatgccgatg tcggccttct      840
tcagcgccgg cgcgtcgttc acgccgtcgc ccgtcatccc gcacacgtgg ccttgcgcct      900
gcaggatccg cacgatctcg tgcttgtgct ccgggaacac gcccgcaaac ccgtccgcgc      960
tctccacgag ctcctccacc ggagccgccg cccgatcgcc accgcggccg aacagcgcct     1020
ccgacgggtg catgttggtc cctgtcccga ggcgccggcc tgtctccttg gcgatggcca     1080
ggtggtcgcc ggtgaccatc ttcacgcaca cgccgagatc cagtgccttg cggatggtgt     1140
cggcactgtc gtgccgcggc gggtcgaaca gcggcagcaa gccgcagaag acccacggcc     1200
cgccatggcc gtgccttgat ttctccggga cctcctgatc tcagtcatca aatgacggtg     1260
cttcagaatt tagactacag tgtttcactt ggtgctacca gactactact tgaactacta     1320
tgagtctgat attacttaat tacaagtacc tggtaagcaa ctgctagtga tcggaggccc     1380
ctctccgcaa atctgttgac gacacgctcc accttctcgg cgatgtcatc cttgttgtag     1440
cacaggttga ggatctgtaa gatgatcaaa gtcagatcag agatgttcta ggctatggct     1500
aaacactgta aataaagtcc cattttgttg acagttagca tttagcagca ctgagataca     1560
ctgatgaatt tcttcaacag gtggagagga gtacctgctc agcagcacct ttgctgaccc     1620
ggaaccaatt gccaccataa tcaatgtatg ttatcgccgt cctttgtcg acgggattga     1680 atgggagaaa gtgaacttca gtgatgttag cgcgtgcctg acgatgaaca ggtaacgtcc     1740
gtgaaccatt attaatgtgc aggctcagat caagtgaaac agattcagaa cctctttggg     1800
atcagcaagc atgtttatga tggccatgtc gatagcatct tggttctcca ctcttgatgc     1860
tcttgcagcc aacaggataa tcatgtccct gtccattcct ccgctgaaaa cctgaactta     1920
ccaaaatgat ggatggataa gctttgcatg aaaaccgtta cactgcataa ttttttaaat     1980
ttgaaaggtg actatactcc ttttttaggt gcaaagggaa gcacctcgat taggtttttg     2040
tcgacagtaa gatggttgac agtgagcgtt ccggttttgt cacagcagag aacatccatt     2100
cctgccatct cctcaatggc tgtcatcctt ttggtgatgg caccctgcaa agtttcagaa     2160
aaaaatctgt gatccacaat acatatactc tgttaactga acagaggtgg cagcaatata     2220
tccagacacc acctgttgag ataggtgatg agaacctatt gcaagtgtga ccgacaaaac     2280
agtcggcatc gcaatcggta tccctccgat cagaagcaca agcacattgt taattccgac     2340
ccggtatgac cggtgctgga ccgcgaacat gacgataacc tcgacgatca ccccaaccac     2400
gatggagcag atacaaaagt tgcctatgca ggtaagaacc tgaaattttc agtaggaaaa     2460
ttcagctcac cccatagaca cttccgtgca actaatgctc aacacatcaa atgacattct     2520
agtgtggtga cttgccttct ggaaatggcc aacaacctct gtagagtcca ccaaatgagc     2580
tgccttcccg aagaaagagc ggaccccggt tgcaatgacg acagcttcga tctcaccatg     2640
```

```
cttgcatgtt gaaccagtga atactaggtc gccagtcctt ttggtgacag gtagggattc    2700
tccagtgaga gctgactgaa atattgaaaa ttaacagtaa gagaccagat cacttgacag    2760
aacaatcagg cctacacggt aaatgtgatt gcctgatcaa ttttgagaga atcccctcg     2820 agcagtcgcg catctgcagg gacaatgtca ccaagcctga tgctgatgat gtccccgggt    2880
accaatacag aagcatccag ctcttgccat ttcccatctc taagaacctg cattcacacc    2940
aaggcatggt cagacaaaat caatgcatca tcacttgcat gctattccta caaacctttg    3000
ttttaggcgc aagcgggcc atgagacaag ccgcggcatt gcctgcgttg ttctcctcca     3060
cgaagctgat cgttgagttg atgaaaagaa ggcagacgat tcccacgaag tcttcccagt    3120
ccggaccctg actctgaaga aataagaaag caacaccaaa taattccacc actcgtcttc    3180
tgttaaacaa tagtgcattt cccctgaaaa ttcagagact ttcttgactg aaccggcagc    3240
agaagatagc atagtatcag tgtacttaca cccccatttg ccaagaccag tgccatgatt    3300
gctgctgcct ccattaccca tgacagtggg ttccacatga agctgatgaa cttgagaacc    3360
ttgttctcct gtcagaaata tgttttttta aattaggaat tcaggacagg taaacagaga    3420
gatagtactt agtagtatag atggtgaatt tacacgcttc tcctctagtc ggtttgcgcc    3480
gaacagctgc agtcgttccg cgacatccgc tgaagagagt ccactgcggg acgtgctcag    3540
ctgctcaaag acgtcttcca ggggcaggtt ccctgctca cacccgttg tcatgaacgt      3600 catttgcaca caatgctggg agtatgaaca ttgcagtccc tatcctgact gatgaaacta    3660
acttaccaga tcaatgtctt cggtgcagaa actctcaggt ccaagcaacg gttttcccaa    3720
cccgccatca tccatgcctg cagcttctgg acggcacgaa ggtctgcaag gttcatcgat    3780
cggattagga agagaactgc acgtctgcgg atttgtttca agaaaaatat ttggggagac    3840
gaagtgtgac gcgggatgga agaactcacc gttcaagtct tctagaatct ggtggaatgg    3900
agtcgctagt gtactgttgg caatgtattt tggtggttac tgtcgatgag gagtgaagag    3960 ggagggagg ttgctgcta cccttttcc cgcgttttgg gagcatggct cgtccaagcc       4020
caaccaccat tcaaactttc cacggcagtg agcagacggt cgcttcaaac caaccggtcg    4080
agtggaagtg tggaacagca ccgtagcggc ttcacagctc cgaaatacct ctcccatcgt    4140
gcttgcatct cagaactttg agttaattgc aaaaacataa ttatggctag attttccaaa    4200
accaccggtt tcttttttt tccaaaaaaa ccaccttcca agtgtaataa ttgttttttc     4260
agaaaacacc aaattgacac cattttgag cggtggcgcc cactataagc aatgacggag     4320
taccaaatat tcacacattt ttaacggaga agttaaaaca aacatagggc ccaccgctca    4380
cacttcaact atatcttcct cctacacatg ctggaatttg gggcatttgg tctttggccc    4440
atggcccatt atcaaattct gaaactcaca tgacccattc caaaaatcag tgacaacact    4500 agtggggct aaaatttagt cccacattgc tagttgagag agagttggag tggtatataa     4560
ggtggactgt tctagtccta gtaagtgagt gagaagagag agagcccacg cgcactcctc    4620
ctcctctgct gcccggcgta gatgcaatcg atttgtcttg tttagatgtg atttgttcat    4680
ctaccttact agtctgcacg attagtttac ttgttatttt catagtcatg atttatcaat    4740
tacttgtacg gattatttca tatggatatt ttcttatata ttcaacaaca cattccctct    4800
ttaactcttg gttccctcc ctccactact cttgggccgc tgcttcgccg atcccagcag     4860
tcgcgccacc atattctaca ccagcgtcca aaaacaaacc tttccacgtc gcttgtctta    4920
aaggtgaaat gatcgaaaag gtcgactaga gggggtgaat aggaaactgc atatttgtaa    4980
```

-continued

```
tgttttttct taaatttacg dacaacaata ataggttt tctagatatg gaactaggtg    5040
acaacaatct atatgcaaga tacaattagc tcaacaaaat cgacaagata ataggctagt    5100
gaacaaataa gtaaaggcaa ggatgtgaaa tgaccacaca gggagacgta tatgtatccc    5160
gaagttcaca tccctagagg tgcagggtag tctctattgg aggatgtgcg gaggcaaaat    5220
gccccctcaa caccgcaaat gccccatctt cttctccttg tgactttcac acaaggaaaa    5280
tgcctcaatc tactaatagt acgcttgaag gtagtcacca aacctttata aacttgttcg    5340
gagccactcc acaccettga gtctcccgaa gcttgcccaa cgcacaatct acaaagtaat    5400
ggcgcctaga caatctcctt ccttctacgg agcccaaaca ccaagagtaa ccagattcat    5460
aaagaaaaaa acaaaggaaa tcgtatatcc tttgatgaag tggtagatgt aagtatgctc    5520
tatcttttcg taaataaac atgattcaag tgttgggagc gagatcacaa agtttcgtac    5580
tttgcaacaa tatatgagag actaatggag tttttttttt gagagagaga ctaatggagc    5640
agtctcacct tcgtgaggta gaagatgggc ttatatattt ggggcaaaaa tccaattcta    5700
ggcccgatgg tttcggggga aaccctagcg gctcgacttc ttgatagtaa ttcatataat    5760
ttatttcatt gattcatccg cactaaattt aactcgggta tgaaaacata aatccaattc    5820
agcatttggg gaagaatcct ccactttttc tttgcacaat caaacgttca tgcaatcttt    5880
gtagttcgcg tgttttccat atcttacttt gttttgctct aaatacttat cgcgagttca    5940
gtaaatcacg acataattca gcctaaattt tagctaagtc tacaacacac atatttagag    6000
ctgaaggagt acaacaaaag aggctcaagt attttaagcc ggcgaaattg tgttgaacc    6060 ggccggtgtg ctcagctgaa ccgtgcgaag tgcggtatat tccagggaaa acgtagagcg    6120
cagcaggcgc caaacggcat cctccgccac cacatcttct tcgcctcagt gatccctcc    6180 gctttgtcgc tttcccaccg cccaaaaacc tccaactcca gccggcgacg agccttatcc    6240
cgcaccataa atatacctc cgcgctccca ttcccctccc gttgacccaa gcctcgccgc    6300
tccctctccg cctacggtaa gcctcctccg cgcgcgcacc ttcctgcacg aacccgctgg    6360
ctgcgggtgg ggctaatcct ccgcgccgcc gcggttccag ttcctcgttt tttcggattg    6420
gtgctctagt aggaagaatt cgcgttgggg tggggtgggg attagctttg gaattgggga    6480
ttttctcagg gtttatagga gtactttaga ggcgttggaa attcccgatt gactggaaaa    6540
atcgacgcta ggcttaccac taaggctgca tatgcttgat tattctaatt catttgctta    6600
ctgtacagcc acacagatcc cagttgccca tttcatgcat tatttgttca gcaaattact    6660
tgaatgaacc acaactcagg gaattattta gttaataatg aactcatgtt tctactgtaa    6720
aaataaatgg atcccttaag cctatcatat ccggttgaac ttacactata caactgccct    6780
gctccttctg tctttacttt tatgccgcat ttccacgaat tcaaagacca caccacgttc    6840
agtggatcga attctggctt ctcagcaaat tgtgactttt gtttaccaag ttatgctagt    6900
ctcgatcagc cgacccgtga cacctggctg ccattcatac cagagggcct cgtcatgaat    6960
tgctcttctt gactatgcag ttctcttccc acgctcaatc gttgactaaa ccagggctga    7020
caagaatcta ccagcggttg cttcattatg gataccggct gtttatcatc tatgaacata    7080
actggagctg cgcaagtgcg gtcctttgtg ggcaacttc atacacagag gtgcttcaca    7140
agcagcagtg tccagccgct gaaaagtagt tccccaacga gcgctggctt ggcgtctctt    7200
ggctcaagga atagagggaa aaaatcacgc cgtgggcttg ctgctctgca ggttaagatt    7260
tcgtccctgt tcggaaaata aagtgggttc tctattttat ctcaccacag ccgtttcttg    7320
tgaagtaatt gttggcattg tttgcaggtt gtttcccagg atttaccaag acctccactg    7380
```

```
gaaaacacaa ttaactatct ggaagctggg cagctttctt catcttttag aagcagtgaa    7440
cgacccagta aaccattaca gatcgtgatt gctggtgcag gtctgatgta actcctggac    7500
tagaacatat atgaatttca caaattagat acccctttga gtgaattaaa ttgcctctaa    7560
gcgttactac tctctgacgt gagttgtgca ggattggctg gactatcaac tgcaaagtat    7620
ctagcagatg ctggccataa acccatatta cttgaggcca gagatgtttt gggtggaaag    7680
gtttgataat ttcttacatc atttcttatc taatctctaa aattatactg gtaacttaat    7740
ctgagttttc atttgttgtc atcattctga atagctcacc ttcactttta ccattattgt    7800
tgcttgattc cttctatcct tgtgtgcctt gaacagttag ctgcttggaa ggatgaagat    7860
ggtgattggt atgagactgg tcttcatatt ttctgtaagt tatgatactt cctttgtact    7920
ctgtgtatag gttatatcca ttggcagtgt acagatagta tttgatgcct cagacaaata    7980
tgtacacaat aataagatag aacaccttga gtgaagtaca aagtgatttt tgaggagcca    8040
cattgaggtt ctgaaattgc aaataagaga agagtttcat actgtcaaat ttttaggttg    8100
tttgcatttt attaatgggc ctcattctct taataatatt tttagtgggt tttttgcgtg    8160
actgtatgaa aatatataag ggattcacgc atacaatagc ttagatttta atgttccata    8220
catcattgtt ggcctggttg aattcttttt tgtctataaa ttctcttcta ccagcctttc    8280
ctccctgccg gtagcttgtg tacggtactt ctcattctgt gcatgtatgt aaccatatgt    8340
ttttttttgg gttttaagtt ggagcttatc ccaacgtaca gaatttgttt ggtgagcttg    8400
gtattaatga tcgcttgcaa tggaaggaac actctatgat atttgccatg ccaaacaagc    8460
caggagaata cagccgtttt gatttcccag aggttttgcc agcgccttta aacggtaaga    8520
tcatacatag ccctggtatt tgcaatggaa ggaacactct atgacaatgt tgcttaatag    8580
atgaaagaat ggcaagaaaa tttaggaatg cacctagcgt tagttctttc attttgctaa    8640
tatttgaatg caactagtgg ggtatattag tgcaaacaac attgtcatgg ccatccagct    8700
gttctcttcc catcaacgtc agtttatcat tgattatgca tgtatttaac aggaatatgg    8760
gccatactga agaacaatga aatgcttact tggccggaga aggtgaagtt cgctattgga    8820
cttcttccag caatgcttgg tggccaagct tatgttgaag ctcaagatgg cttaactgtt    8880
tcagagtgga tggaaaagca ggtatgagcc caccaagtca gttagactca tctctttgta    8940
ctgaacacag ctgtctcaat tcacacttga tatatgagga tatgttgtaa cgcgataaat    9000
tgctgccttc cttctattgt tatatttta tgaagaagtg tggctaggtc cataaatgaa    9060
actatatgct caagtttcca tactttttc cacccagccc ttctgtatgc aatgtaggct    9120
taagtaatac ttatatttct attaatcttg taattaaatt ccaaatgcac aacgatgtgc    9180
tacctcctcc cct                                                       9193
```

<210> SEQ ID NO 56
<211> LENGTH: 1573
<212> TYPE: DNA
<213> ORGANISM: Lolium rigidum

<400> SEQUENCE: 56

```
tttggctaag aaggaatcat tattgaactt aaaattatag ataccttggg cattgcaaat     60
tggagttatg aattactgaa gtatagcatt tttgtcattg ctaacatgtc cgttggctgt    120
tgatttcgtg aagcattta gttagaataa ctgaataacc gtgctagctt aactgaaaga    180
acgaaggaca tggatgcata ctcgtaattt tatttttcc ttgttcttta actctatgca    240
```

```
ggagtactat gatccagacc gttcaatgct ggagttggtg tttgctccag cagaggaatg       300
gattggacgt agcgacgctg aaatcatcga agcaaccatg caagagctag ccaagttatt       360
tcctgatgaa attgctgctg atcagagtaa agcaaaaatt cgtaaatacc atgttgtcaa       420
gacgccgagg tgaggacatt ttgctaacac ccatcctgat gattaatcaa aaggacacct       480
gatgtggtct tgttctctta cactgtttat attttctgg ctcgctgtta cagatctgtt        540
tacaagacca tcccagattg tgagccttgc cgacctctgc aacgatcacc gatcgaaggg       600
ttctatctgg ctggcgatta cacgaagcag aaatatttgg cttccatgga gggtgcagtt       660
ttatccggga agctctgtgc ccagtccata gtccaggtaa atgctctcca cggttttggt       720
tgcacataga taagtcaaac ttctattgtt gtgttggtgc gttatggtat ggcattattg       780
tggtctaatc acctctctgc ttgcaggatt ctaaattgtt gtcccgtagg agccaggaaa       840
gcctgaagac aaaatccgaa gttcccgtcg cttcctaggt gtatttagtt agcacacaat       900
tcattcttag cacattctgt ggtattttca cactgttgta gagttaaaca ggtgattgag       960
ctgatatcca tattgtgaaa aaggaaatct gtaaaacgag aagctgcata aaagcagctc      1020
tgatccatat agcaattctt acgttagacc tttccggaag gcaaaagtga taaaaaaggg      1080
atcttagata ttatcttcgt ttgcaacaat tgggaactgg atcattaacc gcttactttt      1140
ctggaattgt gtaaacatta aaacctaagg ttcgtgtcag caaaaggaga tgaaatcatg      1200
gataatatcc tagcatctaa atcttgtaag caaatgggat ttatgatatt tggcagttgc      1260
aacaccaagt tgcagttaca aaaaggaggc acagagacaa gccctgagat aaccttctcc      1320
cgagatagat gacggggcct cagtaagtga gatatttgct gcgctcccta caggaggtat      1380
tggtagtagt aggctggtat agtaggtcat gcccgagatg ctagtaggtt acatcagttt      1440
tgggaaggta atggctgtcc tgcatgatgg atttctggaa gatacttgag cttgggggtt      1500
tccttcgcat acctgaacgg agcatcagaa tagaagatat tatgagaggc ttgaattagt      1560
agagtactag tat                                                         1573

<210> SEQ ID NO 57
<211> LENGTH: 932
<212> TYPE: DNA
<213> ORGANISM: Lolium rigidum

<400> SEQUENCE: 57
ccgctaccat cacggcggcg ctaccgctcc gcctccgggt ccccgcgcgc tcccgacgcg        60
gacagacgcg ctgcgcggtc gcgagcgacg ccaccgaggc tccggccgcg cccagcgcac       120
ggctgtccgc ggattgcgtc atcgtgggcg gcggcatcag cggcctctgc accgcacagg       180
cgctggccac caagtacggt gtcagcgact tgctcgtgac ggaggcccgc gctcgcgcag       240
gcggcaacat caccaccgtc gagcgccccg acgaggggta cctctgggag gaggggccca       300
acagcttcca gccctccgac cccgtcctca ccatggccgt acgcatcttg ctcgcttttct      360 ccttcttttc ggattcttgg ggacgtacgt gtacaggata cagatacgat ccctgcatgg       420
attggttgcg caggtagaca gcggcctcaa ggatgacttg tgttcgggg accccaatgc       480 gccgcgcttc gtgctgtggc aggggaagct gaggccggtg ccgtccaagc ccggcgacct       540
gcctttcttc gacctcatga gtattcctgg gaagctcagg gccggccttg gcgcgctcgg       600
cattcgcgcg cctcctccag tttgtgctct gcccgtgctc tctattcttt tgtgaatttt       660
gattgtcaaa gatgggctg agcgttcccg gcgaaggttt caggggcgtg aggagtcggt       720
ggaggagttt gtgcgccgca acctgggtgc ggaggtcttt gagcgcctca tcgagccctt       780
```

```
ctgctcaggt aatgtgcagt agtatctgtc tgttctgttc tgctccttgc attgattccg      840
ataacatttc gatatcaatg ttaggtgtgt atgccggtga cccttcaaag ctcagtatga      900
gggctgcgtt tgggaaggta tggagactgg ag                                    932
```

```
<210> SEQ ID NO 58
<211> LENGTH: 244
<212> TYPE: DNA
<213> ORGANISM: Lolium rigidum

<400> SEQUENCE: 58
gtgcatatac ctaagttatg ctatcggtaa tgttttttgta tgtccatgtc ccttgtactc       60
agagatgatc atgaattata gtaattattt catgcttggt cttaagacgt aaccttgtca      120
tgttctgcat tccttcattt ccaggttggg tagtaaagtc aaactctcgt ggaagcttac      180
gggcattaca aagtcggaca accagggata tctgttagca tatgaaacac cggaaggagt      240
tgtt                                                                   244
```

```
<210> SEQ ID NO 59
<211> LENGTH: 616
<212> TYPE: DNA
<213> ORGANISM: Lolium rigidum

<400> SEQUENCE: 59
tttgggaagg tatggagact ggaggagaat ggaggcagta ttattggtgg aaccatcaag       60
gcaattcagg atagaggcaa gaaccccaaa ccgccgaggg atccgtaagt ggagactgca      120
attttctatt tagtcagtta actgttccat tagactcgta ttaatttgtt tcaccacttt      180
tagccgactt ccgacaccaa aggggcagac ggtggcatct ttcaggaagg gtctagccat      240
gcttccaaat gctatcgctt ctaggtttgt tatcatcact tgtgcacata cctaagttat      300
gctatcagta tacgaggtga tgtatattgt tcagatagag gggacagctc tgttggtaga      360
cctactattt gctgaactca ataccatatg aatatcatta catcagcacc caaagtacat      420
gtggctcgat tcttatatca gccattctcg cattgttcac cttttttcatc ttgggttcat      480 cttttttcatc ttgcctttttt ggttggggcc tgtactatat aggaaattcc acgagggatg      540
agttatagag catgtttgtg ctttttccgtg tcccttgtac tcggagatga tcatgagtta      600
tagtaataat ttcatg                                                      616
```

```
<210> SEQ ID NO 60
<211> LENGTH: 1255
<212> TYPE: DNA
<213> ORGANISM: Lolium rigidum
<220> FEATURE:
<221> NAME/KEY: unsure
<222> LOCATION: (1)..(1255)
<223> OTHER INFORMATION: unsure at all n locations

<400> SEQUENCE: 60
catcccaatc tgttcaaata gctggctgtc actggcatt tttttttcaa gaattcaagc        60
ctggttctac gtaccatttg caaccctatc ttgccaaccg gtagggtgca gttgcaagca      120
tttactttat ttcacattgc ttagactttc taagttagtc taactatact tccttctgtg      180
ttcattgaac ttttttcccc tcctgttacc gcagagtgat gcagcagatg gtctctcaaa      240 atttattat ccaccggttg ctgctgtaac tgtttcatat ccaacagaag ctattagaaa       300
agaatgctta attgatgggg agctccaggg tttcggccag ttgcatccac gtagccaagg     360
```

-continued

```
agttgagact ttaggtattt cgtggaatag aaccttagca tgaaacaact gcgagcatta    420
ctcttccttc tccattttca tttatcatgg gattggtttt ggtattattc tactaattcg    480
tggtattttt atgtagggac aatatatagc tcttctctct ttccgaatcg tgctcctgct    540
ggaagagtgt tacttctgaa ctatatcggg ggtgctacaa atacagggat cgtctccaag    600
gttctctcga cctgcttgat actcatgtca ttttcttatt gtgtgatacc tggttacggt    660
attcagttag tgttggtcac ctattcattt atgattaata taaataactg gactgcattt    720
ttcacctcca gctgcaattg tcaacacaaa tagattaaat ggtttggtta gatgctacat    780
tcaatctcga tagtattgtt agattttttt tggctggcca tatttatact gatcccattt    840
tgtttgcaga ctgagagtga cttggtggaa gcagttgatc gtgacctcag aaaaatgttg    900
ataaatccta cagcaccaga ccctttagcc ttaggcgtcc gagtgtggcc acaagccatt    960
ccacagtttt tgattgggca ccttgatcgc cttgatgcgg caaaatctgc cttggccaga   1020
ggcggctgca gtgggttgtt cctnggagga aactatgtag caggagttgc cttgggccga   1080
tgcatcgagg gtgcgtacga gagtgcctca gaagtatctg acttcttgac caagtatgcc   1140
tacaagtgat gaaagaagtg taattcatca ccttgctgca tatttgaggt gcggccagaa   1200
tcagtaataa ttcagaaaat cttgtaatct tctctactta tacctcctat cgttt        1255
```

<210> SEQ ID NO 61
<211> LENGTH: 883
<212> TYPE: DNA
<213> ORGANISM: Lolium rigidum

<400> SEQUENCE: 61

```
attcataggg tttagctcca catttgtttc agagaacata gcctctacat tgttacacat     60
gcgactgttt cttgtatagg aaccctcttc tcctctatga tgttcccaga tcgagctcct    120
aatgaccaac acttatttac aacattcgtt gggggaagcc acaataggga tctcgctgga    180
gctccaacgt atggaatttc tatatgttga atgttatgct tatttttagg tggatcattc    240
atattctata cttctgcagg gctatcttga aacaacttgt gacctctgac cttagaaagc    300
tcttgggtgt agaggggcag ccaacttttg tgaggtaagt gtccaagcgt attgccttaa    360
tagtagaagt cattgatata tgtcccattt gagcttgtgt tgtggtttgc tatcttctag    420
gaatttttga atttccgtaa aataaaaatt accactacat gctcattaat ttaacacgga    480
cattcttcat tacacagaca tatacattgg aaaaatgctt ttcctctgta tggccatgat    540
tatgattcgg cattggaagc tataggaaag atggagagtg atcttccagg gttcttctat    600
gcaggcaagt caataaaggc accatattgt taatttgtta ttggtttcca tgaaaatgta    660
actccatgcc ttcttggtct gccgaaaatg atgctctgat aaaagaaaac atgcatttgc    720
atctcattag tcttgttgga gttctctaga gcaaaccaga aatagtaatg ccattaagta    780
acactattat ctgatgttaa cttaaatagt cattgaactt tggttatgtc ttacaggaaa    840
taacaaggat ggcttggctg ttggaaatgt tatagcttca gga                      883
```

<210> SEQ ID NO 62
<211> LENGTH: 363
<212> TYPE: DNA
<213> ORGANISM: Lolium rigidum

<400> SEQUENCE: 62

```
ccaaatccaa gttcactccg tcagacaatt ctcacctgct cgatggagaa gaagagggtg     60
gccatcatcg gcgccggcgt gagcggcctg gcggcgtgca agcacctgct ggagcgcggc    120
```

```
tgccggcccg tcgtcttcga ggcggacacg ctcctcggcg gcgtgtgggc gcggacgccg    180
gactgcacct cgctgcagtc tgagcgggcc atgtaccagt actccgactt cccgtggccg    240
gactccgtca ccgagatgtt ccccaactgc cgccaggtcg ccgactacct caacgcctat    300
gcgcgccact tcggcgtgct cgactgcgtc aggttccggc atcgtgtcgt agggatggag    360
tat                                                                  363

<210> SEQ ID NO 63
<211> LENGTH: 293
<212> TYPE: DNA
<213> ORGANISM: Lolium rigidum

<400> SEQUENCE: 63
tttccctgtt ttgacacatt ttcagtgttg ggagcttctt tgaacgccac tttggaaagg     60
aagtgagttt ttcctggaca atcttgaat aactagtcat atgtaatcaa aagctctgca    120
gttcattgta accagacatg gctaagaatt tccttgttta ttacaggttg tcgactatct    180
tattgatcca tttgtagctg aacaagtgc aggagatcct gagtcattat ctgtaagtta    240
ttattgtgtc atgtccaact atttgcatta gttagatata tatttttatt ttc          293

<210> SEQ ID NO 64
<211> LENGTH: 1054
<212> TYPE: DNA
<213> ORGANISM: Lolium rigidum

<400> SEQUENCE: 64
acatatatgt accatacttt attttaatga catgaataca gaattggagt aaagatagtt     60
ttacatttct ccattgcaaa agaggtcctt gattgttaaa ttttatatga ttttgattcc    120
cataatggaa ccataacttc ttaagatgct tgttgtact aatttcacta ttatttcata    180
ttttcatttg gagaatactt taaattattg caacatacta cttctagagc ctacgagcta    240
ctgcatcaca agtttacagt tatgacttat gggatgggtg actctgattt tgtctcatga    300
aatacatgga cgttttcgaa ctctacatgt atagcagaat cctgccttaa ttgatattta    360
ttatgcaggt ggattatctg ccgttatccc tcatggtaac agcttttaag aaggaagatg    420
tcaaaagacc cctggaagga tttggggtgt ggtaccccta taaggaacag caaaaacatg    480
gtctgaaaac ccttggtagg ttagctcggc tatgaattgc cattatgtac acaaaacaac    540
cttgctgtat cagtttactt gtactcatgt ttttgttaac tctgattcat agggtttagc    600
tccatatttt tttcagagaa catagcctct acattgttac acacgtgact gtttcttgta    660
taggaaccct cttctcctct atgatgttcc cagatcgagc tcctaatgac caacacttat    720
ttacaacatt cgttggggga agccacaata gggatctcgc tggagctcca acgtatggaa    780
tttctatatg ttgaatgtta tgcttatttt taggtggatc attcatattc tatacttctg    840
cagggctatc ttgaaacaac ttgtgacctc tgaccttaga aagctcttgg gtgtagaggg    900
gcagccaact tttgtgaggt aagtgtccaa acgtattgcc ttaatagtag aagtcattga    960
tatatgtttc atttgagctt gtgttgtggt ttgctatctt ctaggaattt ttgaatttcc   1020
gtaaaataaa aattaccact acatgctcat taat                              1054

<210> SEQ ID NO 65
<211> LENGTH: 566
<212> TYPE: DNA
<213> ORGANISM: Lolium rigidum
```

<400> SEQUENCE: 65

```
gcttatttgg attttttct aaaatttact atacttgatg tatatcactc tctgatactt      60
agatagataa ttttgttatc atctgttgaa gcttcaaaag gcaattaaag aggtgcagtg    120
gtagaccact ggaactactt aggttaaaag tttgtaatct gcatcggtca tgataataag    180
cattgcactt atcgtgtcca aatagatcta gcagtttcaa cttgacattt acactgcagc    240
atcttgttat cataaatgag gatagcaact tttgtcttcc cagttatgtt ttttaatctt    300
tccctttttc ctttcaaatc tgttgttcat gctccttcaa tgctctcagg tatggttcta    360
tcattgctgg tgccatcttg tctaaactaa cagctaaagg tgattcgact aagaaaggaa    420
gggctgtatc aggaaaagga aggaataagc gggtgtcatt ttcatttcat ggtggtatgc    480
aggtattcat atgatgatat cctgtcattt tatttgttag tgccaaagat ttcaaaggca    540
aaccctatta actctgtgcc atttaa                                        566
```

<210> SEQ ID NO 66
<211> LENGTH: 577
<212> TYPE: DNA
<213> ORGANISM: Lolium rigidum

<400> SEQUENCE: 66

```
atgtaccata ctttatttta atgacatgaa tacagaattg gagtaaagat agttttacat     60
ttctccattg caaagaggt ccttgattgt taaattttat atgatttga ttcccataat    120
ggaaccataa cttcttaaga tgctttgttg tactaatttc actattattt catattttca    180
tttggagaat actttaaatt attgcaacat actacttcta gagcctacga gctattgtat    240
cacaagttta cagttatgac ttatgggatg ggtgactctg atttcgtctc atgaaataca    300
tggacgtttt cgaactctac atgtatagca gaatcctgcc gtaattgata tttattatgc    360
aggtggatta tctgccgtta tccctcatgg taacagcttt taagaaggaa gatgtcaaaa    420
gaccctgga aggatttggg gtgttggtac cctataagga acagcaaaa catggtctga    480
aaacccttgg taggttagct cagctatgaa ttgccattat gtacacaaaa caaccttgct    540
atatcagttt acttgtactc atgttttgt taactct                             577
```

<210> SEQ ID NO 67
<211> LENGTH: 30
<212> TYPE: DNA
<213> ORGANISM: Lolium rigidum

<400> SEQUENCE: 67

```
ggaagagccg attctccggc atgtggagcc                                     30
```

<210> SEQ ID NO 68
<211> LENGTH: 30
<212> TYPE: DNA
<213> ORGANISM: Lolium rigidum

<400> SEQUENCE: 68

```
gggcaagtct ggtttccaga ttctgctacc                                     30
```

<210> SEQ ID NO 69
<211> LENGTH: 30
<212> TYPE: DNA
<213> ORGANISM: Lolium rigidum

<400> SEQUENCE: 69

```
ggagaggctt ctctggtggg caaagagacc                                     30
```

<210> SEQ ID NO 70
<211> LENGTH: 30
<212> TYPE: DNA
<213> ORGANISM: Lolium rigidum

<400> SEQUENCE: 70
ggaaaagtta tatcctcttg tgcggcaacc                                    30

<210> SEQ ID NO 71
<211> LENGTH: 30
<212> TYPE: DNA
<213> ORGANISM: Lolium rigidum

<400> SEQUENCE: 71
ggagagatac gcactaatgt tgattacacc                                    30

<210> SEQ ID NO 72
<211> LENGTH: 30
<212> TYPE: DNA
<213> ORGANISM: Lolium rigidum

<400> SEQUENCE: 72
gggctgttaa tgcaggtaaa catatttacc                                    30

<210> SEQ ID NO 73
<211> LENGTH: 30
<212> TYPE: DNA
<213> ORGANISM: Lolium rigidum

<400> SEQUENCE: 73
ggatggttct catgtggttg ctgatacacc                                    30

<210> SEQ ID NO 74
<211> LENGTH: 30
<212> TYPE: DNA
<213> ORGANISM: Lolium rigidum

<400> SEQUENCE: 74
ggaagtggag gtcatgaaga tgtgcatgcc                                    30

<210> SEQ ID NO 75
<211> LENGTH: 30
<212> TYPE: DNA
<213> ORGANISM: Lolium rigidum

<400> SEQUENCE: 75
ggcctctggc gtcattcact ttgtcatgcc                                    30

<210> SEQ ID NO 76
<211> LENGTH: 30
<212> TYPE: DNA
<213> ORGANISM: Lolium rigidum

<400> SEQUENCE: 76
ggactttaag acatatacgt tggctaaccc                                    30

<210> SEQ ID NO 77
<211> LENGTH: 30
<212> TYPE: DNA
<213> ORGANISM: Lolium rigidum

<400> SEQUENCE: 77
ggaggagccg atgctccgcc atgtggaacc                                          30

<210> SEQ ID NO 78
<211> LENGTH: 30
<212> TYPE: DNA
<213> ORGANISM: Lolium rigidum

<400> SEQUENCE: 78
ggcattgttg cttggaagat gaagctctcc                                          30

<210> SEQ ID NO 79
<211> LENGTH: 30
<212> TYPE: DNA
<213> ORGANISM: Lolium rigidum

<400> SEQUENCE: 79
ggctctacaa ttgttgagaa cctgaggacc                                          30

<210> SEQ ID NO 80
<211> LENGTH: 30
<212> TYPE: DNA
<213> ORGANISM: Lolium rigidum

<400> SEQUENCE: 80
ggaagttgag gttatgaaga tgtgcatgcc                                          30

<210> SEQ ID NO 81
<211> LENGTH: 30
<212> TYPE: DNA
<213> ORGANISM: Lolium rigidum

<400> SEQUENCE: 81
gggaccgaga aggccattct cctggtggcc                                          30

<210> SEQ ID NO 82
<211> LENGTH: 30
<212> TYPE: DNA
<213> ORGANISM: Lolium rigidum

<400> SEQUENCE: 82
ggcctggctg gggccatgct tctgagaacc                                          30

<210> SEQ ID NO 83
<211> LENGTH: 30
<212> TYPE: DNA
<213> ORGANISM: Lolium rigidum

<400> SEQUENCE: 83
ggagaaggga atcattttc ttgggccacc                                           30

<210> SEQ ID NO 84
<211> LENGTH: 30
<212> TYPE: DNA
<213> ORGANISM: Lolium rigidum

<400> SEQUENCE: 84
ggtggctagt tgtcaggtgg tggggtatcc                                          30

<210> SEQ ID NO 85
<211> LENGTH: 30
<212> TYPE: DNA
<213> ORGANISM: Lolium rigidum

<400> SEQUENCE: 85

```
ggcgctatgg gctactgcat ttcggcggcc                                       30

<210> SEQ ID NO 86
<211> LENGTH: 30
<212> TYPE: DNA
<213> ORGANISM: Lolium rigidum

<400> SEQUENCE: 86
ggagttggag cagcagaaaa gggagtttcc                                       30

<210> SEQ ID NO 87
<211> LENGTH: 30
<212> TYPE: DNA
<213> ORGANISM: Lolium rigidum

<400> SEQUENCE: 87
gggatacaaa actttcgggg aggccatccc                                       30

<210> SEQ ID NO 88
<211> LENGTH: 30
<212> TYPE: DNA
<213> ORGANISM: Lolium rigidum

<400> SEQUENCE: 88
ggttatactt cttgtgtaaa tattaggacc                                       30

<210> SEQ ID NO 89
<211> LENGTH: 30
<212> TYPE: DNA
<213> ORGANISM: Lolium rigidum

<400> SEQUENCE: 89
ggtcacattt aggttaacta gatttacacc                                       30

<210> SEQ ID NO 90
<211> LENGTH: 30
<212> TYPE: DNA
<213> ORGANISM: Lolium rigidum

<400> SEQUENCE: 90
ggctataggt gccacagtct gcctagtacc                                       30

<210> SEQ ID NO 91
<211> LENGTH: 30
<212> TYPE: DNA
<213> ORGANISM: Lolium rigidum

<400> SEQUENCE: 91
ggtattcccc atcgataggg aattcgaccc                                       30

<210> SEQ ID NO 92
<211> LENGTH: 30
<212> TYPE: DNA
<213> ORGANISM: Lolium rigidum

<400> SEQUENCE: 92
gggcgggccc cgatgaactt agggaagtcc                                       30

<210> SEQ ID NO 93
<211> LENGTH: 30
<212> TYPE: DNA
<213> ORGANISM: Lolium rigidum
```

<400> SEQUENCE: 93
gggcctcctc acgccgcgcc ctcgccgccc                                               30

<210> SEQ ID NO 94
<211> LENGTH: 30
<212> TYPE: DNA
<213> ORGANISM: Lolium rigidum

<400> SEQUENCE: 94
ggttatactt cttgtgtaaa tattaggacc                                               30

<210> SEQ ID NO 95
<211> LENGTH: 30
<212> TYPE: DNA
<213> ORGANISM: Lolium rigidum

<400> SEQUENCE: 95
ggtcacattt aggttaacta gatttacacc                                               30

<210> SEQ ID NO 96
<211> LENGTH: 30
<212> TYPE: DNA
<213> ORGANISM: Lolium rigidum

<400> SEQUENCE: 96
ggcatttcac gtattacaac agttgttccc                                               30

<210> SEQ ID NO 97
<211> LENGTH: 30
<212> TYPE: DNA
<213> ORGANISM: Lolium rigidum

<400> SEQUENCE: 97
gggagatact agatatcggt caaatcttcc                                               30

<210> SEQ ID NO 98
<211> LENGTH: 30
<212> TYPE: DNA
<213> ORGANISM: Lolium rigidum

<400> SEQUENCE: 98
ggttatactt cttgtgtaaa tattaggacc                                               30

<210> SEQ ID NO 99
<211> LENGTH: 30
<212> TYPE: DNA
<213> ORGANISM: Lolium rigidum

<400> SEQUENCE: 99
ggtcacattt aggttaacta gatttacacc                                               30

<210> SEQ ID NO 100
<211> LENGTH: 30
<212> TYPE: DNA
<213> ORGANISM: Lolium rigidum

<400> SEQUENCE: 100
ggcatttcac gtattacaac agttgttccc                                               30

<210> SEQ ID NO 101
<211> LENGTH: 30
<212> TYPE: DNA
<213> ORGANISM: Lolium rigidum -continued

```
<400> SEQUENCE: 101
gggagatact agatatcggt caaatcttcc                                            30

<210> SEQ ID NO 102
<211> LENGTH: 30
<212> TYPE: DNA
<213> ORGANISM: Lolium rigidum

<400> SEQUENCE: 102
ggctataggt gccacagtct gcctagtacc                                            30

<210> SEQ ID NO 103
<211> LENGTH: 30
<212> TYPE: DNA
<213> ORGANISM: Lolium rigidum

<400> SEQUENCE: 103
gggggtaagt ttcaagaagt ggaagctgcc                                            30

<210> SEQ ID NO 104
<211> LENGTH: 30
<212> TYPE: DNA
<213> ORGANISM: Lolium rigidum

<400> SEQUENCE: 104
ggttttcatg aaacttctcc tcgtgactcc                                            30

<210> SEQ ID NO 105
<211> LENGTH: 30
<212> TYPE: DNA
<213> ORGANISM: Lolium rigidum

<400> SEQUENCE: 105
ggtgttgttg caggtcctgt gtttttacc                                             30

<210> SEQ ID NO 106
<211> LENGTH: 30
<212> TYPE: DNA
<213> ORGANISM: Lolium rigidum

<400> SEQUENCE: 106
ggccggcgcg gaggaggtcg tgctgcagcc                                            30

<210> SEQ ID NO 107
<211> LENGTH: 30
<212> TYPE: DNA
<213> ORGANISM: Lolium rigidum

<400> SEQUENCE: 107
ggcggcaggt tcccgattga gaaggatgcc                                            30

<210> SEQ ID NO 108
<211> LENGTH: 30
<212> TYPE: DNA
<213> ORGANISM: Lolium rigidum

<400> SEQUENCE: 108
ggtgcgaatg ttgattgttt cctcggcacc                                            30

<210> SEQ ID NO 109
<211> LENGTH: 30
<212> TYPE: DNA
```

<213> ORGANISM: Lolium rigidum

<400> SEQUENCE: 109
ggttccatca gcagccagta cttgagttcc           30

<210> SEQ ID NO 110
<211> LENGTH: 30
<212> TYPE: DNA
<213> ORGANISM: Lolium rigidum

<400> SEQUENCE: 110
ggtccaactg ctatcagaga tggtaaaccc           30

<210> SEQ ID NO 111
<211> LENGTH: 30
<212> TYPE: DNA
<213> ORGANISM: Lolium rigidum

<400> SEQUENCE: 111
gggaccctgg gtgcacccgc aagaccttcc           30

<210> SEQ ID NO 112
<211> LENGTH: 30
<212> TYPE: DNA
<213> ORGANISM: Lolium rigidum

<400> SEQUENCE: 112
ggttccatca gcagccaata cttgagttcc           30

<210> SEQ ID NO 113
<211> LENGTH: 30
<212> TYPE: DNA
<213> ORGANISM: Lolium rigidum

<400> SEQUENCE: 113
ggtccaactg ctatcagaga tggtaaaccc           30

<210> SEQ ID NO 114
<211> LENGTH: 30
<212> TYPE: DNA
<213> ORGANISM: Lolium rigidum

<400> SEQUENCE: 114
ggcaagcacg agaccgctga catccacacc           30

<210> SEQ ID NO 115
<211> LENGTH: 30
<212> TYPE: DNA
<213> ORGANISM: Lolium rigidum

<400> SEQUENCE: 115
ggcctcttgg ctggcctgtt ggagggtacc           30

<210> SEQ ID NO 116
<211> LENGTH: 30
<212> TYPE: DNA
<213> ORGANISM: Lolium rigidum

<400> SEQUENCE: 116
ggccagccct ttggtcaaat catatttccc           30

<210> SEQ ID NO 117
<211> LENGTH: 30

<212> TYPE: DNA
<213> ORGANISM: Lolium rigidum

<400> SEQUENCE: 117
ggtacggtat cgagcaggag tacaccctcc                                    30

<210> SEQ ID NO 118
<211> LENGTH: 30
<212> TYPE: DNA
<213> ORGANISM: Lolium rigidum

<400> SEQUENCE: 118
ggtgcgcctg gtcagagcct tccaagttcc                                    30

<210> SEQ ID NO 119
<211> LENGTH: 30
<212> TYPE: DNA
<213> ORGANISM: Lolium rigidum

<400> SEQUENCE: 119
ggcggcagag tagctaccta ctagctagcc                                    30

<210> SEQ ID NO 120
<211> LENGTH: 30
<212> TYPE: DNA
<213> ORGANISM: Lolium rigidum

<400> SEQUENCE: 120
gggggaaggg tgtgggcgt caggagggcc                                     30

<210> SEQ ID NO 121
<211> LENGTH: 30
<212> TYPE: DNA
<213> ORGANISM: Lolium rigidum

<400> SEQUENCE: 121
ggcatgtgag ttaaaatgat ttttttttgcc                                   30

<210> SEQ ID NO 122
<211> LENGTH: 30
<212> TYPE: DNA
<213> ORGANISM: Lolium rigidum

<400> SEQUENCE: 122
ggcgatcagg ctgctctccg acaatgatcc                                    30

<210> SEQ ID NO 123
<211> LENGTH: 30
<212> TYPE: DNA
<213> ORGANISM: Lolium rigidum

<400> SEQUENCE: 123
ggcattgcac gggagacata ggaattagcc                                    30

<210> SEQ ID NO 124
<211> LENGTH: 30
<212> TYPE: DNA
<213> ORGANISM: Lolium rigidum

<400> SEQUENCE: 124
ggccatcagg ctgctctctg acaatgatcc                                    30

<210> SEQ ID NO 125

```
<211> LENGTH: 30
<212> TYPE: DNA
<213> ORGANISM: Lolium rigidum

<400> SEQUENCE: 125
ggtaattgct gtgcctggtc agagccttcc                                              30

<210> SEQ ID NO 126
<211> LENGTH: 30
<212> TYPE: DNA
<213> ORGANISM: Lolium rigidum

<400> SEQUENCE: 126
ggccatcagg ctgctctcgg acaatgatcc                                              30

<210> SEQ ID NO 127
<211> LENGTH: 30
<212> TYPE: DNA
<213> ORGANISM: Lolium rigidum

<400> SEQUENCE: 127
ggcatgtgag ttaaaatgat ttttttgcc                                               30

<210> SEQ ID NO 128
<211> LENGTH: 30
<212> TYPE: DNA
<213> ORGANISM: Lolium rigidum

<400> SEQUENCE: 128
ggcctcttgg ctggcctgtt ggagggtacc                                              30

<210> SEQ ID NO 129
<211> LENGTH: 30
<212> TYPE: DNA
<213> ORGANISM: Lolium rigidum

<400> SEQUENCE: 129
ggccagccga ttggtcaaat catatttccc                                              30

<210> SEQ ID NO 130
<211> LENGTH: 30
<212> TYPE: DNA
<213> ORGANISM: Lolium rigidum

<400> SEQUENCE: 130
ggcggggagc tgcggtcgtg catggccacc                                              30

<210> SEQ ID NO 131
<211> LENGTH: 30
<212> TYPE: DNA
<213> ORGANISM: Lolium rigidum

<400> SEQUENCE: 131 ggtaccttt ctttcaccg ccgcctcacc                                                30

<210> SEQ ID NO 132
<211> LENGTH: 30
<212> TYPE: DNA
<213> ORGANISM: Lolium rigidum

<400> SEQUENCE: 132
ggtcgcgtcc cccggctttt tcctcatccc                                              30
```

```
<210> SEQ ID NO 133
<211> LENGTH: 30
<212> TYPE: DNA
<213> ORGANISM: Lolium rigidum

<400> SEQUENCE: 133
ggccccatca ccgacgcgag ccagctgccc                              30

<210> SEQ ID NO 134
<211> LENGTH: 30
<212> TYPE: DNA
<213> ORGANISM: Lolium rigidum

<400> SEQUENCE: 134
ggaacaatgc tgccaagatc ttcgacaacc                              30

<210> SEQ ID NO 135
<211> LENGTH: 30
<212> TYPE: DNA
<213> ORGANISM: Lolium rigidum

<400> SEQUENCE: 135
ggtacggtat cgagcaggag tacaccctcc                              30

<210> SEQ ID NO 136
<211> LENGTH: 30
<212> TYPE: DNA
<213> ORGANISM: Lolium rigidum

<400> SEQUENCE: 136
ggcgactgga acggcgccgg cgcgcacacc                              30

<210> SEQ ID NO 137
<211> LENGTH: 30
<212> TYPE: DNA
<213> ORGANISM: Lolium rigidum

<400> SEQUENCE: 137
ggacaccacg agaccgccga catcaacacc                              30

<210> SEQ ID NO 138
<211> LENGTH: 30
<212> TYPE: DNA
<213> ORGANISM: Lolium rigidum

<400> SEQUENCE: 138
ggatatcaat ctcaatgtgt ttagtgagcc                              30

<210> SEQ ID NO 139
<211> LENGTH: 30
<212> TYPE: DNA
<213> ORGANISM: Lolium rigidum

<400> SEQUENCE: 139
ggcttctatg ttttccaata cttcgatgcc                              30

<210> SEQ ID NO 140
<211> LENGTH: 30
<212> TYPE: DNA
<213> ORGANISM: Lolium rigidum

<400> SEQUENCE: 140
gggctcggcg tgccactcgc cgcgcagtcc                              30
```

<210> SEQ ID NO 141
<211> LENGTH: 30
<212> TYPE: DNA
<213> ORGANISM: Lolium rigidum

<400> SEQUENCE: 141
ggagccacgt cgagacgttc ctggaccacc                                    30

<210> SEQ ID NO 142
<211> LENGTH: 30
<212> TYPE: DNA
<213> ORGANISM: Lolium rigidum

<400> SEQUENCE: 142
ggcccaggca tacagcacct ggcaatgacc                                    30

<210> SEQ ID NO 143
<211> LENGTH: 30
<212> TYPE: DNA
<213> ORGANISM: Lolium rigidum

<400> SEQUENCE: 143
ggcgcgctca ggaaaatccg agctcggtcc                                    30

<210> SEQ ID NO 144
<211> LENGTH: 30
<212> TYPE: DNA
<213> ORGANISM: Lolium rigidum

<400> SEQUENCE: 144
gggcgggttt gagctcctgc cgccgccgcc                                    30

<210> SEQ ID NO 145
<211> LENGTH: 30
<212> TYPE: DNA
<213> ORGANISM: Lolium rigidum

<400> SEQUENCE: 145
ggaggtttac ttgtttgaac cgaatgttcc                                    30

<210> SEQ ID NO 146
<211> LENGTH: 30
<212> TYPE: DNA
<213> ORGANISM: Lolium rigidum

<400> SEQUENCE: 146
ggaccataaa tggaggaaaa tcgtattccc                                    30

<210> SEQ ID NO 147
<211> LENGTH: 30
<212> TYPE: DNA
<213> ORGANISM: Lolium rigidum

<400> SEQUENCE: 147
ggtaagcaac tgctagtgat cggaggcccc                                    30

<210> SEQ ID NO 148
<211> LENGTH: 30
<212> TYPE: DNA
<213> ORGANISM: Lolium rigidum

<400> SEQUENCE: 148
ggctatggct aaacactgta aataaagtcc                                    30

```
<210> SEQ ID NO 149
<211> LENGTH: 30
<212> TYPE: DNA
<213> ORGANISM: Lolium rigidum

<400> SEQUENCE: 149
ggttgcaatg acgacagctt cgatctcacc                                        30

<210> SEQ ID NO 150
<211> LENGTH: 30
<212> TYPE: DNA
<213> ORGANISM: Lolium rigidum

<400> SEQUENCE: 150
ggcgcccact ataagcaatg acggagtacc                                        30

<210> SEQ ID NO 151
<211> LENGTH: 30
<212> TYPE: DNA
<213> ORGANISM: Lolium rigidum

<400> SEQUENCE: 151
ggagaagtta aaacaaacat agggcccacc                                        30

<210> SEQ ID NO 152
<211> LENGTH: 30
<212> TYPE: DNA
<213> ORGANISM: Lolium rigidum

<400> SEQUENCE: 152
ggatatgttg taacgcgata aattgctgcc                                        30

<210> SEQ ID NO 153
<211> LENGTH: 30
<212> TYPE: DNA
<213> ORGANISM: Lolium rigidum

<400> SEQUENCE: 153
ggttggggcc tgtactatat aggaaattcc                                        30

<210> SEQ ID NO 154
<211> LENGTH: 30
<212> TYPE: DNA
<213> ORGANISM: Lolium rigidum

<400> SEQUENCE: 154
gggggtgcta caaatacagg gatcgtctcc                                        30

<210> SEQ ID NO 155
<211> LENGTH: 30
<212> TYPE: DNA
<213> ORGANISM: Lolium rigidum

<400> SEQUENCE: 155
ggttacggta ttcagttagt gttggtcacc                                        30
```

METHODS AND COMPOSITIONS FOR WEED CONTROL

CROSS REFERENCE TO RELATED APPLICATIONS

This application is a U.S. National Stage Application of PCT/US2014/023503, filed on Mar. 11, 2014, which claims the benefit of U.S. Provisional Application No. 61/779,532, filed on Mar. 13, 2013, which is incorporated by reference in its entirety herein.

INCORPORATION OF SEQUENCE LISTING

A computer readable form of a sequence listing is filed with this application by electronic submission and is incorporated into this application by reference in its entirety. The sequence listing is contained in the file named P34107US01_SEQ.txt, which is 179,123 bytes in size (measured in operating system MS windows) and was created on Sep. 10, 2015.

FIELD OF THE INVENTION

The invention relates generally to the field of weed management. More specifically, the invention relates to control of *Lolium* weed species and compositions containing polynucleotide molecules. The invention further provides methods and compositions useful for *Lolium* control.

BACKGROUND OF THE INVENTION

Weeds are plants that compete with cultivated plants in an agronomic environment and cost farmers billions of dollars annually in crop losses and the expense of efforts to keep weeds under control. Weeds also serve as hosts for crop diseases and insect pests. Weeds are plants that are unwanted in any particular environment. The losses caused by weeds in agricultural production environments include decreases in crop yield, reduced crop quality, increased irrigation costs, increased harvesting costs, reduced land value, injury to livestock, and crop damage from insects and diseases harbored by the weeds. The principal means by which weeds cause these effects are: 1) competing with crop plants for water, nutrients, sunlight and other essentials for growth and development, 2) production of toxic or irritant chemicals that cause human or animal health problem, 3) production of immense quantities of seed or vegetative reproductive parts or both that contaminate agricultural products and perpetuate the species in agricultural lands, and 4) production on agricultural and nonagricultural lands of vast amounts of vegetation that must be disposed of Herbicide tolerant weeds are a problem with nearly all herbicides in use, there is a need to effectively manage these weeds. There are over 365 weed biotypes currently identified as being herbicide resistant to one or more herbicides by the Herbicide Resistance Action Committee (HRAC), the North American Herbicide Resistance Action Committee (NAHRAC), and the Weed Science Society of America (WSSA).

*Lolium* species, include but are not limited to, *Lolium canariense* Steud.—Canary Islands ryegrass, *Lolium edwardii* H. Scholz, Stierst. & Gaisberg, *Lolium multiflorum* Lam.—Italian ryegrass, *Lolium perenne* L.—Perennial ryegrass, *Lolium persicum*—Persian ryegrass or Persian darnel, *Lolium remotum* Schrank, *Lolium rigidum* Gaudin—Stiff darnel, Wimmera ryegrass and *Lolium temulentum* L.—Darnel, poison darnelryegrass that include members that are difficult to control weeds and that have been shown to develop tolerance to several classes of frequently used herbicides.

The present invention provides herbicidal compositions that comprise polynucleotide compositions useful for modulating gene expression in the *Lolium* weed species, *Lolium rigidium* in particular, genes providing the production of herbicide target proteins, such as, acetyl-CoA carboxylase (ACCase), acetolactate synthase (ALS large subunit and ALS small subunit, also known as acetohydroxyacid synthase, AHAS), dihydropteroate synthetase (DHPS), 5-enolpyruvylshikimate-3-phosphate synthase (EPSPS), glutamine synthetase (GS2), 4-hydroxyphenyl-pyruvate-dioxygenase (HPPD), phytoene desaturase (PDS), protoporphyrinogen IX oxidase (PPDX) in plants for the purpose of enhancing control of *Lolium* in an agronomic environment and for the management of herbicide resistant *Lolium* species.

SUMMARY OF THE INVENTION

The invention comprises a method of *Lolium* species weed control, in particular *Lolium rigidum* plant control comprising an external application of a herbicidal composition to a *Lolium rigidum* plant or a part of the *Lolium rigidum* plant in need of control, said herbicidal composition comprising a polynucleotide, an organosilicone surfactant concentration of about 0.2 percent or greater, and an effective dose of a nonpolynucleotide herbicide, wherein the polynucleotide is at least 19 contiguous polynucleotides in length and essentially identical or essentially complementary to a segment of a *Lolium rigidum* gene polynucleotide selected from the group consisting of SEQ ID NO: 1-66, wherein said treated plant is more sensitive to said nonpolynucleotide herbicide relative to a similar plant treated with a herbicide composition not containing said polynucleotide.

In another aspect of the invention, the herbicide composition comprises a polynucleotide at least 19 contiguous polynucleotides in length and essentially identical or essentially complementary to a segment of a *Lolium rigidum* gene polynucleotide selected from the group consisting of SEQ ID NO: 1-10, and an organosilicone surfactant concentration of about 0.2 percent or greater, and a nonpolynucleotide herbicide selected from the group consisting of aryloxyphenoxypropionates, cyclohexanediones and phenylpyrazoline.

In another aspect of the invention, the herbicide composition comprises a polynucleotide at least 19 contiguous polynucleotides in length and essentially identical or essentially complementary to a segment of a *Lolium rigidum* gene polynucleotide selected from the group consisting of SEQ ID NO: 11-21, and an organosilicone surfactant concentration of about 0.2 percent or greater, and a nonpolynucleotide herbicide selected from the group consisting of sulfonylureas, imidazolinones, triazolopyrimidines, pyrimidinyl(thio) benzoates, and sulfonylaminocarbonyl-triazolinones.

In another aspect of the invention, the herbicide composition comprises a polynucleotide at least 19 contiguous polynucleotides in length and essentially identical or essentially complementary to a segment of a *Lolium rigidum* gene polynucleotide selected from the group consisting of SEQ ID NO: 22-27, and an organosilicone surfactant concentration of about 0.2 percent or greater, and a nonpolynucleotide herbicide selected from the group consisting of sulfonylureas, imidazolinones, triazolopyrimidines, pyrimidinyl(thio) benzoates, and sulfonylaminocarbonyl-triazolinones.

In another aspect of the invention, the herbicide composition comprises a polynucleotide at least 19 contiguous polynucleotides in length and essentially identical or essentially complementary to a segment of a *Lolium rigidum* gene polynucleotide selected from the group consisting of SEQ ID NO: 28-32, and an organosilicone surfactant concentration of about 0.2 percent or greater, and a nonpolynucleotide herbicide selected from the group consisting of sulfonamides and asulam.

In another aspect of the invention, the herbicide composition comprises a polynucleotide at least 19 contiguous polynucleotides in length and essentially identical or essentially complementary to a segment of a *Lolium rigidum* gene polynucleotide selected from the group consisting of SEQ ID NO: 33-37, and an organosilicone surfactant concentration of about 0.2 percent or greater, and a nonpolynucleotide herbicide selected from the group consisting of glyphosate.

In another aspect of the invention, the herbicide composition comprises a polynucleotide at least 19 contiguous polynucleotides in length and essentially identical or essentially complementary to a segment of a *Lolium rigidum* gene polynucleotide selected from the group consisting of SEQ ID NO: 38-45, and an organosilicone surfactant concentration of about 0.2 percent or greater, and a nonpolynucleotide herbicide selected from the group consisting of glufosinate.

In another aspect of the invention, the herbicide composition comprises a polynucleotide at least 19 contiguous polynucleotides in length and essentially identical or essentially complementary to a segment of a *Lolium rigidum* gene polynucleotide selected from the group consisting of SEQ ID NO: 46-50, and an organosilicone surfactant concentration of about 0.2 percent or greater, and a nonpolynucleotide herbicide selected from the group consisting of triketones, isoxazoles, and pyrazoles.

In another aspect of the invention, the herbicide composition comprises a polynucleotide at least 19 contiguous polynucleotides in length and essentially identical or essentially complementary to a segment of a *Lolium rigidum* gene polynucleotide selected from the group consisting of SEQ ID NO: 51-56, and an organosilicone surfactant concentration of about 0.2 percent or greater, and a nonpolynucleotide herbicide selected from the group consisting of pyridazinones, pyridinecarboxamides, beflubutamid, fluridone, fluorochloridone and flurtamone.

In another aspect of the invention, the herbicide composition comprises a polynucleotide at least 19 contiguous polynucleotides in length and essentially identical or essentially complementary to a segment of a *Lolium rigidum* gene polynucleotide selected from the group consisting of SEQ ID NO: 57-66, and an organosilicone surfactant concentration of about 0.2 percent or greater, and a nonpolynucleotide herbicide selected from the group consisting of acifluorfen-Na, bifenox, chlomethoxyfen, fluoroglycofen-ethyl, fomesafen, halosafen, lactofen, oxyfluorfen, fluazolate, pyraflufen-ethyl, cinidon-ethyl, flumioxazin, flumiclorac-pentyl, fluthiacet-methyl, thidiazimin, oxadiazon, oxadiargyl, azafenidin, carfentrazone-ethyl, sulfentrazone, pentoxazone, benzfendizone, butafenacil, pyrazogyl, and profluazol.

The polynucleotide of the herbicide composition is at least 19 contiguous nucleotides, and at least 85 percent identical to a gene sequence selected from the group consisting of SEQ ID NO:1-66. The polynucleotide can also be sense or anti-sense ssDNA or ssRNA, dsRNA, or dsDNA, or dsDNA/RNA hybrids.

In another aspect of the invention, the herbicide composition comprises a polynucleotide at least 19 contiguous nucleotide in length or at least 85 percent homologous to polynucleotides selected from the group consisting of SEQ ID NO: 67-155. The polynucleotide can also be sense or anti-sense ssDNA or ssRNA, dsRNA, or dsDNA, or dsDNA/RNA hybrids.

In a further aspect of the invention, the polynucleotide molecule containing composition of the invention may be combined with other herbicidal compounds in a premix or tankmix to provide additional control of unwanted ryegrass plants in a field of crop plants or combined with other agricultural chemicals to provide additional benefit to crop plants in a field treated with the herbicide composition of the invention.

DETAILED DESCRIPTION

The invention provides a method and herbicide compositions containing a polynucleotide that provide for regulation of herbicide target gene expression in a *Lolium* plant and enhanced control of weedy *Lolium* plant species and important herbicide resistant *Lolium* weed biotypes. Aspects of the method can be applied to manage *Lolium* plants in agronomic and other cultivated environments.

The following definitions and methods are provided to better define the present invention and to guide those of ordinary skill in the art in the practice of the present invention. Unless otherwise noted, terms are to be understood according to conventional usage by those of ordinary skill in the relevant art. Where a term is provided in the singular, the inventors also contemplate aspects of the invention described by the plural of that term.

Herbicide activity is often directed to known enzymes in a plant cell. These enzymes include acetyl-CoA carboxylase (ACCase), acetolactate synthase (ALS large subunit and ALS small subunit, also known as acetohydroxyacid synthase, AHAS), dihydropteroate synthetase (DHPS), 5-enolpyruvylshikimate-3-phosphate synthase (EPSPS), glutamine synthetase (GS2), 4-hydroxyphenyl-pyruvate-dioxygenase (HPPD), phytoene desaturase (PDS), and protoporphyrinogen IX oxidase (PPDX). Plant genes encode for these enzymes and the polynucleotides that provide for the expression of these enzymes have been isolated from *Lolium rigidum* in the invention. The genes that encode for these enzymes are herein referred to as herbicide target genes.

The Acetyl-CoA carboxylase (ACCase) enzyme catalyzes the biotin-dependent carboxylation of acetyl-CoA to produce malonyl-CoA, this is the first and the committed step in the biosynthesis of long-chain fatty acids. This enzyme is the target of many herbicides that include members of the chemical families of aryloxyphenoxypropionates, cyclohexanediones and phenylpyrazoline, that include, but are not limited to an aryloxyphenoxypropionate comprising clodinafop (Propanoic acid, 2-[4-[(5-chloro-3-fluoro-2-pyridinyl)oxy]phenoxy]-,2-propynyl ester, (2R)), cyhalofop (butyl (2R)-2-[4-(4-cyano-2-fluorophenoxy)phenoxy]propionate), diclofop (methyl 2-[4-(2,4-dichlorophenoxy)phenoxy]propanoate), fenoxaprop (ethyl (R)-2-[4-(6-chloro-1,3-benzoxazol-2-yloxy)phenoxy]propionate), fluazifop (2R)-2-[4-[[5-(trifluoromethyl)-2-pyridinyl]oxy]phenoxy]propanoic acid), haloxyfop (2-[4-[[3-chloro-5-(trifluoromethyl)-2-pyridinyl]oxy]phenoxy]propanoic acid), propaquizafop (2-[[(1-methylethylidene)amino]oxy]ethyl (2R)-2-[4-[(6-chloro-2quinoxalinyl)oxy]phenoxy]propanoate) and quizalofop (2R)-2-[4-[(6-chloro-2-quinoxalinyl)oxy]phenoxy]propanoic acid; a cyclohexanedione comprising alloxydim (methyl 2,2-dimethyl-4,6-dioxo-5-[(1E)-1-[(2-propen-1-yloxy)imino]butyl]cyclohexanecarboxylate), butroxydim (2-[1-(ethoxyimino)propyl]-3-hydroxy-5-[2,4,6-trimethyl-3-(1-oxobutyl)phenyl]-2-cyclohexen-1-one), clethodim (2-

[1-[[[(2E)-3-chloro-2-propen-1-yl]oxy]imino]propyl]-5-[2-(ethylthio)propyl]-3-hydroxy-2-cyclohexen-1-one), cycloxydim (2-[1-(ethoxyimino)butyl]-3-hydroxy-5-(tetrahydro-2H-thiopyran-3-yl)-2-cyclohexen-1-one), profoxydim (2-[1-[[2-(4-chlorophenoxy)propoxy]imino]butyl]-3-hydroxy-5-(tetrahydro-2H-thiopyran-3-yl)-2-cyclohexen-1-one), sethoxydim (2-[1-(ethoxyimino)butyl]-5-[2-(ethylthio)propyl]-3-hydroxy-2-cyclohexen-1-one), tepraloxydim (2-[1-[[[(2E)-3-chloro-2-propen-1-yl]oxy]imino]propyl]-3-hydroxy-5-(tetrahydro-2H-pyran-4-yl)-2-cyclohexen-1-one) and tralkoxydim (2-[1-(ethoxyimino) propyl]-3-hydroxy-5-(2,4,6-trimethylphenyl)-2-cyclohexen-1-one); a phenylpyrazoline comprising pinoxaden (8-(2,6-diethyl-4-methylphenyl)-1,2,4,5-tetrahydro-7-oxo-7H-pyrazolo[1,2-d][1,4,5]oxadiazepin-9-yl 2,2-dimethylpropanoate).

The ALS (acetolactate synthase, also known as acetohydroxyacid synthase, AHAS) enzyme catalyzes the first step in the synthesis of the branched-chain amino acids (valine, leucine, and isoleucine). This enzyme is the target of many herbicides that include members of the chemical families of Sulfonylureas, Imidazolinones, Triazolopyrimidines, Pyrimidinyl(thio)benzoates, and Sulfonylaminocarbonyl-triazolinones, amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flupyrsulfuron-methyl-Na, foramsulfuron, halosulfuron-methyl, imazosulfuron, iodosulfuron, metsulfuron-methyl, nicosulfuron, oxasulfuron, primisulfuron-methyl, prosulfuron, pyrazosulfuron-ethyl, rimsulfuron, sulfometuron-methyl, sulfosulfuron, thifensulfuron-methyl, triasulfuron, tribenuron-methyl, trifloxysulfuron, triflusulfuron-methyl, tritosulfuron, imazapic, imazamethabenz-methyl, imazamox, imazapyr, imazaquin, imazethapyr, cloransulam-methyl, diclosulam, florasulam, flumetsulam, metosulam, bispyribac-Na, pyribenzoxim, pyriftalid, pyrithiobac-Na, pyriminobac-methyl, flucarbazone-Na, and procarbazone-Na.

The dihydropteroate synthetase (DHPS) is an enzyme involved in folic acid synthesis which is needed for purine nucleotide biosynthesis. This enzyme is the target of herbicides that include the carbamate chemical family and sulfonamides and asulam.

The EPSPS (5-enolpyruvylshikimate-3-phosphate synthase) enzyme catalyzes the conversion of shikimate-3-phosphate into 5-enolpyruvyl-shikimate-3-phosphate, an intermediate in the biochemical pathway for creating three essential aromatic amino acids (tyrosine, phenylalanine, and tryptophan). The EPSPS enzyme is the target for the herbicide N-phosphonomethyl glycine also known as glyphosate.

The glutamine synthetase (GS2) enzyme is an essential enzyme in the metabolism of nitrogen by catalyzing the condensation of glutamate and ammonia to form glutamine. This enzyme is the target of phosphinic acids herbicides that include glufosinate-ammonium and bialaphos.

The 4-hydroxyphenyl-pyruvate-dioxygenase (HPPD) is an Fe-containing enzyme, that catalyzes the second reaction in the catabolism of tyrosine, the conversion of 4-hydroxyphenylpyruvate to homogentisate. This enzyme is the target of many herbicides that include members of the chemical families of Triketones, Isoxazoles, and Pyrazoles, includes but are not limited to Triketones, such as, mesotrione, tefuryltrione, tembotrione, and sulcotrione; Isoxazoles, such as, isoxachlortole, pyrasulfotole, and isoxaflutole; Pyrazoles, such as, benzofenap, pyrazolynate, topramezone and pyrazoxyfen. Additional HPPD inhibitors include benzobicyclon and bicyclopyrone, The phytoene desaturase (PDS) enzyme is an essential enzyme in the carotenoid biosysnthesis pathway. This enzyme is the target of herbicides that include Pyridazinones, Pyridinecarboxamides, beflubutamid, fluridone, flurochloridone and flurtamone.

Protoporphyrinogen oxidase (PPDX) catalyses the oxidation of protoporphyrinogen IX to protoporphyrin IX during the synthesis of tetrapyrrole molecules. PPDX inhibitor herbicide, which include but is not limited to acifluorfen-Na, bifenox, chlomethoxyfen, fluoroglycofen-ethyl, fomesafen, halosafen, lactofen, oxyfluorfen, fluazolate, pyraflufen-ethyl, cinidon-ethyl, flumioxazin, flumiclorac-pentyl, fluthiacet-methyl, thidiazimin, oxadiazon, oxadiargyl, azafenidin, carfentrazone-ethyl, sulfentrazone, pentoxazone, benzfendizone, butafenacil, pyrazogyl, and profluazol.

As used herein "solution" refers to homogeneous mixtures and non-homogeneous mixtures such as suspensions, colloids, micelles, and emulsions.

Weedy plants are plants that compete with cultivated plants, those of particular importance include, but are not limited to important invasive and noxious weeds and herbicide resistant biotypes in crop production, such as, *Amaranthus* species—*A. albus, A. blitoides, A. hybridus, A. palmeri, A. powellii, A. retroflexus, A. spinosus, A. tuberculatus,* and *A. viridis; Ambrosia* species—*A. trifida, A. artemisifolia; Lolium* species—*L. multiflorum, L. rigidium, L perenne; Digitaria* species—*D. insularis; Euphorbia* species—*E. heterophylla; Kochia* species—*K. scoparia; Lolium* species—*S. halepense; Conyza* species—*C. bonariensis, C. canadensis, C. sumatrensis; Chloris* species—*C. truncate; Echinochola* species—*E. colona, E. crus-galli; Eleusine* species—*E. indica; Poa* species—*P. annua; Plantago* species—*P. lanceolata; Avena* species—*A. fatua; Chenopodium* species—*C. album; Setaria* species—*S. viridis, Abutilon theophrasti, Ipomoea* species, *Sesbania*, species, *Cassia* species, *Sida* species, *Brachiaria*, species and *Solanum* species.

*Lolium* weed species include, but are not limited to *Lolium canariense* Steud.—Canary Islands ryegrass, *Lolium edwardii* H. Scholz, Stierst. & Gaisberg, *Lolium multiflorum* Lam.—Italian ryegrass, *Lolium perenne* L.—Perennial ryegrass, *Lolium persicum*—Persian ryegrass or Persian darnel, *Lolium remotum* Schrank, *Lolium rigidum* Gaudin—Stiff darnel, Wimmera ryegrass and *Lolium temulentum* L.—Darnel, poison darnelryegrass. The polynucleotide molecules of the invention were isolated from *Lolium rigidum* and may be applicable in the method and compositions to provide control of the *Lolium* weed species other than *Lolium rigidum* where sufficient homology and complementarity of the molecules exist.

It is contemplated that the composition of the present invention will contain multiple polynucleotides and herbicides that include any one or more polynucleotides identical or complementary to a segment of the any one or more herbicide target gene sequences, and the corresponding nonpolynucleotide herbicides. Additionally, the composition may contain a pesticide, where the pesticide is selected from the group consisting of insecticides, fungicides, nematocides, bactericides, acaricides, growth regulators, chemosterilants, semiochemicals, repellents, attractants, pheromones, feeding stimulants, and biopesticides. Any one or more of these compounds can be added to the trigger oligonucleotide to form a multi-component pesticide giving an even broader spectrum of agricultural protection. Examples of such agricultural protectants with which compounds of this invention can be formulated are: insecticides such as abamectin, acephate, azinphos-methyl, bifenthrin, buprofezin, carbofuran, chlorfenapyr, chlorpyrifos, chlorpyrifos-methyl, cyfluthrin, beta-cyfluthrin, cyhalothrin, lambda-cyhalothrin, deltamethrin, diafenthiuron, diazinon, diflubenzuron, dimethoate, esfenvalerate, fenoxycarb, fenpropathrin, fenvalerate, fipronil, flucythrinate, tau-fluvalinate, fonophos, imidacloprid, isofenphos, malathion, metaldehyde, methamidophos, methidathion, methomyl, methoprene, methoxychlor, methyl 7-chloro-2,5-dihydro-2-[[N-(methoxycarbonyl)-N-[4-(trifluoromethoxy)phenyl]amino]carbonyl]indeno[1,2-e][1,3,4]oxadiazine-4a(3H)-carboxylate (DPX-JW062), monocrotophos, oxamyl, parathion, parathion-methyl, permethrin, phorate, phosalone, phosmet, phosphamidon, pirimicarb, profenofos, rotenone, sulprofos, tebufenozide, tefluthrin, terbufos, tetrachlorvinphos, thiodicarb, tralomethrin, trichlorfon and triflumuron; most preferably a glyphosate compound is formulated with a fungicide compound or combinations of fungicides, such as azoxystrobin, benomyl, blasticidin-S, Bordeaux mixture (tribasic copper sulfate), bromuconazole, captafol, captan, carbendazim, chloroneb, chlorothalonil, copper oxychloride, copper salts, cymoxanil, cyproconazole, cyprodinil (CGA 219417), diclomezine, dicloran, difenoconazole, dimethomorph, diniconazole, diniconazole-M, dodine, edifenphos, epoxiconazole (BAS 480F), famoxadone, fenarimol, fenbuconazole, fenpiclonil, fenpropidin, fenpropimorph, fluazinam, fluquinconazole, flusilazole, flutolanil, flutriafol, folpet, fosetyl-aluminum, furalaxyl, hexaconazole, ipconazole, iprobenfos, iprodione, isoprothiolane, kasugamycin, kresoxim-methyl, mancozeb, maneb, mepronil, metalaxyl, metconazole, S-methyl 7-benzothiazolecarbothioate (CGA 245704), myclobutanil, neo-asozin (ferric methanearsonate), oxadixyl, penconazole, pencycuron, probenazole, prochloraz, propiconazole, pyrifenox, pyroquilon, quinoxyfen, spiroxamine (KWG4168), sulfur, tebuconazole, tetraconazole, thiabendazole, thiophanate-methyl, thiram, triadimefon, triadimenol, tricyclazole, trifloxystrobin, triticonazole, validamycin and vinclozolin; combinations of fungicides are common for example, cyproconazole and azoxystrobin, difenoconazole, and metalaxyl-M, fludioxonil and metalaxyl-M, mancozeb and metalaxyl-M, copper hydroxide and metalaxyl-M, cyprodinil and fludioxonil, cyproconazole and propiconazole; commercially available fungicide formulations for control of Asian soybean rust disease include, but are not limited to Quadris® (Syngenta Corp), Bravo® (Syngenta Corp), Echo 720® (Sipcam Agro Inc), Headline® 2.09EC (BASF Corp), Tilt® 3.6EC (Syngenta Corp), PropiMax™ 3.6 EC (Dow AgroSciences), Bumper® 41.8EC (MakhteshimAgan), Folicur® 3.6F (Bayer CropScience), Laredo® 25EC (Dow AgroSciences), Laredo™ 25EW (Dow AgroSciences), Stratego® 2.08F (Bayer Corp), Domark™ 125SL (Sipcam Agro USA), and Pristine®38% WDG (BASF Corp) these can be combined with glyphosate compositions as described in the present invention to provide enhanced protection from soybean rust disease; nematocides such as aldoxycarb and fenamiphos; bactericides such as streptomycin; acaricides such as amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad; and biological agents such as Bacillus thuringiensis, Bacillus thuringiensis delta endotoxin, baculovirus, and entomopathogenic bacteria, virus and fungi.

Numerous nonpolynucleotide herbicides are available that can be added to the composition of the present invention at effective rates for weed control, for example, members of the herbicide families that include but are not limited to amide herbicides, aromatic acid herbicides, arsenical herbicides, benzothiazole herbicides, benzoylcyclohexanedione herbicides, benzofuranyl alkylsulfonate herbicides, carbamate herbicides, cyclohexene oxime herbicides, cyclopropylisoxazole herbicides, dicarboximide herbicides, dinitroaniline herbicides, dinitrophenol herbicides, diphenyl ether herbicides, dithiocarbamate herbicides, halogenated aliphatic herbicides, imidazolinone herbicides, inorganic herbicides, nitrile herbicides, organophosphorus herbicides, oxadiazolone herbicides, oxazole herbicides, phenoxy herbicides, phenylenediamine herbicides, pyrazole herbicides, pyridazine herbicides, pyridazinone herbicides, pyridine herbicides, pyrimidinediamine herbicides, pyrimidinyloxybenzylamine herbicides, quaternary ammonium herbicides, thiocarbamate herbicides, thiocarbonate herbicides, thiourea herbicides, triazine herbicides, triazinone herbicides, triazole herbicides, triazolone herbicides, triazolopyrimidine herbicides, uracil herbicides, and urea herbicides. In particular, the rates of use of the added herbicides can be reduced in compositions comprising the polynucleotides of the invention. Use rate reductions of the additional added herbicides can be 10-25 percent, 26-50 percent, 51-75 percent or more can be achieved that enhance the activity of the polynucleotides and herbicide composition and is contemplated as an aspect of the invention.

An agronomic field in need of *Lolium* plant control is treated by application of the herbicide composition of the present invention directly to the surface of the growing plants, such as by a spray. For example, the method is applied to control *Lolium* in a field of crop plants by spraying the field with the composition. The composition can be provided as a tank mix, a sequential treatment of components (generally the polynucleotide containing composition followed by the herbicide), or a simultaneous treatment or mixing of one or more of the components of the composition from separate containers. Treatment of the field can occur as often as needed to provide weed control and the components of the composition can be adjusted to target specific *Lolium* herbicide target genes through utilization of specific polynucleotides or polynucleotide compositions identical or complementary to the gene sequences. The composition can be applied at effective use rates according to the time of application to the field, for example, preplant, at planting, post planting, post-harvest. The nonpolynucleotide herbicides can be applied to a field at effective rates of 1 to 2000 g ai/ha (active ingredient per hectare) or more. The polynucleotides of the composition can be applied at rates of 1 to 30 grams per acre depending on the number of polynucleotide molecules as needed for effective *Lolium* control.

Crop plants in which *Lolium* weed control is needed include but are not limited to, i) corn, soybean, cotton, canola, sugar beet, alfalfa, sugarcane, rice, and wheat; ii) vegetable plants including, but not limited to, tomato, sweet pepper, hot pepper, melon, watermelon, cucumber, eggplant, cauliflower, broccoli, lettuce, spinach, onion, peas, carrots, sweet corn, Chinese cabbage, leek, fennel, pumpkin, squash or gourd, radish, Brussels sprouts, tomatillo, garden beans, dry beans, or okra; iii) culinary plants including, but not limited to, basil, parsley, coffee, or tea; or, iv) fruit plants including but not limited to apple, pear, cherry, peach, plum, apricot, banana, plantain, table grape, wine grape, citrus, avocado, mango, or berry; v) a tree grown for ornamental or commercial use, including, but not limited to, a fruit or nut tree; or, vi) an ornamental plant (e.g., an ornamental flowering plant or shrub or turf grass). The methods and compositions provided herein can also be applied to plants produced by a cutting, cloning, or grafting process (i.e., a plant not grown from a seed) include fruit trees and plants that include, but are not limited to, citrus, apples, avocados, tomatoes, eggplant, cucumber, melons, watermelons, and grapes as well as various ornamental plants. The crop plants can be transgenic and genetically engineered or genetically selected to be resistant to one or more of the nonpolynucleotide herbicides.

Polynucleotides

As used herein, the term "DNA", "DNA molecule", "DNA polynucleotide molecule" refers to a single-stranded DNA (ssDNA) or double-stranded DNA (dsDNA) molecule of genomic or synthetic origin, such as, a polymer of deoxyribonucleotide bases or a DNA polynucleotide molecule. As used herein, the term "DNA sequence", "DNA nucleotide sequence" or "DNA polynucleotide sequence" refers to the nucleotide sequence of a DNA molecule. As used herein, the term "RNA", "RNA molecule", "RNA polynucleotide molecule" refers to a single-stranded RNA (ssRNA) or double-stranded RNA (dsRNA) molecule of genomic or synthetic origin, such as, a polymer of ribonucleotide bases that comprise single or double stranded regions. Unless otherwise stated, nucleotide sequences in the text of this specification are given, when read from left to right, in the 5' to 3' direction. The nomenclature used herein is that required by Title 37 of the United States Code of Federal Regulations § 1.822 and set forth in the tables in WIPO Standard ST.25 (1998), Appendix 2, Tables 1 and 3.

As used herein, "polynucleotide" refers to a DNA or RNA molecule containing multiple nucleotides and generally refers both to "oligonucleotides" (a polynucleotide molecule of typically 50 or fewer nucleotides in length) and polynucleotides of 51 or more nucleotides. Embodiments of this invention include compositions including oligonucleotides having a length of 19-25 nucleotides (19-mers, 20-mers, 21-mers, 22-mers, 23-mers, 24-mers, or 25-mers), or medium-length polynucleotides having a length of 26 or more nucleotides (polynucleotides of 26, 27, 28, 29, 30, 46, 32, 33, 34, 35, 36, 37, 38, 39, 40, 41, 42, 43, 44, 45, 46, 47, 48, 49, 50, 51, 52, 53, 54, 55, 56, 57, 58, 59, 60, about 65, about 70, about 75, about 80, about 85, about 90, about 95, about 100, about 110, about 120, about 130, about 140, about 150, about 160, about 170, about 180, about 190, about 200, about 210, about 220, about 230, about 240, about 250, about 260, about 270, about 280, about 290, or about 300 nucleotides), or long polynucleotides having a length greater than about 300 nucleotides (for example, polynucleotides of between about 300 to about 400 nucleotides, between about 400 to about 500 nucleotides, between about 500 to about 600 nucleotides, between about 600 to about 700 nucleotides, between about 700 to about 800 nucleotides, between about 800 to about 900 nucleotides, between about 900 to about 1000 nucleotides, between about 300 to about 500 nucleotides, between about 300 to about 600 nucleotides, between about 300 to about 700 nucleotides, between about 300 to about 800 nucleotides, between about 300 to about 900 nucleotides, or about 1000 nucleotides in length, or even greater than about 1000 nucleotides in length, for example up to the entire length of a herbicide target gene including coding or non-coding or both coding and non-coding portions of the target gene). A herbicide target gene comprises any polynucleotide molecule of the gene in a plant cell or fragment thereof for which the modulation of the expression of the herbicide target gene product is provided by the methods and compositions of the present invention. Where a polynucleotide is double-stranded, its length can be similarly described in terms of base pairs. Oligonucleotides and polynucleotides of the present invention can be made that are essentially identical or essentially complementary to adjacent genetic elements of a gene, for example, spanning the junction region of an intron and exon, the junction region of a promoter and a transcribed region, the junction region of a 5' leader and a coding sequence, the junction of a 3' untranslated region and a coding sequence.

Polynucleotide compositions used in the various embodiments of this invention include compositions including oligonucleotides or polynucleotides or a mixture of both, including RNA or DNA or RNA/DNA hybrids or chemically modified oligonucleotides or polynucleotides or a mixture thereof. In some embodiments, the polynucleotide may be a combination of ribonucleotides and deoxyribonucleotides, for example, synthetic polynucleotides consisting mainly of ribonucleotides but with one or more terminal deoxyribonucleotides or synthetic polynucleotides consisting mainly of deoxyribonucleotides but with one or more terminal dideoxyribonucleotides. In some embodiments, the polynucleotide includes non-canonical nucleotides such as inosine, thiouridine, or pseudouridine. In some embodiments, the polynucleotide includes chemically modified nucleotides. Examples of chemically modified oligonucleotides or polynucleotides are well known in the art; see, for example, US Patent Publication 20110171287, US Patent Publication 20110171176, and US Patent Publication 20110152353, US Patent Publication, 20110152346, US Patent Publication 20110160082, herein incorporated by reference. For example, including but not limited to the naturally occurring phosphodiester backbone of an oligonucleotide or polynucleotide can be partially or completely modified with phosphorothioate, phosphorodithioate, or methylphosphonate internucleotide linkage modifications, modified nucleoside bases or modified sugars can be used in oligonucleotide or polynucleotide synthesis, and oligonucleotides or polynucleotides can be labeled with a fluorescent moiety (for example, fluorescein or rhodamine) or other label (for example, biotin).

The polynucleotides can be single- or double-stranded RNA or single- or double-stranded DNA or double-stranded DNA/RNA hybrids or modified analogues thereof, and can be of oligonucleotide lengths or longer. In more specific embodiments of the invention the polynucleotides that provide single-stranded RNA in the plant cell are selected from the group consisting of (a) a single-stranded RNA molecule (ssRNA), (b) a single-stranded RNA molecule that self-hybridizes to form a double-stranded RNA molecule, (c) a double-stranded RNA molecule (dsRNA), (d) a single-stranded DNA molecule (ssDNA), (e) a single-stranded DNA molecule that self-hybridizes to form a double-stranded DNA molecule, and (f) a single-stranded DNA molecule including a modified Pol III gene that is transcribed to an RNA molecule, (g) a double-stranded DNA molecule (dsDNA), (h) a double-stranded DNA molecule including a modified Pol III gene that is transcribed to an RNA molecule, (i) a double-stranded, hybridized RNA/DNA molecule, or combinations thereof. In some embodiments these polynucleotides include chemically modified nucleotides or non-canonical nucleotides. In embodiments of the method the polynucleotides include double-stranded DNA formed by intramolecular hybridization, double-stranded DNA formed by intermolecular hybridization, double-stranded RNA formed by intramolecular hybridization, or double-stranded RNA formed by intermolecular hybridization. In one embodiment the polynucleotides include single-stranded DNA or single-stranded RNA that self-hybridizes to form a hairpin structure having an at least partially double-stranded structure including at least one segment that will hybridize to RNA transcribed from the gene targeted for suppression. Not intending to be bound by any mechanism, it is believed that such polynucleotides are or will produce single-stranded RNA with at least one segment that will hybridize to RNA transcribed from the gene targeted for suppression. In certain other embodiments the polynucleotides further includes a promoter, generally a promoter functional in a plant, for example, a pol II promoter, a pol III promoter, a pol IV promoter, or a pol V promoter.

The term "gene" refers to chromosomal DNA, plasmid DNA, cDNA, intron and exon DNA, artificial DNA polynucleotide, or other DNA that encodes a peptide, polypeptide, protein, or RNA transcript molecule, and the genetic elements flanking the coding sequence that are involved in the regulation of expression, such as, promoter regions, 5' leader regions, 3' untranslated regions. Any of the components of the herbicide target gene are potential targets for the oligonucleotides and polynucleotides of the present invention.

The polynucleotide molecules of the present invention are designed to modulate expression by inducing regulation or suppression of an endogenous herbicide target gene in a ryegrass plant and are designed to have a nucleotide sequence essentially identical or essentially complementary to the nucleotide sequence of the gene or to the sequence of RNA transcribed from the target gene, which can be coding sequence or non-coding sequence. These effective polynucleotide molecules that modulate expression are referred to as "a trigger, or triggers". By "essentially identical" or "essentially complementary" is meant that the trigger polynucleotides (or at least one strand of a double-stranded polynucleotide or portion thereof, or a portion of a single strand polynucleotide) are designed to hybridize to the endogenous gene noncoding sequence (including promoters and regulatory elements of the gene) or to RNA transcribed (known as messenger RNA or an RNA transcript) from the endogenous gene to effect regulation or suppression of expression of the endogenous gene. Trigger molecules are identified by "tiling" the gene targets with partially overlapping probes or non-overlapping probes of antisense or sense polynucleotides that are essentially identical or essentially complementary to the nucleotide sequence of an endogenous gene. Multiple target sequences can be aligned and sequence regions with homology in common, according to the methods of the present invention, are identified as potential trigger molecules for the multiple targets. Multiple trigger molecules of various lengths, for example 19-25 nucleotides, 26-50 nucleotides, 51-100 nucleotides, 101-200 nucleotides, 201-300 nucleotides or more can be pooled into a few treatments in order to investigate polynucleotide molecules that cover a portion of a gene sequence (for example, a portion of a coding versus a portion of a noncoding region, or a 5' versus a 3' portion of a gene) or an entire gene sequence including coding and noncoding regions of a target gene. Polynucleotide molecules of the pooled trigger molecules can be divided into smaller pools or single molecules in order to identify trigger molecules that provide the desired effect.

The herbicide target gene RNA and DNA polynucleotide molecules are sequenced by any number of available methods and equipment. Some of the sequencing technologies are available commercially, such as the sequencing-by-hybridization platform from Affymetrix Inc. (Sunnyvale, Calif.) and the sequencing-by-synthesis platforms from 454 Life Sciences (Bradford, Conn.), Illumina/Solexa (Hayward, Calif.) and Helicos Biosciences (Cambridge, Mass.), and the sequencing-by-ligation platform from Applied Biosystems (Foster City, Calif.), as described below. In addition to the single molecule sequencing performed using sequencing-by-synthesis of Helicos Biosciences, other single molecule sequencing technologies are encompassed by the method of the invention and include the SMRT™ technology of Pacific Biosciences, the Ion Torrent™ technology, and nanopore sequencing being developed for example, by Oxford Nanopore Technologies.

Embodiments of single-stranded polynucleotides functional in this invention have sequence complementarity that need not be 100 percent, but is at least sufficient to permit hybridization to RNA transcribed from the herbicide target gene or DNA of the herbicide target gene to form a duplex to permit a gene silencing mechanism. Thus, in embodiments, a polynucleotide fragment is designed to be essentially identical to, or essentially complementary to, a sequence of 19 or more contiguous nucleotides in either DNA gene sequence or messenger RNA transcribed from the target gene. By "essentially identical" is meant having 100 percent sequence identity or at least about 83, 84, 85, 86, 87, 88, 89, 90, 91, 92, 93, 94, 95, 96, 97, 98, or 99 percent sequence identity when compared to the sequence of 19 or more contiguous nucleotides in either the target gene or RNA transcribed from the target gene; by "essentially complementary" is meant having 100 percent sequence complementarity or at least about 83, 84, 85, 86, 87, 88, 89, 90, 91, 92, 93, 94, 95, 96, 97, 98, or 99 percent sequence complementarity when compared to the sequence of 19 or more contiguous nucleotides in either the target gene or RNA transcribed from the target gene. In some embodiments of this invention polynucleotide molecules are designed to have 100 percent sequence identity with or complementarity to one allele or one family member of a given target gene (coding or non-coding sequence of a gene for of the present invention); in other embodiments the polynucleotide molecules are designed to have 100 percent sequence identity with or complementarity to multiple alleles or family members of a given target gene.

In certain embodiments, the polynucleotides used in the compositions that are essentially identical or essentially complementary to the target gene or transcript will comprise the predominant nucleic acid in the composition. Thus in certain embodiments, the polynucleotides that are essentially identical or essentially complementary to the target gene or transcript will comprise at least about 50%, 75%, 95%, 98% or 100% of the nucleic acids provided in the composition by either mass or molar concentration. However, in certain embodiments, the polynucleotides that are essentially identical or essentially complementary to the target gene or transcript can comprise at least about 1% to about 50%, about 10% to about 50%, about 20% to about 50%, or about 30% to about 50% of the nucleic acids provided in the composition by either mass or molar concentration. Also provided are compositions where the polynucleotides that are essentially identical or essentially complementary to the target gene or transcript can comprise at least about 1% to 100%, about 10% to 100%, about 20% to about 100%, about 30% to about 50%, or about 50% to a 100% of the nucleic acids provided in the composition by either mass or molar concentration.

"Identity" refers to the degree of similarity between two polynucleic acid or protein sequences. An alignment of the two sequences is performed by a suitable computer program. A widely used and accepted computer program for performing sequence alignments is CLUSTALW v1.6 (Thompson, et al. Nucl. Acids Res., 22: 4673-4680, 1994). The number of matching bases or amino acids is divided by the total number of bases or amino acids, and multiplied by 100 to obtain a percent identity. For example, if two 580 base pair sequences had 145 matched bases, they would be 25 percent identical. If the two compared sequences are of different lengths, the number of matches is divided by the shorter of the two lengths. For example, if there are 100 matched amino acids between a 200 and a 400 amino acid protein, they are 50 percent identical with respect to the shorter sequence. If the shorter sequence is less than 150 bases or 50 amino acids in length, the number of matches are divided by 150 (for nucleic acid bases) or 50 (for amino acids), and multiplied by 100 to obtain a percent identity.

Trigger molecules for specific herbicide target gene family members can be identified from coding and/or non-coding sequences of gene families of a plant or multiple plants, by aligning and selecting 200-300 polynucleotide fragments from the least homologous regions amongst the aligned sequences and evaluated using topically applied polynucleotides (as sense or anti-sense ssDNA or ssRNA, dsRNA, or dsDNA) to determine their relative effectiveness in inducing the herbicidal phenotype. The effective segments are further subdivided into 50-60 polynucleotide fragments, prioritized by least homology, and reevaluated using topically applied polynucleotides. The effective 50-60 polynucleotide fragments are subdivided into 19-30 polynucleotide fragments, prioritized by least homology, and again evaluated for induction of the yield/quality phenotype. Once relative effectiveness is determined, the fragments are utilized singly, or again evaluated in combination with one or more other fragments to determine the trigger composition or mixture of trigger polynucleotides for providing the yield/quality phenotype.

Trigger molecules for broad activity against *Lolium* weed species can be identified from coding and/or non-coding sequences of gene families of a plant or multiple plants, by aligning and selecting 200-300 polynucleotide fragments from the most homologous regions amongst the aligned sequences and evaluated using topically applied polynucleotides (as sense or anti-sense ssDNA or ssRNA, dsRNA, or dsDNA) to determine their relative effectiveness in inducing the yield/quality phenotype. The effective segments are subdivided into 50-60 polynucleotide fragments, prioritized by most homology, and reevaluated using topically applied polynucleotides. The effective 50-60 polynucleotide fragments are subdivided into 19-30 polynucleotide fragments, prioritized by most homology, and again evaluated for induction of the yield/quality phenotype. Once relative effectiveness is determined, the fragments may be utilized singly, or in combination with one or more other fragments to determine the trigger composition or mixture of trigger polynucleotides for providing the yield/quality phenotype.

Methods of making polynucleotides are well known in the art. Chemical synthesis, in vivo synthesis and in vitro synthesis methods and compositions are known in the art and include various viral elements, microbial cells, modified polymerases, and modified nucleotides. Commercial preparation of oligonucleotides often provides two deoxyribonucleotides on the 3' end of the sense strand. Long polynucleotide molecules can be synthesized from commercially available kits, for example, kits from Applied Biosystems/Ambion (Austin, Tex.) have DNA ligated on the 5' end in a microbial expression cassette that includes a bacterial T7 polymerase promoter that makes RNA strands that can be assembled into a dsRNA and kits provided by various manufacturers that include T7 RiboMax Express (Promega, Madison, Wis.), AmpliScribe T7-Flash (Epicentre, Madison, Wis.), and TranscriptAid T7 High Yield (Fermentas, Glen Burnie, Md.). dsRNA molecules can be produced from microbial expression cassettes in bacterial cells (Ongvarrasopone et al. ScienceAsia 33:35-39; Yin, Appl. Microbiol. Biotechnol 84:323-333, 2009; Liu et al., BMC Biotechnology 10:85, 2010) that have regulated or deficient RNase III enzyme activity or the use of various viral vectors to produce sufficient quantities of dsRNA. In some embodiments design parameters such as Reynolds score (Reynolds et al. Nature Biotechnology 22, 326-330 (2004) and Tuschl rules (Pei and Tuschl, Nature Methods 3(9): 670-676, 2006) are known in the art and are used in selecting polynucleotide sequences effective in gene silencing. In some embodiments random design or empirical selection of polynucleotide sequences is used in selecting polynucleotide sequences effective in gene silencing. In some embodiments the sequence of a polynucleotide is screened against the genomic DNA of the intended plant to minimize unintentional silencing of other genes.

The polynucleotide compositions of this invention are useful in compositions, such as solutions of polynucleotide molecules, at low concentrations, alone or in combination with other components either in the same solution or in separately applied solutions that provide a permeability-enhancing agent. While there is no upper limit on the concentrations and dosages of polynucleotide molecules that can useful in the methods of this invention, lower effective concentrations and dosages will generally be sought for efficiency. The concentrations can be adjusted in consideration of the volume of spray or treatment applied to plant leaves or other plant part surfaces, such as flower petals, stems, tubers, fruit, anthers, pollen, or seed. In one embodiment, a useful treatment for herbaceous plants using 25-mer oligonucleotide molecules is about 1 nanomole (nM) of oligonucleotide molecules per plant, for example, from about 0.05 to 1 nM per plant. Other embodiments for herbaceous plants include useful ranges of about 0.05 to about 100 nM, or about 0.1 to about 20 nM, or about 1 nM to about 10 nM of polynucleotides per plant. To illustrate embodiments of the invention, the factor 1×, when applied to oligonucleotide molecules is arbitrarily used to denote a treatment of 0.8 nM of polynucleotide molecule per plant; 10×, 8 nM of polynucleotide molecule per plant; and 100×, 80 nM of polynucleotide molecule per plant.

The polynucleotide compositions of this invention are useful in compositions, such as liquids that comprise polynucleotide molecules, alone or in combination with other components either in the same liquid or in separately applied liquids that provide a transfer agent. As used herein, a transfer agent is an agent that, when combined with a polynucleotide in a composition that is topically applied to a target plant surface, enables the polynucleotide to enter a plant cell. In certain embodiments, a transfer agent is an agent that conditions the surface of plant tissue, e.g., leaves, stems, roots, flowers, or fruits, to permeation by the polynucleotide molecules into plant cells. The transfer of polynucleotides into plant cells can be facilitated by the prior or contemporaneous application of a polynucleotide-transferring agent to the plant tissue. In some embodiments the transferring agent is applied subsequent to the application of the polynucleotide composition. The polynucleotide transfer agent enables a pathway for polynucleotides through cuticle wax barriers, stomata and/or cell wall or membrane barriers into plant cells. Suitable transfer agents to facilitate transfer of the polynucleotide into a plant cell include agents that increase permeability of the exterior of the plant or that increase permeability of plant cells to oligonucleotides or polynucleotides. Such agents to facilitate transfer of the composition into a plant cell include a chemical agent, or a physical agent, or combinations thereof. Chemical agents for conditioning or transfer include (a) surfactants, (b) an organic solvent or an aqueous solution or aqueous mixtures of organic solvents, (c) oxidizing agents, (d) acids, (e) bases, (f) oils, (g) enzymes, or combinations thereof. Embodiments of the method can optionally include an incubation step, a neutralization step (e.g., to neutralize an acid, base, or oxidizing agent, or to inactivate an enzyme), a rinsing step, or combinations thereof. Embodiments of agents or treatments for conditioning of a plant to permeation by polynucleotides include emulsions, reverse emulsions, liposomes, and other micellar-like compositions. Embodiments of agents or treatments for conditioning of a plant to permeation by polynucleotides include counter-ions or other molecules that are known to associate with nucleic acid molecules, e.g., inorganic ammonium ions, alkyl ammonium ions, lithium ions, polyamines such as spermine, spermidine, or putrescine, and other cations. Organic solvents useful in conditioning a plant to permeation by polynucleotides include DMSO, DMF, pyridine, N-pyrrolidine, hexamethylphosphoramide, acetonitrile, dioxane, polypropylene glycol, other solvents miscible with water or that will dissolve phosphonucleotides in non-aqueous systems (such as is used in synthetic reactions). Naturally derived or synthetic oils with or without surfactants or emulsifiers can be used, e.g., plant-sourced oils, crop oils, such as those listed in the 9$^{th}$ Compendium of Herbicide Adjuvants, can be used, e.g., paraffinic oils, polyol fatty acid esters, or oils with short-chain molecules modified with amides or polyamines such as polyethyleneimine or N-pyrrolidine. Transfer agents include, but are not limited to, organosilicone preparations.

In certain embodiments, an organosilicone preparation that is commercially available as Silwet® L-77 surfactant having CAS Number 27306-78-1 and EPA Number: CAL. REG. NO. 5905-50073-AA, and currently available from Momentive Performance Materials, Albany, N.Y. can be used to prepare a polynucleotide composition. In certain embodiments where a Silwet L-77 organosilicone preparation is used as a pre-spray treatment of plant leaves or other plant surfaces, freshly made concentrations in the range of about 0.015 to about 2 percent by weight (wt percent) (e.g., about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.5 wt percent) are efficacious in preparing a leaf or other plant surface for transfer of polynucleotide molecules into plant cells from a topical application on the surface. In certain embodiments of the methods and compositions provided herein, a composition that comprises a polynucleotide molecule and an organosilicone preparation comprising Silwet L-77 in the range of about 0.015 to about 2 percent by weight (wt percent) (e.g., about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.5 wt percent) is used or provided.

In certain embodiments, any of the commercially available organosilicone preparations provided such as the following Breakthru S 321, Breakthru S 200 Cat #67674-67-3, Breakthru OE 441 Cat #68937-55-3, Breakthru S 278 Cat #27306-78-1, Breakthru S 243, Breakthru S 233 Cat #134180-76-0, available from manufacturer Evonik Goldschmidt (Germany), Silwet® HS 429, Silwet® HS 312, Silwet® HS 508, Silwet® HS 604 (Momentive Performance Materials, Albany, N.Y.) can be used as transfer agents in a polynucleotide composition. In certain embodiments where an organosilicone preparation is used as a pre-spray treatment of plant leaves or other surfaces, freshly made concentrations in the range of about 0.015 to about 2 percent by weight (wt percent) (e.g., about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.5 wt percent) are efficacious in preparing a leaf or other plant surface for transfer of polynucleotide molecules into plant cells from a topical application on the surface. In certain embodiments of the methods and compositions provided herein, a composition that comprises a polynucleotide molecule and an organosilicone preparation in the range of about 0.015 to about 2 percent by weight (wt percent) (e.g., about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.5 wt percent) is used or provided.

Organosilicone preparations used in the methods and compositions provided herein can comprise one or more effective organosilicone compounds. As used herein, the phrase "effective organosilicone compound" is used to describe any organosilicone compound that is found in an organosilicone preparation that enables a polynucleotide to enter a plant cell. In certain embodiments, an effective organosilicone compound can enable a polynucleotide to enter a plant cell in a manner permitting a polynucleotide mediated suppression of a target gene expression in the plant cell. In general, effective organosilicone compounds include, but are not limited to, compounds that can comprise: i) a trisiloxane head group that is covalently linked to, ii) an alkyl linker including, but not limited to, an n-propyl linker, that is covalently linked to, iii) a poly glycol chain, that is covalently linked to, iv) a terminal group. Trisiloxane head groups of such effective organosilicone compounds include, but are not limited to, heptamethyltrisiloxane. Alkyl linkers can include, but are not limited to, an n-propyl linker. Poly glycol chains include, but are not limited to, polyethylene glycol or polypropylene glycol. Poly glycol chains can comprise a mixture that provides an average chain length "n" of about "7.5". In certain embodiments, the average chain length "n" can vary from about 5 to about 14. Terminal groups can include, but are not limited to, alkyl groups such as a methyl group. Effective organosilicone compounds are believed to include, but are not limited to, trisiloxane ethoxylate surfactants or polyalkylene oxide modified heptamethyl trisiloxane.

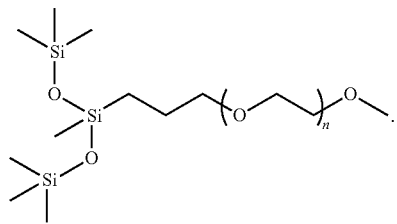

(Compound I: polyalkyleneoxide heptamethyltrisiloxane, average n = 7.5)

In certain embodiments, an organosilicone preparation that comprises an organosilicone compound comprising a trisiloxane head group is used in the methods and compositions provided herein. In certain embodiments, an organosilicone preparation that comprises an organosilicone compound comprising a heptamethyltrisiloxane head group is used in the methods and compositions provided herein. In certain embodiments, an organosilicone composition that comprises Compound I is used in the methods and compositions provided herein. In certain embodiments, an organosilicone composition that comprises Compound I is used in the methods and compositions provided herein. In certain embodiments of the methods and compositions provided herein, a composition that comprises a polynucleotide molecule and one or more effective organosilicone compound in the range of about 0.015 to about 2 percent by weight (wt percent) (e.g., about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.5 wt percent) is used or provided.

Compositions of the present invention include but are not limited components that are one or more polynucleotides essentially identical to, or essentially complementary to herbicide target gene sequence (promoter, intron, exon, 5' untranslated region, 3' untranslated region), a transfer agent that provides for the polynucleotide to enter a plant cell, a herbicide that complements the action of the polynucleotide, one or more additional herbicides that further enhance the herbicide activity of the composition or provide an additional mode of action different from the complementing herbicide, various salts and stabilizing agents that enhance the utility of the composition as an admixture of the components of the composition.

In aspects of the invention, methods include one or more applications of a polynucleotide composition and one or more applications of a permeability-enhancing agent for conditioning of a plant to permeation by polynucleotides. When the agent for conditioning to permeation is an organosilicone composition or compound contained therein, embodiments of the polynucleotide molecules are double-stranded RNA oligonucleotides, single-stranded RNA oligonucleotides, double-stranded RNA polynucleotides, single-stranded RNA polynucleotides, double-stranded DNA oligonucleotides, single-stranded DNA oligonucleotides, double-stranded DNA polynucleotides, single-stranded DNA polynucleotides, chemically modified RNA or DNA oligonucleotides or polynucleotides or mixtures thereof.

In various embodiments, a Lolium herbicide target gene includes coding (protein-coding or translatable) sequence, non-coding (non-translatable) sequence, or both coding and non-coding sequence. Compositions of the invention can include polynucleotides and oligonucleotides designed to target multiple genes, or multiple segments of one or more genes. The target gene can include multiple consecutive segments of a target gene, multiple non-consecutive segments of a target gene, multiple alleles of a target gene, or multiple target genes from one or more species.

An aspect of the invention provides a method for modulating expression of an herbicide target gene in a Lolium plant including (a) conditioning of a plant to permeation by polynucleotides and (b) treatment of the plant with the polynucleotide molecules, wherein the polynucleotide molecules include at least one segment of 19 or more contiguous nucleotides cloned from or otherwise identified from the target gene in either anti-sense or sense orientation, whereby the polynucleotide molecules permeate the interior of the plant and induce modulation of the target gene. The conditioning and polynucleotide application can be performed separately or in a single step. When the conditioning and polynucleotide application are performed in separate steps, the conditioning can precede or can follow the polynucleotide application within minutes, hours, or days. In some embodiments more than one conditioning step or more than one polynucleotide molecule application can be performed on the same plant. In embodiments of the method, the segment can be cloned or identified from (a) coding (protein-encoding), (b) non-coding (promoter and other gene related molecules), or (c) both coding and non-coding parts of the target gene. Non-coding parts include DNA, such as promoter regions or the RNA transcribed by the DNA that provide RNA regulatory molecules, including but not limited to: introns, 5' or 3' untranslated regions, and microRNAs (miRNA), trans-acting siRNAs, natural anti-sense siRNAs, and other small RNAs with regulatory function or RNAs having structural or enzymatic function including but not limited to: ribozymes, ribosomal RNAs, t-RNAs, aptamers, and riboswitches.

The following examples are included to demonstrate examples of certain preferred embodiments of the invention. It should be appreciated by those of skill in the art that the techniques disclosed in the examples that follow represent approaches the inventors have found function well in the practice of the invention, and thus can be considered to constitute examples of preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLES

Example 1. Polynucleotides Related to the Herbicide Target Genes *Lolium rigidum*

Polynucleotides were isolated from *Lolium rigidum* and sequenced and those identified as noncoding or coding regions of herbicide target genes acetyl-CoA carboxylase (ACCase), acetolactate synthase (ALS large subunit and ALS small subunit, also known as acetohydroxyacid synthase, AHAS), dihydropteroate synthetase (DHPS), 5-enolpyruvylshikimate-3-phosphate synthase (EPSPS), glutamine synthetase (GS2), 4-hydroxyphenyl-pyruvate-dioxygenase (HPPD), phytoene desaturase (PDS), protoporphyrinogen IX oxidase (PPDX) were selected. These are shown as SEQ ID NO:1-66.

Polynucleotide molecules were extracted from *Lolium rigidum* tissues by methods standard in the field, for example, total RNA was extracted using Trizol Reagent (Invitrogen Corp, Carlsbad, Calif. Cat. No. 15596-018), following the manufacturer's protocol or modifications thereof by those skilled in the art of polynucleotide extraction that may enhance recover or purity of the extracted RNA. Briefly, starting with approximately 1 gram of ground plant tissue for extraction. Prealiquot 10 milliliters (mL) Trizol reagent to 15 mL conical tubes. Add ground powder to tubes and shake to homogenize. Incubate the homogenized samples for 5 minutes (min) at room temperature (RT) and then add 3 mL of chloroform. Shakes tubes vigorously by hand for 15-30 seconds (sec) and incubate at RT for 3 min. Centrifuge the tubes at 7,000 revolutions per minute (rpm) for 10 min at 4 degrees C. (centigrade). Transfer the aqueous phase to a new 1.5 mL tube and add 1 volume of cold isopropanol. Incubate the samples for 20-30 min at RT and centrifuge at 10,000 rpm for 10 min at 4 degrees C. Wash pellet with Sigma-grade 80 percent ethanol. Remove the supernatant and briefly air-dry the pellet. Dissolve the RNA pellet in approximately 200 microliters of Diethylpyrocarbonate (DEPC) treated water. Heat briefly at 65 C to dissolve pellet and vortex or pipet to resuspend RNA pellet. Adjust RNA concentration to 1-2 microgram/microliter. RNA was used to make cDNA libraries by standard methods that were then sequenced.

Genomic DNA (gDNA) was extracted using EZNA SP Plant DNA Mini kit (Omega Biotek, Norcross Ga., Cat # D5511) and Lysing Matrix E tubes (Q-Biogen, Cat #6914), following the manufacturer's protocol or modifications thereof by those skilled in the art of polynucleotide extraction that may enhance recover or purity of the extracted DNA. Briefly, aliquot ground tissue to a Lysing Matrix E tube on dry ice, add 800 μl Buffer SP1 to each sample, homogenize in a bead beater for 35-45 sec, incubate on ice for 45-60 sec, centrifuge at ≥14000 rpm for 1 min at RT, add 10 microliter RNase A to the lysate, incubate at 65° C. for 10 min, centrifuge for 1 min at RT, add 280 μl Buffer SP2 and vortex to mix, incubate the samples on ice for 5 min, centrifuge at ≥10,000 g for 10 min at RT, transfer the supernatant to a homogenizer column in a 2 ml collection tube, centrifuge at 10,000 g for 2 min at RT, transfer the cleared lysate into a 1.5 ml microfuge tube, add 1.5 volumes Buffer SP3 to the cleared lysate, vortex immediately to obtain a homogeneous mixture, transfer up to 650 μl supernatant to the Hi-Bind column, centrifuge at 10,000 g for 1 min, repeat, apply 100 μl 65° C. Elution Buffer to the column, centrifuge at 10,000 g for 5 min at RT.

Next-generation DNA sequencers, such as the 454-FLX (Roche, Branford, Conn.), the SOLiD (Applied Biosystems), and the Genome Analyzer (HiSeq2000, Illumina, San Diego, Calif.) are used to provide polynucleotide sequence from the DNA and RNA extracted from the plant tissues. Raw sequence data is assembled into contigs. The contig sequence is used to identify trigger molecules that can be applied to the plant to enable regulation of the gene expression. SEQ ID NO: 1-66 (summarized in Table 1) contains the target cDNA and gDNA sequence contigs from the various herbicide target genes of *Lolium rigidum*.

TABLE 1

*Lolium rigidum* herbicide target gene sequences and fragments SEQ ID NO: 1-66.

| SEQ ID NO | GENE | TYPE |
|---|---|---|
| 1 | ACCase | gDNAContig |
| 2 | ACCase | gDNAContig |
| 3 | ACCase | gDNAContig |
| 4 | ACCase | gDNAContig |
| 5 | ACCase | gDNAContig |
| 6 | ACCase | gDNAContig |
| 7 | ACCase | gDNAContig |
| 8 | ACCase | gDNAContig |
| 9 | ACCase | gDNAContig |
| 10 | ACCase | gDNAContig |
| 11 | ALS | gDNAContig |
| 12 | ALS | gDNAContig |
| 13 | ALS | gDNAContig |
| 14 | ALS | gDNAContig |
| 15 | ALS | gDNAContig |
| 16 | ALS | gDNAContig |
| 17 | ALS | gDNAContig |
| 18 | ALS | gDNAContig |
| 19 | ALS | gDNAContig |
| 20 | ALS | gDNAContig |
| 21 | ALS | gDNAContig |
| 22 | ALS_small | gDNAContig |
| 23 | ALS_small | gDNAContig |
| 24 | ALS_small | gDNAContig |
| 25 | ALS_small | gDNAContig |
| 26 | ALS_small | gDNAContig |
| 27 | ALS_small | gDNAContig |
| 28 | DHPS | gDNAContig |
| 29 | DHPS | gDNAContig |
| 30 | DHPS | gDNAContig |
| 31 | DHPS | gDNAContig |
| 32 | DHPS | gDNAContig |
| 33 | EPSPS | gDNAContig |
| 34 | EPSPS | gDNAContig |
| 35 | EPSPS | gDNAContig |
| 36 | EPSPS | gDNAContig |
| 37 | EPSPS | gDNAContig |
| 38 | GS2 | gDNAContig |
| 39 | GS2 | gDNAContig |
| 40 | GS2 | gDNAContig |
| 41 | GS2 | gDNAContig |
| 42 | GS2 | gDNAContig |
| 43 | GS2 | gDNAContig |
| 44 | GS2 | gDNAContig |
| 45 | GS2 | gDNAContig |
| 46 | HPPD | gDNAContig |
| 47 | HPPD | gDNAContig |
| 48 | HPPD | gDNAContig |
| 49 | HPPD | gDNAContig |
| 50 | HPPD | gDNAContig |
| 51 | PDS | gDNAContig |
| 52 | PDS | gDNAContig |
| 53 | PDS | gDNAContig |
| 54 | PDS | gDNAContig |
| 55 | PDS | gDNAContig |
| 56 | PDS | gDNAContig |
| 57 | PPOX | gDNAContig |
| 58 | PPOX | gDNAContig |
| 59 | PPOX | gDNAContig |
| 60 | PPOX | gDNAContig |
| 61 | PPOX | gDNAContig |
| 62 | PPOX | gDNAContig |
| 63 | PPOX | gDNAContig |
| 64 | PPOX | gDNAContig |
| 65 | PPOX | gDNAContig |
| 66 | PPOX | gDNAContig |

Example 2. Polynucleotides of the Invention Related to Trigger Molecules of the *Lolium rigidum* Herbicide Target Genes The gene sequences and fragments of SEQ ID NO: 1-66 were selected into short polynucleotide lengths of 30 contiguous nucleotides as shown in Table 2, SEQ ID NO: 67-155. These polynucleotides are tested to select an efficacious trigger to any of the herbicide target gene sequence regions. The trigger polynucleotides are constructed as sense or anti-sense ssDNA or ssRNA, dsRNA, or dsDNA, or dsDNA/RNA hybrids and combined with an organosilicone based transfer agent and nonpolynucleotide herbicide to provide a new herbicidal composition. The polynucleotides are combined into sets of two to three polynucleotides per set, using 4-8 nM of each polynucleotide. Each polynucleotide set is prepared with the organosilicone transfer agent and applied to a *Lolium* plant or to a field of crop plants containing ryegrass plants in combination with a nonpolynucleotide herbicide that targets one or more of the enzymes of the herbicide target genes, or followed by the nonpolynucleotide herbicide treatment one to three days later. The effect is measured as stunting the growth and/or killing of the plant and is measured 8-14 days after treatment with the herbicidal composition. The most efficacious trigger sets are identified and the individual polynucleotides are tested in the same methods as the sets are and the most efficacious single polynucleotide is identified. By this method it is possible to identify one oligonucleotide or several oligonucleotides that effect plant sensitivity to nonpolynucleotide herbicide.

It is contemplated that additional 19-30 polynucleotides can be selected from the sequences of SEQ ID NO: 1-66 that are specific for a herbicide target gene in *Lolium rigidum* or include activity against a related weed species, for example, *Lolium canariense* Steud.—Canary Islands ryegrass, *Lolium edwardii* H. Scholz, Stierst. & Gaisberg, *Lolium multiflorum* Lam.—Italian ryegrass, *Lolium perenne* L.—Perennial ryegrass, *Lolium persicum*—Persian ryegrass or Persian darnel, *Lolium remotum* Schrank, and *Lolium temulentum* L.—Darnel, poison darnelryegrass

TABLE 2

Polynucleotides SEQ ID NO: 67-155.

| SEQ ID NO | SEQ | GENE |
|---|---|---|
| 67 | GGAAGAGCCGATTCTCCGGCATGTGGAGCC | ACCase |
| 68 | GGGCAAGTCTGGTTTCCAGATTCTGCTACC | ACCase |
| 69 | GGAGAGGCTTCTCTGGTGGGCAAAGAGACC | ACCase |
| 70 | GGAAAAGTTATATCCTCTTGTGCGGCAACC | ACCase |
| 71 | GGAGAGATACGCACTAATGTTGATTACACC | ACCase |
| 72 | GGGCTGTTAATGCAGGTAAACATATTTACC | ACCase |
| 73 | GGATGGTTCTCATGTGGTTGCTGATACACC | ACCase |
| 74 | GGAAGTGGAGGTCATGAAGATGTGCATGCC | ACCase |
| 75 | GGCCTCTGGCGTCATTCACTTTGTCATGCC | ACCase |
| 76 | GGACTTTAAGACATATACGTTGGCTAACCC | ACCase |
| 77 | GGAGGAGCCGATGCTCCGCCATGTGGAACC | ACCase |
| 78 | GGCATTGTTGCTTGGAAGATGAAGCTCTCC | ACCase |
| 79 | GGCTCTACAATTGTTGAGAACCTGAGGACC | ACCase |
| 80 | GGAAGTTGAGGTTATGAAGATGTGCATGCC | ACCase |
| 81 | GGGACCGAGAAGGCCATTCTCCTGGTGGCC | ACCase |
| 82 | GGCCTGGCTGGGGCCATGCTTCTGAGAACC | ACCase |
| 83 | GGAGAAGGGAATCATTTTTCTTGGGCCACC | ACCase |
| 84 | GGTGGCTAGTTGTCAGGTGGTGGGGTATCC | ACCase |
| 85 | GGCGCTATGGGCTACTGCATTTCGGCGGCC | ALS |
| 86 | GGAGTTGGAGCAGCAGAAAAGGGAGTTTCC | ALS |
| 87 | GGGATACAAAACTTTCGGGGAGGCCATCCC | ALS |
| 88 | GGTTATACTTCTTGTGTAAATATTAGGACC | ALS |
| 89 | GGTCACATTTAGGTTAACTAGATTTACACC | ALS |
| 90 | GGCTATAGGTGCCACAGTCTGCCTAGTACC | ALS |
| 91 | GGTATTCCCCATCGATAGGGAATTCGACCC | ALS |
| 92 | GGGCGGGCCCCGATGAACTTAGGGAAGTCC | ALS |
| 93 | GGGCCTCCTCACGCCGCGCCCTCGCCGCCC | ALS |
| 94 | GGTTATACTTCTTGTGTAAATATTAGGACC | ALS_small |
| 95 | GGTCACATTTAGGTTAACTAGATTTACACC | ALS_small |
| 96 | GGCATTTCACGTATTACAACAGTTGTTCCC | ALS_small |
| 97 | GGGAGATACTAGATATCGGTCAAATCTTCC | ALS_small |
| 98 | GGTTATACTTCTTGTGTAAATATTAGGACC | ALS_small |
| 99 | GGTCACATTTAGGTTAACTAGATTTACACC | ALS_small |
| 100 | GGCATTTCACGTATTACAACAGTTGTTCCC | ALS_small |
| 101 | GGGAGATACTAGATATCGGTCAAATCTTCC | ALS_small |
| 102 | GGCTATAGGTGCCACAGTCTGCCTAGTACC | ALS_small |
| 103 | GGGGGTAAGTTTCAAGAAGTGGAAGCTGCC | DHPS |
| 104 | GGTTTTCATGAAACTTCTCCTCGTGACTCC | DHPS |
| 105 | GGTGTTGTTGCAGGTCCTGTGTTTTTTACC | DHPS |
| 106 | GGCCGGCGCGGAGGAGGTCGTGCTGCAGCC | EPSPS |
| 107 | GGCGGCAGGTTCCCGATTGAGAAGGATGCC | EPSPS |
| 108 | GGTGCGAATGTTGATTGTTTCCTCGGCACC | EPSPS |
| 109 | GGTTCCATCAGCAGCCAGTACTTGAGTTCC | EPSPS |
| 110 | GGTCCAACTGCTATCAGAGATGGTAAACCC | EPSPS |
| 111 | GGGACCCTGGGTGCACCCGCAAGACCTTCC | EPSPS |
| 112 | GGTTCCATCAGCAGCCAATACTTGAGTTCC | EPSPS |
| 113 | GGTCCAACTGCTATCAGAGATGGTAAACCC | EPSPS |
| 114 | GGCAAGCACGAGACCGCTGACATCCACACC | GS2 |
| 115 | GGCCTCTTGGCTGGCCTGTTGGAGGGTACC | GS2 |
| 116 | GGCCAGCCCTTTGGTCAAATCATATTTCCC | GS2 |
| 117 | GGTACGGTATCGAGCAGGAGTACACCCTCC | GS2 |
| 118 | GGTGCGCCTGGTCAGAGCCTTCCAAGTTCC | GS2 |
| 119 | GGCGGCAGAGTAGCTACCTACTAGCTAGCC | GS2 |
| 120 | GGGGGAAGGGTGTGGGCGTCAGGAGGGCC | GS2 |
| 121 | GGCATGTGAGTTAAAATGATTTTTTTTGCC | GS2 |
| 122 | GGCGATCAGGCTGCTCTCCGACAATGATCC | GS2 |
| 123 | GGCATTGCACGGGAGACATAGGAATTAGCC | GS2 |
| 124 | GGCCATCAGGCTGCTCTCTGACAATGATCC | GS2 |
| 125 | GGTAATTGCTGTGCCTGGTCAGAGCCTTCC | GS2 |
| 126 | GGCCATCAGGCTGCTCTCGGACAATGATCC | GS2 |
| 127 | GGCATGTGAGTTAAAATGATTTTTTTTGCC | GS2 |
| 128 | GGCCTCTTGGCTGGCCTGTTGGAGGGTACC | GS2 |

TABLE 2-continued

Polynucleotides SEQ ID NO: 67-155.

| SEQ ID NO | SEQ | GENE |
|---|---|---|
| 129 | GGCCAGCCGATTGGTCAAATCATATTTCCC | GS2 |
| 130 | GGCGGGGAGCTGCGGTCGTGCATGGCCACC | GS2 |
| 131 | GGTACCTTTTCTTTTCACCGCCGCCTCACC | GS2 |
| 132 | GGTCGCGTCCCCCGGCTTTTTCCTCATCCC | GS2 |
| 133 | GGCCCCATCACCGACGCGAGCCAGCTGCCC | GS2 |
| 134 | GGAACAATGCTGCCAAGATCTTCGACAACC | GS2 |
| 135 | GGTACGGTATCGAGCAGGAGTACACCCTCC | GS2 |
| 136 | GGCGACTGGAACGGCGCCGGCGCGCACACC | GS2 |
| 137 | GGACACCACGAGACCGCCGACATCAACACC | GS2 |
| 138 | GGATATCAATCTCAATGTGTTTAGTGAGCC | GS2 |
| 139 | GGCTTCTATGTTTTCCAATACTTCGATGCC | HPPD |
| 140 | GGGCTCGGCGTGCCACTCGCCGCGCAGTCC | HPPD |
| 141 | GGAGCCACGTCGAGACGTTCCTGGACCACC | HPPD |
| 142 | GGCCCAGGCATACAGCACCTGGCAATGACC | HPPD |
| 143 | GGCGCGCTCAGGAAAATCCGAGCTCGGTCC | HPPD |
| 144 | GGGCGGGTTTGAGCTCCTGCCGCCGCCGCC | HPPD |
| 145 | GGAGGTTTACTTGTTTGAACCGAATGTTCC | PDS |
| 146 | GGACCATAAATGGAGGAAAATCGTATTCCC | PDS |
| 147 | GGTAAGCAACTGCTAGTGATCGGAGGCCCC | PDS |
| 148 | GGCTATGGCTAAACACTGTAAATAAAGTCC | PDS |
| 149 | GGTTGCAATGACGACAGCTTCGATCTCACC | PDS |
| 150 | GGCGCCCACTATAAGCAATGACGGAGTACC | PDS |
| 151 | GGAGAAGTTAAAACAAACATAGGGCCCACC | PDS |
| 152 | GGATATGTTGTAACGCGATAAATTGCTGCC | PDS |
| 153 | GGTTGGGGCCTGTACTATATAGGAAATTCC | PPOX |
| 154 | GGGGGTGCTACAAATACAGGGATCGTCTCC | PPOX |
| 155 | GGTTACGGTATTCAGTTAGTGTTGGTCACC | PPOX |

Example 3. Methods Used in the Invention Related to Treating Plants or Plant Parts with a Topical Mixture of the Trigger Molecules

*Lolium* plants are grown in the greenhouse (30/20 C day/night T; 14 hour photoperiod) in 4 inch square pots containing Sun Gro® Redi-Earth and 3.5 kg/cubic meter Osmocote® 14-14-14 fertilizer. When the plants at 5 to 10 cm in height are pre-treated with a mixture of single-strand antisense or double-strand polynucleotides (ssDNA ro dsRNA targeting one or more of the herbicide target gene sequences from SEQ ID NO: 1-66) at 16 nM, formulated in 10 millimolar sodium phosphate buffer (pH 6.8) containing 2% ammonium sulfate and 0.5% Silwet L-77. Plants are treated manually by pipetting 10 μL of polynucleotide solution on fully expanded mature leaves, for a total of 40 microliters of solution per plant. Twenty-four and forty-eight hours later, the plants are treated with and effective dose of the nonpolynucleotide herbicide corresponding to the herbicide target gene in which the polynucleotides have homology. Four replications of each treatment is conducted. Plant height is determined just before treatment and at intervals up to twelve days after herbicide treatments to determine effect of the polynucleotide and herbicide treatments.

Example 4. A Method to Control *Lolium* in a Field

A method to control *Lolium* in a field comprises the use of trigger polynucleotides that can modulate the expression of one or more herbicide target genes in *Lolium*. In Table 2, an analysis of herbicide target gene sequences provided a collection of 30-mer polynucleotides that can be used in compositions to affect the growth or develop or sensitivity to a nonpolynucleotide herbicide to control multiple weed species in a field. A composition containing 1 or 2 or 3 or 4 or more of the polynucleotides of Table 2 or fragments thereof would enable broad activity of the composition against the herbicide resistant ryegrass species or multiple *Lolium* weed species that occur in a field environment.

The method includes creating a composition that comprises components that include at least one polynucleotide of Table 2 or fragment thereof or any other effective gene expression modulating polynucleotide essentially identical or essentially complementary to SEQ ID NO:1-66, a transfer agent that mobilizes the polynucleotide into a plant cell and nonpolynucleotide herbicide. The polynucleotide of the composition includes a dsRNA, ssDNA or dsDNA or a combination thereof. A composition containing a polynucleotide can have a use rate of about 1 to 30 grams or more per acre depending on the size of the polynucleotide and the number of polynucleotides in the composition. The composition may include one or more additional herbicides as needed to provide effective multi-species weed control in addition to control of ryegrass and related weed species. A field of crop plants in need of weed plant control is treated by spray application of the composition. The composition can be provided as a tank mix, a sequential treatment of components (generally the polynucleotide followed by the nonpolynucleotide herbicide), a simultaneous treatment or mixing of one or more of the components of the composition from separate containers or as a premix of all of the components of the herbicidal composition. Members of the nonpolynucleotide herbicide families include but are not limited to amide herbicides, aromatic acid herbicides, arsenical herbicides, benzothiazole herbicides, benzoylcyclohexanedione herbicides, benzofuranyl alkylsulfonate herbicides, carbamate herbicides, cyclohexene oxime herbicides, cyclopropylisoxazole herbicides, dicarboximide herbicides, dinitroaniline herbicides, dinitrophenol herbicides, diphenyl ether herbicides, dithiocarbamate herbicides, halogenated aliphatic herbicides, imidazolinone herbicides, inorganic herbicides, nitrile herbicides, organophosphorus herbicides, oxadiazolone herbicides, oxazole herbicides, phenoxy herbicides, phenylenediamine herbicides, pyrazole herbicides, pyridazine herbicides, pyridazinone herbicides, pyridine herbicides, pyrimidinediamine herbicides, pyrimidinyloxybenzylamine herbicides, quaternary ammonium herbicides, thiocarbamate herbicides, thiocarbonate herbicides, thiourea herbicides, triazine herbicides, triazinone herbicides, triazole herbicides, triazolone herbicides, triazolopyrimidine herbicides, uracil herbicides, and urea herbicides. Treatment of the plants in the field can occur as often as needed to provide weed control and the components of the composition can be adjusted to target specific weed species or weed families.

I claim:

1. A method of *Lolium* species plant control comprising: treating a *Lolium* species plant or a part thereof in need of control with a first herbicidal composition comprising a double-stranded RNA (dsRNA) polynucleotide, an organo-silicone surfactant in a concentration of about 0.2 percent or greater by weight, and an effective dose of a nonpolynucleotide herbicide, wherein said dsRNA polynucleotide is identical or complementary to at least 21 contiguous nucleotides of a *Lolium* species gene polynucleotide selected from the group consisting of SEQ ID NOs: 46, 65, 88, 89, 91, 92, 94, 95, 98, 99, 104, 105, 114, 122-126, 129-134, 136, 138, 139, and 145-151, wherein said *Lolium* species plant is more sensitive to said nonpolynucleotide herbicide, relative to a similar plant treated with a second herbicidal composition not containing said dsRNA polynucleotide.

2. The method of claim 1, wherein said *Lolium* species is selected from the group consisting of *Lolium rigidum, Lolium canariense, Lolium edwardii, Lolium multiflorum, Lolium perenne, Lolium persicum, Lolium remotum,* and *Lolium temulentum.*

3. The method of claim 1, wherein
(a) said *Lolium* species gene polynucleotide is SEQ ID NO: 88, 89, 91, 92, 94, 95, 98, and 99, and said nonpolynucleotide herbicide is selected from the group consisting of sulfonylureas, imidazolinones, triazolopyrimidines, pyrimidinyl(thio)benzoates, and sulfonylaminocarbonyl-triazolinones;
(b) said *Lolium* species gene polynucleotide is SEQ ID NO: 104 or 105, and said nonpolynucleotide herbicide is sulfonamides or asulam;
(c) said *Lolium* species gene polynucleotide is selected from the group consisting of SEQ ID NOs: 114, 122-126, 129-134, 136, and 138, and said nonpolynucleotide herbicide is glufosinate;
(c) said *Lolium* species gene polynucleotide is selected from the group consisting of SEQ ID NOs: 114, 122-126, 129-134, 136, and 138, and said nonpolynucleotide herbicide is glufosinate;
(d) said *Lolium* species gene polynucleotide is SEQ ID NO: 46 or 139, and said nonpolynucleotide herbicide is selected from the group consisting of triketones, isoxazoles, and pyrazoles;
(e) said *Lolium* species gene polynucleotide is selected from the group consisting of SEQ ID NOs: 145-151, and said nonpolynucleotide herbicide is selected from the group consisting of pyridazinones, pyridinecarboxamides, beflubutamid, fluridone, flurochioridone, and flurtamone; or
(f) said *Lolium* species gene polynucleotide is SEQ ID NO: 65 and said nonpolynucleotide herbicide is selected from the group consisting of acifluorfen-Na, bifenox, chlomethoxyfen, fluoroglycofen-ethyl, fomesafen, halosafen, lactofen, oxyfluorfen, fluazolate, pyraflufen-ethyl, cinidon-ethyl, flumioxazin, flumiclorac-pentyl, fluthiacet-methyl, thidiazimin, oxadiazon, oxadiargyl, azafenidin, carfentrazone-ethyl, sulfentrazone, pentoxazone, benzfendizone, butafenacil, pyrazogyl, and profluazol.

4. The method of claim 1, wherein said first herbicidal composition comprises any combination of two or more of said dsRNA polynucleotides and two or more of said nonpolynucleotide herbicides that inhibit the activity of two or more proteins selected from the group consisting of acetolactate synthase (ALS) large subunit, ALS small subunit, 7,8-dihydropteroate synthase (DHPS), glutamine synthetase 2 (GS2), 4-hydroxyphenyl-pyruvate-dioxygenase (HPPD), phytoene desaturase (PDS), protoporphyrinogen IX oxidase (PPDX), and wherein said *Lolium* species plant is more sensitive to said two or more nonpolynucleotide herbicides, relative to said similar plant treated with said second herbicidal composition not containing said two or more dsRNA polynucleotides.

5. The method of claim 1, wherein said first or second herbicidal composition further comprises one or more herbicides selected from the group consisting of: 5-diarylpyrazole herbicides, 2-thiopyrimidine herbicides, 3-CF3-benzene herbicides, acetamide herbicides, amide herbicides, aminoacrylate herbicides, aminotriazine herbicides, aromatic acid herbicides, arsenical herbicides, arylcarboxamide herbicides, arylcyclodione herbicides, aryloxyphenoxy-propionate herbicides, azolecarboxamide herbicides, azoloazinone herbicides, azolotriazine herbicides, benzamide herbicides, benzenesulfonamide herbicides, benzhydryl herbicides, benzimidazole herbicides, benzofuran herbicides, benzofuranyl alkylsulfonate herbicides, benzohydrazide herbicides, benzoic acid herbicides, benzophenylmethanone herbicides, benzothiadiazinone herbicides, benzothiazole herbicides, benzothiazoleacetate herbicides, benzoxazole herbicides, benzoylcyclohexanedione herbicides, benzyloxymethylisoxazole herbicides, benzylpyrazole herbicides, benzylpyridine herbicides, benzylpyrimidone herbicides, bipyridylium herbicides, carbamate herbicides, chloroacetamide herbicides, chloroacetamide herbicides, chlorocarbonic acid herbicides, cyclohexene oxime herbicides, cyclopropylisoxazole herbicides, diarylether herbicides, dicarboximide herbicides, dihydropyrancarboxamide herbicides, diketo-epoxide herbicides, diketopiperazine herbicides, dinitroaniline herbicides, dinitrophenol herbicides, diphenylether herbicides, diphenylfuranone herbicides, dithiocarbamate herbicides, fluoroalkene herbicides, glyphosate herbicides, halogenated aliphatic herbicides, hydantocidin herbicides, hydroxypyrazole herbicides, imidazolinone herbicides, indazole herbicides, indenedione herbicides, inorganic herbicides, isoxazole herbicides, isoxazolesulfone herbicides, isoxazolidinone herbicides, nicotinohydrazide herbicides, nitrile herbicides, nitrile-amide herbicides, nitropyrazole herbicides, N-phenylphthalimide herbicides, organoarsenical herbicides, organophosphates herbicides, organophosphorus herbicides, oxabicycloheptane herbicides, oxadiazole herbicides, oxadiazolebenzamide herbicides, oxadiazolone herbicides, oxazole herbicides, oxazolidinedione herbicides, oxyacetamide herbicides, phenoxy herbicides, phenoxyalkyne herbicides, phenoxycarboxylic acid herbicides, phenoxypyridazinol herbicides, phenylalkanoate herbicides, phenylcarbamate herbicides, phenylenediamine herbicides, phenylethylurea herbicides, phenylimidazole herbicides, phenylisoxazole herbicides, phenylpyrazole herbicides, phenylpyridazine herbicides, phenylpyridine herbicides, phenylpyrrolidone herbicides, phosphinic acid herbicides, phosphonate herbicides, phosphoroamidate herbicides, phosphorodithioate herbicides, phthalamate herbicides, propionamide herbicides, pyrazole herbicides, pyrazole-arylether herbicides, pyrazolium herbicides, pyridazine herbicides, pyridazinone herbicides, pyridine herbicides, pyridinecarboxamide herbicides, pyridinecarboxylic acid herbicides, pyridinone herbicides, pyridyl-benzylamide herbicides, pyridyl-ether-carboxamide herbicides, pyrimidinecarboxylic acid herbicides, pyrimidinediamine herbicides, pyrimidinedione herbicides, pyrimidinetrione herbicides, pyrimidinone herbicides, pyrimidinyl(thio)benzoate herbicides, pyrimidinyloxybenzylamine herbicides, pyrimidylmethanol herbicides, pyrrolidone herbicides, quaternary ammonium herbicides, quinoline-carboxylic acid herbicides, quinoxaline herbicides, semicarbazone herbicides, sulfonamide herbicides, sulfonylamino-carbonyl-triazolinone herbicides, sulfonylurea herbicides, sulfonylurea herbicides, tetrazolinone herbicides, thiadiazole herbicides, thiatriazine herbicides, thienopyrimidine herbicides, thiocarbamate herbicides, thiocarbonate herbicides, thiourea herbicides, tolyltriazole herbicides, triazine herbicides, triazinedione herbicides, triazine-sulfonanilide herbicides, triazinone herbicides, triazole herbicides, triazolecarboxamide herbicides, triazoleimine herbicides, triazolinone herbicides, triazolone herbicides, triazolopyrimidine herbicides, triketone herbicides, uracil herbicides, and urea herbicides.

6. The method of claim 1, wherein said organosilicone surfactant is in a concentration of about 0.2 percent to about 2.0 percent by weight.

7. A herbicidal composition comprising an admixture of a dsRNA polynucleotide, an organosilicone surfactant in a concentration of about 0.2 percent or greater by weight, and an effective dose of a nonpolynucleotide herbicide, wherein said dsRNA polynucleotide is identical or complementary to at least 21 contiguous nucleotides of a *Lolium* species gene polynucleotide selected from the group consisting of SEQ ID NOs: 46, 65, 88, 89, 91, 92, 94, 95, 98, 99, 104, 105, 114, 122-126, 129-132, 134, 136, 138, 139, and 145-151, wherein a *Lolium* species plant treated with said herbicidal composition is more sensitive to said nonpolynucleotide herbicide, relative to a similar plant treated with a herbicidal composition not containing said dsRNA polynucleotide.

8. The herbicidal composition of claim 7, further comprising a pesticide, wherein said pesticide is selected from the group consisting of insecticides, fungicides, nematicides, bactericides, acaricides, growth regulators, chemosterilants, semiochemicals, repellents, attractants, pheromones, feeding stimulants, and biopesticides.

9. The herbicidal composition of claim 7, comprising a premix or a tankmix combination.

* * * * *